(12) United States Patent
Miao et al.

(10) Patent No.: US 9,488,660 B2
(45) Date of Patent: Nov. 8, 2016

(54) METHODS AND COMPOSITIONS COMPRISING NON-NATURAL AMINO ACIDS

(75) Inventors: Zhenwei Miao, San Diego, CA (US); Feng Tian, San Diego, CA (US); Anna-Maria A. Hays Putnam, San Diego, CA (US); Ying Buechler, San Diego, CA (US)

(73) Assignee: AMBRX, INC., La Jolla, CA (US)

( * ) Notice: Subject to any disclaimer, the term of this patent is extended or adjusted under 35 U.S.C. 154(b) by 0 days.

(21) Appl. No.: 12/902,010

(22) Filed: Oct. 11, 2010

(65) Prior Publication Data

US 2011/0144307 A1 Jun. 16, 2011

Related U.S. Application Data

(63) Continuation of application No. 12/092,791, filed as application No. PCT/US2006/044682 on Nov. 16, 2006, now abandoned.

(60) Provisional application No. 60/737,855, filed on Nov. 16, 2005.

(51) Int. Cl.
*A61K 38/00* (2006.01)
*G01N 33/68* (2006.01)

(52) U.S. Cl.
CPC ................................. *G01N 33/6812* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. |
| 4,289,872 A | 9/1981 | Denkewalter et al. |
| 4,412,989 A | 11/1983 | Iwashita et al. |
| 4,414,148 A | 11/1983 | Jansen et al. |
| 4,485,045 A | 11/1984 | Regen |
| 4,511,502 A | 4/1985 | Builder et al. |
| 4,511,503 A | 4/1985 | Olson et al. |
| 4,512,922 A | 4/1985 | Jones et al. |
| 4,544,545 A | 10/1985 | Ryan et al. |
| 4,551,433 A | 11/1985 | DeBoer |
| 4,569,789 A | 2/1986 | Blattler et al. |
| 4,619,794 A | 10/1986 | Hauser |
| 4,659,839 A | 4/1987 | Nicolotti et al. |
| 4,670,417 A | 6/1987 | Iwasaki et al. |
| 4,671,958 A | 6/1987 | Rodwell et al. |
| 4,680,338 A | 7/1987 | Sundoro |
| 4,689,406 A | 8/1987 | Banks et al. |
| 4,699,784 A | 10/1987 | Shih et al. |
| 4,738,921 A | 4/1988 | Belagaje et al. |
| 4,755,465 A | 7/1988 | Gray et al. |
| 4,837,148 A | 6/1989 | Cregg |
| 4,859,600 A | 8/1989 | Gray et al. |
| 4,876,197 A | 10/1989 | Burke et al. |
| 4,880,734 A | 11/1989 | Burke et al. |
| 4,902,502 A | 2/1990 | Nitecki et al. |
| 4,904,584 A | 2/1990 | Shaw |
| 4,929,555 A | 5/1990 | Cregg et al. |
| 5,021,234 A | 6/1991 | Ehrenfeld |
| 5,089,398 A | 2/1992 | Rosenberg et al. |
| 5,122,614 A | 6/1992 | Zalipsky |
| 5,162,601 A | 11/1992 | Slightom |
| 5,219,564 A | 6/1993 | Zalipsky et al. |
| 5,229,490 A | 7/1993 | Tam |
| 5,231,178 A | 7/1993 | Holtz et al. |
| 5,252,714 A | 10/1993 | Harris et al. |
| 5,281,698 A | 1/1994 | Nitecki |
| 5,290,686 A | 3/1994 | Kendal et al. |
| 5,324,639 A | 6/1994 | Brierley et al. |
| 5,324,844 A | 6/1994 | Zalipsky |
| 5,382,657 A | 1/1995 | Karasiewicz et al. |
| 5,446,090 A | 8/1995 | Harris |
| 5,468,478 A | 11/1995 | Saifer et al. |
| 5,473,034 A | 12/1995 | Yasui et al. |
| 5,476,653 A | 12/1995 | Pitt et al. |
| 5,516,657 A | 5/1996 | Murphy et al. |
| 5,516,673 A | 5/1996 | Margel et al. |
| 5,532,142 A | 7/1996 | Johnston et al. |
| 5,559,213 A | 9/1996 | Hakimi et al. |
| 5,571,709 A | 11/1996 | Devauchelle et al. |

(Continued)

FOREIGN PATENT DOCUMENTS

DE  3218121 A1  11/1983
EP  036 676 A1  9/1981

(Continued)

OTHER PUBLICATIONS

Hendrickson et al. High sensitivity multianalyte immunoassay using covalent DNA-labeled antibodies and polymerase chain reaction. Nucleic Acids Research. 1995, vol. 23, No. 3, pp. 522-529.*
Halpin et al. DNA Display III. Solid-Phase Organic Synthesis on Unprotected DNA. Jul. 2004. PLoS Biology. vol. 2, Issue 7, pp. 1031-1038.*
Skolnick, et al. From genes to protein structure and function: novel applications of computational approaches in the genomic era. Jan. 2000. Trends in Biotechnology. vol. 18, pp. 34-39.*
MacCallum, et al. Antibody-antigen Interactions: Contact Analysis and Binding Site Topography. 1996. Journal of Molecular Biology, vol. 262, pp. 732-745.*

(Continued)

*Primary Examiner* — Catherine S Hibbert
*Assistant Examiner* — Channing S Mahatan
(74) *Attorney, Agent, or Firm* — Kristin S. Eaton; John W. Wallen, III

(57) ABSTRACT

Disclosed herein are methods of detecting non-natural amino acids and polypeptides that include at least one non-natural amino acid. The non-natural amino acids, by themselves or as a part of a polypeptide, can include a wide range of functionalities, including but not limited to oxime, carbonyl, and/or hydroxylamine groups. Also disclosed herein are non-natural amino acid polypeptides that are further modified post-translationally, and methods for detecting such polypeptides.

2 Claims, 22 Drawing Sheets

(56) References Cited

U.S. PATENT DOCUMENTS

| | | |
|---|---|---|
| 5,580,723 A | 12/1996 | Wells et al. |
| 5,583,023 A | 12/1996 | Cerutti et al. |
| 5,602,034 A | 2/1997 | Tekamp-Olson |
| 5,605,827 A | 2/1997 | Jackwood et al. |
| 5,612,460 A | 3/1997 | Zalipsky |
| 5,629,203 A | 5/1997 | Shuster |
| 5,629,384 A | 5/1997 | Veronese et al. |
| 5,643,575 A | 7/1997 | Martinez et al. |
| 5,650,234 A | 7/1997 | Dolence et al. |
| 5,672,662 A | 9/1997 | Harris et al. |
| 5,674,706 A | 10/1997 | Shuster |
| RE35,749 E | 3/1998 | Rosenberg et al. |
| 5,736,625 A | 4/1998 | Callstrom et al. |
| 5,739,208 A | 4/1998 | Harris |
| 5,747,646 A | 5/1998 | Hakimi et al. |
| 5,750,373 A | 5/1998 | Garrard et al. |
| 5,753,220 A | 5/1998 | Suzuki et al. |
| 5,762,939 A | 6/1998 | Smith et al. |
| 5,766,885 A | 6/1998 | Carrington et al. |
| 5,808,096 A | 9/1998 | Zalipsky |
| 5,824,778 A | 10/1998 | Ishikawa et al. |
| 5,824,784 A | 10/1998 | Kinstler et al. |
| 5,834,250 A | 11/1998 | Wells et al. |
| 5,834,594 A | 11/1998 | Hakimi et al. |
| 5,843,733 A | 12/1998 | Estes |
| 5,849,860 A | 12/1998 | Hakimi et al. |
| 5,858,368 A | 1/1999 | Smith et al. |
| 5,861,279 A | 1/1999 | Zhang et al. |
| 5,871,986 A | 2/1999 | Boyce |
| 5,891,676 A | 4/1999 | Estes |
| 5,900,461 A | 5/1999 | Harris |
| 5,932,462 A | 8/1999 | Harris et al. |
| 5,939,285 A | 8/1999 | Devauchelle et al. |
| 5,965,393 A | 10/1999 | Hasnain et al. |
| 5,980,948 A | 11/1999 | Goedemoed et al. |
| 5,989,868 A | 11/1999 | Harrison et al. |
| 5,990,237 A | 11/1999 | Bentley et al. |
| 6,004,573 A | 12/1999 | Rathi et al. |
| 6,013,433 A | 1/2000 | Pellett et al. |
| 6,013,478 A | 1/2000 | Wells et al. |
| 6,017,731 A | 1/2000 | Tekamp-Olson et al. |
| 6,083,723 A | 7/2000 | Tekamp-Olson |
| 6,096,304 A | 8/2000 | McCutchen |
| 6,126,944 A | 10/2000 | Pellett et al. |
| 6,129,912 A | 10/2000 | Hortin et al. |
| 6,168,932 B1 | 1/2001 | Uckun et al. |
| 6,183,985 B1 | 2/2001 | Shuster |
| 6,183,987 B1 | 2/2001 | Van De Wiel et al. |
| 6,201,072 B1 | 3/2001 | Rathi et al. |
| 6,214,966 B1 | 4/2001 | Harris |
| 6,225,060 B1 | 5/2001 | Clark et al. |
| 6,245,528 B1 | 6/2001 | Chao |
| 6,261,805 B1 | 7/2001 | Wood |
| RE37,343 E | 8/2001 | Tekamp-Olson |
| 6,281,211 B1 | 8/2001 | Cai et al. |
| 6,306,821 B1 | 10/2001 | Mikos et al. |
| 6,312,923 B1 | 11/2001 | Tekamp-Olson |
| 6,337,191 B1 | 1/2002 | Swartz et al. |
| 6,338,846 B1 | 1/2002 | Kang et al. |
| 6,342,216 B1 | 1/2002 | Fidler et al. |
| 6,361,969 B1 | 3/2002 | Galeotti |
| 6,368,825 B1 | 4/2002 | Chao |
| 6,420,339 B1 | 7/2002 | Gegg et al. |
| 6,423,685 B1 | 7/2002 | Drummond et al. |
| 6,428,954 B1 | 8/2002 | Wells et al. |
| 6,436,386 B1 | 8/2002 | Roberts et al. |
| 6,451,346 B1 | 9/2002 | Shah et al. |
| 6,451,561 B1 | 9/2002 | Wells et al. |
| 6,461,603 B2 | 10/2002 | Bentley et al. |
| 6,515,100 B2 | 2/2003 | Harris |
| 6,521,427 B1 | 2/2003 | Evans |
| 6,552,167 B1 | 4/2003 | Rose |
| 6,586,207 B2 | 7/2003 | Tirrell et al. |
| 6,602,498 B2 | 8/2003 | Shen |
| 6,608,183 B1 | 8/2003 | Cox, III |
| 6,610,281 B2 | 8/2003 | Harris |
| 6,646,110 B2 | 11/2003 | Nissen et al. |
| 6,927,042 B2 | 8/2005 | Schultz et al. |
| 7,045,337 B2 | 5/2006 | Schultz et al. |
| 7,083,970 B2 | 8/2006 | Schultz et al. |
| 2001/0021763 A1 | 9/2001 | Harris |
| 2001/0044526 A1 | 11/2001 | Shen |
| 2001/0056171 A1 | 12/2001 | Kozlowski |
| 2002/0002250 A1 | 1/2002 | Bentley et al. |
| 2002/0019061 A1 | 2/2002 | Lai et al. |
| 2002/0037949 A1 | 3/2002 | Harris et al. |
| 2002/0040076 A1 | 4/2002 | Harris et al. |
| 2002/0042097 A1 | 4/2002 | Tirrell et al. |
| 2002/0052009 A1 | 5/2002 | Hornauer et al. |
| 2002/0052430 A1 | 5/2002 | Harris et al. |
| 2002/0055169 A1 | 5/2002 | Tekamp-Olson |
| 2002/0072573 A1 | 6/2002 | Bentley et al. |
| 2002/0081660 A1 | 6/2002 | Swartz et al. |
| 2002/0082345 A1 | 6/2002 | Kozlowski et al. |
| 2002/0086939 A1 | 7/2002 | Kozlowski |
| 2002/0099133 A1 | 7/2002 | Kozlowski |
| 2002/0156047 A1 | 10/2002 | Zhao |
| 2003/0023023 A1 | 1/2003 | Harris et al. |
| 2003/0082575 A1 | 5/2003 | Schultz et al. |
| 2003/0105224 A1 | 6/2003 | Roberts et al. |
| 2003/0105275 A1 | 6/2003 | Bentley et al. |
| 2003/0106797 A1 | 6/2003 | Schneider et al. |
| 2003/0108885 A1 | 6/2003 | Schultz et al. |
| 2003/0114647 A1 | 6/2003 | Harris et al. |
| 2003/0143596 A1 | 7/2003 | Bentley et al. |
| 2003/0158333 A1 | 8/2003 | Roberts |
| 2003/0162949 A1 | 8/2003 | Cox, III |
| 2003/0220447 A1 | 11/2003 | Harris |
| 2003/0228274 A1 | 12/2003 | Rose |
| 2003/0235851 A1 | 12/2003 | Roberts et al. |
| 2004/0001838 A1 | 1/2004 | Zhao et al. |
| 2004/0013637 A1 | 1/2004 | Bentley et al. |
| 2004/0138106 A1 | 7/2004 | Schultz et al. |
| 2004/0171085 A1 | 9/2004 | Joazeiro |
| 2004/0198637 A1 | 10/2004 | Schultz et al. |
| 2005/0009049 A1 | 1/2005 | Chin et al. |
| 2005/0019755 A1 | 1/2005 | Marchessault et al. |
| 2005/0053973 A1 | 3/2005 | Kolkman et al. |
| 2005/0085619 A1 | 4/2005 | Wilson et al. |
| 2005/0136513 A1 | 6/2005 | Zhang et al. |
| 2005/0170404 A1 | 8/2005 | Cho et al. |
| 2005/0220762 A1 | 10/2005 | Cho et al. |

FOREIGN PATENT DOCUMENTS

| | | |
|---|---|---|
| EP | 036 776 A2 | 9/1981 |
| EP | 052 322 A2 | 5/1982 |
| EP | 058 481 A1 | 8/1982 |
| EP | 073 657 A1 | 3/1983 |
| EP | 102 324 A2 | 3/1984 |
| EP | 121 775 A1 | 10/1984 |
| EP | 127 839 A2 | 12/1984 |
| EP | 133 988 A2 | 3/1985 |
| EP | 143 949 A1 | 6/1985 |
| EP | 154 316 A2 | 9/1985 |
| EP | 155 476 A1 | 9/1985 |
| EP | 164 556 A2 | 12/1985 |
| EP | 183 503 A2 | 6/1986 |
| EP | 188 256 A2 | 7/1986 |
| EP | 229 108 B1 | 7/1987 |
| EP | 244 234 A2 | 11/1987 |
| EP | 267 851 A2 | 5/1988 |
| EP | 284 044 A1 | 9/1988 |
| EP | 324 274 A1 | 7/1989 |
| EP | 329 203 A1 | 8/1989 |
| EP | 340 986 A2 | 11/1989 |
| EP | 400 472 A2 | 12/1990 |
| EP | 402 378 B1 | 12/1990 |
| EP | 439 508 B1 | 8/1991 |
| EP | 480 480 A2 | 4/1992 |
| EP | 510 356 A1 | 10/1992 |
| EP | 605 963 A1 | 7/1994 |
| EP | 732 403 A1 | 9/1996 |
| EP | 809 996 A2 | 12/1997 |

(56) References Cited

FOREIGN PATENT DOCUMENTS

| | | |
|---|---|---|
| EP | 921 131 A1 | 6/1999 |
| EP | 946 736 B1 | 10/1999 |
| EP | 1396498 A1 | 3/2004 |
| JP | 60-007934 A | 1/1985 |
| WO | 88/07082 A1 | 9/1988 |
| WO | 89/01037 A1 | 2/1989 |
| WO | 89/01038 A1 | 2/1989 |
| WO | 90/01556 A1 | 2/1990 |
| WO | 90/02186 A1 | 3/1990 |
| WO | 90/02566 A1 | 3/1990 |
| WO | 90/05785 A1 | 5/1990 |
| WO | 90/10078 A1 | 9/1990 |
| WO | 90/10277 A1 | 9/1990 |
| WO | 90/13540 A1 | 11/1990 |
| WO | 90/14428 A1 | 11/1990 |
| WO | 91/00357 A1 | 1/1991 |
| WO | 92/01801 A1 | 2/1992 |
| WO | 92/02628 A1 | 2/1992 |
| WO | 92/16555 A1 | 10/1992 |
| WO | 92/16619 A1 | 10/1992 |
| WO | 93/03173 A1 | 2/1993 |
| WO | 93/15189 A1 | 8/1993 |
| WO | 93/21259 A1 | 10/1993 |
| WO | 94/04193 A1 | 3/1994 |
| WO | 94/09027 A1 | 4/1994 |
| WO | 94/14758 A1 | 7/1994 |
| WO | 94/15625 A1 | 7/1994 |
| WO | 94/17039 A1 | 8/1994 |
| WO | 94/18247 A1 | 8/1994 |
| WO | 94/28024 A1 | 12/1994 |
| WO | 95/00162 A1 | 1/1995 |
| WO | 95/06058 A1 | 3/1995 |
| WO | 95/11924 A1 | 5/1995 |
| WO | 95/13090 A1 | 5/1995 |
| WO | 95/13312 A1 | 5/1995 |
| WO | 95/20672 A1 | 8/1995 |
| WO | 95/33490 A1 | 12/1995 |
| WO | 96/00080 A1 | 1/1996 |
| WO | 96/06161 A1 | 2/1996 |
| WO | 96/07670 A1 | 3/1996 |
| WO | 96/21469 A1 | 7/1996 |
| WO | 96/25496 A1 | 8/1996 |
| WO | 96/29400 A1 | 9/1996 |
| WO | 96/40791 A1 | 12/1996 |
| WO | 96/41813 A2 | 12/1996 |
| WO | 97/03106 A1 | 1/1997 |
| WO | 97/18832 A1 | 5/1997 |
| WO | 97/26332 A1 | 7/1997 |
| WO | 97/32607 A2 | 9/1997 |
| WO | 98/05363 A2 | 2/1998 |
| WO | 98/26080 A1 | 6/1998 |
| WO | 98/32466 A1 | 7/1998 |
| WO | 98/37208 A1 | 8/1998 |
| WO | 98/41562 A1 | 9/1998 |
| WO | 98/48837 A1 | 11/1998 |
| WO | 99/03887 A1 | 1/1999 |
| WO | 99/05297 A1 | 2/1999 |
| WO | 99/07862 A1 | 2/1999 |
| WO | 99/09193 A1 | 2/1999 |
| WO | 99/10515 A1 | 3/1999 |
| WO | 99/31257 A2 | 6/1999 |
| WO | 99/32134 A1 | 7/1999 |
| WO | 99/32139 A1 | 7/1999 |
| WO | 99/32140 A1 | 7/1999 |
| WO | 99/45130 A1 | 9/1999 |
| WO | 99/51721 A1 | 10/1999 |
| WO | 99/67291 A2 | 12/1999 |
| WO | 00/20032 A1 | 4/2000 |
| WO | 00/26354 A1 | 5/2000 |
| WO | 00/55345 A2 | 9/2000 |
| WO | 00/55353 A1 | 9/2000 |
| WO | 01/05956 A2 | 1/2001 |
| WO | 01/27301 A2 | 4/2001 |
| WO | 01/90390 A1 | 11/2001 |
| WO | 02/06305 A1 | 1/2002 |
| WO | 02/085923 A2 | 10/2002 |
| WO | 02/086075 A2 | 10/2002 |
| WO | 03/101972 A1 | 12/2003 |
| WO | 2004/035605 A2 | 4/2004 |
| WO | 2004/035743 A2 | 4/2004 |
| WO | 2004/058946 A2 | 7/2004 |
| WO | 2004/094593 A2 | 11/2004 |
| WO | 2005/007624 A2 | 1/2005 |
| WO | 2005/007870 A2 | 1/2005 |
| WO | 2005/019415 A2 | 3/2005 |
| WO | 2005/035727 A2 | 4/2005 |
| WO | 2005/074524 A2 | 8/2005 |
| WO | 2005/074546 A2 | 8/2005 |
| WO | 2005/074650 A2 | 8/2005 |

OTHER PUBLICATIONS

De Pascalis et al. Grafting of "Abbreviated" Complementarity-Determining Regions Containing Specificity-Determining Residues Essential for Ligand Contact to Engineer a Less Immunogenic Humanized Monoclonal Antibody. 2002. Journal of Immunology. vol. 169, pp. 3076-3084.*

Casset, et al. A peptide mimetic of an anti-CD4 monoclonal antibody by rational design. 2003. Biochemical and Biophysical Research Communications. vol. 307, pp. 198-205.*

Vajdos, et al. Comprehensive Functional Maps of the Antigen-binding Site of an Anti-ErbB2 Antibody Obtained with Shotgun Scanning Mutagenesis. 2002. Journal of Molecular Biology. vol. 320, pp. 415-428.*

Holm et al. Functional mapping and single chain construction of the anti-cytokeratin 8 monoclonal antibody TS1. 2007. Molecular Immunology. vol. 44, pp. 1075-1084.*

Chen et al. Selection and Analysis of an Optimized Anti-VEGF Antibody: Crystal Structure of an Affinity-matured Fab in Complex with Antigen. 1999. Journal of Molecular Biology. vol. 293, pp. 865-881.*

Wu et al. Humanization of a Murine Monoclonal Antibody by Simultaneous Optimization of Framework and CDR Residues. 1999. Journal of Molecular Biology. vol. 294, pp. 151-162.*

Mallender et al. Inter-Active-Site Distance and Solution Dynamics of a Bivalent-Bispecific Single-Chain Antibody Molecule. 1994. Biochemistry. vol. 33, pp. 10100-10108.*

Duncan, R. "The dawning era of polymer therapeutics," Nat Rev Drug Discov May 2003;2(5):347-60.

Gaertner, HF et RE Offord. "Site-specific attachment of functionalized poly(ethylene glycol) to the amino terminus of proteins," Bioconjug Chem Jan.-Feb. 1996;7(1):38-44.

Gu, Z et al. "Chromatographic methods for the isolation of, and refolding of proteins from, *Escherichia coli* inclusion bodies," Protein Expr Purif. Jun. 2002;25(1):174-9.

Hohsaka, T et M Sisido. "Incorporation of non-natural amino acids into proteins," Curr Opin Chem Biol. Dec. 2002;6(6):809-15.

Lilie, H et al. "Advances in refolding of proteins produced in *E. coli*," Curr Opin Biotechnol. Oct. 1998;9(5):497-501.

Tsumoto, K et al. "Practical considerations in refolding proteins from inclusion bodies," Protein Expr Purif. Mar. 2003;28(1):1-8.

Wang, W. "Instability, stabilization, and formulation of liquid protein pharmaceuticals," Int J Pharm. Aug. 20, 1999;185 (2):129-88.

Doherty et al., "Site Specific PEGylation of Engineered Cysteine Analogs of Recombinant Human GranulocyteMacrophage Colony-Stimulating Factor", Bioconjugate Chemistry, Sep. 2005, 16(5):1291-1298.

Ferra et al., "Engineering of Peptide Synthetases, The Journal of Biological Chemistry", Oct. 1997, 272(40): 25304-25309.

Kobayashi et al., "Structural Basis of Orthogonal tRNA Specificities of tyrosyl-tRNA Synthetases for Genetic Code Expansion", Nature Structural Biology, Jun. 2003, 10(6):425-432.

Sisido et al., "Introduction of Speciality Functions by the Position-Specific Incorporation of Nonnatural Amino Acids into Proteins through Four-Based Codon/Anticodon Pairs", Appl. Microbiol Biotechnol., Oct. 2001, 57(3)274-281.

(56) References Cited

OTHER PUBLICATIONS

Gakh et al., "Fluorine as an NMR Probe for Structural Studies of Chemical and Biological Systems", Magnetic Resonance in Chemistry, Jun. 2000, 38(7):551-558.
Karginov et al., "Facile Characterization of Translation Initiation via Nonsense Codon Suppression", Nucleic Acid Research, Aug. 15, 1999, 27(16):3283-3290.
Kurfurst et al., "Detection and Molecular Weight Determination of Polyethylene Glycol-Modified Hirudin by Staining After Sodium Dodecyl Sulfate-Polyacrylamide gel Electrorphoresis", Analytical Biochemistry, Feb. 1, 1992, 200 (2):244-248.).
Abuchowski, A. et al. "Cancer therapy with chemically modified enzymes. I. Antitumor properties of polyethylene glycol-asparaginase conjugates," Cancer Biochem Biophys. Jun. 1984;7(2):175-86.
Altschul, SF et al. "Gapped Blast and PSI-BLAST: A new generation of protein database search programs," Nucleic Acids Res. Sep. 1, 1997;25(17):3389-402.
Altschul, SF et al. "Basic local alignment search tool," J Mol Biol. Oct. 5, 1990;215(3):403-10.
Amann, E et al., "Vectors bearing a hybrid trp-lac promoter useful for regulated expression of cloned genes in *Escherichia coli*," Gene. Nov. 1983;25(2-3):167-78.
Anderson, JC et al., "Exploring the limits of codon and anticodon size," Chem Biol. Feb. 2002;9(2):237-44.
Arnold, FH. "Protein engineering for unusual environments," Curr Opin Biotechnol. Aug. 1993;4(4):450-5.
Azoulay, M., et al. "Glutamine analogues as Potential Antimalarials," Eur. J. Med. Chem. (1991); 26(2):201-5.
Bain, JD, et al. "Biosynthetic site-specific incorporation of a nonnatural amino acid into a polypeptide," J. Am Chem Soc 1989;111(20):8013-8014.
Ballance, DJ et al., "Transformation of Aspergillus nidulans by the orotidine-5'-phosphate decarboxylase gene of Neurospora crassa," Biochem Biophys Res Commun. Apr. 15, 1983;112(1):284-9.
Barany, F. et al., "Genetic disease detection and DNA amplification using cloned thermostable ligase," Proc Natl Acad Sci U S A. Jan. 1, 1991;88(1):189-93.
Barton, DHR et al., "Synthesis of Novel alpha-Amino-Acids and Derivatives Using Radical Chemistry: Synthesis of L- and D-alpha-Amino-Adipic Acids, L-alpha-aminopimelic Acid and Appropriate Unsaturated Derivatives," Tetrahedron (1987) 43:4297-4308.
Bass, Set al., "Mutant Trp repressors with new DNA-binding specificities," Science (1988) 242:240-245.
Batzer, MA et al., "Enhanced evolutionary PCR using oligonucleotides with inosine at the 3'-terminus," Nucleic Acids Res. Sep. 25, 1991;19(18):5081.
Beach, D et al., "Functionally homologous cell cycle control genes in budding and fission yeast," Nature Dec. 1982; 300:706-709.
Beauchamp, CO et al., "A new procedure for the synthesis of polyethylene glycol-protein adducts; effects on function, receptor recognition, and clearance of superoxide dismutase, lactoferrin, and alpha 2-macroglobulin," Anal Biochem. May 1983;131(1):25-33.
Bernstein, FC, et al. "The protein data bank: a computer-based archival file for macromolecular structures," J. Mol. Biol, 1977; 112:535-542.
Boissel, JP et al., "Erythropoietin structure-function relationships. Mutant proteins that test a model of tertiary structure," J Biol Chem. Jul. 25, 1993;268(21):15983-93.
Botstein, D et D Shortie, "Strategies and applications of in vitro mutagenesis," Science. Sep. 20, 1985;229 (4719):1193-201.
Brunner, J. "New photolabeling and crosslinking methods," Annu Rev Biochem. 1993;62:483-514.
Buchner, J. et al., "A method for increasing the yield of properly folded recombinant fusion proteins: Single-chain immunotoxins from renaturation of bacterial inclusion bodies," Anal. Biochem. 1992; 205(2): 263-270.
Bückmann et al. "Functionalization of Poly(ethylene glycol) and Monomethoxy-Poly(ethylene glycol)," "Makromol. Chem. 1981;182:1379-84.

Budisa, N. et al. "High-level biosynthetic substitution of methionine in proteins by its analogs 2-aminohexanoic acid, selenomethionine, telluromethionine and ethionine in *Escherichia coli*," Eur J Biochem. Jun. 1, 1995;230(2):788-96.
Budisa, N. et al., "Bioincorporation of telluromethionine into proteins: a promising new approach for X-ray structure analysis of proteins," J Mol Biol. Jul. 25, 1997;270(4):616-23.
Budisa, N. et al., "Toward the experimental codon reassignment in vivo: protein building with an expanded amino acid repertoire," FASEB J. Jan. 1999;13(1):41-51.
Cai, X-Y et al., "Expression, Purification, and Characterization of an Activated Cytokine-Suppressive Anti-inflammatory Drug-Binding Protein 2 (CSBP2) Kinase from Baculovirus-Infected Insect Cells," Protein Expression and Purification 1997; 10(2):263-74.
Carbonell, LF et al., "Baculovirus-mediated expression of bacterial genes in dipteran and mammalian cells," J Virol. Oct. 1985;56(1):153-60.
Carrasco, M. and R. Brown, "A Versatile Set of Aminooxy Amino Acids for the Synthesis of Neoglycopeptides," J. Org. Chem. (2003); 68(23): 8853-8858.
Carter, P. "Site-directed mutagenesis," Biochem J. Jul. 1, 1986; 237(1):1-7.
Carter, P et al. "Improved oligonucleotide site-directed mutagenesis using M13 vectors" Nucleic Acids Res. Jun. 25, 1985;13(12):4431-43.
Carter, P. "Improved oligonucleotide-directed mutagenesis using M13 vectors" Methods Enzymol. 1987;154:382-403.
Chaiken, Im. "Semisynthetic peptides and proteins," CRC Crit Rev Biochem. 1981;11(3):255-301.
Chin, JW et al., "Addition of p-azido-L-phenylalanine to the genetic code of *E. coli*," J Am Chem Soc. Aug. 7, 2002;124(31):9026-7.
Chin, JW et al., "Addition of a photocrosslinking amino acid to the genetic code of *Escherichia coli*," Proc Nati Acad SCi U S A. Aug. 20, 2002;99(17):11020-4. Epub Aug. 1, 2002.
Chin, JW et al., "An expanded eukaryotic genetic code," Science. Aug. 15, 2003;301(5635):964-7.
Chin, JW & P. G. Schultz, "In vivo photocrosslinking with unnatural amino acid mutagenesis," Chembiochem. Nov. 4, 2002; 3(11): 1135-7.
Christie, B.D. & Rapoport, H. "Synthesis of Optically Pure Pipecolates from L-Asparagine. Application to the Total Synthesis of (+)-Apovincamine through Amino Acid Decarbonylation and Iminium Ion Cyclization," J. Org. Chem. 1985;50(8):1239-1246.
Clark, R et al., "Long-acting growth hormones produced by conjugation with polyethylene glycol," J Biol Chem. Sep. 6, 1996;271(36):21969-77.
Corey, D.R., Schultz, P.G. "Generation of a hybrid sequence-specific single-stranded deoxyribonuclease," Science 1987; 238(4832):1401-1403.
Cornish, VW, et al., "Site-Specific Protein Modification Using a Ketone Handle," J. Am. Chem. Soc. 1996; 118 (34):8150-8151.
Cornish, VW et al., "Probing Protein Structure and Function with an Expanded Genetic Code,"Angew Chem Int Ed Eng1,1995;34(6):621-33.
Craig, J.C. et al. "Absolute Configuration of the Enantiomers of 7-Chloro-4 [[4-(diethylamino)-1-methylbutyl]amino] quinoline (Chloroquine)," J. Org. Chem. 1988; 53(6):1167-1170.
Cregg, JM et al., "Pichia pastoris as a host system for transformations," Mol Cell Biol. Dec. 1985;5(12):3376-85.
Crick, FHC, et al. "General nature of the genetic code for proteins," Nature. Dec. 30, 1961;192:1227-32.
Dale et al., Oligonucleotide-directed random mutagenesis using the phosphorothioate method, Methods Mol. Bio1.1996;57:369-374.
Das, S et al., "Transformation of Kluyveromyces fragilis," J Bacteriol. Jun. 1984;158(3):1165-7.
Dawson, P. E. and S. B. H. Kent, "Synthesis of native proteins by chemical ligation," Annu. Rev. Biochem. 2000; 69:923-60.
De Boer, HA et al., "The tac promoter: a functional hybrid derived from the trp and lac promoters," Proc Natl Acad Sci U S A. Jan. 1983;80(1):21-5.
De Louvencourt, L et al., "Transformation of Kluyveromyces lactis by killer plasmid DNA," J Bacteriol. May 1983;154(2):737-42.

(56) References Cited

OTHER PUBLICATIONS

Tondelli, L. et al. "Poly(ethylene Glycol) Imidazolyl Formates as Oligomeric Drug-Binding Matrices," J. Controlled Release 1985;1(4):251-7.

Tornoe, CW et al., "Peptidotriazoles on solid phase: [1,2,3]-triazoles by regiospecific copper(i)-catalyzed 1,3-dipolar cycloadditions of terminal alkynes to azides," J Org Chem. May 3, 2002;67(9):3057-64.

Tschumper, G. et al., "Sequence of a yeast DNA fragment containing a chromosomal replicator and the TRP1 gene," Gene 1980; 10(2):157-66.

Turcatti, G et al. "Probing the structure and function of the tachykinin neurokinin-2 receptor through biosynthetic incorporation of fluorescent amino acids at specific sites," J Biol Chem. Aug. 16, 1996;271(33):19991-8.

Van Den Berg, JA et al., "Kluyveromyces as a host for heterologous gene expression: expression and secretion of prochymosin," Biotechnology (N. Y). Feb. 1990;8(2):135-9.

Van Hest, JC and DA Tirrell, "Efficient introduction of alkene functionality into proteins in vivo," FEBS Lett. May 22, 1998;428(1-2):68-70.

Doherty et al., "Site Specific PEGylation of Engineered Cysteine Analogs of Recombinant Human Granulocyte Macrophage Colony-Stimulating Factor", Bioconjugate Chemistry, Sep. 2005, 16(5):1291-1298.

Braun et al., "A Biological Transporter for the Delivery of Peptide Nucleic Acids (PNAs) to the Nuclear Compartment of Living Cells", J. Mol, Biol. (2002) 318(2):237-243.

Cutrona et al., "Effects in Live Cells of a c-myc Anti-gene PNA Linked to a Nuclear Localization Signal", Nature Biotech. (2000) 18(3):3003-303.

Wilson et al., "In Vitro Selection of Functional Nucleic Acids", Ann. Rev. Biotech. (1999) (68):611-647.

Debinski, W et al. "A wide range of human cancers express interleukin 4 (IL4) receptors that can be targeted with chimeric toxin composed of IL4 and Pseudomonas exotoxin," J Biol Chem. Jul. 5, 1993;268(19):14065-70.

Deiters, A., et al., "Adding Amino Acids with Novel Reactivity to the Genetic Code of *Saccharomyces Cerevisiae*," J. Am. Chem. Soc. 2003; 125(39):11782-11783.

Delgado, C et al., "The uses and properties of PEG-linked proteins," Crit Rev Ther Drug Carrier Syst. 1992;9 (3-4):249-304.

Dennis, MS et al., "Albumin binding as a general strategy for improving the pharmacokinetics of proteins," J Biol Chem. Sep. 20, 2002;277(38):35035-43. Epub Jul. 15, 2002.

Dolphin, CT et al., "Missense mutation in flavin-containing monooxygenase 3 gene, FMO3, underlies fish-odour syndrome," Nat Genet. Dec. 1997;17(4):491-4.

Doring, V et al., "Enlarging the amino acid set of *Escherichia coli* by infiltration of the valine coding pathway," Science. Apr. 20, 2001;292(5516):501-4.

Dougherty, DA. "Unnatural amino acids as probes of protein structure and function," Curr Opin Chem Biol. Dec. 2000;4(6):645-52.

Duewel, H et al., "Incorporation of trifluoromethionine into a phage lysozyme: implications and a new marker for use in protein 19F NMR," Biochemistry. Mar. 18, 1997;36(11):3404-16.

Eghtedarzadeh MK & S Henikoff "Use of oligonucleotides to generate large deletions" Nucleic Acids Res. Jun. 25, 1986;14(12):5115.

Elling L et MR Kula., "Immunoaffinity partitioning: synthesis and use of polyethylene glycol-oxirane for coupling to bovine serum albumin and monoclonal antibodies," Biotechnol Appl Biochem. Jun. 1991;13(3):354-62.

Elliott, S et al., "Yeast-derived recombinant human insulin-like growth factor I: production, purification, and structural characterization," J Protein Chem. Feb. 1990;9(1):95-104.

Ellman, J.A., Mendel, D., Anthony-Cahill, S., Noren, C.J., Schultz, P.G. "Biosynthetic method for introducing unnatural amino acids site-specifically into proteins," Methods in Enz., 1992; 202:301-336.

Ellman, JA, et al. "Site-specific incorporation of novel backbone structures into proteins," Science. Jan. 10, 1992;255 (5041):197-200.

England, P. M., et al., "Backbone mutations in transmembrane domains of a ligand-gated ion channel: implications for the mechanism of gating," Cell. Jan. 8, 1999;96(1):89-98.

Eppstein et al., "Biological Activity of Liposome-Encapsulated Murine Interferon is Mediated by a Cell Membrane Receptor," Proc. Natl. Acad. Sci. U.S.A.(1985); 82: 3688-3692.

Fieschko, JC et al., "Controlled expression and purification of human immune interferon from high-cell-density fermentations of *Saccharomyces cerevisiae*," Biotech. Bioeng. (1987) 29(9):1113-21.

Forster, AC et al., "Programming peptidomimetic syntheses by translating genetic codes designed de novo," Proc Natl Acad Sci U S A. May 27, 2003;100(11):6353-7. Epub May 16, 2003.

Frankel, A et al., "Encodamers: unnatural peptide oligomers encoded in RNA," Chem Biol. Nov. 2003;10 (11):1043-50.

Fraser, MJ et al., "Expression of eucaryotic genes in insect cell cultures," in Vitro Cell. Dev. Biol. 1989; 25:225-235.

Friedman, O.M. & R. Chatterrji. "Synthesis of Derivatives of Glutamine as Model Substrates for Anti-Tumor Agents," J. Am. Chem. Soc. 1959; 81(14):3750-3752.

Fritz HJ et al., "Oligonucleotide-directed construction of mutations: a gapped duplex DNA procedure without enzymatic reactions in vitro," Nucleic Acids Res. Jul. 25, 1988;16(14B):6987-99.

Fromm, M. et al., "Expression of Genes Transferred into Monocot and Dicot Plant Cells by Electroporation," Proc. Natl. Acad. Sci. USA (1985) 82:5824-8.

Furter, R. "Expansion of the genetic code: site-directed p-fluorophenylalanine incorporation in *Escherichia coli*," Protein Sci. Feb. 1998;7(2):419-26.

Gaertner, HF et al., "Construction of protein analogues by site-specific condensation of unprotected fragments," Bioconjug Chem. May-Jun. 1992;3(3):262-8.

Gaertner, HF et al., "Chemo-enzymic backbone engineering of proteins. Site-specific incorporation of synthetic peptides that mimic the 64-74 disulfide loop of granulocyte colony-stimulating factor," J Biol Chem. Mar. 11, 1994;269 (10):7224-30.

Gallivan, JP et al., "Site-specific incorporation of biotinylated amino acids to identify surface-exposed residues in integral membrane proteins," Chem Biol. Oct. 1997;4(10):739-49.

Gellissen, G et al., "Heterologous protein production in yeast," Antonie Van Leeuwenhoek. Aug. 1992;62(1-2):79-93.

Geoghegan, KF and JG Stroh, "Site-directed conjugation of nonpeptide groups to peptides and proteins via periodate oxidation of a 2-amino alcohol. Application to modification at N-terminal serine," Bioconjug Chem. Mar.-Apr. 1992; 3(2):138-46.

Gillam, S. & M Smith, "Site-specific mutagenesis using synthetic oligodeoxyribonucleotide primers: I. Optimum conditions and minimum oligodeoxyribonucleotide length," Gene 1979; 8(1):81-97.

Gleeson, MA et al., "Transformation of the methylotrophic yeast hansenula polymorphica," J. Gen. Microbiol. (1986) 132:3459-3465.

Goeddel, DV, "Systems for heterologous gene expression," Methods Enzymol. 1990;185:3-7.

Goeddel, DV et al., "Synthesis of human fibroblast interferon by *E. coli*," Nucleic Acids Res. Sep. 25, 1980;8 (18):4057-74.

Goodson RJ et NV Katre. "Site-directed pegylation of recombinant interleukin-2 at its glycosylation site," Biotechnology (N Y). Apr. 1990;8(4):343-6.

Graves, SW et al., "Expression, purification, and initial kinetic characterization of the large subunit of the human mitochondrial DNA polymerase," Biochemistry. Apr. 28, 1998;37(17):6050-8.

Griffin, BA et al., "Specific Covalent Labeling of Recombinant Protein Molecules Inside Live Cells," Science (1998) 281:269-272.

(56) References Cited

OTHER PUBLICATIONS

Grundström T et al., "Oligonucleotide-directed mutagenesis by microscale 'shot-gun' gene synthesis," Nucleic Acids Res. May 10, 1985;13(9):3305-16.
Guckian, KM and ET Kool, "Highly Precise Shape Mimicry by a Difluorotoluene Deoxynucleoside, a Replication-Competent Substitute for Thymidine," Angew. Chem. Int. Ed. Engl (1998) 36(24):2825-8.
Hamano-Takaku, F et al., "A mutant *Escherichia coli* tyrosyl-tRNA synthetase utilizes the unnatural amino acid azatyrosine more efficiently than tyrosine," J Biol Chem. Dec. 22, 2000;275(51):40324-8.
Hang, HC and CR Bertozzi, "Chemoselective approaches to glycoprotein assembly," Acc Chem Res. Sep. 2001;34 (9):727-36.
Harris, JM et al. "Synthesis and Characterization of Poly(ethylene Glycol) Derivatives," J. Polym. Sci. Chem. Ed. 1984; 22:341-352.
Harris, JM. "Laboratory Synthesis of Polyethylene Glycol Derivatives," JMS-Rev. Macromol. Chem. Phys. 1985;C25 (3): 325-373.
Hendrickson, WA et al., "Selenomethionyl proteins produced for analysis by multiwavelength anomalous diffraction (MAD): a vehicle for direct determination of three-dimensional structure," EMBO J. May 1990;9(5):1665-72.
Henikoff, S and JG Henikoff "Amino Acid Substitution Matrices from Protein Blocks," Proc. Natl. Acad. Sci. USA 1992; 89:10915-9.
Hess, B. et al., "Cooperation of glycolytic enzymes," J. Adv. Enzyme Reg. (1969) 7:149-67.
Hinnen, A et al., "Transformation of yeast," Proc Natl Acad Sci U S A. Apr. 1978;75(4):1929-33.
Hirao, I et al., "An unnatural base pair for incorporating amino acid analogues into proteins," Nat Biotechnol. Feb. 2002;20(2):177-82.
Hitzeman, RA et al., "Isolation and characterization of the yeast 3-phosphoglycerokinase gene (PGK) by an immunological screening technique," J. Biol Chem. Dec. 25, 1980;255(24):12073-80.
Hofmann, K., et H. Bohn. "Studies on polypeptides. XXXVI. The effect of pyrazole-imidazole replacements on the S-protein activating potency of an S-peptide fragment," J. Am Chem, (1966); 88(24):5914-5919.
Hohsaka, T et al., "Efficient Incorporation of Nonnatural Amino Acids with Large Aromatic Groups into Streptavidin in In Vitro Protein Synthesizing Systems," J. Am. Chem. Soc. 1999; 121(1); 34-40.
Hohsaka, T et al., "Incorporation of Two Different Nonnatural Amino Acids Independently into a Single Protein through Extension of the Genetic Code," J. Am. Chem. Soc. 1999; 121(51):12194-12195.
Zoller, MJ & Smith M, "Oligonucleotide-directed mutagenesis: a simple method using two oligonucleotide primers and a single-stranded DNA template," Methods Enzymol. 1987;154:329-50.
Mehl, RA et al. "Generation of a bacterium with a 21 amino acid genetic code," J Am Chem Soc. Jan. 29, 2003;125 (4):935-9.
Santoro, SW et al. "An efficient system for the evolution of aminoacyl-tRNA synthetase specificity," Nat Biotechnol. Oct. 2002;20(10):1044-8. Epub Sep. 16, 2002.
Caliceti, P. et FM Veronese. "Pharmacokinetic and biodistribution properties of poly(ethylene glycol)-protein conjugates," Adv Drug Deliv Rev. Sep. 26, 2003;55(10):1261-77.
Clark, EDB, "Refolding of recombinant proteins," Curr Opin Biotechnol Apr. 1, 1998;9(2):157-63.
Clark, EDB, "Protein refolding for industrial processes," Curr Opin Biotechnol Apr. 2001;12(2):202-7.
Davis, GD et al., "New fusion protein systems designed to give soluble expression in *Escherichia coli*," Biotechnol Bioeng Nov. 20, 1999;65(4):382-8.
Holland, MJ et JP Holland., "Isolation and identification of yeast messenger ribonucleic acids coding for enolase, glyceraldehyde-3-phosphate dehydrogenase, and phosphoglycerate kinase," Biochemistry. Nov. 14, 1978;17 (23):4900-7.
Holland, MJ et al., "The primary structures of two yeast enolase genes. Homology between the 5' noncoding flanking regions of yeast enolase and glyceraldehyde-3-phosphate dehydrogenase genes," J Biol Chem. Feb. 10, 1981;256(3):1385-95.
Hsiao, CL et J Carbon, "High-frequency transformation of yeast by plasmids containing the cloned yeast ARG4 gene," Proc Natl Acad Sci U S A. Aug. 1979;76(8):3829-33.
Huisgen, R. in 1,3-Dipolar Cycloaddition Chemistry, vol. 1, 1984; Ed. Padwa A.; John Wiley and Sons, New York, p. 1-176.
Hwang, KJ et al., "Hepatic uptake and degradation of unilamellar sphingomyelin/cholesterol liposomes: a kinetic study," Proc Natl Acad Sci U S A. Jul. 1980;77(7):4030-4.
Ibba, M et al., "Substrate specificity is determined by amino acid binding pocket size in *Escherichia coli* phenylalanyltRNA synthetase," Biochemistry. Jun. 14, 1994;33(23)1107-12.
Ibba, M and H Hennecke, "Relaxing the substrate specificity of an aminoacyl-tRNA synthetase allows in vitro and in vivo synthesis of proteins containing unnatural amino acids," FEBS Lett. May 15, 1995;364(3):272-5.
Ito, H. et al., "Transformation of intact yeast cells treated with alkali cations," J. Bacteriol. 1983; 153(1):163-8.
Jackson, Dy et al. "A designed peptide ligase for total synthesis of ribonuclease a with unnatural catalytic residues," Science. Oct. 14, 1994;266(5183):243-7.
Jakobsson, PJ et al., "Identification and characterization of a novel human microsomal glutathione S-transferase with leukotriene C4 synthase activity and significant sequence identity to 5-lipoxygenase-activating protein and leukotriene C4 synthase," J Biol Chem. Sep. 6, 1996;271(36):22203-10.
Jencks, W.P., "Studies on the Mechanism of Oxime and Semicarbazone Formation," J. Am. Chem. Soc.; 1959; 81.
Joppich, M. et al. "Peptides Flanked by Two Polymer Chains, 1; Synthesis of Glycl-L-tryptohylglycine Substituted by Poly(eyhylene oxide) at both the Carboxy and the Amino End Groups," Makromol. Chem. 1979;180:1381-4.
Kaiser, ET. "Synthetic approaches to biologically active peptides and proteins including enzymes," Acc Chem Res, (1989); 22(2):47-54.
Kaiser, ET et al. "The chemical modification of enzymatic specificity," Annu Rev Biochem. 1985;54:565-95.
Kaiser, ET and DS Lawrence. "Chemical mutation of enzyme active sites," Science. Nov. 2, 1984;226(4674):505-11.
Karlin, S and SF Altschul "Applications and statistics for multiple high-scoring segments in molecular sequences," Proc Natl Acad Sci U S A. Jun. 15, 1993;90(12):5873-7.
Kayser, B., et al., "Alkyne bridged alpha- amino acids by palladium mediated coupling of alkynes with N-t-Boc-4- iodo-phenylalanine methyl ester," Tetrahedron (1997); 53(7): 2475-2484.
Kelly, JM and MJ Hynes, "Transformation of Aspergillus niger by the amdS gene of Aspergillus nidulans," EMBO J. 1985; 4(2):475-479.
Kiick, K. L. And D. A. Tirrell, "Protein Engineering by in Vivo Incorporation of Non-Natural Amino Acids: Control of Incorporation of Methionine Analogues by Methionyl-tRNA Synthetase," Tetrahedron (2000), 56:9487-9493.
Kiick, KL et al., "Incorporation of azides into recombinant proteins for chemoselective modification by the Staudinger ligation," Proc Batl Acad Sci U S A. Jan. 8, 2002;99(1):19-24. Epub Dec. 18, 2001.
Kim, DM and JR Swartz, "Regeneration of adenosine triphosphate from glycolytic intermediates for cell-free protein synthesis," Biotechnol Bioeng. Aug. 20, 2001;74(4):309-16.
Kim, DM and JR Swartz, "Oxalate improves protein synthesis by enhancing ATP supply in a cell-free system derived from *Escherichia coli*," Biotechnology Letters, 2000; 22:1537-1542.
Kim, DM, and JR Swartz, "Prolonging cell-free protein synthesis by selective reagent additions," Biotechnol Prog. May-Jun. 2000;16(3):385-90.
Kim, DM, and JR Swartz, "Prolonging cell-free protein synthesis with a novel ATP regeneration system," Biotechnol Bioeng. 1999;66(3):180-8.
King, F.E. & Kidd, D.A.A. "A New Synthesis of Glutamine and of gamma-Dipeptides of Glutamic Acid from Phthylated Intermediates," J. Chem. Soc. 1949; 3315-3319.

(56) References Cited

OTHER PUBLICATIONS

Kingsman, AJ et al., "Replication in Saccharomyces cerevisiae of plasmid pBR313 carrying DNA from the yeast trpl region," Gene. Oct. 1979;7(2):141-52.
Kitts, PA et al. "Linearization of baculovirus DNA enhances the recovery of recombinant virus expression vectors," Nucleic Acids Res. Oct. 11, 1990;18(19):5667-72.
Klein, TM et al., "High-velocity microprojectiles for delivering nucleic acids into living cells," Nature 1987; 327 (6117):70-73.
Kobayashi, T. et al., "Structural basis for orthogonal tRNA specificities of tyrosyl-tRNA synthetases for genetic code expansion," Nature Structural Biology (2003); 10(6):425-432.
Kogan, TP. "The synthesis of substituted methoxy-poly(ethyleneglycol) derivatives suitable for selective protein modification," Synthetic Comm. 1992; 22(16):2417-24.
Kool, ET. "Synthetically modified DNAs as substrates for polymerases," Curr Opin Chem Biol. Dec. 2000;4(6):602-8.
Koskinen, A.M.P. & Rapoport, H. "Synthesis of 4-Substituted Prolines as Conformationally Constrained Amino Acid Analogues," J. Org. Chem. (1989) 54(8):1859-1866.
Kost, TA et al., "Production of a urokinase plasminogen activator-IgG fusion protein (uPA-IgG) in the baculovirus expression system," Gene. Apr. 29, 1997;190(1):139-44.
Kramer, W et al., "The gapped duplex DNA approach to oligonucleotide-directed mutation construction," Nucleic Acids Res. Dec. 21, 1984;12(24):9441-56.
Kramer, W & Fritz HJ. "Oligonucleotide-directed construction of mutations via gapped duplex DNA" Methods Enzymol. 1987;154:350-67.
Kramer, W. et al., "Improved enzymatic in vitro reactions in the gapped duplex DNA approach to oligonucleotide-directed construction of mutations," Nucleic Acids Res. Jul. 25, 1988;16(14B):7207.
Kramer, B. et al., "Different base/base mismatches are corrected with different efficiencies by the methyl-directed DNA mismatch-repair system of E. coli," Cell. Oct. 1984;38(3):879-87.
Kreitman, RJ and I. Pastan "Purification and characterization of IL6-PE4E, a recombinant fusion of interleukin 6 with Pseudomonas exotoxin," Bioconjug Chem. Nov.-Dec.1993;4(6):581-5.
Krieg, UC, et al. "Photocrosslinking of the signal sequence of nascent preprolactin to the 54-kilodalton polypeptide of the signal recognition particle," Proc Natl Acad Sci U S A. Nov. 1986;83(22):8604-8.
Kunitani, M. et al., "Reversed-phase chromatography of interleukin-2 muteins," J Chromatogr. May 30, 1986;359:391-402.
Kunkel, "The efficiency of oligonucleotide directed mutagenesis," in Nucleic Acids & Molecular Biology 1987; Eckstein, F. and Lilley, D.M.J. eds.; Springer Verlag, Berlin; 124-135.
Kunkel, TA "Rapid and efficient site-specific mutagenesis without phenotypic selection," Proc Natl Acad Sci U S A. Jan. 1985;82(2):488-92.
Kunkel, TA et al., "Rapid and efficient site-specific mutagenesis without phenotypic selection," Methods Enzymol. 1987;154:367-82.
Kunze, G et al., "Transformation of the industrially important yeasts Candida maltosa and Pichia guilliermondii," J. Basic Microbiol. 1985; 25:141-4.
Kurtz et al., "Integrative transformation of Candida albicans, using a cloned Candida ADE2 gene," Mol Cell Biol. Jan. 1986;6(1):142-9.
Kurtzhals, P. et al., "Albumin binding of insulins acylated with fatty acids: characterization of the ligand-protein interaction and correlation between binding affinity and timing of the insulin effect in vivo," Biochem J. Dec. 15, 1995;312 ( Pt 3):725-31.
Langer, R et al., "Biocompatibility of polymeric delivery systems for macromolecules," J Biomed Mater Res. Mar. 1981;15(2):267-77.
Langer, R. "Controlled release of macromolecules, " Chem. Tech. 1982; 12: 98-105.

Liebman, JM et al., "When less is more: enhanced baculovirus production of recombinant proteins at very low multiplicities of infection," Biotechniques. Jan. 1999;26(1):36-8, 40, 42.
Ling, MM et BH Robinson, "Approaches to DNA mutagenesis: an overview" Anal Biochem. Dec. 15, 1997;254 (2):157-78.
Wang, L & Pg. Schultz, "Expanding the genetic code," Chem Commun (Camb). Jan. 7, 2002;1:1-11.
Weissmann, C. "The cloning of interferon and other mistakes." in Interferon 3 1981; ed. I. Gresser; Academic Press, London, 101-134.
Wells, JA et al., "Importance of hydrogen-bond formation in stabilizing the transition state of subtilisin," Phil. Trans. R. Soc. Lond. A 1986; 317: 415-423.
Wells, JA et al., "Cassette mutagenesis: an efficient method for generation of multiple mutations at defined sites," Gene. 1985;34(2-3):315-23.
Woghiren, C et al. "Protected thiol-polyethylene glycol: a new activated polymer for reversible protein modification," Bioconjug Chem. Sep.-Oct. 1993;4(5):314-8.
Wong, SS et LJ Wong, "Chemical crosslinking and the stabilization of proteins and enzymes," Enzyme Microb Technol. Nov. 1992;14(11):866-74.
Wright, K. "Biotechnology: Insect virus as super-vector?," Nature (1986) 321(6072):718.
Liu, H. et al. "A Method for the Generation of Glycoprotein Mimetics," J. Am. Chem. Soc. 2003 125(7): 1702-1703.
Liu, D.R. & Schultz, P.G. "Progress toward the evolution of an organism with an expanded genetic code," Proc Natl Acad Sci U S A. Apr. 27, 1999;96(9):4780-5.
Lorimer, I. A. et I. Pastan, "Random recombination of antibody single chain Fv sequences after fragmentation with DNaseI in the presence of Mn2+," Nucleic Acids Res. Aug. 11, 1995;23(15):3067-8.
Lu, T. et al. "Probing ion permeation and gating in a K +channel with backbone mutations in the selectivity filter," Nature Neurosci. Mar. 2001;4(3):239-246.
Luckow, VA and MD Summers, "High level expression of nonfused foreign genes with Autographa californica nuclear polyhedrosis virus expression vectors," Virology. May 1989;170(1):31-9.
Ma, C et al., "In vitro protein engineering using synthetic tRNA(Ala) with different anticodons," Biochemistry. Aug. 10, 1993;32(31):7939-45.
Magliery, TJ et al. "Expanding the Genetic Code: Selection of Efficient Suppressors of Four-base Codons and Identification of "Shifty" Four-base Codons with a Library Approach in *Escherichia coli*," J Mol Biol. Mar. 30, 2001;307 (3):755-69.
Mahal, L. K., et al., "Engineering chemical reactivity on cell surfaces through oligosaccharide biosynthesis," Science. May 16, 1997;276(5315):1125-8.
Makrides, SC et al., "Extended in vivo half-life of human soluble complement receptor type 1 fused to a serum albumin-binding receptor," J Pharmacol Exp Ther. Apr. 1996;277(1):534-42.
Mamot, C, et al., "Epidermal growth factor receptor (EGFR)-targeted immunoliposomes mediate specific and efficient drug delivery to EGFR- and EGFRvIII-overexpressing tumor cells," Cancer Res. Jun. 15, 2003;63(12):3154-61.
Mandecki, W. 'Oligonucleotide-directed double-strand break repair in plasmids of *Escherichia coli*: a method for sitespecific mutagenesis, Proc Natl Acad Sci U S A. Oct. 1986;83(19):7177-81.
Mann, SG and LA King, "Efficient transfection of insect cells with baculovirus DNA using electroporation," J Gen Virol. Dec. 1989;70 (Pt 12):3501-5.
Matsoukas, JM et al., "Differences in backbone structure between angiotensin II agonists and type I antagonists," J Med Chem. Nov. 10, 1995;38(23):4660-9.
McMinn, DL et al., "Efforts toward Expansion of the Genetic Alphabet: DNA Polymerase Recognition of a Highly Stable, Self-Pairing Hydrophobic Base," J. Am. Chem. Soc. 1999; 121(49):11585-6.
Meggers, E et al., "A Novel Copper-Mediated DNA Base Pair," J. Am. Chem. Soc. 2000; 122(43):10714-10715.
Mehvar, R.,"Modulation of the pharmacokinetics and pharmacodynamics of proteins by polyethylene glycol conjugation" J Pharm Pharm Sci. Jan.-Apr. 2000;3(1):125-36.

(56) References Cited

OTHER PUBLICATIONS

Mendel, D, et al. "Site-directed mutagenesis with an expanded genetic code," Annu Rev Biophys Biomol Struct. 1995;24:435-62.
Miller, LK, "Baculoviruses as gene expression vectors," Ann. Rev. Microbiol. 1988; 42:177-99.
Miller, LK. "Insect baculoviruses: powerful gene expression vectors," Bioessays. Oct. 1989;11(4):91-5.
Miller, JC et al. "Flash decaging of tyrosine sidechains in an ion channel," Neuron. Apr. 1998;20(4):619-24.
Minks, C. et al., Noninvasive tracing of recombinant proteins with "fluorophenylalanine-fingers," Anal Biochem. Aug. 15, 2000;284(1):29-34.
Miyanohara, A et al., "Expression of hepatitis B surface antigen gene in yeast," Proc Natl Acad Sci U S A. Jan. 1983;80(1):1-5.
Moore, B. et al., "Quadruplet implications for code expansion and the specification of translation step size," J Mol. Biol. 2000; 298(2):195-209.
Mosbach, K. et al., "Formation of proinsulin by immobilized Bacillus subtilis," Nature Apr. 1983; 302:543-545.
Nakamaye, KL & Eckstein F, "Inhibition of restriction endonuclease NCI I cleavage by phosphorothioate groups and its application to oligonucleotide-directed mutagenesis" Nucleic Acids Res. Dec. 22, 1986;14(24):9679-98.
Nakatsuka, T., et al. "Peptide segment coupling catalyzed by the semisynthetic enzyme thiosubtilisin," J Am Chem Soc, 1987; 109(12): 3808-3810.
Nambiar, KP et al., "Total synthesis and cloning of a gene coding for the ribonuclease S protein," Science (1984) 223: 1299-1301.
Needleman, SB and Wunsch CD, "A general method applicable to the search for similarities in the amino acid sequence of two proteins," J Mol Biol. Mar. 1970;48(3):443-53.
Neet, Ke et al. "Properties of thiol-subtilisin. The consequences of converting the active serine residue to cysteine in a serine protease," J Biol Chem. Dec. 25, 1968;243(24):6392-401.
Nielsen, UB, et al., "Therapeutic efficacy of anti-ErbB2 immunoliposomes targeted by a phage antibody selected for cellular endocytosis," Biochim Biophys Acta. Aug. 19, 2002;1591(1-3):109-118.
Nomura, T. et al., "Purification, cDNA Cloning, and Expression of UDP-Gal: Glucosylceramide -1,4- Galactosyltransferase from Rat Brain," J Biol. Chem. 1998; 273(22):13570-7.
Noren, CJ et al. "A general method for site-specific incorporation of unnatural amino acids into proteins," Science Apr. 14, 1989; 244(4901): 182-8.
Nowak, MW et al., "Nicotinic receptor binding site probed with unnatural amino acid incorporation in intact cells," Science. Apr. 21, 1995;268(5209):439-42.
Ogawa, AK et al., "Efforts toward the Expansion of the Genetic Alphabet: Information Storage and Replication with Unnatural Hydrophobic Base Pairs," J. Am. Chem. Soc. 2000; 122(14):3274-3287.
Ogawa, AK et al., "Rational Design of an Unnatural Base Pair with Increased Kinetic Selectivity," J. Am. Chem. Soc. 2000; 122(36): 8803-8804.
Ohtsuka, E et al., "An alternative approach to deoxyoligonucleotides as hybridization probes by insertion of deoxyinosine at ambiguous codon positions," J Biol Chem. Mar. 10, 1985;260(5):2605-8.
Olson et al. "Preparation and Characterization of Poly(ethylene glycol)yated Human Growth Hormone Antagonist," in Poly(ethylene glycol) Chemistry & Biological Applications, 1997; Eds. JM Harris & S. Zalipsky; ACS, Washington, D.C., 170-181.
Padwa, A. "Intermolecular 1,3-Dipolar Cycloadditions," in Comprehensive Organic Synthesis, vol. 4, (1991) Ed. Trost, B. M.; Pergamon, Oxford, 1069-1109.
Palva, I et al., "Secretion of interferon by Bacillus subtilis," Gene. May-Jun. 1983;22(2-3):229-35.
Park, JW, et al., "Development of anti-p185HER2 immunoliposomes for cancer therapy," Proc Natl Acad Sci U S A. Feb. 28, 1995;92(5):1327-31.

Park, JW, et al., "Anti-HER2 immunoliposomes: enhanced efficacy attributable to targeted delivery," Clin Cancer Res. Apr. 2002;8(4):1172-81.
Patnaik, R. and JR Swartz, "*E. coli*-based in vitro transcription/translation: in vivo-specific synthesis rates and high yields in a batch system," Biotechniques. May 1998;24(5):862-8.
Pearson, WR and DJ Lipman, "Improved tools for biological sequence comparison," Proc Natl Acad Sci U S A. Apr. 1988;85(8):2444-8.
Pepinsky, RB., et al., "Improved pharmacokinetic properties of a polyethylene glycol-modified form of interferonbeta-la with preserved in vitro bioactivity," J Pharmacol Exp Ther. Jun. 2001;297(3):1059-66.
Piccirilli, JA et al., "Enzymatic incorporation of a new base pair into DNA and RNA extends the genetic alphabet," Nature 1990; 343:33-37.
Pintar, A et al. "CX, an algorithm that identifies protruding atoms in proteins," Bioinformatics. Jul. 2002;18(7):980-4.
Pitha, J et al. "Detergents linked to polysaccharides: preparation and effects on membranes and cells," Eur J Biochem. Feb. 15, 1979;94(1):11-8.
Polgar, L. and ML Bender. "A new enzyme containing a synthetically formed active site. Thiol-subtilisin." J. Am Chem Soc., 1966; 88(13): 3153-3154.
Pollack, SJ et al. "Introduction of nucleophiles and spectroscopic probes into antibody combining sites," Science. Nov. 18, 1988;242(4881):1038-40.
Preneta, AZ. "Separation on the basis of size: gel permeation chromatography," in Protein Purification Methods, a practical approach, 1989; Eds. Harris & Angal; IRL Press, Oxford; 293-306.
Yelton, MM et al., "Transformation of Aspergillus nidulans by using a trpC plasmid," Proc Natl Acad Sci U S A. Mar. 1984;81(5):1470-4.
Yelverton, E et al., "Bacterial synthesis of a novel human leukocyte interferon," Nucleic Acids Res. Feb. 11, 1981;9 (3):731-41.
Zalipsky, S et al. "Attachment of drugs to polyethylene glycols," Eur. Polymer Journal. 1983 19(12):1177-83.
Zalipsky, S. "Functionalized poly(ethylene glycol) for preparation of biologically relevant conjugates," Bioconjug Chem. Mar.-Apr. 1995;6(2):150-65.
Zhang, Z., et al. "A new strategy for the site-specific modification of proteins in vivo," Biochemistry. Jun. 10, 2003;42 (22):6735-46.
Zoller, MJ & M Smith, "Oligonucleotide-directed mutagenesis using M13-derived vectors: an efficient and general procedure for the production of point mutations in any fragment of DNA" Nucleic Acids Res. Oct. 25, 1982;10 (20):6487-500.
Zoller, MJ & M. Smith, "Oligonucleotide-directed mutagenesis of DNA fragments cloned into M13 vectors" Methods Enzymol. 1983;100:468-500.
Raibaud, O et M Schwartz. "Positive control of transcription initiation in bacteria," Annu Rev Genet. 1984;18:173-206.
Reverey, H. et al., "Differential Fatty Acid Selection during Biosynthetic S-Acylation of a Transmembrane Protein (HEF) and Other Proteins in Insect Cells (Sf9) and in Mammalian Cells (CV1)," J. Biol. Chem. 1996; 271 (39):23607-10.
Rivier, J et R McClintock, "Reversed-phase high-performance liquid chromatography of insulins from different species," J Chromatogr. Sep. 23, 1983;268(1):112-9.
Roberts, et al., "Generation of an antibody with enhanced affinity and specificity for its antigen by protein engineering," Nature 1987;328:731-734.
Roberts, RW and JW Szostak, "RNA-peptide fusions for the in vitro selection of peptides and proteins," Proc Natl Acad Sci U S A. Nov. 11, 1997;94(23):12297-302.
Roggenkamp, R. et al., "Transformation of the methylotrophic yeast Hansenula polymorpha by autonomous replication and integration vectors," Mol. Genetics and Genomics 1986;202(2):302-8.
Romani et al. "Synthesis of unsymmetrical cystine peptides: directed disulfide pairing with the sulfenohydrazide method," in Chemistry of Peptides and Proteins 1984; eds. Voelter, W. et al.; Walter de Gruyter et al., Berlin; vol. 2:29-33.
Romanos, MA et al., "Foreign gene expression in yeast: a review," Yeast. Jun. 1992;8(6):423-88.

(56) References Cited

OTHER PUBLICATIONS

Rosenthal, GA. "L-canaline: a potent antimetabolite and anti-cancer agent from leguminous plants," Life Sci.1997;60(19):1635-41.

Rossolini, GM et al., "Use of deoxyinosine-containing primers vs degenerate primers for polymerase chain reaction based on ambiguous sequence information," Mol. Cell. Probes 1994; 8:91-98.

Rostovtsev, VV et al., "A stepwise huisgen cycloaddition process: copper(I)-catalyzed regioselective "ligation" of azides and terminal alkynes," Angew Chem Int Ed Engl Jul. 15, 2002;41(14):2596-9.

Rowles, J et al., "Cloning and characterization of PDK4 on 7q21.3 encoding a fourth pyruvate dehydrogenase kinase isoenzyme in human," J Biol Chem. Sep. 13, 1996;271(37):22376-82.

Sakmar, TP and Khorana HG, "Total synthesis and expression of a gene for the alpha-subunit of bovine rod outer segment guanine nucleotide-binding protein (transducin)" Nucleic Acids Res. Jul. 25, 1988;16(14A):6361-72.

Sandler and Karo, "Polyoxyalkylation of hydroxyl compounds," in Polymer Synthesis, vol. 3, 1980; Academic Press, New York, 138-161.

Sartore, L et al., "Enzyme modification by Mpeg with an amino acid or peptide as spacer arms," Appl Biochem Biotechnol. Jan. 1991;27(1):45-54.

Sawhney, AS et al., "Bioerodible Hydrogels Based on Photopolymerized Poly(ethylene glycol)-co-poly(alpha-hydroxy acid) Diacrylate Macromers," Macromolecules 1993; 26(4):581-7.

Saxon, E and C. Bertozzi, "Cell Surface Engineering by a Modified Staudinger Reaction," Science (2000); 287 (5460):2007-2010.

Sayers, JR et al., "Strand specific cleavage of phosphorothioate-containing DNA by reaction with restriction endonucleases in the presence of ethidium bromide" Nucleic Acids Res. Feb. 11, 1988;16(3):803-14.

Sayers, JR, et al. "5'-3' exonucleases in phosphorothioate-based oligonucleotide-directed mutagenesis," Nucleic Acids Res. Feb. 11, 1988;16(3):791-802.

Schanbacher, FL et al. "Galactosyltransferase Acceptor Specificity of the Lactose Synthetase a Protein," J. Biol. Chem. 1970; 245(19):5057-5061.

Schmidt, M et al., "Baculovirus-mediated large-scale expression and purification of a polyhistidine-tagged rubella virus capsid protein," Protein Expr Purif. Apr. 1998;12(3):323-30.

Schneider, E., et al., "Functional Purification of a Bacterial ATP-Binding Cassette Transporter Protein (MalK) from the Cytoplasmic Fraction of an Overproducing Strain," Protein Expr. Purif. 1995; 6(1):10-14.

Schnolzer, M. and SBH Kent. "Constructing proteins by dovetailing unprotected synthetic peptides: backbone-engineered HIV protease," Science. Apr. 10, 1992;256(5054):221-5.

Scouten, WH. "A survey of enzyme coupling techniques," Methods Enzymol. 1987;135:30-65.

Shao, J and JP Tam, "Unprotected Peptides as Building Blocks for the Synthesis of Peptide Dendrimers with Oxime Hydrazone, and Thiazolidine Linkages," J. Am. Chem. Soc. 1995; 117(14):3893-3899.

Sharma, N. et al., "Efficient introduction of aryl bromide functionality into proteins in vivo," FEBS Lett. Feb. 4, 2000;467 (1):37-40.

Shimatake, H et M Rosenberg, "Purified gamma regulatory protein cII positively activates promoters for lysogenic development," Nature Jul. 1981; 292:128-132.

Shine, J and L Dalgarno, "Determinant of cistron specificity in bacterial ribosomes," Nature. Mar. 6, 1975;254 (5495):34-8.

Sidman, KR et al., "Controlled release of macromolecules and pharmaceuticals from synthetic polypeptides based on glutamic acid," Biopolymers. Jan. 1983;22(1):547-56.

Sieber, V. et al., "Libraries of hybrid proteins from distantly related sequences," Nature Biotechnology, May 2001;19:456-460.

Siffert, W et al., "Association of a human G-protein beta3 subunit variant with hypertension," Nat Genet. Jan. 1998;18(1):45-8.

Sikorski, RS et al., "A System of Shuttle Vectors and Yeast Host Strains Designed for Efficient Manipulation of DNA in Saccharomyces cerevisiae," Genetics (1989) 122:19-27.

Sisk, WP et al., "High-level expression and purification of secreted forms of herpes simplex virus type 1 glycoprotein gD synthesized by baculovirus-infected insect cells," J Virol. Feb. 1994;68(2):766-75.

Sjolander, A et al., "The serum albumin-binding region of streptococcal protein G: a bacterial fusion partner with carrier-related properties," J Immunol Methods. Feb. 14, 1997;201(1):115-23.

Smith, M. "In vitro mutagenesis" Ann. Rev. Genet. 1985; 19:423-462.

Smith, GE et al., "Production of human beta interferon in insect cells infected with a baculovirus expression vector," Mol Cell Biol. Dec. 1983;3(12):2156-65.

Stanley, SL et al., "The serine-rich Entamoeba histolytica protein is a phosphorylated membrane protein containing O-linked terminal N-acetylglucosamine residues," J Biol Chem. Feb. 24, 1995;270(8):4121-6.

Steitz, JA et al. "Genetic signals and nucleotide sequences in messenger RNA," in Biological Regulation and Development: Gene Expression 1979; ed. R. F. Goldberger; Plenum Press, New York; 349-399.

Stemmer, WPC, "Rapid evolution of a protein in vitro by DNA shuffling," Nature 1994;370(4):389-391.

Stemmer, WP "DNA shuffling by random fragmentation and reassembly: in vitro recombination for molecular evolution," Proc Natl Acad Sci U S A. Oct. 25, 1994;91(22):10747-51.

Studier, FW et BA Moffatt, "Use of bacteriophage T7 RNA polymerase to direct selective high-level expression of cloned genes," J. Mol Biol. May 5, 1986;189(1):113-30.

Subasinghe, N. et al., "Quisqualic acid analogues: synthesis of beta-heterocyclic 2-aminopropanoic acid derivatives and their activity at a novel quisqualate-sensitized site," J Med Chem. Nov. 27, 1992;35(24):4602-7.

Switzer, C et al., "Enzymatic incorporation of a new base pair into DNA and RNA," J. Am. Chem. Soc. 1989; 111 (21):8322-8323.

Tabor, S et CC Richardson, "A bacteriophage T7 RNA polymerase/promoter system for controlled exclusive expression of specific genes," Proc Natl Acad Sci U S A. Feb. 1985;82(4):1074-8.

Tae, EL et al., "Efforts toward Expansion of the Genetic Alphabet: Replication of DNA with Three Base Pairs," J. Am. Chem. Soc. 2001; 123(30):7439-7440.

Tang, Y et al., "Fluorinated Coiled-Coil Proteins Prepared in Vivo Display Enhanced Thermal and Chemical Stability," Angew Chem Int Ed Engl. Apr. 17, 2001;40(8):1494-1496.

Taylor, JW et al., "The use of phosphorothioate-modified DNA in restriction enzyme reactions to prepare nicked DNA," Nucleic Acids Res. Dec. 20, 1985;13(24):8749-64.

Taylor, JW et al., "The rapid generation of oligonucleotide-directed mutations at high frequency using phosphorothioate-modified DNA," Nucleic Acids Res. Dec. 20, 1985;13(24):8765-85.

Tijssen, P. "Overview of principles of hybridization and the strategy of nucleic acid assays," in Laboratory Techniques in Biochemistry and Molecular Biology—Hybridization with Nucleic Probes, Part I, 1993; Elsevier Science Publishers, Amsterdam, 19-78.

Tilburn, J. et al., "Transformation by integration in Aspergillus nidulans," Gene. Dec. 1983;26(2-3):205-21.

Van Hest, J. C. et al., "Efficient Incorporation of Unsaturated Methionine Analogues into Proteins in Vivo," J. Am. Chem. Soc2000 ;122 (7); 1282-1288.

Van Solingen, P. et JB van der Plaat. "Fusion of yeast spheroplasts," J Bacteriol. May 1977;130(2):946-7.

Veronese, FM et al., "Surface modification of proteins. Activation of monomethoxy-polyethylene glycols by phenylchloroformates and modification of ribonuclease and superoxide dismutase," Appl Biochem Biotechnol. Apr. 1985; 11(2):141-52.

Vlak, JM et al., "Functional studies on the p10 gene of Autographa californica nuclear polyhedrosis virus using a recombinant expressing a p10-beta-galactosidase fusion gene," J Gen Virol. Apr. 1988;69 ( Pt 4):765-76.

(56) References Cited

OTHER PUBLICATIONS

Wang, Q., et al., "Bioconjugation by Copper(I)-Catalyzed Azide-Alkyne [3 + 2] Cycloaddition," J. Am. Chem. Soc. 2003; 125(11):3192-3193.

Wang, L. et al., "Addition of the keto functional group to the genetic code of *Escherichia coli*," Proc. Natl. Acad. Sci. (2003); 100(1):56-61.

Wang, L et al., "Expanding the genetic code of *Escherichia coli*," Science. Apr. 20, 2001;292(5516):498-500.

\* cited by examiner

Figure 2

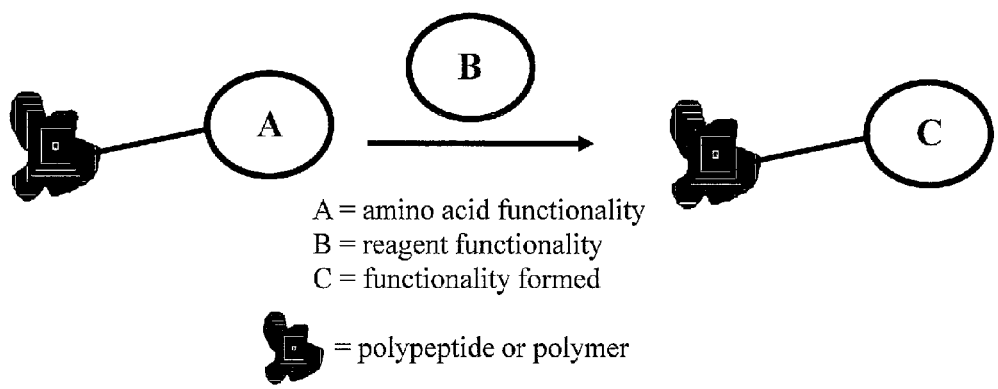

A = amino acid functionality
B = reagent functionality
C = functionality formed

= polypeptide or polymer

| Amino Acid Functionality | Reagent Functionality | Functionality Formed |
|---|---|---|
| Carbonyl | Hydroxylamine | Oxime |
| Hydroxylamine | Carbonyl | Oxime |
| Oxime | Carbonyl | Oxime Exchange |
| Dicarbonyl | Hydroxylamine | Oxime |
| Hydroxylamine | Dicarbonyl | Oxime |
| Oxime | Dicarbonyl | Oxime Exchange |

*Formation of Oxime-Containing Non-Natural Amino Acid Components by Reaction of Carbonyl-Containing Non-Natural Amino Acid Components with Hydroxylamine-Containing Reagents*

Figure 4
*Formation of Oxime-Containing Non-Natural Amino Acid Components by Reaction of Hydroxylamine-Containing Non-Natural Amino Acid Components with Carbonyl-Containing Reagents*
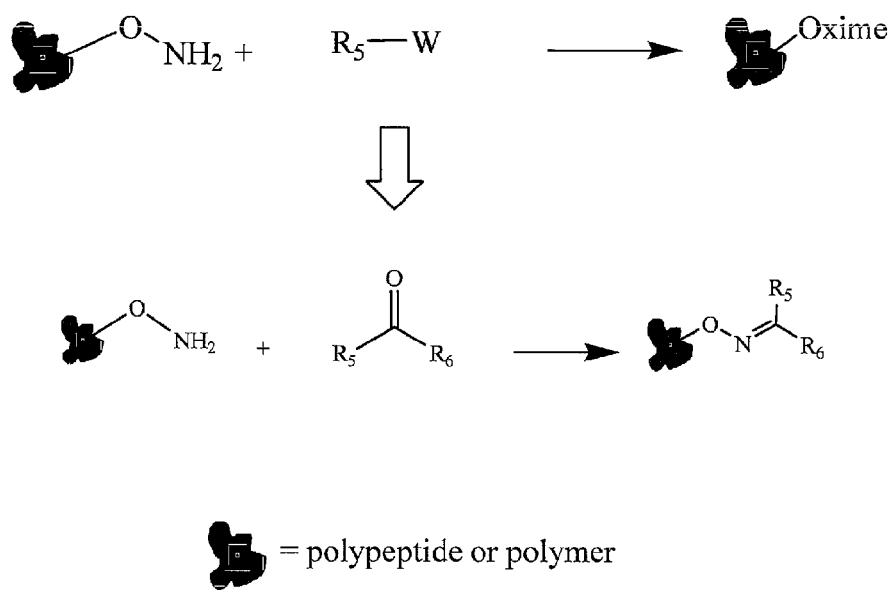
 = polypeptide or polymer

*Formation of Oxime-Containing Non-Natural Amino Acid Components by Oxime Exchange Reactions of Oxime-Containing Non-Natural Amino Acid Components with Carbonyl-Containing Reagents*

= polypeptide or polymer

*Formation of Oxime-Containing Non-Natural Amino Acid Components by Reactions of Dicarbonyl-Containing Non-Natural Amino Acid Components with Hydroxylamine-Containing Reagents*

= polypeptide or polymer

Figure 7
*Formation of Oxime-Containing Non-Natural Amino Acid Components by Reactions of Hydroxylamine-Containing Non-Natural Amino Acid Components with Dicarbonyl-Containing Reagents*
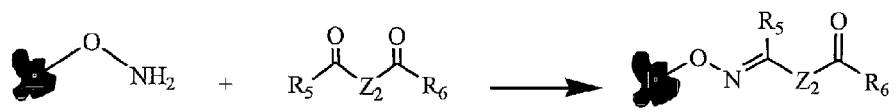
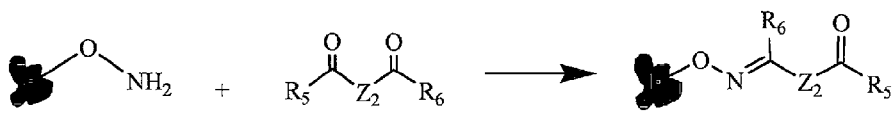
= polypeptide or polymer

*Formation of Oxime-Containing Non-Natural Amino Acid Components by Oxime Exchange Reactions of Oxime-Containing Non-Natural Amino Acid Components with Carbonyl or Dicarbonyl-Containing Reagents*

Figure 9
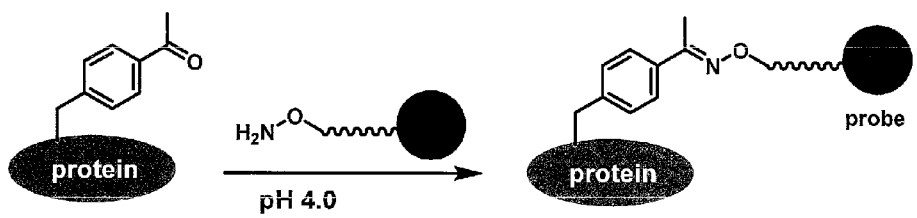
Fluorophores:
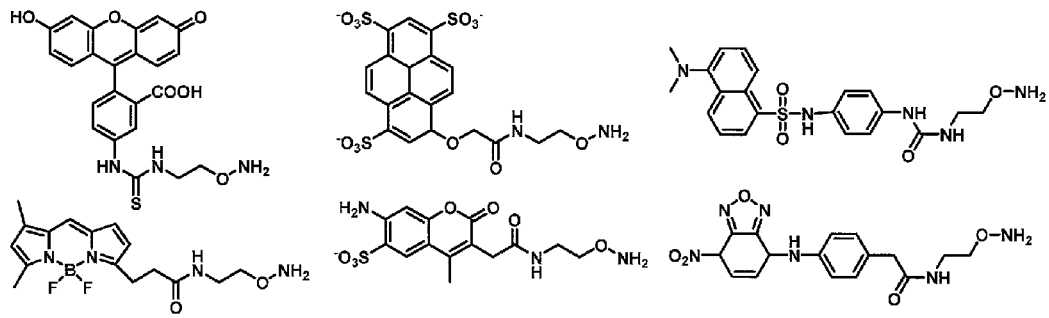
Biotin:
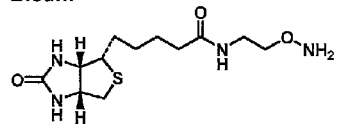
Chelators:
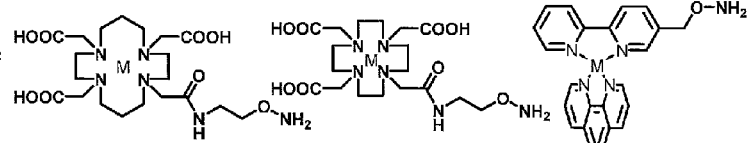
M = transition metal ions or radioactive metal ions Figure 12
Resin selection: 
Must be are water compatible
(resin can swell well in water)
PEGA resin: polyamide, 0.2-0.4 mmol/g
ChemMatrix resin: PEG, 0.8-1.0 mmol/g
Resin functionalization:
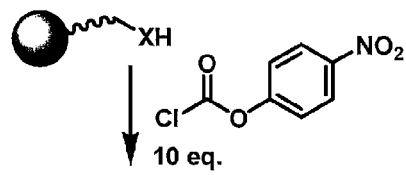
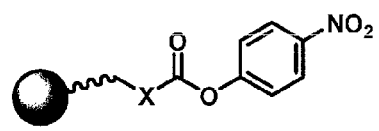
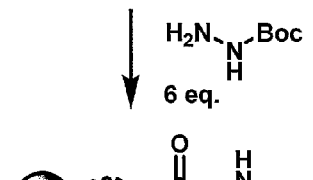
X = O, S, NH, NR Figure 14
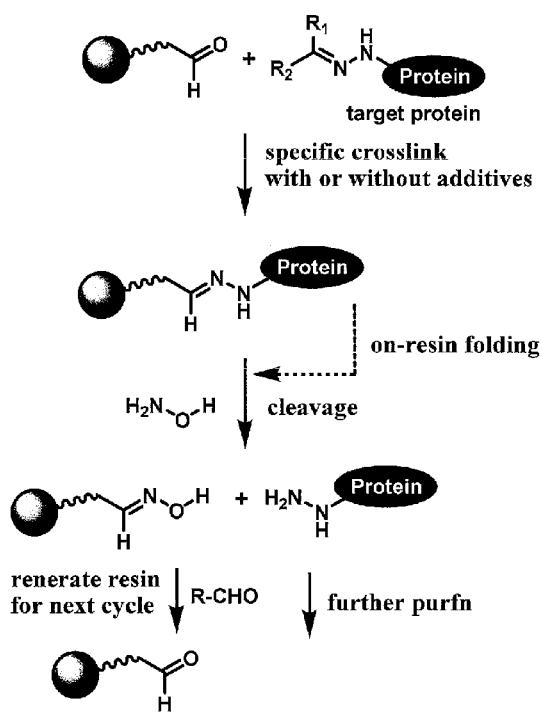
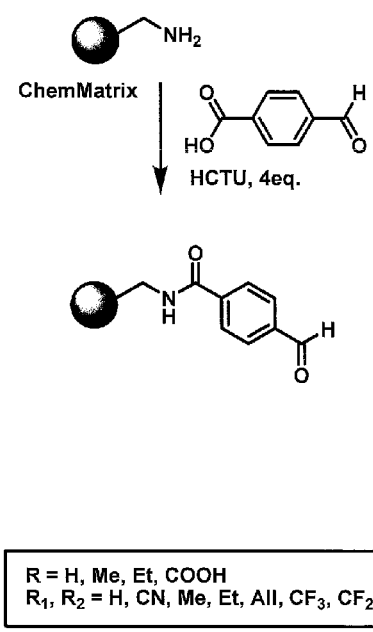

SEQUENCE LISTING

<160> NUMBER OF SEQ ID NOS: 30

<210> SEQ ID NO 1
<211> LENGTH: 217
<212> TYPE: PRT
<213> ORGANISM: Homo sapiens

<400> SEQUENCE: 1

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys

-continued

```
                85                  90                  95
Ser Asn Leu Glu Leu Arg Ile Ser Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
        130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
        210                 215
```

<210> SEQ ID NO 2
<211> LENGTH: 191
<212> TYPE: PRT
<213> ORGANISM: Homo sapiens

<400> SEQUENCE: 2

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 3
<211> LENGTH: 176
<212> TYPE: PRT
<213> ORGANISM: Homo sapiens

<400> SEQUENCE: 3

Phe Pro Thr Ile Pro Leu Ser Arg Leu Phe Asp Asn Ala Met Leu Arg

```
            1               5                  10                 15
        Ala His Arg Leu His Gln Leu Ala Phe Asp Thr Tyr Gln Glu Phe Asn
                        20                 25                 30
        Pro Gln Thr Ser Leu Cys Phe Ser Glu Ser Ile Pro Thr Pro Ser Asn
                        35                 40                 45
        Arg Glu Glu Thr Gln Gln Lys Ser Asn Leu Glu Leu Leu Arg Ile Ser
                        50                 55                 60
        Leu Leu Leu Ile Gln Ser Trp Leu Glu Pro Val Gln Phe Leu Arg Ser
         65                 70                 75                 80
        Val Phe Ala Asn Ser Leu Val Tyr Gly Ala Ser Asp Ser Asn Val Tyr
                        85                 90                 95
        Asp Leu Leu Lys Asp Leu Glu Glu Gly Ile Gln Thr Leu Met Gly Arg
                       100                105                110
        Leu Glu Asp Gly Ser Pro Arg Thr Gly Gln Ile Phe Lys Gln Thr Tyr
                       115                120                125
        Ser Lys Phe Asp Thr Asn Ser His Asn Asp Asp Ala Leu Leu Lys Asn
                       130                135                140
        Tyr Gly Leu Leu Tyr Cys Phe Arg Lys Asp Met Asp Lys Val Glu Thr
        145                150                155                160
        Phe Leu Arg Ile Val Gln Cys Arg Ser Val Glu Gly Ser Cys Gly Phe
                       165                170                175

<210> SEQ ID NO 4
<211> LENGTH: 77
<212> TYPE: DNA
<213> ORGANISM: Methanococcus jannaschii

<400> SEQUENCE: 4
ccggcggtag ttcagcaggg cagaacggcg gactctaaat ccgcatggcg ctggttcaaa    60
tccggcccgc cggacca                                                    77

<210> SEQ ID NO 5
<211> LENGTH: 88
<212> TYPE: DNA
<213> ORGANISM: Halobacterium sp. NRC-1

<400> SEQUENCE: 5
cccagggtag ccaagctcgg ccaacggcga cggactctaa atccgttctc gtaggagttc    60
gagggttcga atcccttccc tgggacca                                        88

<210> SEQ ID NO 6
<211> LENGTH: 89
<212> TYPE: DNA
<213> ORGANISM: Halobacterium sp. NRC-1

<400> SEQUENCE: 6
gcgagggtag ccaagctcgg ccaacggcga cggacttcct aatccgttct cgtaggagtt    60
cgagggttcg aatccctccc ctcgcacca                                       89

<210> SEQ ID NO 7
<211> LENGTH: 306
<212> TYPE: PRT
<213> ORGANISM: Methanococcus jannaschii

<400> SEQUENCE: 7

Met Asp Glu Phe Glu Met Ile Lys Arg Asn Thr Ser Glu Ile Ile Ser
        1               5                  10                 15
```

```
Glu Glu Glu Leu Arg Glu Val Leu Lys Lys Asp Glu Lys Ser Ala Gly
             20                  25                  30

Ile Gly Phe Glu Pro Ser Gly Lys Ile His Leu Gly His Tyr Leu Gln
         35                  40                  45

Ile Lys Lys Met Ile Asp Leu Gln Asn Ala Gly Phe Asp Ile Ile Ile
     50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 8
<211> LENGTH: 306
<212> TYPE: PRT
<213> ORGANISM: Methanococcus jannaschii

<400> SEQUENCE: 8

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Gly
             20                  25                  30

Ile Gly Phe Glu Pro Ser Gly Lys Ile His Leu Gly His Tyr Leu Gln
         35                  40                  45

Ile Lys Lys Met Ile Asp Leu Gln Asn Ala Gly Phe Asp Ile Ile Ile
     50                  55                  60

Leu Leu Ala Asp Leu His Ala Tyr Leu Asn Gln Lys Gly Glu Leu Asp
 65                  70                  75                  80
```

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Thr Ser His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
                180                 185                 190

Asn Pro Val Leu Thr Gly Leu Asp Gly Glu Gly Lys Met Ser Ser Ser
                195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
                275                 280                 285

Asn Ala Val Ala Glu Leu Ile Lys Ile Leu Glu Pro Ile Arg Lys
290                 295                 300

Arg Leu
305

<210> SEQ ID NO 9
<211> LENGTH: 305
<212> TYPE: PRT
<213> ORGANISM: Methanococcus jannaschii

<400> SEQUENCE: 9

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro

```
            130                 135                 140
Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
                195                 200                 205

Gly Asn Phe Ile Ala Val Asp Asp Ser Pro Glu Glu Ile Arg Ala Lys
            210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
            245                 250                 255

Pro Glu Lys Phe Gly Gly Asp Leu Thr Val Asn Ser Tyr Glu Glu Leu
                260                 265                 270

Glu Ser Leu Phe Lys Asn Lys Glu Leu His Pro Met Asp Leu Lys Asn
            275                 280                 285

Ala Val Ala Glu Glu Leu Ile Lys Ile Leu Glu Pro Ile Arg Lys Arg
            290                 295                 300

Leu
305

<210> SEQ ID NO 10
<211> LENGTH: 305
<212> TYPE: PRT
<213> ORGANISM: Methanococcus jannaschii

<400> SEQUENCE: 10

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
            130                 135                 140

Lys Val Ala Glu Val Ile Tyr Pro Ile Met Gln Val Asn Ile Pro Tyr
145                 150                 155                 160

Leu Pro Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190
```

```
Pro Val Leu Thr Gly Leu Asp Gly Glu Gly Lys Met Ser Ser Lys
            195                 200                 205

Gly Asn Phe Ile Ala Val Asp Asp Ser Pro Glu Glu Ile Arg Ala Lys
    210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Leu
                260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
    290                 295                 300

Leu
305

<210> SEQ ID NO 11
<211> LENGTH: 305
<212> TYPE: PRT
<213> ORGANISM: Methanococcus jannaschii

<400> SEQUENCE: 11

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Lys Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
    210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255
```

```
Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
290                 295                 300

Leu
305

<210> SEQ ID NO 12
<211> LENGTH: 306
<212> TYPE: PRT
<213> ORGANISM: Methanococcus jannaschii

<400> SEQUENCE: 12

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Asn Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
```

<210> SEQ ID NO 13
<211> LENGTH: 306
<212> TYPE: PRT
<213> ORGANISM: Methanococcus jannaschii

<400> SEQUENCE: 13

| Met | Asp | Glu | Phe | Glu | Met | Ile | Lys | Arg | Asn | Thr | Ser | Glu | Ile | Ile | Ser |
|---|---|---|---|---|---|---|---|---|---|---|---|---|---|---|---|
| 1 | | | | 5 | | | | | 10 | | | | | 15 | |

Glu Glu Glu Leu Arg Glu Val Leu Lys Lys Asp Glu Lys Ser Ala Thr
           20                  25                  30

Ile Gly Phe Glu Pro Ser Gly Lys Ile His Leu Gly His Tyr Leu Gln
       35                  40                  45

Ile Lys Lys Met Ile Asp Leu Gln Asn Ala Gly Phe Asp Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                       85                  90                  95

Gly Leu Lys Ala Lys Tyr Val Tyr Gly Ser Ser Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 14
<211> LENGTH: 306
<212> TYPE: PRT
<213> ORGANISM: Methanococcus jannaschii

<400> SEQUENCE: 14

Met Asp Glu Phe Glu Met Ile Lys Arg Asn Thr Ser Glu Ile Ile Ser

```
  1               5                  10                 15
Glu Glu Glu Leu Arg Glu Val Leu Lys Lys Asp Glu Lys Ser Ala Leu
            20                  25                 30

Ile Gly Phe Glu Pro Ser Gly Lys Ile His Leu Gly His Tyr Leu Gln
            35                  40                 45

Ile Lys Lys Met Ile Asp Leu Gln Asn Ala Gly Phe Asp Ile Ile Ile
     50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Thr Phe Gln Leu Asp Lys
            100                 105                110

Asp Tyr Thr Leu Asn Val Tyr Arg Leu Ala Leu Lys Thr Thr Leu Lys
            115                 120                125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Pro Val His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
        210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
        290                 295                 300

Arg Leu
305

<210> SEQ ID NO 15
<211> LENGTH: 306
<212> TYPE: PRT
<213> ORGANISM: Methanococcus jannaschii

<400> SEQUENCE: 15

Met Asp Glu Phe Glu Met Ile Lys Arg Asn Thr Ser Glu Ile Ile Ser
 1               5                  10                 15

Glu Glu Glu Leu Arg Glu Val Leu Lys Lys Asp Glu Lys Ser Ala Thr
            20                  25                 30

Ile Gly Phe Glu Pro Ser Gly Lys Ile His Leu Gly His Tyr Leu Gln
            35                  40                 45

Ile Lys Lys Met Ile Asp Leu Gln Asn Ala Gly Phe Asp Ile Ile Ile
     50                  55                  60
```

-continued

```
Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Ser His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 16
<211> LENGTH: 306
<212> TYPE: PRT
<213> ORGANISM: Methanococcus jannaschii

<400> SEQUENCE: 16

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125
```

```
Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 17
<211> LENGTH: 306
<212> TYPE: PRT
<213> ORGANISM: Methanococcus jannaschii

<400> SEQUENCE: 17

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Thr His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
```

```
                180                 185                 190
Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
        210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 18
<211> LENGTH: 306
<212> TYPE: PRT
<213> ORGANISM: Methanococcus jannaschii

<400> SEQUENCE: 18

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Gly His
145                 150                 155                 160

Tyr Leu Gly Val Asp Val Ile Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240
```

Ile Met Glu Ile Ala Lys Tyr Phe Leu Glu Tyr Pro Leu Thr Ile Lys
            245                 250                 255

Arg Pro Glu Lys Phe Gly Gly Asp Leu Thr Val Asn Ser Tyr Glu Glu
        260                 265                 270

Leu Glu Ser Leu Phe Lys Asn Lys Glu Leu His Pro Met Asp Leu Lys
    275                 280                 285

Asn Ala Val Ala Glu Glu Leu Ile Lys Ile Leu Glu Pro Ile Arg Lys
290                 295                 300

Arg Leu
305

<210> SEQ ID NO 19
<211> LENGTH: 306
<212> TYPE: PRT
<213> ORGANISM: Methanococcus jannaschii

<400> SEQUENCE: 19

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Arg Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Val Ile His
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 20
<211> LENGTH: 306
<212> TYPE: PRT
<213> ORGANISM: Methanococcus jannaschii

<400> SEQUENCE: 20

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 21
<211> LENGTH: 654
<212> TYPE: DNA
<213> ORGANISM: Homo sapiens

<400> SEQUENCE: 21

```
atggctacag gctcccggac gtccctgctc ctggcttttg gcctgctctg cctgccctgg      60
cttcaagagg gcagtgcctt cccaaccatt cccttatcca ggcttttga caacgctatg     120 ctccgcgccc atcgtctgca ccagctggcc tttgacacct accaggagtt tgaagaagcc     180
tatatcccaa aggaacagaa gtattcattc ctgcagaacc cccagacctc cctctgtttc     240
tcagagtcta ttccgacacc ctccaacagg aggaaacac aacagaaatc caacctagag      300
ctgctccgca tctccctgct gctcatccag tcgtggctgg agcccgtgca gttcctcagg     360
agtgtcttcg ccaacagcct ggtgtacggc gcctctgaca gcaacgtcta tgacctccta     420
aaggacctag aggaaggcat ccaaacgctg atggggaggc tggaagatgg cagccccgg     480 actgggcaga tcttcaagca gacctacagc aagttcgaca caaactcaca caacgatgac     540
gcactactca agaactacgg gctgctctac tgcttcagga aggacatgga caaggtcgag     600
acattcctgc gcatcgtgca gtgccgctct gtggagggca gctgtggctt ctag           654

<210> SEQ ID NO 22
<211> LENGTH: 576
<212> TYPE: DNA
<213> ORGANISM: Homo sapiens

<400> SEQUENCE: 22
ttcccaacca ttcccttatc caggcttttt gacaacgcta tgctccgcgc ccatcgtctg      60
caccagctgg cctttgacac ctaccaggag tttgaagaag cctatatccc aaaggaacag     120
aagtattcat cctgcagaaa cccccagacc tccctctgtt tctcagagtc tattccgaca     180
ccctccaaca gggaggaaac acaacagaaa tccaacctag agctgctccg catctccctg     240
ctgctcatcc agtcgtggct ggagcccgtg cagttcctca ggagtgtctt cgccaacagc     300
ctggtgtacg gcgcctctga cagcaacgtc tatgacctcc taaaggacct agaggaaggc     360
atccaaacgc tgatggggag ctggaagat ggcagccccc ggactgggca gatcttcaag     420
cagacctaca gcaagttcga cacaaactca cacaacgatg acgcactact caagaactac     480
gggctgctct actgcttcag gaaggacatg gacaaggtcg agacattcct gcgcatcgtg     540
cagtgccgct ctgtggaggg cagctgtggc ttctag                                576

<210> SEQ ID NO 23
<211> LENGTH: 567
<212> TYPE: DNA
<213> ORGANISM: Homo sapiens

<400> SEQUENCE: 23
atggccttga cctttgcttt actggtggcc ctcctggtgc tcagctgcaa gtcaagctgc      60
tctgtgggct gtgatctgcc tcaaacccac agcctgggta gcaggaggac cttgatgctc     120
ctggcacaga tgaggagaat ctctcttttc tcctgcttga aggacagaca tgactttgga     180
tttccccagg aggagtttgg caaccagttc caaaaggctg aaaccatccc tgtcctccat     240
gagatgatcc agcagatctt caatctcttc agcacaaagg actcatctgc tgcttgggat     300
gagaccctcc tagacaaatt ctacactgaa ctctaccagc agctgaatga cctggaagcc     360
tgtgtgatac aggggtggg ggtgacagag actcccctga tgaaggagga ctccattctg     420
gctgtgagga aatacttcca aagaatcact ctctatctga agagaagaa atacagccct     480 tgtgcctggg aggttgtcag agcagaaatc atgagatctt tttcttttgtc aacaaacttg     540 caagaaagtt taagaagtaa ggaatga                                          567
```

<210> SEQ ID NO 24
<211> LENGTH: 498
<212> TYPE: DNA
<213> ORGANISM: Homo sapiens

<400> SEQUENCE: 24

```
tgtgatctgc ctcaaaccca cagcctgggt agcaggagga ccttgatgct cctggcacag    60
atgaggagaa tctctctttt ctcctgcttg aaggacagac atgactttgg atttccccag   120
gaggagtttg gcaaccagtt ccaaaaggct gaaaccatcc ctgtcctcca tgagatgatc   180
cagcagatct tcaatctctt cagcacaaag gactcatctg ctgcttggga tgagaccctc   240
ctagacaaat tctacactga actctaccag cagctgaatg acctggaagc ctgtgtgata   300 caggggtgg gggtgacaga gactcccctg atgaaggagg actccattct ggctgtgagg   360
aaatacttcc aaagaatcac tctctatctg aaagagaaga atacagccc ttgtgcctgg   420 gaggttgtca gagcagaaat catgagatct ttttctttgt caacaaactt gcaagaaagt   480
ttaagaagta aggaatga                                                  498
```

<210> SEQ ID NO 25
<211> LENGTH: 30
<212> TYPE: DNA
<213> ORGANISM: Artificial Sequence
<220> FEATURE:
<223> OTHER INFORMATION: PCR Cloning Primer

<400> SEQUENCE: 25

```
cgtgcacgct ggctgcgtgc acgctggctg                                      30
```

<210> SEQ ID NO 26
<211> LENGTH: 31
<212> TYPE: DNA
<213> ORGANISM: Artificial Sequence
<220> FEATURE:
<223> OTHER INFORMATION: PCR Cloning Primer

<400> SEQUENCE: 26

```
cgtgcacgct ggctgtcgtg cacgctggct g                                    31
```

<210> SEQ ID NO 27
<211> LENGTH: 32
<212> TYPE: DNA
<213> ORGANISM: Artificial Sequence
<220> FEATURE:
<223> OTHER INFORMATION: PCR Cloning Primer

<400> SEQUENCE: 27

```
cgtgcacgct ggctgttcgt gcacgctggc tg                                   32
```

<210> SEQ ID NO 28
<211> LENGTH: 45
<212> TYPE: DNA
<213> ORGANISM: Artificial Sequence
<220> FEATURE:
<223> OTHER INFORMATION: PCR Cloning Primer

<400> SEQUENCE: 28

```
cgtgcacgct ggctgcgtgc acgctggctg cgtgcacgct ggctg                     45
```

<210> SEQ ID NO 29
<211> LENGTH: 47
<212> TYPE: DNA
<213> ORGANISM: Artificial Sequence

```
<220> FEATURE:
<223> OTHER INFORMATION: PCR Cloning Primer

<400> SEQUENCE: 29
cgtgcacgct ggctgtcgtg cacgctggtc tgcgtgcacg ctggctg                47

<210> SEQ ID NO 30
<211> LENGTH: 49
<212> TYPE: DNA
<213> ORGANISM: Artificial Sequence
<220> FEATURE:
<223> OTHER INFORMATION: PCR Cloning Primer

<400> SEQUENCE: 30
cgtgcacgct ggctgttcgt gcacgctggt tctgcgtgca cgctggctg              49
```

METHODS AND COMPOSITIONS COMPRISING NON-NATURAL AMINO ACIDS

RELATED APPLICATIONS

This application is a continuation of U.S. patent application Ser. No. 12/092,791 filed on May 6, 2008, and claims the benefit of International Patent Application No. PCT/US2006/044682 filed on Nov. 16, 2006, and U.S. Provisional Application No. 60/737,855, filed on Nov. 16, 2005, the specifications and disclosures of which are incorporated herein in their entirety.

BACKGROUND OF THE INVENTION

The ability to incorporate non-genetically encoded amino acids (i.e., "non-natural amino acids") into proteins permits the introduction of chemical functional groups that could provide valuable alternatives to the naturally-occurring functional groups, such as the epsilon —NH2 of lysine, the sulfhydryl —SH of cysteine, the imino group of histidine, etc. Certain chemical functional groups are known to be inert to the functional groups found in the 20 common, genetically-encoded amino acids but react cleanly and efficiently to form stable linkages with functional groups that can be incorporated onto non-natural amino acids.

Methods are now available to selectively introduce chemical functional groups that are not found in proteins, that are chemically inert to all of the functional groups found in the 20 common, genetically-encoded amino acids and that may be used to react efficiently and selectively with reagents comprising certain functional groups to form stable covalent linkages.

SUMMARY OF THE INVENTION

Described herein and incorporated by reference are methods, compositions, techniques and strategies for making, purifying, detecting, characterizing, and using non-natural amino acids, non-natural amino acid polypeptides and modified non-natural amino acid polypeptides.

This invention provides a method of detecting a polypeptide that comprises detecting a non-naturally encoded amino acid side chain in the polypeptide. In some embodiments, the polypeptide is ribosomally synthesized. The invention also provides methods of detecting a polypeptide that comprise detecting a non-naturally encoded amino acid side chain in the polypeptide that has been post-translationally modified. Also provided are methods of detecting a non-naturally encoded amino acid side chain in said polypeptide that comprise contacting the non-naturally encoded amino acid side chain with a molecule comprising a functional group that specifically interacts with the non-naturally encoded amino acid side chain. Also provided are methods of purifying a polypeptide having a non-naturally encoded amino acid in the polypeptide chain. In some embodiments the method comprises contacting the polypeptide with a substance that interacts with the non-naturally encoded amino acid side chain in the polypeptide. In other embodiments, the method of purifying a polypeptide having a non-naturally encoded amino acid in the polypeptide chain comprises precipitation of the polypeptide, wherein the non-naturally encoded amino acid alters the solubility of the polypeptide when compared to the solubility of the polypeptide without a non-naturally encoded amino acid in the polypeptide chain. Methods of purifying a ribosomally made polypeptide having a non-naturally encoded amino acid in the polypeptide side chain comprises electrophoresis of the polypeptide, wherein the non-naturally encoded amino acid alters the electrophoretic mobility of the polypeptide when compared to the electrophoretic mobility of the polypeptide without a non-naturally encoded amino acid in the polypeptide chain are also provided. In other embodiments, the method of purifying a ribosomally made polypeptide having a non-naturally encoded amino acid in the polypeptide side chain, comprises dialysis of the polypeptide, wherein the non-naturally encoded amino acid alters the diffusion rate of the polypeptide when compared to the diffusion rate of the polypeptide without a non-naturally encoded amino acid in the polypeptide chain.

The invention also provides a method for screening a library of molecules, comprising: a) combining a polypeptide comprising a non-naturally encoded amino acid with the library molecules under conditions to allow interaction of the library molecules with the polypeptide comprising a non-naturally encoded amino acid, and b) identifying the library molecules which interact with the polypeptide comprising a non-naturally encoded amino acid. In some embodiments, a library of ribosomally made polypeptide comprising a plurality of polypeptides having different amino acid sequences, wherein each polypeptide comprises a non-natural amino acid is screened.

The invention also provides methoda, comprising: a) substituting a non-naturally encoded amino acid for a naturally encoded amino acid at a single pre-selected site in a pre-selected polypeptide having at least one known biological activity; and b) measuring a biological activity of the pre-selected polypeptide comprising the non-naturally encoded amino acid; and c) comparing the biological activity of the pre-selected polypeptide of step b) with the pre-selected polypeptide having a non-naturally encoded amino acid substituted for a naturally encoded amino acid at a different position in the pre-selected polypeptide chain or with the pre-selected polypeptide without a substituted non-naturally encoded amino acid in the polypeptide chain. In some embodiments, a method for selecting a position for post-translational modification of a pre-selected polypeptide comprises a) substituting a non-naturally encoded amino acid for a naturally encoded amino acid at a single pre-selected site in a pre-selected polypeptide having at least one known biological activity; and b) measuring a biological activity of the pre-selected polypeptide comprising the non-naturally encoded amino acid; and c) comparing the biological activity of the pre-selected polypeptide of step b) with the pre-selected polypeptide having a non-naturally encoded amino acid substituted for a naturally encoded amino acid at a different position in the pre-selected polypeptide chain or with the pre-selected polypeptide without a substituted non-naturally encoded amino acid in the polypeptide chain.

It is to be understood that the methods and compositions described herein and incorporated by reference are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

Definitions

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which the inventions described herein belong. Although any methods, devices, and materials similar or equivalent to those described herein can be used in the practice or testing of the inventions described herein, the preferred methods, devices and materials are now described.

All publications and patents mentioned herein are incorporated herein by reference for the purpose of describing and disclosing, for example, the constructs and methodologies that are described in the publications, which might be used in connection with the presently described inventions. The publications discussed herein are provided solely for their disclosure prior to the filing date of the present application. Nothing herein is to be construed as an admission that the inventors described herein are not entitled to antedate such disclosure by virtue of prior invention or for any other reason.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by the structures —$CH_2CH_2$— and —$CH_2CH_{12}CH_2CH_2$—, and further includes those groups described below as "heteroalkylene." Typically, an alkyl (or alkylene) group will have from 1 to 24 carbon atoms, with those groups having 10 or fewer carbon atoms being a particular embodiment of the methods and compositions described herein. A "lower alkyl" or "lower alkylene" is a shorter chain alkyl or alkylene group, generally having eight or fewer carbon atoms.

The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include but are not limited to various water soluble polymers, peptides or proteins such as serum albumin, or other moieties that increase serum half-life of peptides.

The term "aryl" means, unless otherwise stated, a polyunsaturated, aromatic, hydrocarbon substituent which can be a single ring or multiple rings (including but not limited to, from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (including but not limited to, aryloxy, arylthioxy, aralkyl) includes both aryl and heteroaryl rings as defined above. Thus, the term "aralkyl" or "alkaryl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by, for example, an oxygen atom (including but not limited to, phenoxymethyl, 2-pyridyloxymethyl, 3-(1-naphthyloxy)propyl, and the like).

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No. 188,256; U.S.

Pat. Nos. 4,671,958, 4,659,839, 4,414,148, 4,699,784; 4,680,338; and 4,569,789 which are incorporated by reference herein. A "multi-functional polymer" refers to a polymer comprising two or more discrete functional groups that are capable of reacting specifically with other moieties (including but not limited to, amino acid side groups) to form covalent or non-covalent linkages. A bi-functional polymer or multi-functional polymer may be any desired length or molecular weight, and may be selected to provide a particular desired spacing or conformation between one or more molecules linked to the polypeptide and its binding partner or the polypeptide.

The term "biologically active molecule", "biologically active moiety" or "biologically active agent" when used herein means any substance which can affect any physical or biochemical properties of a biological system, pathway, molecule, or interaction relating to an organism, including but not limited to viruses, bacteria, bacteriophage, transposon, prion, insects, fungi, plants, animals, and humans. In particular, as used herein, biologically active molecules include but are not limited to any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, hard drugs, soft drugs, carbohydrates, inorganic atoms or molecules, dyes, lipids, nucleosides, radionuclides, oligonucleotides, toxins, cells, viruses, liposomes, microparticles and micelles. Classes of biologically active agents that are suitable for use with the methods and compositions described herein include, but are not limited to, drugs, prodrugs, radionuclides imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

"Cofolding," as used herein, refers specifically to refolding processes, reactions, or methods which employ at least two polypeptides which interact with each other and result in the transformation of unfolded or improperly folded polypeptides to native, properly folded polypeptides.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, including but not limited to, by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of an algorithm that is suitable for determining percent sequence identity and sequence similarity are the BLAST and BLAST 2.0 algorithms, which are described in Altschul et al. (1997) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, $M=5$, $N=-4$ and a comparison of both strands. For amino acid sequences, the BLASTP program uses as defaults a wordlength of 3, and expectation (E) of 10, and the BLOSUM62 scoring matrix (see Henikoff and Henikoff (1992) *Proc. Natl. Acad. Sci. USA* 89:10915) alignments (B) of 50, expectation (E) of 10, $M=5$, $N=-4$, and a comparison of both strands. The BLAST algorithm is typically performed with the "low complexity" filter turned off.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, less than about 0.01, or less than about 0.001.

The term "conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the methods and compositions described herein.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins: Structures and Molecular Properties* (W H Freeman & Co.; 2nd edition (December 1993)

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated, partially unsaturated and fully unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-piperidinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses bicyclic and tricyclic ring structures. Similarly, the term "heterocycloalkylene" by itself or as part of another substituent means a divalent radical derived from heterocycloalkyl, and the term "cycloalkylene" by itself or as part of another substituent means a divalent radical derived from cycloalkyl.

"Denaturing agent" or "denaturant," as used herein, is defined as any compound or material which will cause a reversible unfolding of a protein. The strength of a denaturing agent or denaturant will be determined both by the properties and the concentration of the particular denaturing agent or denaturant. Suitable denaturing agents or denaturants may be chaotropes, detergents, organic, water miscible solvents, phospholipids, or a combination of two or more such agents. Suitable chaotropes include, but are not limited to, urea, guanidine, and sodium thiocyanate. Useful detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N->2,3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Organic, water miscible solvents such as acetonitrile, lower alkanols (especially $C_2$-$C_4$ alkanols such as ethanol or isopropanol), or lower alkandiols (especially $C_2$-$C_4$ alkandiols such as ethylene-glycol) may be used as denaturants. Phospholipids useful in the methods and compositions described herein may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

The term "effective amount" as used herein refers to that amount of the (modified) non-natural amino acid polypeptide being administered which will relieve to some extent one or more of the symptoms of the disease, condition or disorder being treated. Compositions containing the (modified) non-natural amino acid polypeptide described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "halogen" includes fluorine, chlorine, iodine, and bromine.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CCH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, optionally about 65%, about 70%, about 75%, about 80%, about 85%, about 90%, or about 95% identity over a specified region), when compared and aligned for maximum correspondence over a comparison window, or designated region as measured using one of the following sequence comparison algorithms or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "isolated," when applied to a nucleic acid or protein, denotes that the nucleic acid or protein is free of at least some of the cellular components with which it is associated in the natural state, or that the nucleic acid or protein has been concentrated to a level greater than the concentration of its in vivo or in vitro production. It can be in a homogeneous state. Isolated substances can be in either a dry or semi-dry state, or in solution, including but not limited to an aqueous solution. It can be a component of a pharmaceutical composition that comprises additional pharmaceutically acceptable carriers and/or excipients. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it may mean that the nucleic acid or protein is at least 85% pure, at least 90% pure, at least 95% pure, at least 99% or greater pure.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include but are not limited to carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which the polypeptide has been secreted, including medium either before or after a proliferation step. The term also may encompass buffers or reagents that contain host cell lysates, such as in the case where the polypeptide is produced intracellularly and the host cells are lysed or disrupted to release the polypeptide.

A "metabolite" of a (modified) non-natural amino acid polypeptide disclosed herein is a derivative of that (modified) non-natural amino acid polypeptide that is formed when the (modified) non-natural amino acid polypeptide is metabolized. The term "active metabolite" refers to a biologically active derivative of a (modified) non-natural amino acid polypeptide that is formed when the (modified) non-natural amino acid polypeptide is metabolized. The term "metabolized" refers to the sum of the processes (including, but not limited to, hydrolysis reactions and reactions catalyzed by enzymes) by which a particular substance is changed by an organism. Further information on metabolism may be obtained from The Pharmacological Basis of Therapeutics, 9th Edition, McGraw-Hill (1996). Metabolites of the (modified) non-natural amino acid polypeptide disclosed herein can be identified either by administration of (modified) non-natural amino acid polypeptide to a host and analysis of tissue samples from the host, or by incubation of (modified) non-natural amino acid polypeptide with hepatic cells in vitro and analysis of the resulting compounds.

The term "modified," as used herein refers to the presence of a post-translational modification on a polypeptide. The form "(modified)" term means that the polypeptides being discussed are optionally modified, that is, the polypeptides under discussion can be modified or unmodified.

As used herein, the term "modulated serum half-life" means the positive or negative change in circulating half-life of a (modified) polypeptide relative to its non-modified form. Serum half-life is measured by taking blood samples at various time points after administration of the polypeptide, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of a (modified) polypeptide, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as proteases, or an increase or decrease in another parameter or mechanism of action of the non-modified molecule.

As used herein, the term "non-eukaryote" refers to non-eukaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax voleanii* and *Halobacterium* species NRC-1, *Archaeoglobus fulgidus, Pyrococcus furiosus, Pyrococcus horikoshii, Aeuropyrum pernix*, etc.) phylogenetic domain.

A "non-natural amino acid" refers to an amino acid that is not one of the 20 common amino acids or pyrrolysine or selenocysteine; other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids that occur naturally by modification of a naturally encoded amino acid (including but not limited to, the 20 common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine.

The term "nucleic acid" refers to deoxyribonucleotides, deoxyribonucleosides, ribonucleosides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

"Oxidizing agent," as used hereinwith respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. A wide variety of oxidizing agents are suitable for use in the methods and compositions described herein.

As used herein, the term "polyalkylene glycol" refers to polyethylene glycol, polypropylene glycol, polybutylene glycol, and derivatives thereof. The term "polyalkylene glycol" encompasses both linear and branched polymers and average molecular weights of between 1 kDa and 100 kDa. Other exemplary embodiments are listed, for example, in commercial supplier catalogs, such as Shearwater Corporation's catalog "Polyethylene Glycol and Derivatives for Biomedical Applications" (2001).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. As used herein, the terms encompass amino acid chains of any length, including full length proteins, wherein the amino acid residues are linked by covalent peptide bonds.

The term "post-translationally modified" refers to any modification of a natural or non-natural amino acid that occurs to such an amino acid after it has been incorporated into a polypeptide chain. The term encompasses, by way of example only, co-translational in vivo, modifications, co-translational in vitro modifications (such as in a cell-free translation system), post-translational in vivo modifications, and post-translational in vitro modifications.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug.

In prophylactic applications, compositions containing the (modified) non-natural amino acid polypeptide are administered to a patient susceptible to or otherwise at risk of a particular disease, disorder or condition. Such an amount is defined to be a "prophylactically effective amount." In this use, the precise amounts also depend on the patient's state of health, weight, and the like. It is considered well within the skill of the art for one to determine such prophylactically effective amounts by routine experimentation (e.g., a dose escalation clinical trial).

The term "protected" refers to the presence of a "protecting group" or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in or with the methods and compositions described herein, including photolabile groups such as Nvoc and MeNvoc.

By way of example only, blocking/protecting groups may be selected from:

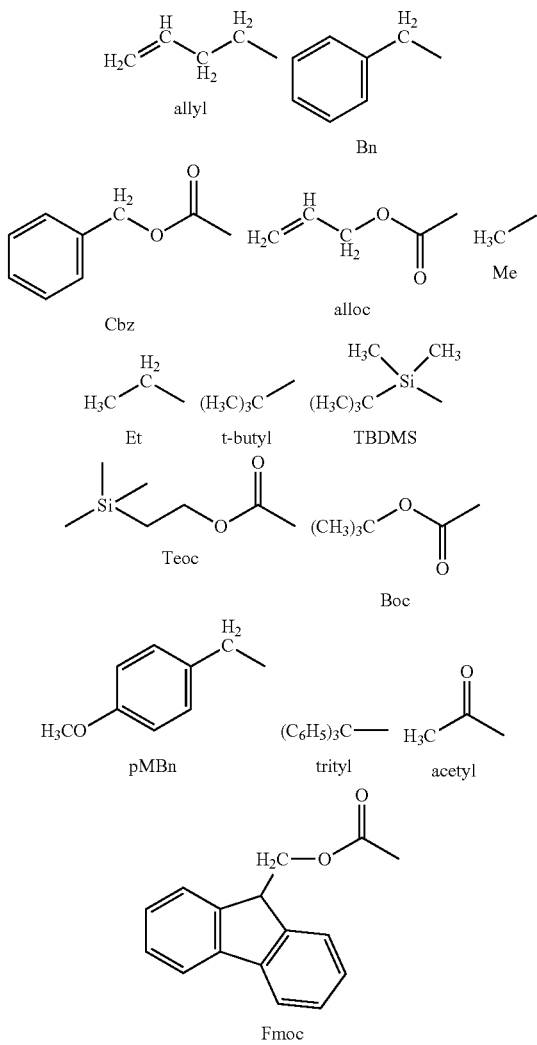

Other protecting groups are described in Greene and Wuts, Protective Groups in Organic Synthesis, 3rd Ed., John Wiley & Sons, New York, N.Y., 1999, which is incorporated herein by reference in its entirety.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptoethanol, dithioerythritol, cysteine, cysteamine (2-aminoethanethiol), and reduced glutathione. A wide variety of reducing agents are suitable for use in the methods and compositions described herein.

"Refolding," as used herein describes any process, reaction or method which transforms disulfide bond containing polypeptides from an improperly folded or unfolded state to a native or properly folded conformation with respect to disulfide bonds.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, *Laboratory Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3 and the temperature is at least about 30° C. for short probes (including but not limited to, 10 to 50 nucleotides) and at least about 60° C. for long probes (including but not limited to, greater than 50 nucleotides). Stringent conditions may also be achieved with the addition of destabilizing agents such as formamide. For selective or specific hybridization, a positive signal may be at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

The term "subject" as used herein, refers to an animal, in some embodiments a mammal, and in other embodiments a human, who is the object of treatment, observation or experiment.

The term "substantially purified" refers to a polypeptide that may be substantially or essentially free of components that normally accompany or interact with the protein as found in its naturally occurring environment, i.e. a native cell, or host cell in the case of recombinantly produced polypeptide. A polypeptide that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the polypeptide or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the polypeptide or variant thereof is recombinantly produced by the host cells, the protein may be present in the culture medium at about 5 g/L, about 4 g/L, about 3 g/L, about 2 g/L, about 1 g/L, about 750 mg/L, about 500 mg/L, about 250 mg/L, about 10 mg/L, about 50 mg/L, about 10 mg/L, or about 1 mg/L or less of the dry weight of the cells. Thus, "substantially purified" polypeptide as produced by the methods described herein may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

The term "substituents" includes but is not limited to "non-interfering substituents." "Non-interfering substituents" are those groups that yield stable compounds. Suitable non-interfering substituents or radicals include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, substituted phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —NRC(O)—($C_1$-$C_{10}$ alkyl), —C(O)—($C_1$-$C_{10}$ alkyl), $C_2$-$C_{10}$ alkthioalkyl, —C(O)O—($C_1$-$C_{10}$ alkyl), —OH, —$SO_2$, =S, —COOH, —$NR_2$, carbonyl, —C(O)—($C_1$-$C_{10}$ alkyl)-CF3, —C(O)—CF3, —C(O)NR2, —($C_1$-$C_{10}$ aryl)-S—($C_6$-$C_{10}$ aryl), —C(O)—($C_6$-$C_{10}$ aryl), —$(CH_2)_m$—O—$(CH_2)_m$—O—($C_1$-$C_{10}$ alkyl) wherein each m is from 1 to 8, —C(O)$NR_2$, —C(S)$NR_2$, —$SO_2NR_2$, —NRC(O)$NR_2$, —NRC(S)$NR_2$, salts thereof, and the like. Each R group in the preceding list is independently selected from the group consisting of H, alkyl or substituted alkyl, aryl or substituted aryl, or alkaryl. Where substituent groups are specified by their conventional chemical formulas, written from left to right, they equally encompass the chemically identical substituents that would result from writing the structure from right to left, for example, —$CH_2O$— is equivalent to —$OCH_2$—.

Substituents for alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR, =O, =NR, =N—OR, —$NR_2$, —SR, -halogen, —$SiR_3$, —OC(O)R, —C(O)R, —$CO_2R$, —$CONR_2$, —OC(O)$NR_2$, —NRC(O)R, —NR—C(O)$NR_2$, —NR(O)$_2$R, —NR—C($NR_2$)=NR, —S(O)R, —S(O)$_2$R, —S(O)$_2NR_2$, —$NRSO_2R$, —CN and —$NO_2$ in a number ranging from zero to (2m'+1), where m' is the total number of carbon atoms in such a radical. Each R group in the preceding list is independently selected from the group consisting of hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or aralkyl groups. When two R groups are attached to the same nitrogen atom, they can be combined with the nitrogen atom to form a 5-, 6-, or 7-membered ring. For example, —$NR_2$ is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —$CF_3$ and —$CH_2CF_3$) and acyl (including but not limited to, —C(O)$CH_3$, —C(O)$CF_3$, —C(O)$CH_2OCH_3$, and the like).

Similar to the substituents described for the alkyl radical, substituents for aryl and heteroaryl groups are varied and are selected from, but are not limited to —OR, =O, =NR, =N—OR, —$NR_2$, —SR, -halogen, —$SiR_3$, —OC(O)R, —C(O)R, —$CO_2R$, —$CONR_2$, —OC(O)$NR_2$, —NRC(O)R, —NR—C(O)$NR_2$, —NR(O)$_2$R, —NR—C($NR_2$)=NR, —S(O)R, —S(O)$_2$R, —S(O)$_2NR_2$, —$NRSO_2R$, —CN, —$NO_2$, —R, —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where each R group in the preceding list is independently selected from hydrogen, alkyl, heteroalkyl, aryl and heteroaryl.

In therapeutic applications, compositions containing the (modified) non-natural amino acid polypeptide are administered to a patient already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

As used herein, the term "test ligand" refers to an agent, which can be a compound, molecule or complex, which is being tested for its ability to bind to a non-natural amino acid polypeptide, such as a protein or -protein complex in its native form is known to be associated with or causative of a disease or condition in a living organism, such as a vertebrate, particularly a mammal and even more particularly a human. Since binding of a ligand to its non-natural amino acid polypeptide must occur for the ligand to have a direct effect on the non-natural amino acid polypeptide, binding as indicated by the present assay method is a strong indication of the therapeutic potential of a ligand identified as described herein.

A test ligand which can be assessed by the present method can be virtually any agent, including, but not limited to, metals, polypeptides, proteins, lipids, polysaccharides, polynucleotides and small organic molecules. A test ligand which is shown to bind a non-natural amino acid polypeptide is referred to as a ligand. Complex mixtures of substances, including but not limited to, natural product extracts, which include more than one test ligand can be tested and if there is a positive response (i.e., if binding to the non-natural amino acid polypeptide occurs), the ligand which bound the non-natural amino acid polypeptide can be purified from the mixture prior to further assessment of its therapeutic potential.

The term "treating" is used to refer to either prophylactic and/or therapeutic treatments.

As used herein, the term "water soluble polymer" refers to any polymer that is soluble in aqueous solvents. Linkage of water soluble polymers to a polypeptide can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding, altered binding to one or more binding partners, and altered receptor dimerization or multimerization. The water soluble polymer may or may not have its own biological activity and may be utilized as a linker for attaching the polypeptide to other substances, including but not limited to one or more polypeptides, or one or more biologically active molecules. Suitable polymers include, but are not limited to, polyethylene glycol, polyethylene glycol propionaldehyde, mono C1-C10 alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include but are not limited to polyethylene glycol and serum albumin.

Unless otherwise indicated, conventional methods of mass spectroscopy, NMR, HPLC, protein chemistry, biochemistry, recombinant DNA techniques and pharmacology, within the skill of the art are employed.

Compounds (including, but not limited to non-natural amino acids, (modified) non-natural amino acid polypeptides and reagents for producing either of the aforementioned compounds) presented herein include isotopically-labelled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^{2}H$, $^{3}H$. $^{13}C$, $^{14}C$, $^{15}N$, $^{18}O$, $^{17}O$, $^{35}S$, $^{18}F$, $^{36}Cl$, respectively. Certain isotopically-labelled compounds described herein, for example those into which radioactive isotopes such as $^{3}H$ and $^{14}C$ are incorporated, are useful in drug and/or substrate tissue distribution assays. Further, substitution with isotopes such as deuterium, i.e., $^{2}H$, can afford certain therapeutic advantages resulting from greater metabolic stability, for example increased in vivo half-life or reduced dosage requirements.

Some of the compounds herein (including, but not limited to non-natural amino acids, (modified) non-natural amino acid polypeptides and reagents for producing either of the aforementioned compounds) have asymmetric carbon atoms and can therefore exist as enantiomers or diastereomers. Diasteromeric mixtures can be separated into their individual diastereomers on the basis of their physical chemical differences by methods known, for example, by chromatography and/or fractional crystallization. Enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

In additional or further embodiments, the compounds described herein (including, but not limited to non-natural amino acids, (modified) non-natural amino acid polypeptides and reagents for producing either of the aforementioned compounds) are used in the form of pro-drugs. In additional or further embodiments, the compounds described herein (including, but not limited to non-natural amino acids, (modified) non-natural amino acid polypeptides and reagents for producing either of the aforementioned compounds) are metabolized upon administration to an organism in need to produce a metabolite that is then used to produce a desired effect, including a desired therapeutic effect. In further or additional embodiments are active metabolites of non-natural amino acids and (modified) non-natural amino acid polypeptides.

The methods and formulations described herein include the use of N-oxides, crystalline forms (also known as polymorphs), or pharmaceutically acceptable salts of non-natural amino acids and (modified) non-natural amino acid polypeptides. In some situations, non-natural amino acids and (modified) non-natural amino acid polypeptides may exist as tautomers. All tautomers are included within the scope of the non-natural amino acids and (modified) non-natural amino acid polypeptides presented herein. In addition, the non-natural amino acids and (modified) non-natural amino acid polypeptides described herein can exist in unsolvated as well as solvated forms with pharmaceutically acceptable solvents such as water, ethanol, and the like. The solvated forms of the non-natural amino acids and (modified) non-natural amino acid polypeptides presented herein are also considered to be disclosed herein.

Those skilled in the art will recognize that some of the compounds herein (including, but not limited to non-natural amino acids, (modified) non-natural amino acid polypeptides and reagents for producing either of the aforementioned compounds) can exist in several tautomeric forms. All such tautomeric forms are considered as part of the compositions described herein. Also, for example all enol-keto forms of any compounds (including, but not limited to non-natural amino acids, (modified) non-natural amino acid polypeptides and reagents for producing either of the aforementioned compounds) herein are considered as part of the compositions described herein.

Some of the compounds herein (including, but not limited to non-natural amino acids, (modified) non-natural amino acid polypeptides and reagents for producing either of the aforementioned compounds) are acidic and may form a salt with a pharmaceutically acceptable cation. Some of the compounds herein (including, but not limited to non-natural amino acids, (modified) non-natural amino acid polypeptides and reagents for producing either of the aforementioned compounds) can be basic and accordingly, may form a salt with a pharmaceutically acceptable anion. All such salts, including di-salts are within the scope of the compositions described herein and they can be prepared by conventional methods. For example, salts can be prepared by contacting the acidic and basic entities, in either an aqueous, non-aqueous or partially aqueous medium. The salts are recovered by using at least one of the following techniques: filtration, precipitation with a non-solvent followed by filtration, evaporation of the solvent, or, in the case of aqueous solutions, lyophilization.

Salts, for example, include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

INCORPORATION BY REFERENCE

All publications, patents, and patent applications mentioned in this specification are herein incorporated by reference in their entirety for all purposes to the same extent as if each individual publication, patent, or patent application was specifically and individually indicated to be incorporated by reference for all purposes.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 presents an illustrative, non-limiting example of reactions where an amino acid functionality (A), translationally incorporated (or otherwise incorporated) into a polypeptide, reacts with reactant (B) to yield a modified polypeptide.

FIG. 4 presents an illustrative, non-limiting example of formation of oxime-containing non-natural amino acid components by reaction of hydroxylamine-containing non-natural amino acid components with carbonyl-containing reagents.

FIG. 7 presents an illustrative, non-limiting example of formation of oxime-containing non-natural amino acid components by reactions of hydroxylamine-containing non-natural amino acid components with dicarbonyl-containing reagents.

FIG. 9 presents non-limiting examples of molecules that are site specifically attached to proteins through oxime formation between carbonyl of non-natural amino acid incorporated into a polypeptide and the hydroxylamine of the molecule.

FIG. 12 shows an example of resin selection and functionalization.

FIG. 14 shows an example of purification of a non-natural amino acid polypeptide using an aldehyde resin.

DETAILED DESCRIPTION OF THE INVENTION

I. Introduction

Recently, an entirely new technology in the protein sciences has been reported, which promises to overcome many of the limitations associated with site-specific modifications of proteins. Specifically, new components have been added to the protein biosynthetic machinery of the prokaryote *Escherichia coli* (*E. coli*) (e.g., L. Wang, et al., (2001), *Science* 292:498-500) and the eukaryote *Saccharomyces cerevisiae* (*S. cerevisiae*) (e.g., J. Chin et al., *Science* 301: 964-7 (2003)), which has enabled the incorporation of non-natural amino acids to proteins in vivo. A number of new amino acids with novel chemical, physical or biological properties, including photoaffinity labels and photoisomerizable amino acids, keto amino acids, and glycosylated amino acids have been incorporated efficiently and with high fidelity into proteins in *E. coli* and in yeast in response to the amber codon, TAG, using this methodology. See, e.g., J. W. Chin et al., (2002), *Journal of the American Chemical Society* 124:9026-9027 (incorporated by reference in its entirety); J. W. Chin, & P. G. Schultz, (2002), *Chem Bio Chem* 3(11):1135-1137 (incorporated by reference in its entirety); J. W. Chin, et al., (2002), *PNAS United States of America* 99:11020-11024 (incorporated by reference in its entirety); and, L. Wang, & P. G. Schultz, (2002), *Chem. Comm.*, 1:1-11 (incorporated by reference in its entirety). These studies have demonstrated that it is possible to selectively and routinely introduce chemical functional groups that are not found in proteins, that are chemically inert to all of the functional groups found in the 20 common, genetically-encoded amino acids and that may be used to react efficiently and selectively to form stable covalent linkages.

II. Overview

Figure 1:
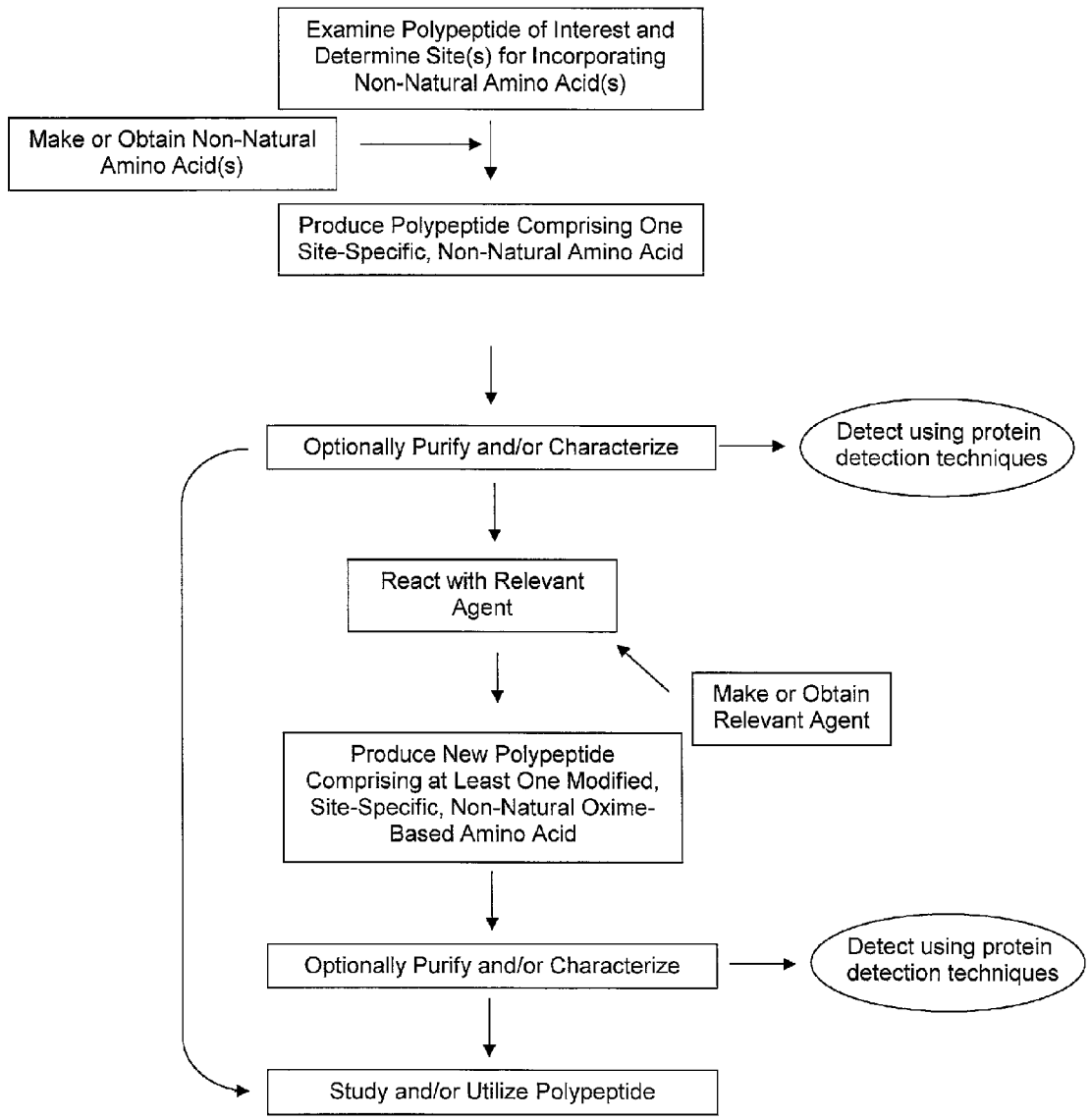
FIG. 1 presents a schematic representation of the relationship of certain aspects of the methods, compositions, strategies and techniques described herein.

FIG. 1 is an overview of the compositions, methods and techniques that are described herein. At one level, incorporated by reference from U.S. Patent Application Nos. 60/638,418, 60/638,527, 60/639,195, 60/696,210, 60/696, 302, and 60/696,068 in their entirety are the tools (methods, compositions, techniques) for creating and using a polypeptide comprising at least one non-natural amino acid or modified non-natural amino acid. Such non-natural amino acid polypeptides may contain further functionality, including but not limited to, a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; and any combination of the above.

As shown in FIG. 1, in one aspect are methods for selecting and designing a polypeptide to be modified using the methods, compositions and techniques are further described in U.S. Patent Application Nos. 60/638,418, 60/638,527, 60/639,195, 60/696,210, 60/696,302, and 60/696,068 which are incorporated by reference in their entirety. The new polypeptide may be designed de novo, including by way of example only, as part of high-throughput screening process (in which case numerous polypeptides may be designed, synthesized, characterized and/or tested) or based on the interests of the researcher. The new polypeptide may also be designed based on the structure of a known or partially characterized polypeptide. By way of example only, the Growth Hormone Gene Superfamily (see infra) has been the subject of intense study by the scientific community; a new polypeptide may be designed based on the structure of a member or members of this gene superfamily. The principles for selecting which amino acid(s) to substitute and/or modify are described separately herein. The choice of which modification to employ is also described herein, and can be used to meet the need of the experimenter or end user. Modifications include, by way of example only, manipulating the therapeutic effectiveness of the polypeptide, improving the safety profile of the polypeptide, adjusting the pharmacokinetics of the polypeptide, providing additional functionality to the polypeptide, incorporating a tag, label or detectable signal into the polypeptide, easing the isolation properties of the polypeptide, and any combination of the aforementioned modifications.

Thus, polypeptides comprising at least one non-natural amino acid or modified non-natural amino acid are further provided and described in U.S. Patent Application Nos. 60/638,418, 60/638,527, 60/639,195, 60/696,210, 60/696, 302, and 60/696,068 which are incorporated by reference in their entirety. A very wide variety of non-naturally encoded amino acids are suitable for use in the present invention. Any number of non-naturally encoded amino acids can be introduced into a polypeptide. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, the side chain (R group) optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof.

Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

A number of non-natural amino acids for incorporation into polypeptides are found in WO 2002/085923 entitled "In vivo incorporation of unnatural amino acids" which is incorporated by reference herein in its entirety. Methods and compositions for the in vivo incorporation of non-naturally encoded amino acids are described in U.S. Patent Application Publication 2003/0082575 (Ser. No. 10/126,927) which is incorporated by reference herein in its entirety. Methods for selecting an orthogonal tRNA-tRNA synthetase pair for use in in vivo translation system of an organism are also described in U.S. Patent Application Publications 2003/0082575 (Ser. No. 10/126,927) and 2003/0108885 (Ser. No. 10/126,931) which are incorporated by reference herein in their entirety. PCT Publication No. WO 04/035743 entitled "Site Specific Incorporation of Keto Amino Acids into Proteins," which is incorporated by reference herein in its entirety, describes orthogonal RS and tRNA pairs for the incorporation of keto amino acids. PCT Publication No. WO 04/094593 entitled "Expanding the Eukaryotic Genetic Code," which is incorporated by reference herein in its entirety, describes orthogonal RS and tRNA pairs for the incorporation of non-naturally encoded amino acids in eukaryotic host cells. Non-naturally encoded amino acids have side chain groups that distinguish them from the natural amino acids. The side chain may comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof.

In certain embodiments, polypeptides with at least one non-natural amino acid or modified non-natural amino acid group include at least one post-translational modification at some position on the polypeptide. In some embodiments the post-translational modification occurs via the cellular machinery (e.g., glycosylation, acetylation, acylation, lipid-modification, palmitoylation, palmitate addition, phosphorylation, glycolipid-linkage modification, and the like), in many instances, such cellular-machinery-based post-translational modifications occur at the naturally occurring amino acid sites on the polypeptide, however, in certain embodiments, the cellular-machinery-based post-translational modifications occur on the non-natural amino acid site(s) on the polypeptide.

In other embodiments the post-translational modification does not utilize the cellular machinery, but is instead providing by attachment of a molecule (including but not limited to, a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule, a quantum dot; a nanotransmitter; and any combination of the above) comprising a second reactive group to the at least one non-natural amino acid comprising a first reactive group (including but not limited to, non-natural amino acid containing a ketone, aldehyde, acetal, hemiacetal, oxime, or hydroxylamine functional group) utilizing chemistry methodology that is known to one of ordinary skill in the art to be suitable for the particular reactive groups. In certain embodiments, the post-translational modification is made in vivo in a eukaryotic cell or in a non-eukaryotic cell. In certain embodiments, the post-translational modification is made in vitro. Also included with this aspect are methods for producing, purifying, characterizing and using such polypeptides containing at least one such post-translationally modified non-natural amino acids.

Also included within the scope of the methods, compositions, strategies and techniques further described in U.S. Patent Application Nos. 60/638,418, 60/638,527, 60/639,195, 60/696,210, 60/696,302, and 60/696,068 which are incorporated by reference in their entirety are reagents capable of reacting with a non-natural amino acid that is part of a polypeptide so as to produce any of the aforementioned post-translational modifications. In general, the resulting post-translationally modified non-natural amino acid will contain at least one non-natural amino acid which may undergo subsequent modification reactions. Also included with this aspect are methods for producing, purifying, characterizing and using such reagents that are capable of any such post-translational modifications of such non-natural amino acid(s).

In certain embodiments, the protein includes at least one post-translational modification that is made in vivo by one host cell, where the post-translational modification is not normally made by another host cell type. In certain embodiments, the protein includes at least one post-translational modification that is made in vivo by a eukaryotic cell, where the post-translational modification is not normally made by a non-eukaryotic cell. Examples of post-translational modifications include, but are not limited to, glycosylation, acetylation, acylation, lipid-modification, palmitoylation, palmitate addition, phosphorylation, glycolipid-linkage modification, and the like. In one embodiment, the post-translational modification comprises attachment of an oligosaccharide to an asparagine by a GlcNAc-asparagine linkage (including but not limited to, where the oligosaccharide comprises (GlcNAc-Man)$_2$-Man-GlcNAc-GlcNAc, and the like). In another embodiment, the post-translational modification comprises attachment of an oligosaccharide (including but not limited to, Gal-GalNAc, Gal-GlcNAc, etc.) to a serine or threonine by a GalNAc-serine, a GalNAc-threonine, a GlcNAc-serine, or a GlcNAc-threonine linkage. In certain embodiments, a protein or polypeptide can comprise a secretion or localization sequence, an epitope tag, a FLAG tag, a polyhistidine tag, a GST fusion, and/or the like. Examples of secretion signal sequences include, but are not limited to, a prokaryotic secretion signal sequence, a eukaryotic secretion signal sequence, a eukaryotic secretion signal sequence 5'-optimized for bacterial expression, a novel secretion signal sequence, pectate lyase secretion signal sequence, Omp A secretion signal sequence, and a phage secretion signal sequence. Examples of secretion signal sequences, include, but are not limited to, STII (prokaryotic), Fd GIII and M13 (phage), Bgl2 (yeast), and the signal sequence bla derived from a transposon. Also included with this aspect are methods for producing, purifying, characterizing and using such polypeptides containing at least one such post-translational modification.

The protein or polypeptide of interest can contain at least one, at least two, at least three, at least four, at least five, at least six, at least seven, at least eight, at least nine, or ten or more non-natural amino acids. The non-natural amino acids can be the same or different, for example, there can be 1, 2, 3, 4, 5, 6, 7, 8, 9, 10 or more different sites in the protein that comprise 1, 2, 3, 4, 5, 6, 7, 8, 9, 10 or more different non-natural amino acids. In certain embodiments, at least one, but fewer than all, of a particular amino acid present in a naturally occurring version of the protein is substituted with an non-natural amino acid.

The methods and compositions provided and described herein include polypeptides comprising at least one non-natural amino acid. Introduction of at least one non-natural amino acid into a polypeptide can allow for the application of conjugation chemistries that involve specific chemical reactions, including, but not limited to, with one or more non-natural amino acids while not reacting with the commonly occurring 20 amino acids. Once incorporated, the amino acid side chains can then be modified by utilizing chemistry methodologies known to those of ordinary skill in the art to be suitable for the particular functional groups or substituents present in the naturally encoded amino acid.

The non-natural amino acid methods and compositions described herein provides conjugates of substances having a wide variety of functional groups, substituents or moieties, with other substances including but not limited to a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; and any combination of the above. Conjugation of a non-natural amino acid polypeptide with a molecule, including but not limited to, biotin may enable purification of the conjugate.

In another aspect of the compositions, methods, techniques and strategies further described in U.S. Patent Application Nos. 60/638,418, 60/638,527, 60/639,195, 60/696,210, 60/696,302, and 60/696,068 which are incorporated by reference in their entirety are methods for studying or using any of the aforementioned (modified) non-natural amino acid polypeptides. Included within this aspect, by way of example only, are therapeutic, diagnostic, assay-based, industrial, cosmetic, plant biology, environmental, energy-production, and/or military uses which would benefit from a polypeptide comprising a (modified) non-natural amino acid polypeptides or protein.

The invention provides a method for detecting the aforementioned (modified) non-natural amino acid polypeptides or a fragment thereof. Such non-natural amino acid polypeptides or a fragment thereof can be obtained by combining the non-natural amino acid polypeptides or a fragment thereof with a library of molecules under conditions suitable to allow specific interactions. The invention also provides a method for detecting the aforementioned (modified) non-natural amino acid polypeptides or a fragment thereof where non-natural amino acid polypeptides or a fragment thereof are obtained by combining the non-natural amino acid polypeptides or a fragment thereof with the library of proteins or a portion thereof under conditions suitable to allow specific interaction. Such interactions include but are not limited to acetylation, carboxylation, acylation, phosphorylation, dephosphorylation, ubiquitination, glycosylation, lipid modification, ADP-ribosylation, bioavailability and half-life. Such libraries include alpha-1 antitrypsin, angiostatin, antihemolytic factor, antibody, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-1 beta, RANTES, I309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, interleukin (IL), IL-1, IL-2, IL-3, IL-4, IL-5, IL-6, IL-7, IL-8, IL-9, IL-10, IL-11, IL-12, keratinocyte growth factor (KGF), lanreotide, lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, pth, pyrogenic exotoxin A, pyrogenic exotoxin B, pyrogenic exotoxin C, pyy, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), urotensin-II, VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone.

III. Location of Non-natural Amino Acids in Polypeptides

The non-natural amino acid polypeptides or a fragment thereof disclosed herein, include incorporation of one or more non-natural amino acids into a polypeptide. One or more non-natural amino acids may be incorporated at a particular position which does not disrupt activity of the polypeptide. This can be achieved by making "conservative" substitutions, including but not limited to, substituting hydrophobic amino acids with hydrophobic amino acids, bulky amino acids for bulky amino acids, hydrophilic amino acids for hydrophilic amino acids and/or inserting the non-natural amino acid in a location that is not required for activity.

A variety of biochemical and structural approaches can be employed to select the desired sites for substitution with a non-natural amino acid within the polypeptide. Any position of the polypeptide chain is suitable for selection to incorporate a non-natural amino acid, and selection may be based on rational design or by random selection for any or no particular desired purpose. Selection of desired sites may be for producing a non-natural amino acid polypeptide (which may be further modified or remain unmodified) having any desired property or activity, including but not limited to agonists, super-agonists, inverse agonists, antagonists, receptor binding modulators, receptor activity modulators, modulators of binding to one or more binding partners, binding partner activity modulators, binding partner conformation modulators, dimer or multimer formation, no change to activity or property compared to the native molecule, or manipulating any physical or chemical property of the polypeptide such as solubility, aggregation, or stability. For example, locations in the polypeptide required for biological activity of a polypeptide can be identified using point mutation analysis, alanine scanning or homolog scanning methods known in the art. Methods similar to those described in Cunningham, B. and Wells, J., *Science*, 244: 1081-1085 (1989) and Cunningham, B., et al. *Science* 243: 1330-1336 (1989) may be used to identify residues that are critical for bioactivity and/or may be used to identify antibody and receptor epitopes. U.S. Pat. Nos. 5,580,723; 5,834,250; 6,013,478; 6,428,954; and 6,451,561, which are incorporated by reference herein, describe methods for the systematic analysis of the structure and function of polypeptides by identifying active domains which influence the activity of the polypeptide with a target substance. Residues other than those identified as critical to biological activity by alanine or homolog scanning mutagenesis may be good candidates for substitution with a non-natural amino acid depending on the desired activity sought for the polypeptide. Alternatively, the sites identified as critical to biological activity may also be good candidates for substitution with a non-natural amino acid, again depending on the desired activity sought for the polypeptide. Another alternative would be to simply make serial substitutions in each position on the polypeptide chain with a non-natural amino acid and observe the effect on the activities of the polypeptide. It is readily apparent to those of ordinary skill in the art that any means, technique, or method for selecting a position for substitution with a non-natural amino acid into any polypeptide is suitable for use in the present invention.

The structure and activity of naturally-occurring mutants of a polypeptide that contain deletions can also be examined to determine regions of the protein that are likely to be tolerant of substitution with a non-natural amino acid. Once residues that are likely to be intolerant to substitution with non-natural amino acids have been eliminated, the impact of proposed substitutions at each of the remaining positions can be examined from the three-dimensional structure of the relevant polypeptide, and any associated ligands or binding proteins. X-ray crystallographic and NMR structures of many polypeptides are available in the Protein Data Bank, a centralized database containing three-dimensional structural data of large molecules of proteins and nucleic acids. Thus, those of ordinary skill in the art can readily identify amino acid positions that can be substituted with non-natural amino acids.

Exemplary sites of incorporation of a non-natural amino acid include, but are not limited to, those that are excluded from potential receptor binding regions, regions for binding to one or more binding partners, may be fully or partially solvent exposed, have minimal or no hydrogen-bonding interactions with nearby residues, may be minimally exposed to nearby reactive residues, may be on one or more of the exposed faces of the polypeptide, may be in regions that are highly flexible or structurally rigid as predicted by the three-dimensional, secondary, tertiary, or quaternary structure of the polypeptide, bound or unbound to its associated receptor, ligand or binding proteins, or coupled or not coupled to another polypeptide or other biologically active molecule, or may modulate the conformation of the polypeptide itself or a dimer or multimer comprising one or more polypeptide, by altering the flexibility or rigidity of the complete structure as desired.

A wide variety of non-natural amino acids can be substituted for, or incorporated into, a given position in a polypeptide. In general, a particular non-natural amino acid may be selected for incorporation based on an examination of the three dimensional crystal structure of a polypeptide with its associated ligand, receptor and/or binding proteins, secondary, tertiary or quaternary structure, a preference for conservative substitutions (i.e., aryl-based non-natural amino acids, such as p-acetylphenylalanine or O-propargyltyrosine substituting for Phe, Tyr or Trp), and the specific conjugation chemistry that one desires to introduce into the polypeptide protein.

The method further includes incorporating into the protein the non-natural amino acid, where the non-natural amino acid comprises a first reactive group; and contacting the protein with a molecule (including but not limited to a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; and any combination of the above) that comprises a second reactive group.

In some cases, the non-natural amino acid substitution(s) or incorporation(s) will be combined with other additions, substitutions, or deletions within the polypeptide to affect other biological traits. In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility (including but not limited to, when expressed in *E. coli* or other host cells) of the polypeptide. In some cases, sites are selected for substitution with a naturally encoded or non-natural amino acid in addition to another site for incorporation of a non-natural amino acid for the purpose of increasing the polypeptide solubility following expression in *E. coli* recombinant host cells. In some cases, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bioavailability, facilitates purification, or improves or alters a particular route of administration. Similarly, polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport through tissues or cell membranes, prodrug release or activation, size reduction, or other traits of the polypeptide.

IV. Growth Hormone Supergene Family as Exemplar

The methods, compositions, strategies and techniques described herein are not limited to a particular type, class or family of polypeptides or proteins. By way of example only, the polypeptide can be homologous to a therapeutic protein selected from the group consisting of: alpha-1 antitrypsin, angiostatin, antihemolytic factor, antibody, antibody fragments, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-i beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, pth, pyrogenic exotoxin A, pyrogenic exotoxin B, pyrogenic exotoxin C, pyy, relaxin, renin, SCF, small biosynthetic protein, soluble complement receptor 1, soluble I-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone.

Antibody fragments herein include antibodies that are smaller components that exist within full-length antibodies, and antibodies that have been engineered. Antibody fragments include but are not limited to Fv, Fc, Fab, and (Fab')2, single chain Fv (scFv), diabodies, triabodies, tetrabodies, bifunctional hybrid antibodies, CDR1, CDR2, CDR3, combinations of CDR's, variable regions, framework regions, constant regions, and the like (Maynard & Georgiou, 2000, Annu. Rev. Biomed. Eng. 2:339-76; Hudson, 1998, Curr. Opin. Biotechnol. 9:395-402). Another functional substructure is a single chain Fv (scFv), comprised of the variable regions of the immunoglobulin heavy and light chain, covalently connected by a peptide linker (S-z Hu et al., 1996, Cancer Research, 56, 3055-3061). These small (Mr 25,000) proteins generally retain specificity and affinity for antigen in a single polypeptide and can provide a convenient building block for larger, antigen-specific molecules. Polypeptides also include the antibody heavy chain, light chain, variable region, alternative scaffold non-antibody molecules, and bispecific antibodies, as well as other antigen-binding polypeptides or fragments thereof.

Thus, the following description of the growth hormone supergene family is provided for illustrative purposes and by way of example only and not as a limit on the scope of the methods, compositions, strategies and techniques described herein. Further, reference to GH polypeptides in this application is intended to use the generic term as an example of any member of the GH supergene family. Thus, it is understood that the modifications and chemistries described herein with reference to GH polypeptides or protein can be equally applied to any member of the GH supergene family, including those specifically listed herein or incorporated by reference.

The following proteins include those encoded by genes of the growth hormone (GH) supergene family (Bazan, F., *Immunology Today* 11: 350-354 (1990); Bazan, J. F. Science 257: 410-413 (1992); Mott, H. R. and Campbell, I. D., *Current Opinion in Structural Biology* 5: 114-121 (1995); Silvennoinen, O. and Ihle, J. N., SIGNALLING BY THE HEMATOPOIETIC CYTOKINE RECEPTORS (1996)): growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-11, IL-12 (p35 subunit), IL-13, IL-15, oncostatin M, ciliary neurotrophic factor, leukemia inhibitory factor, alpha interferon, beta interferon, gamma interferon, omega interferon, tau interferon, granulocyte-colony stimulating factor (G-CSF), granulocyte-macrophage colony stimulating factor (GM-CSF), macrophage colony stimulating factor (M-CSF) and cardiotrophin-1 (CT-1) ("the GH supergene family"). It is anticipated that additional members of this gene family will be identified in the future through gene cloning and sequencing. Members of the GH supergene family have similar secondary and tertiary structures, despite the fact that they generally have limited amino acid or DNA sequence identity. The shared structural features allow new members of the gene family to be readily identified and the non-natural amino acid methods and compositions described herein and incorporated by reference similarly applied.

Structures of a number of cytokines, including G-CSF (Zink et al., FEBS Lett. 314:435 (1992); Zink et al., Biochemistry 33:8453 (1994); Hill et al., Proc. Natl. Acad. Sci. USA 90:5167 (1993)), GM-CSF (Diederichs, K., et al. Science 154: 1779-1782 (1991); Walter et al., *J. Mol. Biol.* 224:1075-1085 (1992)), IL-2 (Bazan, J. F. and McKay, D. B. Science 257: 410-413 (1992)), IL-4 (Redfield et al., *Biochemistry* 30: 11029-11035 (1991); Powers et al., Science 256:1673-1677 (1992)), and IL-5 (Milburn et al., Nature 363: 172-176 (1993)) have been determined by X-ray diffraction and NMR studies and show striking conservation with the GH structure, despite a lack of significant primary sequence homology. IFN is considered to be a member of this family based upon modeling and other studies (Lee et al., J. Interferon Cytokine Res. 15:341 (1995); Murgolo et al., Proteins 17:62 (1993); Radhakrishnan et al., Structure 4:1453 (1996); Klavs et al., J. Mol. Biol. 274:661 (1997)). EPO is considered to be a member of this family based upon modeling and mutagenesis studies (Boissel et al., *J. Biol. Chem.* 268: 15983-15993 (1993); Wen et al., J. Biol. Chem. 269: 22839-22846 (1994)). A large number of additional cytokines and growth factors including ciliary neurotrophic factor (CNTF), leukemia inhibitory factor (LIF), thrombopoietin (TPO), oncostatin M, macrophage colony stimulating factor (M-CSF), IL-3, IL-6, IL-7, IL-9, IL-12, IL-13, IL-15, and granulocyte-colony stimulating factor (G-CSF), as well as the IFN's such as alpha, beta, omega, tau, epsilon, and gamma interferon belong to this family (reviewed in Mott and Campbell, *Current Opinion in Structural Biology* 5: 114-121 (1995); Silvennoinen and Ihle (1996) SIGNALLING BY THE HEMATOPOIETIC CYTOKINE RECEPTORS). All of the above cytokines and growth factors are now considered to comprise one large gene family.

In addition to sharing similar secondary and tertiary structures, members of this family share the property that they must oligomerize cell surface receptors to activate intracellular signaling pathways. Some GH family members, including but not limited to; GH and EPO, bind a single type of receptor and cause it to form homodimers. Other family members, including but not limited to, IL-2, IL4. and IL-6, bind more than one type of receptor and cause the receptors to form heterodimers or higher order aggregates (Davis et al., (1993) Science 260: 1805-1808; Paonessa et al., 1995) EMBO J. 14: 1942-1951; Mott and Campbell, *Current Opinion in Structural Biology* 5: 114-121 (1995)). Mutagenesis studies have shown that, like GH, these other cytokines and growth factors contain multiple receptor binding sites, typically two, and bind their cognate receptors sequentially (Mott and Campbell, *Current Opinion in Structural Biology* 5: 114-121 (1995); Matthews et al., (1996) *Proc. Natl. Acad. Sci. USA* 93: 9471-9476). Like GH, the primary receptor binding sites for these other family members occur primarily in the four alpha helices and the A-B loop. The specific amino acids in the helical bundles that participate in receptor binding differ amongst the family members. Most of the cell surface receptors that interact with members of the GH supergene family are structurally related and comprise a second large multi-gene family. See, e.g. U.S. Pat. No. 6,608,183, which is incorporated by reference herein.

A general conclusion reached from mutational studies of various members of the GH supergene family is that the loops joining the alpha helices generally tend to not be involved in receptor binding. In particular the short B-C loop appears to be non-essential for receptor binding in most, if not all, family members. For this reason, the B-C loop may be substituted with non-natural amino acids as described herein in members of the GH supergene family. The A-B loop, the C-D loop (and D-E loop of interferon/IL-10-like members of the GH superfamily) may also be substituted with a non-natural amino acid. Amino acids proximal to helix A and distal to the final helix also tend not to be involved in receptor binding and also may be sites for introducing non-natural amino acids. In some embodiments, a non-natural amino acid is substituted at any position within a loop structure including but not limited to the first 1, 2, 3, 4, 5, 6, 7, or more amino acids of the A-B, B-C, C-D or D-E loop. In some embodiments, a non-natural amino acid is substituted within the last 1, 2, 3, 4, 5, 6, 7, or more amino acids of the A-B, B-C, C-D or D-E loop.

Certain members of the GH family, including but not limited to, EPO, IL-2, IL-3, IL-4, IL-6, IFN, GM-CSF, TPO, IL-10, IL-12 p35, IL-13, IL-15 and beta interferon contain N-linked and/or O-linked sugars. The glycosylation sites in the proteins occur almost exclusively in the loop regions and not in the alpha helical bundles. Because the loop regions generally are not involved in receptor binding and because they are sites for the covalent attachment of sugar groups, they may be useful sites for introducing non-natural amino acid substitutions into the proteins. Amino acids that comprise the N- and O-linked glycosylation sites in the proteins may be sites for non-natural amino acid substitutions because these amino acids are surface-exposed. Therefore, the natural protein can tolerate bulky sugar groups attached to the proteins at these sites and the glycosylation sites tend to be located away from the receptor binding sites.

Additional members of the GH gene family are likely to be discovered in the future. New members of the GH supergene family can be identified through computer-aided secondary and tertiary structure analyses of the predicted protein sequences. Members of the GH supergene family typically possess four or five amphipathic helices joined by non-helical amino acids (the loop regions). The proteins may contain a hydrophobic signal sequence at their N-terminus to promote secretion from the cell. Such later discovered members of the GH supergene family also are included within the methods and compositions described herein. International Patent Application entitled "Modified Four Helical Bundle Polypeptides and Their Uses" (WO 05/074650 on Aug. 18, 2005), which is incorporated by reference herein in its entirety, provides methods for site selection and incorporation of non-natural amino acids into polypeptides.

V. Non-natural Amino Acids

A very wide variety of non-natural amino acids are suitable for use in the methods and compositions described herein as long as the non-natural amino acid has at least one of the following four properties: (1) at least one functional group on the sidechain of the non-natural amino acid with at least one characteristic and/or activity and/or reactivity orthogonal to the chemical reactivity of the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or at least orthogonal to the chemical reactivity of the naturally occurring amino acids present in the polypeptide that includes the non-natural amino acid; (2) the introduced non-natural amino acid is substantially chemically inert toward the 20 common, genetically-encoded amino acids; (3) the non-natural amino acid can be stably incorporated into a polypeptide; the stability may be commensurate with the naturally-occurring amino acids or under typical physiological conditions, and such incorporation may occur via an in vivo system; and (4) the non-natural amino acid includes an oxime functional group or a functional group that can be transformed into an oxime group by reacting with a reagent, and may be reacted under conditions that do not destroy the biological properties of the polypeptide that includes the non-natural amino acid (unless of course such a destruction of biological properties is the purpose of the modification/transformation), or preferably where the transformation can occur under aqueous conditions at a pH between about 2 and about 10 or a pH between about 4 and about 8, and the reactive site on the non-natural amino acid may be an electrophilic site. Illustrative, non-limiting examples of amino acids that satisfy these four properties for non-natural amino acids that can be used with the compositions and methods further described in U.S. Patent Application Nos. 60/638,418, 60/638,527, 60/639,195, 60/696,210, 60/696,302, and 60/696,068 which are incorporated by reference in their entirety. Any number of non-natural amino acids can be introduced into the polypeptide. Non-natural amino acids may also include protected or masked oximes or protected or masked groups that can be transformed into an oxime group after deprotection of the protected group or unmasking of the masked group.

Non-natural amino acids of interest that may be suitable for use in the methods and compositions described herein include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

The chemical moieties via non-natural amino acids that can be incorporated into proteins offer a variety of advantages and manipulations of the protein. For example, the unique reactivity of a carbonyl functional group (including a keto functional group) allows selective modification of proteins with any of a number of hydrazine- or hydroxylamine-containing reagents in vitro and in vivo. A heavy atom non-natural amino acid, for example, can be useful for phasing X-ray structure data. The site-specific introduction of heavy atoms using non-natural amino acids also provides selectivity and flexibility in choosing positions for heavy atoms. Photoreactive non-natural amino acids (including but not limited to, amino acids with benzophenone and arylazides (including but not limited to, phenylazide) side chains), for example, allow for efficient in vivo and in vitro photocrosslinking of protein. Examples of photoreactive non-natural amino acids include, but are not limited to, p-azido-phenylalanine and p-benzoyl-phenylalanine. The protein with the photoreactive non-natural amino acids can then be crosslinked at will by excitation of the photoreactive group-providing temporal control. In one example, the methyl group of a non-natural amino can be substituted with an isotopically labeled, including but not limited to, methyl group, as a probe of local structure and dynamics, including but not limited to, with the use of nuclear magnetic resonance and vibrational spectroscopy.

Many non-naturally encoded amino acids are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Many non-natural amino acids are based on natural amino acids, such as tyrosine, glutamine, phenylalanine, and the like.

A. Cellular Uptake of Non-natural Amino Acids

Non-natural amino acid uptake by a eukaryotic cell is one issue that is typically considered when designing and selecting non-natural amino acids, including but not limited to, for incorporation into a protein. For example, the high charge density of α-amino acids suggests that these compounds are unlikely to be cell permeable. Natural amino acids are taken up into the eukaryotic cell via a collection of protein-based transport systems. A rapid screen can be done which assesses which non-natural amino acids, if any, are taken up by cells. See, e.g., the toxicity assays in, e.g., U.S. Patent Publication No. US 2004/0198637 entitled "Protein Arrays," which is incorporated by reference; and Liu, D. R. & Schultz, P. G. (1999) *Progress toward the evolution of an organism with an expanded genetic code. PNAS United States* 96:4780-4785. Although uptake is easily analyzed with various assays, an alternative to designing non-natural amino acids that are amenable to cellular uptake pathways is to provide biosynthetic pathways to create amino acids in vivo.

B. Biosynthesis of Non-natural Amino Acids

Many biosynthetic pathways already exist in cells for the production of amino acids and other compounds. While a biosynthetic method for a particular non-natural amino acid may not exist in nature, including but not limited to, in a eukaryotic cell, the methods and compositions described herein include such methods. For example, biosynthetic pathways for non-natural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a eukaryotic cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, for example, in Genbank. Artificially evolved enzymes are also optionally added into a cell in the same manner. In this manner, the cellular machinery and resources of a cell are manipulated to produce non-natural amino acids.

A variety of methods are available for producing novel enzymes for use in biosynthetic pathways or for evolution of existing pathways. For example, recursive recombination, including but not limited to, as developed by Maxygen, Inc. (available on the World Wide Web at www.maxygen.com), is optionally used to develop novel enzymes and pathways. See, e.g., Stemmer (1994), *Rapid evolution of a protein in vitro by DNA shuffling*, Nature 370(4):389-391; and, Stemmer, (1994), *DNA shuffling by random fragmentation and reassembly: In vitro recombination for molecular evolution*, Proc. Natl. Acad. Sci. USA., 91:10747-10751. Similarly DesignPath™, developed by Genencor (available on the World Wide Web at genencor.com) is optionally used for metabolic pathway engineering, including but not limited to, to engineer a pathway to create O-methyl-L-tyrosine in a cell. This technology reconstructs existing pathways in host organisms using a combination of new genes, including but not limited to, identified through functional genomics, and molecular evolution and design. Diversa Corporation also provides technology for rapidly screening libraries of genes and gene pathways, including but not limited to, to create new pathways.

Typically, the non-natural amino acid produced with an engineered biosynthetic pathway is produced in a concentration sufficient for efficient protein biosynthesis, including but not limited to, a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and a non-natural amino acid is generated, in vivo selections are optionally used to further optimize the production of the non-natural amino acid for both ribosomal protein synthesis and cell growth.

VI. Polypeptides with Non-natural Amino Acids

The compositions and methods further described in U.S. Patent Application Nos. 60/638,418, 60/638,527, 60/639,195, 60/696,210, 60/696,302, and 60/696,068; U.S. Patent Application Publications 2003/0082575 (Ser. No. 10/126,927) and 2003/0108885 (Ser. No. 10/126,931); WO 04/035743 entitled "Site Specific Incorporation of Keto Amino Acids into Proteins," and PCT Publication No. WO 04/094593 entitled "Expanding the Eukaryotic Genetic Code," which are incorporated by reference in their entirety provide for the incorporation of at least one non-natural amino acid into a polypeptide. The non-natural amino acid may be present at any location on the polypeptide, including any terminal position or any internal position of the polypeptide. The non-natural amino acid polypeptides described herein may be produced biosynthetically or non-biosynthetically. By biosynthetically is meant any method utilizing a translation system (cellular or non-cellular), including use of at least one of the following components: a polynucleotide, a codon, a tRNA, and a ribosome. By non-biosynthetically is meant any method not utilizing a translation system: this approach can be further divided into methods utilizing solid state peptide synthetic methods, solid phase peptide synthetic methods, methods that utilize at least one enzyme, and methods that do not utilize at least one enzyme; of course any of this sub-divisions may overlap and many methods may utilize a combination of these sub-divisions.

The methods, compositions, strategies and techniques described herein are not limited to a particular type, class or family of polypeptides or proteins. Indeed, virtually any polypeptides may include but are not limited to at least one non-natural amino acids further described in U.S. Patent Application Nos. 60/638,418, 60/638,527, 60/639,195, 60/696,210, 60/696,302, and 60/696,068; U.S. Patent Application Publications 2003/0082575 (Ser. No. 10/126,927) and 2003/0108885 (Ser. No. 10/126,931), WO 04/035743 entitled "Site Specific Incorporation of Keto Amino Acids into Proteins," PCT Publication No. WO 04/094593 entitled "Expanding the Eukaryotic Genetic Code," and PCT Publication WO 05/074650 entitled "Modified Four Helical Bundle Polypeptides and Their Uses," which are incorporated by reference herein. The non-natural amino acid polypeptides may be further modified as described in U.S. Patent Application Nos. 60/638,418, 60/638,527, 60/639,195, 60/696,210, 60/696,302, and 60/696,068; U.S. Patent Application Publications 2003/0082575 (Ser. No. 10/126,927) and 2003/0108885 (Ser. No. 10/126,931), WO 04/035743 entitled "Site Specific Incorporation of Keto Amino Acids into Proteins," PCT Publication No. WO 04/094593 entitled "Expanding the Eukaryotic Genetic Code," and PCT Publication WO 05/074650 entitled "Modified Four Helical Bundle Polypeptides and Their Uses," which are incorporated by reference herein or the non-natural amino acid polypeptide may be used without further modification. In one aspect, a composition includes at least one protein with at least one, including but not limited to, at least two, at least three, at least four, at least five, at least six, at least seven, at least eight, at least nine, or at least ten or more non-natural amino acids. The polypeptides may comprise one or more natural amino acid substitutions.

Although embodiments of the non-natural amino acid polypeptides further described in U.S. Patent Application Nos. 60/638,418, 60/638,527, 60/639,195, 60/696,210, 60/696,302, and 60/696,068 which are incorporated by reference may be chemically synthesized via solid phase peptide synthesis methods (e.g., on a solid resin), by solution phase peptide synthesis methods, and/or without the aid of enzymes, other embodiments of the non-natural amino acid polypeptides described herein allow synthesis via a cell membrane, cellular extract, or lysate system or via an in vivo system, i.e., using the cellular machinery of a prokarote or eukaryote cell.

VII. Compositions and Methods Comprising Nucleic Acids and Oligonucleotides

A. General Recombinant Nucleic Acid Methods for Use

U.S. Patent Application Nos. 60/638,418, 60/638,527, 60/639,195, 60/696,210, 60/696,302, and 60/696,068; and PCT Publication WO 05/074650 entitled "Modified Four Helical Bundle Polypeptides and Their Uses," which are incorporated by reference herein, discuss nucleic acids encoding a polypeptide of interest (including by way of example a GH polypeptide), and how it may be isolated, cloned and often altered using recombinant methods. Such embodiments are used, including but not limited to, for protein expression or during the generation of variants, derivatives, expression cassettes, or other sequences derived from a polypeptide. In some embodiments, the sequences encoding the polypeptides are operably linked to a heterologous promoter.

A nucleotide sequence encoding a polypeptide comprising a non-natural amino acid may be synthesized on the basis of the amino acid sequence of the parent polypeptide, and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction. See, e.g., Barany, et al., *Proc. Natl. Acad. Sci.* 88: 189-193 (1991); U.S. Pat. No. 6,521,427 which are incorporated by reference herein.

B. Selector Codons

Selector codons encompassed within the methods and compositions further described in U.S. Patent Application Nos. 60/638,418, 60/638,527, 60/639,195, 60/696,210, 60/696,302, and 60/696,068; and PCT Publication WO 05/074650 entitled "Modified Four Helical Bundle Polypeptides and Their Uses," which are incorporated by reference in their entirety expand the genetic codon framework of protein biosynthetic machinery. For example, a selector codon includes, but is not limited to, a unique three base codon, a nonsense codon, such as a stop codon, including but not limited to, an amber codon (UAG), or an opal codon (UGA), an ochre codon, a unnatural codon, a four or more base codon, a rare codon, or the like. There is a wide range in the number of selector codons that can be introduced into a desired gene, including but not limited to, one or more, two or more, three or more, 4, 5, 6, 7, 8, 9, 10 or more in a single polynucleotide encoding at least a portion of a polypeptide of interest.

In some cases, it involves the use of a selector codon that is a stop codon for the incorporation of one or more non-natural amino acids in vivo. The incorporation of non-natural amino acids in vivo can be done without significant perturbation of the eukaryotic host cell. Selector codons also comprise extended codons, including but not limited to, four or more base codons, such as, four, five, six or more base codons. For a given system, a selector codon can also include one of the natural three base codons, where the endogenous system does not use (or rarely uses) the natural base codon. Selector codons optionally include unnatural base pairs. These unnatural base pairs further expand the existing genetic alphabet. For in vivo usage, the unnatural nucleoside is membrane permeable and is phosphorylated to form the corresponding triphosphate. In addition, the increased genetic information is stable and not destroyed by cellular enzymes. A translational bypassing system can also be used to incorporate a non-natural amino acid in a desired polypeptide. In certain embodiments, the protein or polypeptide of interest (or portion thereof) is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

VIII. In vivo Generation of Polypeptides Comprising Non-natural Amino Acids

The polypeptides can be generated in vivo using modified tRNA and tRNA synthetases to add to or substitute amino acids that are not encoded in naturally-occurring systems. All the methods for generating, screening methods and organisms used for in vivo generation of polypeptides comprising non-natural amino acids which are further described in U.S. Patent Application Nos. 60/638,418, 60/638,527, 60/639,195, 60/696,210, 60/696,302, and 60/696,068; U.S. Patent Application Publications 2003/0082575 (Ser. No. 10/126,927) and 2003/0108885 (Ser. No. 10/126,931), PCT Publication No. WO 04/094593 entitled "Expanding the Eukaryotic Genetic Code," and PCT Publication WO 05/074650 entitled "Modified Four Helical Bundle Polypeptides and Their Uses," which are incorporated by reference in their entirety.

Methods for generating tRNAs and tRNA synthetases which use amino acids that are not encoded in naturally-occurring systems are described in, e.g., U.S. Patent Application Publications 2003/0082575 (Ser. No. 10/126,927) and 2003/0108885 (Ser. No. 10/126,931) which are incorporated by reference herein. These methods involve generating a translational machinery that functions independently of the synthetases and tRNAs endogenous to the translation system (and are therefore sometimes referred to as "orthogonal"). In further or additional embodiments, the translation system comprises an orthogonal tRNA (O-tRNA) and an orthogonal aminoacyl tRNA synthetase (O-RS). A wide variety of orthogonal tRNAs and aminoacyl tRNA synthetases have been described in the art for inserting particular synthetic amino acids into polypeptides, and are generally suitable for in the methods to produce the non-natural amino acid polypeptides.

Use of O-tRNA/aminoacyl-tRNA synthetases involves selection of a specific codon which encodes the non-natural amino acid. While any codon can be used, it is generally desirable to select a codon that is rarely or never used in the cell in which the O-tRNA/aminoacyl-tRNA synthetase is expressed. Specific selector codon(s) can be introduced into appropriate positions in the polynucleotide coding sequence using mutagenesis methods known in the art (including but not limited to, site-specific mutagenesis, cassette mutagenesis, restriction selection mutagenesis, etc.).

A. Expression in Non-eukaryotes and Eukaryotes

To obtain high level expression of a cloned polynucleotide, one typically subclones polynucleotides encoding a desired polypeptide into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems and eukaryotic host cell or non-eukaryotic host cell systems further described in U.S. Patent Application Nos. 60/638,418, 60/638,527, 60/639,195, 60/696,210, 60/696,302, and 60/696,068; U.S. Patent Application Publications 2003/0082575 (Ser. No. 10/126,927) and 2003/0108885 (Ser. No. 10/126,931), PCT Publication No. WO 04/094593 entitled "Expanding the Eukaryotic Genetic Code," and PCT Publication WO 05/074650 entitled "Modified Four Helical Bundle Polypeptides and Their Uses," which are incorporated by reference in their entirety may be used to biosynthesize proteins that comprise non-natural amino acids in large useful quantities.

1. Expression Systems, Culture, and Isolation

The desired polypeptide may be expressed in any number of suitable expression systems including, for example, yeast, insect cells, mammalian cells, *Pseudomonas* cells, and bacteria. A description of exemplary expression systems is further described in U.S. Patent Application Nos. 60/638,418, 60/638,527, 60/639,195, 60/696,210, 60/696,302, and 60/696,068; U.S. Patent Application Publications 2003/0082575 (Ser. No. 10/126,927) and 2003/0108885 (Ser. No. 10/126,931), PCT Publication No. WO 04/094593 entitled "Expanding the Eukaryotic Genetic Code," and PCT Publication WO 05/074650 entitled "Modified Four Helical Bundle Polypeptides and Their Uses," which are incorporated by reference in their entirety 2. Purification of Non-Natural Amino Acid Polypeptides General Purification Methods Any one of a variety of isolation steps may be performed on the cell lysate, extract, culture medium, inclusion bodies, periplasmic space of the host cells, cytoplasm of the host cells, or other material comprising the desired polypeptide or mixtures resulting from any isolation steps including, but not limited to, affinity chromatography, ion exchange chromatography, hydrophobic interaction chromatography, gel filtration chromatography, high performance liquid chromatography ("HPLC"), reversed phase-HPLC ("RP-HPLC"), expanded bed adsorption, or any combination and/or repetition thereof and in any appropriate order. General purification methods, equipment, preferred embodiments and other purification techniques are further described in U.S. Patent Application Nos. 60/638,418, 60/638,527, 60/639,195, 60/696,210, 60/696,302, and 60/696,068; and WO 05/074650 entitled "Modified Four Helical Bundle Polypeptides and Their Uses which are incorporated by reference in their entirety.

B. In vivo Post-Translational Modifications

By producing proteins or polypeptides of interest with at least one non-natural amino acid in eukaryotic cells, proteins or polypeptides include eukaryotic post-translational modifications. In certain embodiments, a protein includes at least one non-natural amino acid and at least one post-translational modification that is made in vivo by a eukaryotic cell, where the post-translational modification is not made by a prokaryotic cell. For example, the post-translation modification is further described in U.S. Patent Application Nos. 60/638,418, 60/638,527, 60/639,195, 60/696,210, 60/696,302, and 60/696,068; and WO 05/074650 entitled "Modified Four Helical Bundle Polypeptides and Their Uses which are incorporated by reference in their entirety.

One advantage of a non-natural amino acid is that it presents additional chemical moieties that can be used to add additional molecules. These modifications can be made in vivo in a eukaryotic or non-eukaryotic cell, or in vitro. Thus, in certain embodiments, the post-translational modification is through the non-natural amino acid.

IX. Expression in Alternate Systems

Several strategies have been employed to introduce unnatural amino acids into proteins in non-recombinant host cells, mutagenized host cells, or in cell-free systems. These systems are also suitable for use in making the non-natural amino acid polypeptides. Derivatization of amino acids with reactive side-chains such as Lys, Cys and Tyr resulted in the conversion of lysine to $N^2$-acetyl-lysine. Chemical synthesis also provides a straightforward method to incorporate unnatural amino acids. With the recent development of enzymatic ligation and native chemical ligation of peptide fragments, it is possible to make larger proteins. See, e.g., P. E. Dawson and S. B. H. Kent, *Annu. Rev. Biochem*, 69:923 (2000). Chemical peptide ligation and native chemical ligation are described in U.S. Pat. No. 6,184,344, U.S. Patent Publication No. 2004/0138412, U.S. Patent Publication No. 2003/0208046, WO 02/098902, and WO 03/042235, which are incorporated by reference herein. A general in vitro biosynthetic method in which a suppressor tRNA chemically acylated with the desired unnatural amino acid is added to an in vitro extract capable of supporting protein biosynthesis, has been used to site-specifically incorporate over 100 unnatural amino acids into a variety of proteins of virtually any size. See, e.g., V. W. Cornish, D. Mendel and P. G. Schultz, *Angew. Chem. Int. Ed. Engl.*, 1995, 34:621 (1995); C. J. Noren, S. J. Anthony-Cahill, M. C. Griffith, P. G. Schultz, *A general method for site-specific incorporation of unnatural amino acids into proteins*, Science 244:182-188 (1989); and, J. D. Bain, C. G. Glabe, T. A. Dix, A. R. Chamberlin, E. S. Diala, *Biosynthetic site-specific incorporation of a non-natural amino acid into a polypeptide*, J. Am. Chem. Soc. 111:8013-8014 (1989). A broad range of functional groups has been introduced into proteins for studies of protein stability, protein folding, enzyme mechanism, and signal transduction.

An in vivo method, termed selective pressure incorporation, was developed to exploit the promiscuity of wild-type synthetases. See, e.g., N. Budisa, C. Minks, S. Alefelder, W. Wenger, F. M. Dong, L. Moroder and R. Huber, *FASEB J.*, 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. For example, using this strategy, o, m and p-fluorophenylalanines have been incorporated into proteins, and exhibit two characteristic shoulders in the UV spectrum which can be easily identified, see, e.g., C. Minks, R. Huber, L. Moroder and N. Budisa, *Anal. Biochem.*, 284:29 (2000); trifluoromethionine has been used to replace methionine in bacteriophage T4 lysozyme to study its interaction with chitooligosaccharide ligands by $^{19}$F NMR, see, e.g., H. Duewel, E. Daub, V. Robinson and J. F. Honek, *Biochemistry*, 36:3404 (1997); and trifluoroleucine has been incorporated in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, *Angew. Chem. Int. Ed. Engl.*, 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.*, 9:1665 (1990); J. O. Boles, K. Lewinski, M. Kunkle, J. D. Odom, B. Dunlap, L. Lebioda and M. Hatada, *Nat. Struct. Biol.*, 1:283 (1994); N. Budisa, B. Steipe, P. Demange, C. Eckerskorn, J. Kellermann and R. Huber, *Eur. J. Biochem.*, 230:788 (1995); and, N. Budisa, W. Karnbrock, S. Steinbacher, A. Humm, L. Prade, T. Neuefeind, L. Moroder and R. Huber, *J. Mol. Biol.*, 270:616 (1997). Methionine analogs with alkene or alkyne functionalities have also been incorporated efficiently, allowing for additional modification of proteins by chemical means. See, e.g., J. C. van Hest and D. A. Tirrell, *FEBS Lett.*, 428:68 (1998); J. C. van Hest, K. L. Kiick and D. A. Tirrell, *J. Am. Chem. Soc.*, 122:1282 (2000); and, K. L. Kiick and D. A. Tirrell, Tetrahedron, 56:9487 (2000); U.S. Pat. No. 6,586,207; U.S. Patent Publication 2002/0042097, which are incorporated by reference herein.

The success of this method depends on the recognition of the unnatural amino acid analogs by aminoacyl-tRNA synthetases, which, in general, require high selectivity to insure the fidelity of protein translation. One way to expand the scope of this method is to relax the substrate specificity of aminoacyl-tRNA synthetases, which has been achieved in a limited number of cases. For example, replacement of Ala$^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry*, 33:7107 (1994). An *Escherichia coli* strain harboring this mutant PheRS allows the incorporation of p-Cl-phenylalanine or p-Br-phenylalanine in place of phenylalanine. See, e.g., M. Ibba and H. Hennecke, *FEBS Lett.*, 364:272 (1995); and, N. Sharma, R. Furter, P. Kast and D. A. Tirrell, *FEBS Lett.*, 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S. Nishimura, *J. Biol. Chem.*, 275:40324 (2000).

Another strategy to incorporate unnatural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, *Science*, 292:501 (2001). ValRS can misaminoacylate tRNAVal with Cys, Thr, or aminobutyrate (Abu); these noncognate amino acids are subsequently hydrolyzed by the editing domain. After random mutagenesis of the *Escherichia coli* chromosome, a mutant *Escherichia coli* strain was selected that has a mutation in the editing site of ValRS. This edit-defective ValRS incorrectly charges tRNAVal with Cys. Because Abu sterically resembles Cys (—SH group of Cys is replaced with —CH3 in Abu), the mutant ValRS also incorporates Abu into proteins when this mutant *Escherichia coli* strain is grown in the presence of Abu. Mass spectrometric analysis shows that about 24% of valines are replaced by Abu at each valine position in the native protein.

Solid-phase synthesis and semisynthetic methods have also allowed for the synthesis of a number of proteins containing novel amino acids. For example, see the following publications and references cited within, which are as follows: Crick, F. H. C., Barrett, L. Brenner, S. Watts-Tobin, R. *General nature of the genetic code for proteins. Nature*, 192:1227-1232 (1961); Hofmann, K., Bohn, H. *Studies on polypeptides. XXXVI. The effect of pyrazole-imidazole replacements on the S-protein activating potency of an S-peptide fragment, J. Am. Chem,* 88(24):5914-5919 (1966); Kaiser, E. T. *Synthetic approaches to biologically active peptides and proteins including enyzmes, Acc Chem Res,* 22:47-54 (1989); Nakatsuka, T., Sasaki, T., Kaiser, E. T. *Peptide segment coupling catalyzed by the semisynthetic enzyme thiosubtilisin, J Am Chem Soc,* 109:3808-3810 (1987); Schnolzer, M., Kent, S B H. *Constructing proteins by dovetailing unprotected synthetic peptides: backbone-engineered HIV protease, Science,* 256(5054):221-225 (1992); Chaiken, I. M. *Semisynthetic peptides and proteins, CRC Crit Rev Biochem,* 11(3):255-301 (1981); Offord, R. E. *Protein engineering by chemical means? Protein Eng.,* 1(3):151-157 (1987); and, Jackson, D. Y., Burnier, J., Quan, C., Stanley, M., Tom, J., Wells, J. A. *A Designed Peptide Ligase for Total Synthesis of Ribonuclease A with Unnatural Catalytic Residues, Science,* 266(5183):243 (1994).

Chemical modification has been used to introduce a variety of unnatural side chains, including cofactors, spin labels and oligonucleotides into proteins in vitro. See, e.g., Corey, D. R., Schultz, P. G. *Generation of a hybrid sequence-specific single-stranded deoxyribonuclease, Science,* 238(4832):1401-1403 (1987); Kaiser, E. T., Lawrence D. S., Rokita, S. E. *The chemical modification of enzymatic specificity, Annu Rev Biochem,* 54:565-595 (1985); Kaiser, E. T., Lawrence, D. S. *Chemical mutation of enyzme active sites, Science,* 226(4674):505-511 (1984); Neet, K. E., Nanci A, Koshland, D. E. *Properties of thiol-subtilisin, J Biol. Chem,* 243(24):6392-6401 (1968); Polgar, L. et M. L. Bender. *A new enzyme containing a synthetically formed active site. Thiol-subtilisin. J. Am Chem Soc,* 88:3153-3154 (1966); and, Pollack, S. J., Nakayama, G. Schultz, P. G. *Introduction of nucleophiles and spectroscopic probes into antibody combining sites, Science,* 242(4881):1038-1040 (1988).

Alternatively, biosynthetic methods that employ chemically modified aminoacyl-tRNAs have been used to incorporate several biophysical probes into proteins synthesized in vitro. See the following publications and references cited within: Brunner, J. *New Photolabeling and crosslinking methods, Annu. Rev Biochem,* 62:483-514 (1993); and, Krieg, U. C., Walter, P., Hohnson, A. E. *Photocrosslinking of the signal sequence of nascent preprolactin of the 54-kilodalton polypeptide of the signal recognition particle, Proc. Natl. Acad. Sci,* 83(22):8604-8608 (1986).

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. *A general method for site-specific incorporation of unnatural amino acids into proteins, Science,* 244: 182-188 (1989); M. W. Nowak, et al., *Science* 268:439-42 (1995); Bain, J. D., Glabe, C. G., Dix, T. A., Chamberlin, A. R., Diala, E. S. *Biosynthetic site-specific Incorporation of a non-natural amino acid into a polypeptide, J. Am Chem Soc,* 111:8013-8014 (1989); N. Budisa et al., *FASEB J.* 13:41-51 (1999); Ellman, J. A., Mendel, D., Anthony-Cahill, S., Noren, C. J., Schultz, P. G. *Biosynthetic method for introducing unnatural amino acids site-specifically into proteins, Methods in Enz.,* vol. 202, 301-336 (1992); and, Mendel, D., Cornish, V. W. & Schultz, P. G. *Site-Directed Mutagenesis with an Expanded Genetic Code, Annu Rev Biophys. Biomol Struct.* 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. *5'-3' Exonucleases in phosphorothioate-based olignoucleotide-directed mutagensis, Nucleic Acids Res,* 16(3):791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10(6):425-432; and, Ellman, J. A., Mendel, D., Schultz, P. G. *Site-specific incorporation of novel backbone structures into proteins, Science,* 255(5041):197-200 (1992).

A tRNA may be aminoacylated with a desired amino acid by any method or technique, including but not limited to, chemical or enzymatic aminoacylation.

Aminoacylation may be accomplished by aminoacyl tRNA synthetases or by other enzymatic molecules, including but not limited to, ribozymes. The term "ribozyme" is interchangeable with "catalytic RNA." Cech and coworkers (Cech, 1987, Science, 236:1532-1539; McCorkle et al., 1987, Concepts Biochem. 64:221-226) demonstrated the presence of naturally occurring RNAs that can act as catalysts (ribozymes). However, although these natural RNA catalysts have only been shown to act on ribonucleic acid substrates for cleavage and splicing, the recent development of artificial evolution of ribozymes has expanded the repertoire of catalysis to various chemical reactions. Studies have identified RNA molecules that can catalyze aminoacyl-RNA bonds on their own (2')3'-termini (Illangakekare et al., 1995 Science 267:643-647), and an RNA molecule which can transfer an amino acid from one RNA molecule to another (Lohse et al., 1996, Nature 381:442-444).

U.S. Patent Application Publication 2003/0228593, which is incorporated by reference herein, describes methods to construct ribozymes and their use in aminoacylation of tRNAs with naturally encoded and non-naturally encoded amino acids. Substrate-immobilized forms of enzymatic molecules that can aminoacylate tRNAs, including but not limited to, ribozymes, may enable efficient affinity purification of the aminoacylated products. Examples of suitable substrates include agarose, sepharose, and magnetic beads. The production and use of a substrate-immobilized form of ribozyme for aminoacylation is described in Chemistry and Biology 2003, 10:1077-1084 and U.S. Patent Application Publication 2003/0228593, which is incorporated by reference herein.

Chemical aminoacylation methods include, but are not limited to, those introduced by Hecht and coworkers (Hecht, S. M. Ace. Chem. Res. 1992, 25, 545; Heckler, T. G.; Roesser, J. R.; Xu, C.; Chang, P.; Hecht, S. M. Biochemistry 1988, 27, 7254; Hecht, S. M.; Alford, B. L.; Kuroda, Y.; Kitano, S. J. Biol. Chem. 1978, 253, 4517) and by Schultz, Chamberlin, Dougherty and others (Cornish, V. W.; Mendel, D.; Schultz, P. G. Angew. Chem. Int. Ed. Engl. 1995, 34, 621; Robertson, S. A.; Ellman, J. A.; Schultz, P. G. J. Am. Chem. Soc. 1991, 113, 2722; Noren, C. J.; Anthony-Cahill, S. J.; Griffith, M. C.; Schultz, P. G. Science 1989, 244, 182; Bain, J. D.; Glabe, C. G.; Dix, T. A.; Chamberlin, A. R. J. Am. Chem. Soc. 1989, 111, 8013; Bain, J. D. et al. Nature 1992, 356, 537; Gallivan, J. P.; Lester, H. A.; Dougherty, D. A. Chem. Biol. 1997, 4, 740; Turcatti, et al. J. Biol. Chem. 1996, 271, 19991; Nowak, M. W. et al. Science, 1995, 268, 439; Saks, M. E. et al. J. Biol. Chem. 1996, 271, 23169; Hohsaka, T. et al. J. Am. Chem. Soc. 1999, 121, 34), to avoid the use of synthetases in aminoacylation. Such methods or other chemical aminoacylation methods may be used to aminoacylate tRNA molecules of the invention.

Methods for generating catalytic RNA may involve generating separate pools of randomized ribozyme sequences, performing directed evolution on the pools, screening the pools for desirable aminoacylation activity, and selecting sequences of those ribozymes exhibiting desired aminoacylation activity.

Ribozymes can comprise motifs and/or regions that facilitate acylation activity, such as a GGU motif and a U-rich region. For example, it has been reported that U-rich regions can facilitate recognition of an amino acid substrate, and a GGU-motif can form base pairs with the 3' termini of a tRNA. In combination, the GGU and motif and U-rich region facilitate simultaneous recognition of both the amino acid and tRNA simultaneously, and thereby facilitate aminoacylation of the 3' terminus of the tRNA.

Ribozymes can be generated by in vitro selection using a partially randomized r24mini conjugated with tRNA$^{Asn}_{CCG}$, followed by systematic engineering of a consensus sequence found in the active clones. An exemplary ribozyme obtained by this method is termed "Fx3 ribozyme" and is described in U.S. Pub. App. No. 2003/0228593, the contents of which is incorporated by reference herein, acts as a versatile catalyst for the synthesis of various aminoacyl-tRNAs charged with cognate non-natural amino acids.

Aminoacylate tRNAs ribozymes can be immobilized on a substrate so as to enable efficient affinity purification of the aminoacylated tRNAs. Examples of suitable substrates include, but are not limited to, agarose, sepharose, and magnetic beads. Ribozymes can be immobilized on resins by taking advantage of the chemical structure of RNA, such as the 3'-cis-diol on the ribose of RNA can be oxidized with periodate to yield the corresponding dialdehyde to facilitate immobilization of the RNA on the resin. Various types of resins can be used including inexpensive hydrazide resins wherein reductive amination makes the interaction between the resin and the ribozyme an irreversible linkage. Synthesis of aminoacyl-tRNAs can be significantly facilitated by this on-column aminoacylation technique. Kourouklis et al. Methods 2005; 36:239-4 describe a column-based aminoacylation system.

Isolation of the aminoacylated tRNAs can be accomplished in a variety of ways. One suitable method is to elute the aminoacylated tRNAs from a column with a buffer such as a sodium acetate solution with 10 mM EDTA, a buffer containing 50 mM N-(2-hydroxyethyl)piperazine-N'-(3-propanesulfonic acid), 12.5 mM KCl, pH 7.0, 10 mM EDTA, or simply an EDTA buffered water (pH 7.0).

The aminoacylated tRNAs can be added to translation reactions in order to incorporate the amino acid with which the tRNA was aminoacylated in a position of choice in a polypeptide made by the translation reaction. Examples of translation systems in which the aminoacylated tRNAs of the present invention may be used include, but are not limited to cell lysates. Cell lysates provide reaction components necessary for in vitro translation of a polypeptide from an input mRNA. Examples of such reaction components include but are not limited to ribosomal proteins, rRNA, amino acids, tRNAs, GTP, ATP, translation initiation and elongation factors and additional factors associated with translation. Additionally, translation systems may be batch translations or compartmentalized translation. Batch translation systems combine reaction components in a single compartment while compartmentalized translation systems separate the translation reaction components from reaction products that can inhibit the translation efficiency. Such translation systems are available commercially.

Further, a coupled transcription/translation system may be used. Coupled transcription/translation systems allow for both transcription of an input DNA into a corresponding mRNA, which is in turn translated by the reaction components. An example of a commercially available coupled transcription/translation is the Rapid Translation System (RTS, Roche Inc.). The system includes a mixture containing *E. coli* lysate for providing translational components such as ribosomes and translation factors. Additionally, an RNA polymerase is included for the transcription of the input DNA into an mRNA template for use in translation. RTS can use compartmentalization of the reaction components by way of a membrane interposed between reaction compartments, including a supply/waste compartment and a transcription/translation compartment.

Aminoacylation of tRNA may be performed by other agents, including but not limited to, transferases, polymerases, catalytic antibodies, multi-functional proteins, and the like.

Stephan in Scientist 2005 Oct. 10; pages 30-33 describes additional methods to incorporate non-naturally encoded amino acids into proteins. Lu et al. in Mol Cell. 2001 October; 8(4):759-69 describe a method in which a protein is chemically ligated to a synthetic peptide containing unnatural amino acids (expressed protein ligation).

Microinjection techniques have also been use incorporate unnatural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, *Science*, 268:439 (1995); and, D. A. Dougherty, *Curr. Opin. Chem. Biol.*, 4:645 (2000). A *Xenopus* oocyte was coinjected with two RNA species made in vitro: an mRNA encoding the target protein with a UAG stop codon at the amino acid position of interest and an amber suppressor tRNA aminoacylated with the desired unnatural amino acid. The translational machinery of the oocyte then inserts the unnatural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, *J. Biol. Chem.*, 271:19991 (1996); the incorporation of biotinylated amino acids to identify surface-exposed residues in ion channels, see, e.g., J. P. Gallivan, H. A. Lester and D. A. Dougherty, *Chem. Biol.*, 4:739 (1997); the use of caged tyrosine analogs to monitor conformational changes in an ion channel in real time, see, e.g., J. C. Miller, S. K. Silverman, P. M. England, D. A. Dougherty and H. A. Lester, Neuron, 20:619 (1998); and, the use of alpha hydroxy amino acids to change ion channel backbones for probing their gating mechanisms. See, e.g., P. M. England, Y. Zhang, D. A. Dougherty and H. A. Lester, *Cell*, 96:89 (1999); and, T. Lu, A. Y. Ting, J. Mainland, L. Y. Jan, P. G. Schultz and J. Yang, *Nat. Neurosci.*, 4:239 (2001).

The ability to incorporate unnatural amino acids directly into proteins in vivo offers the advantages of high yields of mutant proteins, technical ease, the potential to study the mutant proteins in cells or possibly in living organisms and the use of these mutant proteins in therapeutic treatments. The ability to include unnatural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties. However, the process is difficult, because the complex nature of tRNA-synthetase interactions that are required to achieve a high degree of fidelity in protein translation.

In one attempt to site-specifically incorporate para-F-Phe, a yeast amber suppressor tRNAPheCUA/phenylalanyl-tRNA synthetase pair was used in a p-F-Phe resistant, Phe auxotrophic *Escherichia coli* strain. See, e.g., R. Furter, *Protein Sci.*, 7:419 (1998). It may also be possible to obtain expression of a polynucleotide using a cell-free (in-vitro) translational system. Translation systems may be cellular or cell-free, and may be prokaryotic or eukaryotic. Cellular translation systems include, but are not limited to, whole cell preparations such as permeabilized cells or cell cultures wherein a desired nucleic acid sequence can be transcribed to mRNA and the mRNA translated. Cell-free translation systems are commercially available and many different types and systems are well-known. Examples of cell-free systems include, but are not limited to, prokaryotic lysates such as *Escherichia coli* lysates, and eukaryotic lysates such as wheat germ extracts, insect cell lysates, rabbit reticulocyte lysates, rabbit oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. In these systems, which can include either mRNA as a template (in-vitro translation) or DNA as a template (combined in-vitro transcription and translation), the in vitro synthesis is directed by the ribosomes. Considerable effort has been applied to the development of cell-free protein expression systems. See, e.g., Kim, D. M. and J. R. Swartz, *Biotechnology and Bioengineering*, 74 :309-316 (2001); Kim, D. M. and J. R. Swartz, *Biotechnology Letters*, 22, 1537-1542, (2000); Kim, D. M., and J. R. Swartz, *Biotechnology Progress*, 16, 385-390, (2000); Kim, D. M., and J. R. Swartz, *Biotechnology and Bioengineering*, 66, 180-188, (1999); and Patnaik, R. and J. R. Swartz, *Biotechniques* 24, 862-868, (1998); U.S. Pat. No. 6,337,191; U.S. Patent Publication No. 2002/0081660; WO 00/55353; WO 90/05785, which are incorporated by reference herein. Another approach that may be applied to the expression of non-natural amino acid polypeptides includes the mRNA-peptide fusion technique. See, e.g., R. Roberts and J. Szostak, *Proc. Natl Acad. Sci.* (*USA*) 94:12297-12302 (1997); A. Frankel, et al., *Chemistry & Biology* 10:1043-1050 (2003). In this approach, an mRNA template linked to puromycin is translated into peptide on the ribosome. If one or more tRNA molecules has been modified, non-natural amino acids can be incorporated into the peptide as well. After the last mRNA codon has been read, puromycin captures the C-terminus of the peptide. If the resulting mRNA-peptide conjugate is found to have interesting properties in an in vitro assay, its identity can be easily revealed from the mRNA sequence. In this way, one may screen libraries of non-natural amino acid polypeptides to identify polypeptides having desired properties. More recently, in vitro ribosome translations with purified components have been reported that permit the synthesis of peptides substituted with non-naturally encoded amino acids. See, e.g., A. Forster et al., *Proc. Natl. Acad. Sci.* (*USA*) 100:6353 (2003).

Reconstituted translation systems may also be used. Mixtures of purified translation factors have also been used successfully to translate mRNA into protein as well as combinations of lysates or lysates supplemented with purified translation factors such as initiation factor-1 (IF-1), IF-2, IF-3 ($\alpha$ or $\beta$), elongation factor T (EF-Tu), or termination factors. Cell-free systems may also be coupled transcription/translation systems wherein DNA is introduced to the system, transcribed into mRNA and the mRNA translated as described in *Current Protocols in Molecular Biology* (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

Post-Translational Modifications of Non-Natural Amino Acid Components of a Polypeptide Methods, compositions, techniques and strategies have been developed to site-specifically incorporate non-natural amino acids during the in vivo translation of proteins. By incorporating a non-natural amino acid with a sidechain chemistry that is orthogonal to those of the naturally-occurring amino acids, this technology makes possible the site-specific derivatization of recombinant proteins. As a result, a major advantage of the methods, compositions, techniques and strategies is that derivatized proteins can now be prepared as defined homogeneous products.

The non-natural amino acid polypeptides described above are useful for, including but not limited to, novel therapeutics, diagnostics, catalytic enzymes, industrial enzymes, binding proteins and including but not limited to, the study of protein structure and function. See, e.g., Dougherty, (2000) *Unnatural Amino Acids as Probes of Protein Structure and Function, Current Opinion in Chemical Biology*, 4:645-652. Other uses for the non-natural amino acid polypeptides described above include, by way of example only, assay-based, cosmetic, plant biology, environmental, energy-production, and/or military uses. However, the non-natural amino acid polypeptides described above can undergo further modifications so as to incorporate new or modified functionalities, including manipulating the therapeutic effectiveness of the polypeptide, improving the safety profile of the polypeptide, adjusting the pharmacokinetics, pharmacologics and/or pharmacodynamics of the polypeptide (e.g., increasing water solubility, bioavailability, increasing serum half-life, increasing therapeutic half-life, modulating immunogenicity, modulating biological activity, or extending the circulation time), providing additional functionality to the polypeptide, incorporating a tag, label or detectable signal into the polypeptide, easing the isolation properties of the polypeptide, and any combination of the aforementioned modifications.

The methods, compositions, strategies and techniques described herein are not limited to a particular type, class or family of polypeptides or proteins. Indeed, virtually any polypeptides may include at least one non-natural amino acid. A composition may include at least one protein with at least one, including but not limited to, at least two, at least three, at least four, at least five, at least six, at least seven, at least eight, at least nine, or at least ten or more non-natural amino acids that have been post-translationally modified. The post-translationally-modified non-natural amino acids can be the same or different, including but not limited to, there can be 1, 2, 3, 4, 5, 6, 7, 8, 9, or 10 or more different sites in the protein that comprise 1, 2, 3, 4, 5, 6, 7, 8, 9, or 10 or more different post-translationally-modified non-natural amino acids. A composition may include a protein with at least one, but fewer than all, of a particular amino acid present in the protein as substituted with the post-translationally-modified non-natural amino acid. For a given protein with more than one post-translationally-modified non-natural amino acids, the post-translationally-modified non-natural amino acids can be identical or different (including but not limited to, the protein can include two or more different types of post-translationally-modified non-natural amino acids, or can include two of the same post-translationally-modified non-natural amino acid). For a given protein with more than two post-translationally-modified non-natural amino acids, the post-translationally-modified non-natural amino acids can be the same, different or a combination of a multiple post-translationally-modified non-natural amino acid of the same kind with at least one different post-translationally-modified non-natural amino acid.

For example, the post-translational modification can be through a nucleophilic-electrophilic reaction. Most reactions currently used for the selective modification of proteins involve covalent bond formation between nucleophilic and electrophilic reaction partners, including but not limited to the reaction of $\alpha$-haloketones with histidine or cysteine side chains. Selectivity in these cases is determined by the number and accessibility of the nucleophilic residues in the protein. In proteins of the invention, other more selective reactions can be used such as the reaction of an unnatural keto-amino acid with hydrazides or aminooxy compounds, in vitro and in vivo. See, e.g., Cornish, et al., (1996) *J. Am. Chem. Soc.*, 118:8150-8151; Mahal, et al., (1997) *Science*, 276:1125-1128; Wang, et al., (2001) *Science* 292:498-500; Chin, et al., (2002) *J. Am. Chem. Soc.* 124:9026-9027; Chin, et al., (2002) *Proc. Natl. Acad. Sci.*, 99:11020-11024; Wang, et al., (2003) *Proc. Natl. Acad. Sci.*, 100:56-61; Zhang, et al., (2003) *Biochemistry*, 42:6735-6746; and, Chin, et al., (2003) *Science*, 301:964-7. This allows the selective labeling of virtually any protein with a host of reagents including fluorophores, crosslinking agents, saccharide derivatives and cytotoxic molecules. See also, U.S. Pat. No. 6,927,042 entitled "Glycoprotein synthesis," which is incorporated by reference herein.

A. Modifications of Non-Natural Amino Acid Components

The various modifications of non-natural amino acid components (which includes non-natural amino acids, as well as the non-natural amino acid portion of a polypeptide or other polymer) include, but are not limited to, (i) reactions of carbonyl-containing non-natural amino acid components with hydroxylamine-containing reagents to form oxime-containing non-natural amino acid components;

(ii) reactions of hydroxylamine-containing non-natural amino acid components with carbonyl-containing reagents to form oxime-containing non-natural amino acid components;

(iii) reactions of oxime-containing non-natural amino acid components, formed by reaction of carbonyls and hydroxylamines as in (i) and (ii), with different carbonyl-containing reagents to form new oxime-containing non-natural amino acid components via an oxime exchange reaction;

(iv) reactions of dicarbonyl-containing non-natural amino acid components with hydroxylamine-containing reagents to form oxime-containing non-natural amino acid components;

(v) reactions of hydroxylamine-containing non-natural amino acid components with dicarbonyl-containing reagents to form oxime-containing non-natural amino acid components;

(vi) reactions of oxime-containing non-natural amino acid components, formed by reaction of dicarbonyls and hydroxylamines as in (iv) and (v), with a different dicarbonyl-containing reagents to form new oxime-containing non-natural amino acid components via an oxime exchange reaction;

Such reactions are depicted in FIG. 2 wherein the amino acid functionality (A), translationally incorporated (or otherwise incorporated) into a polypeptide, reacts with reactant (B) to yield a modified polypeptide. Such reactions may further occur with the amino acid functionality (A) on a polymer (including, by way of example, a polynucleotide, a polynucleoside, a polysaccharide, or combinations thereof), wherein reaction with reactant (B) yields a modified polymer. For convenience, the modifications described in this section and other parts herein use "polypeptide" or "polypeptides," by way of example, to illustrate the various modifications. However, the modifications described herein apply equally well to nonnatural amino acids incorporated into other molecules, including, but not limited to, polynucleotide(s), polynucleoside(s), polysaccharide(s), synthetic polymer(s), or combinations thereof.

The term "components", as used herein, refers to non-natural amino acids, nonnatural amino acid polypeptides, polymers which contain nonnatural amino acids, nucleic acid sequences which contain selector codons, nonnatural amino acid polypeptides linked to polymers, nonnatural amino acid polypeptides linked to polymers which contain nonnatural amino acids, nonnatural amino acid polypeptides linked to nucleic acid sequences, nonnatural amino acid polypeptides linked to nucleic acid sequences; each of which may independently be a part of, or incorporated into, a polypeptide, a nonnatural amino acid polypeptide, nucleic acid sequence, or a polymer.

Description of these various reaction schemes have been disclosed in U.S. Provisional Patent Application Nos. 60/638,418, 60/638,527, 60/639,195, 60/696,210, 60/696, 302, and 60/696,068, each of which is herein incorporated by reference in its entirety. The disclosures provided within each of the above provisional patent applications apply fully to the methods, compositions, techniques and strategies for making, detecting, purifying, characterizing, and using non-natural amino acids, non-natural amino acid polypeptides and modified non-natural amino acid polypeptides described herein to the same extent as if such disclosures were fully presented herein.

Reactions of Carbonyl-Containing Non-Natural Amino Acid Components with Hydroxylamine-Containing Reagents to Form Oxime-Containing Non-Natural Amino Acid Components Non-natural amino acids with electrophile-containing sidechains including, but not limited to carbonyl groups such as aldehydes, esters, thioesters and ketones, can be incorporated into polypeptides. The incorporation of such non-natural amino acids with such electrophilic sidechains into polypeptides makes possible site-specific derivatization of this sidechain via nucleophilic attack of the carbonyl group. When the attacking nucleophile is a hydroxylamine, an oxime-derivatized polypeptide will be generated. The methods for derivatizing and/or further modifying may be conducted with a polypeptide that has been purified prior to the derivatization step or after the derivatization step. Further, the derivatization step can occur under mildly acidic to slightly basic conditions, including by way of example, between a pH of about 2 to about 10, or between a pH of about 2 to about 8, or between a pH of about 4 to about 8.

Figure 3:
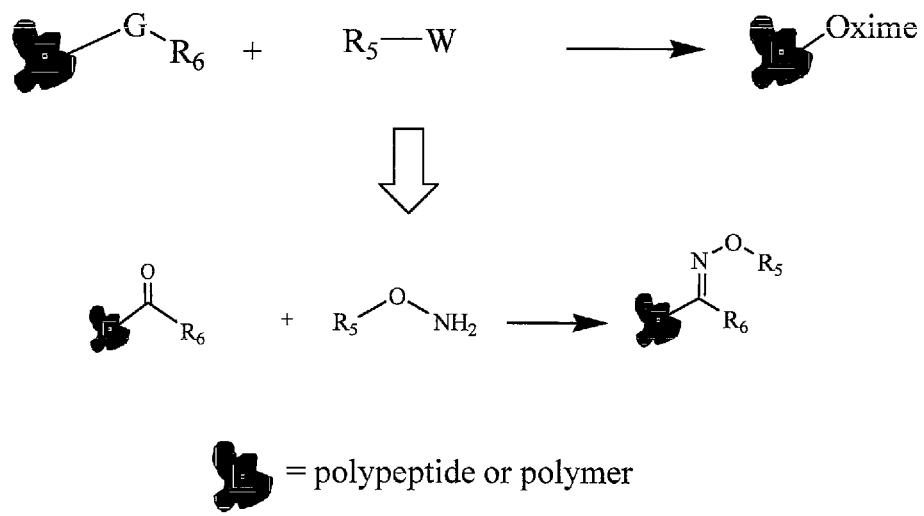
FIG. 3 presents an illustrative, non-limiting example of formation of oxime-containing non-natural amino acid components by reaction of carbonyl-containing non-natural amino acid components with hydroxylamine-containing reagents.

Modification of carbonyl sidechains, of non-natural amino acids incorporated into polypeptides, with hydroxylamine-containing reagents or other functional groups with similar chemical reactivity affords modified polypeptides containing oxime linkages. The reactions and the resulting structures of such modified polypeptides are shown in FIG. 3.

Certain embodiments described herein are polypeptides containing non-natural amino acids with sidechains comprising an oxime group. In other embodiments such oxime groups may be further modified, such as, by way of example only, formation of masked oxime groups (which can be readily converted into oxime groups), protected oxime groups (which upon deprotection can be readily converted into oxime groups available for other chemical reactions), or new oxime groups via oxime exchange reactions.

Non-limiting examples of such modified polypeptide oxime linkages are shown below:

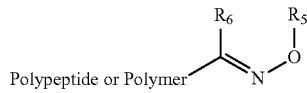

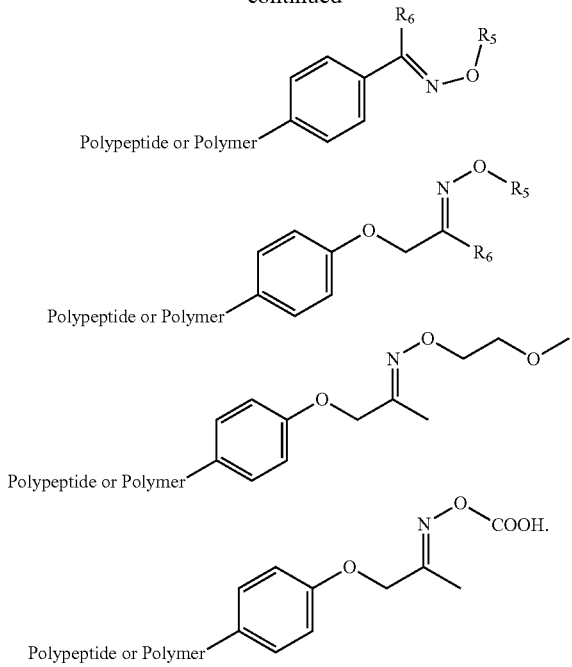

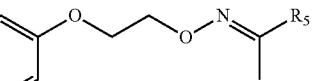

Reactions of Hydroxylamine-Containing Non-Natural Amino Acid Components with Carbonyl-Containing Reagents to Form Oxime-Containing Non-Natural Amino Acid Components The incorporation of non-natural amino acids containing hydroxylamine groups into polypeptides allows for reaction with a variety of electrophilic groups including, but not limited to, carbonyl group such as ketones, esters, thioesters and aldehydes. The nucleophilicity of the hydroxylamine group permits it to react efficiently and selectively with a variety of molecules that contain carbonyl functionality, or other functional groups with similar chemical reactivity, under mild conditions in aqueous solution to form the corresponding oxime linkage. This site-specific derivatization and/or further modifying of such sidechains via nucleophilic attack of the carbonyl group may be conducted with a polypeptide that has been purified prior to the derivatization step or after the derivatization step. Further, the derivatization step can occur under mildly acidic to slightly basic conditions, including by way of example, between a pH of about 2 to about 10, a pH of about 2 to about 8, or between a pH of about 4 to about 8.

Modification of hydroxylamine groups of nonnatural amino acids incorporated into polypeptides with carbonyl-containing reagents affords modified polypeptides containing oxime linkages. The reactions and the resulting structures of such modified polypeptides are shown in FIG. 4.

Certain embodiments described herein are polypeptides containing non-natural amino acids with sidechains comprising an oxime group. In other embodiments such oxime groups may be further modified, such as, by way of example only, formation of masked oxime groups (which can be readily converted into oxime groups), protected oxime groups (which upon deprotection can be readily converted into oxime groups available for other chemical reactions), or new oxime groups via oxime exchange reactions.

Non-limiting examples of such modified polypeptide oxime linkages are shown below:

Reactions of Oxime-Containing Non-Natural Amino Acid Components Formed by Reaction of Carbonyls and Hydroxylamines, with Different Carbonyl-Containing Reagents to Form New Oxime-Containing Non-Natural Amino Acid Components via an Oxime Exchange Reaction Non-natural amino acids containing an oxime group allow for reaction with a variety of reagents that contain certain reactive carbonyl groups (including but not limited to, aldehydes, esters, thioesters and ketones) to form new non-natural amino acids (which can be incorporated into a polypeptide) comprising a new oxime group. Such an oxime exchange reaction allows for the further functionalization of non-natural amino acid polypeptides.

Figure 5:
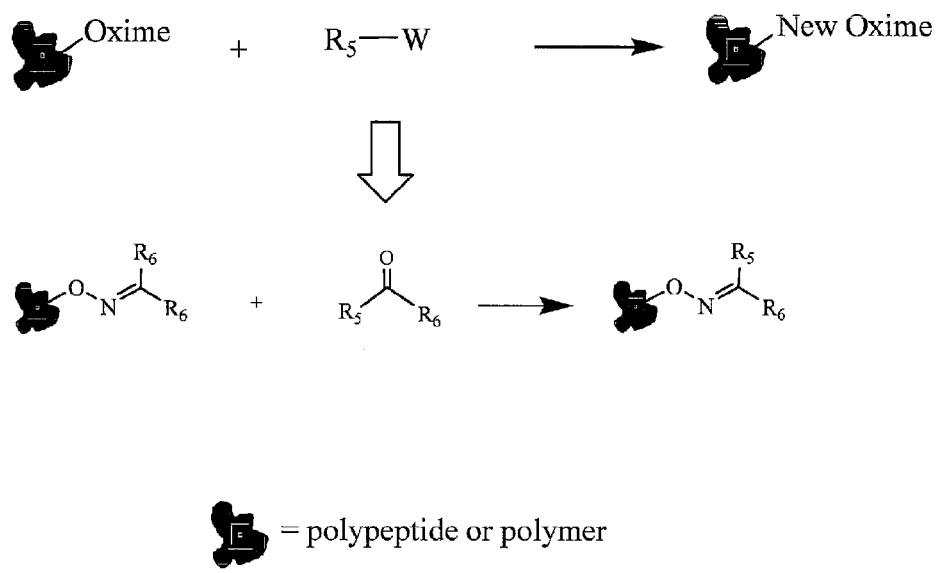
FIG. 5 presents an illustrative, non-limiting example of formation of oxime-containing non-natural amino acid components by oxime-containing non-natural amino acid components with carbonyl-containing reagents.

Modification of oxime sidechains, of nonnatural amino acids incorporated into polypeptides, with carbonyl-containing reagents, or other functional groups with similar chemical reactivity, affords modified polypeptides containing new oxime linkages. The reactions and the resulting structures of such modified polypeptides are shown in FIG. 5.

Certain embodiments described herein are polypeptides containing non-natural amino acids with sidechains comprising an oxime group. In other embodiments such oxime groups may be further modified, such as, by way of example only, formation of masked oxime groups (which can be readily converted into oxime groups), protected oxime groups (which upon deprotection can be readily converted into oxime groups available for other chemical reactions), or new oxime groups via oxime exchange reactions.

Reactions of Dicarbonyl-Containing Non-Natural Amino Acid Components with Hydroxylamine-Containing Reagents to form Oximes Non-natural amino acids with electrophile-containing sidechains including, but not limited to dicarbonyl groups such as a diketone group, a ketoaldehyde group, a ketoacid group, a ketoester group, and a ketothioester group), a dicarbonyl-like group (which has reactivity similar to a dicarbonyl group and is structurally similar to a carbonyl group), a masked dicarbonyl group (which can be readily converted into a dicarbonyl group), or a protected dicarbonyl group (which has reactivity similar to a dicarbonyl group upon deprotection), can be incorporated into polypeptides. The incorporation of such unnatural amino acid with such electrophilic sidechains into polypeptides makes possible site-specific derivatization of this sidechain via nucleophilic attack of the carbonyl group. When the attacking nucleophile is a hydroxylamine, an oxime-derivatized polypeptide will be generated. The methods for derivatizing and/or further modifying may be conducted with a polypeptide that has been purified prior to the derivatization step or after the derivatization step. Further, the derivatization step can occur under mildly acidic to slightly basic conditions, including by way of example, between a pH of about 2 to about 10, a pH of about 2 to about 8, or between a pH of about 4 to about 8.

Figure 6:
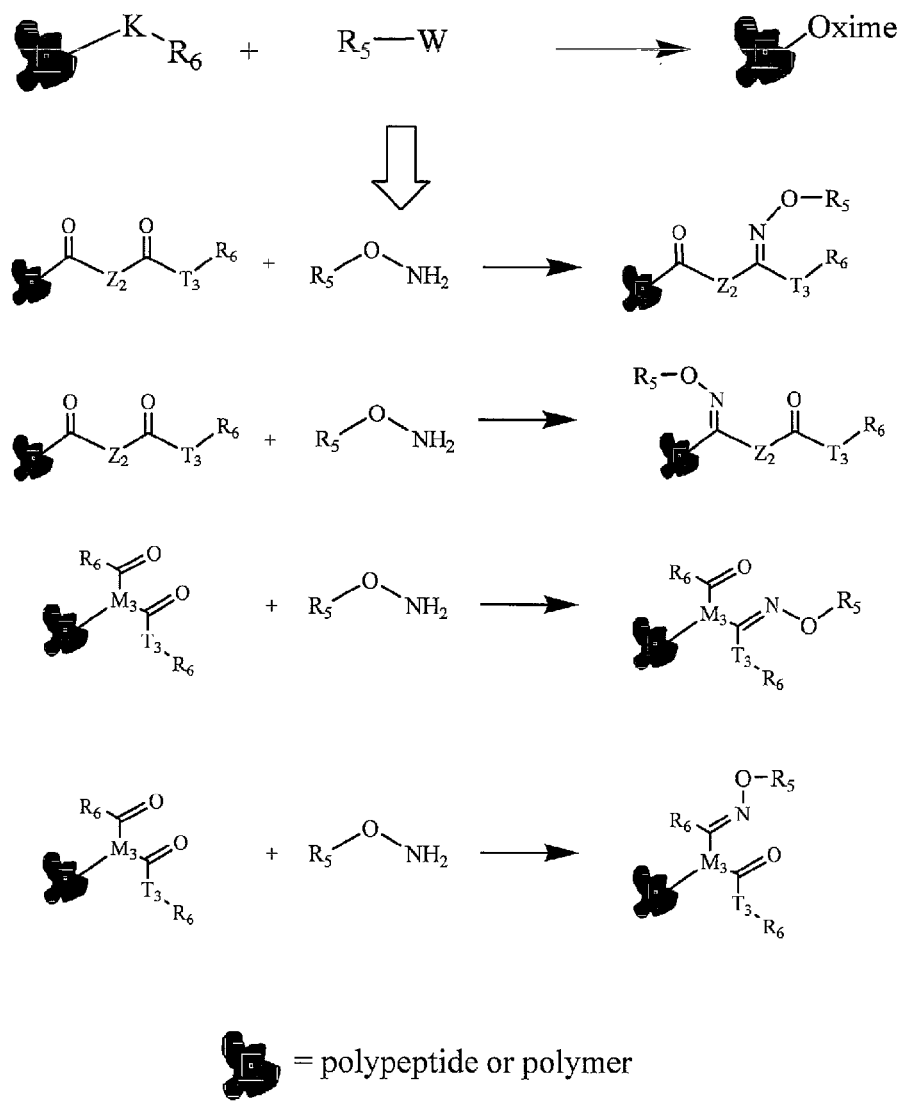
FIG. 6 presents an illustrative, non-limiting example of formation of oxime-containing non-natural amino acid components by reactions of dicarbonyl-containing non-natural amino acid components with hydroxylamine-containing reagents.

Modification of dicarbonyl sidechains, of nonnatural amino acids incorporated into polypeptides, with hydroxylamine-containing reagents, or other functional groups with similar chemical reactivity, affords modified polypeptides containing oxime linkages. The reactions and the resulting structures of such modified polypeptides are shown in FIG. 6.

Certain embodiments described herein are polypeptides containing non-natural amino acids with sidechains comprising an oxime group. In other embodiments such oxime groups may be further modified, such as, by way of example only, formation of masked oxime groups (which can be readily converted into oxime groups), protected oxime groups (which upon deprotection can be readily converted into oxime groups available for other chemical reactions), or new oxime groups via oxime exchange reactions.

Non-limiting examples of such modified polypeptide oxime linkages are shown below:

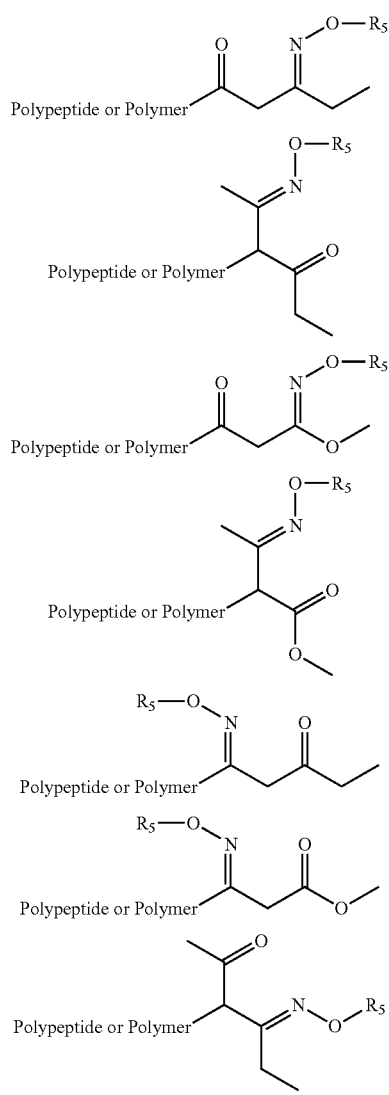

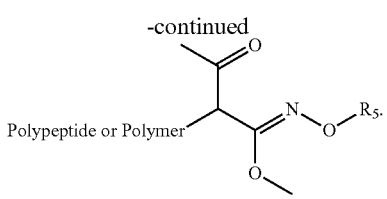

Reactions of Hydroxyalamine-Containing Non-Natural Amino Acid Components with Dicarbonyl-Containing Reagents to Form Oximes The incorporation of non-natural amino acids containing hydroxylamine groups into polypeptides allows for reaction with a variety of electrophilic groups including, but not limited to, dicarbonyl group such as a diketone group, a ketoaldehyde group, a ketoacid group, a ketoester group, and a ketothioester group, a dicarbonyl-like group (which has reactivity similar to a dicarbonyl group and is structurally similar to a carbonyl group), a masked dicarbonyl group (which can be readily converted into a dicarbonyl group), or a protected dicarbonyl group (which has reactivity similar to a dicarbonyl group upon deprotection). The nucleophilicity of the hydroxylamine group permits it to react efficiently and selectively with a variety of molecules that contain such dicarbonyl functionality, or other functional groups with similar chemical reactivity, under mild conditions in aqueous solution to form the corresponding oxime linkage. This site-specific derivatization and/or further modifying of such sidechains via nucleophilic attack of the dicarbonyl group may be conducted with a polypeptide that has been purified prior to the derivatization step or after the derivatization step. Further, the derivatization step can occur under mildly acidic to slightly basic conditions, including by way of example, between a pH of about 2 to about 10, a pH of about 2 to about 8, or between a pH of about 4 to about 8.

Modification of hydroxylamine groups, of nonnatural amino acids incorporated into polypeptides, with dicarbonyl-containing reagents affords modified polypeptides containing oxime linkages. The reactions and the resulting structures of such modified polypeptides are shown in FIG. 7.

Certain embodiments described herein are polypeptides containing non-natural amino acids with sidechains comprising an oxime group. In other embodiments such oxime groups may be further modified, such as, by way of example only, formation of masked oxime groups (which can be readily converted into oxime groups), protected oxime groups (which upon deprotection can be readily converted into oxime groups available for other chemical reactions), or new oxime groups via oxime exchange reactions.

Non-limiting examples of such modified polypeptide oxime linkages are shown below:

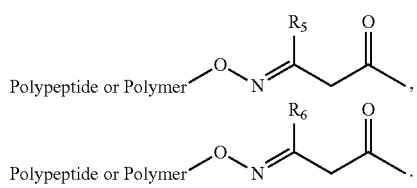

Reactions of Oxime-Containing Non-Natural Amino Acid Components Formed by Reaction of Dicarbonyls and Hydroxylamines, with Carbonyl or Different Dicarbonyl-Containing Reagents to Form New Oximes via an Oxime Exchange Reaction Non-natural amino acids containing an oxime group allow for reaction with a variety of reagents that contain certain reactive dicarbonyl groups, including, but not limited to, diketone groups, ketoaldehyde groups, ketoacid groups, ketoester groups, ketothioester groups, dicarbonyl-like groups (which has reactivity similar to a dicarbonyl group and is structurally similar to a carbonyl group), masked dicarbonyl groups (which can be readily converted into a dicarbonyl group), or protected dicarbonyl groups (which has reactivity similar to a dicarbonyl group upon deprotection) to form new non-natural amino acids (which can be incorporated into a polypeptide) comprising a new oxime group. Such an oxime exchange reaction allows for the further functionalization of non-natural amino acid polypeptides.

Figure 8:
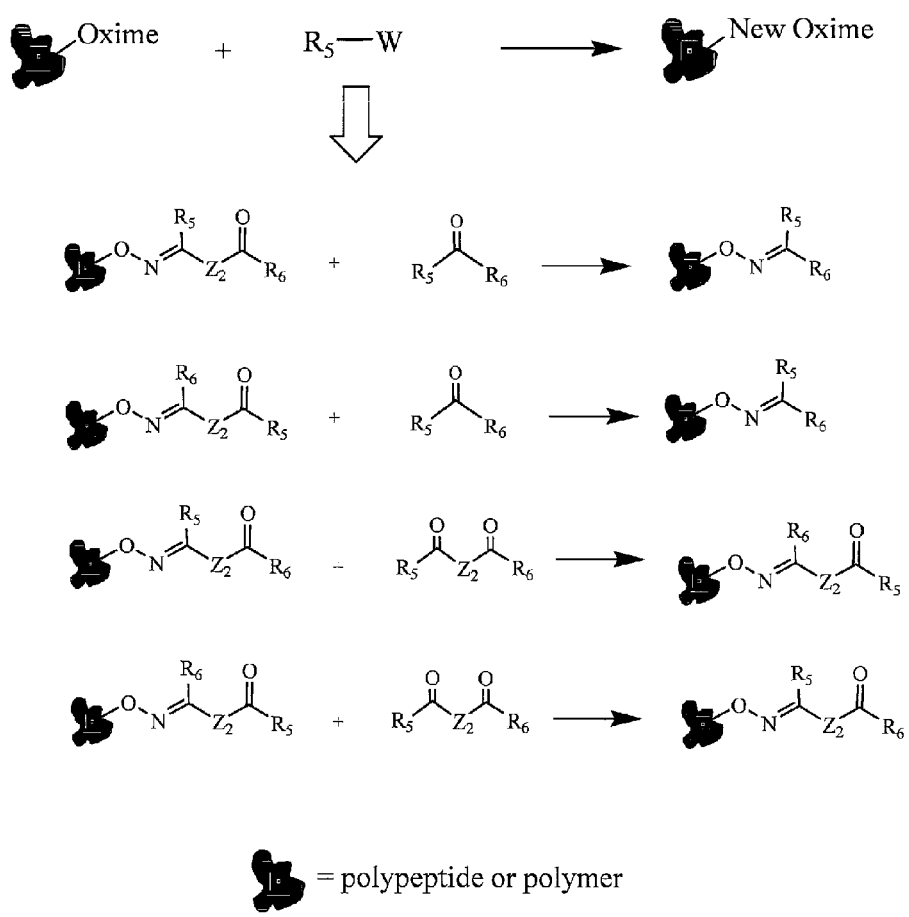
FIG. 8 presents an illustrative, non-limiting example of formation of oxime-containing non-natural amino acid components by oxime exchange reactions of oxime-containing non-natural amino acid components with carbonyl or dicarbonyl-containing reagents.

Modification of oxime sidechains, of nonnatural amino acids incorporated into polypeptides, with dicarbonyl-containing reagents, or other functional groups with similar chemical reactivity, affords modified polypeptides containing new oxime linkages. The reactions and the resulting structures of such modified polypeptides are shown in FIG. 8.

Certain embodiments described herein are polypeptides containing non-natural amino acids with sidechains comprising an oxime group. In other embodiments such oxime groups may be further modified, such as, by way of example only, formation of masked oxime groups (which can be readily converted into oxime groups), protected oxime groups (which upon deprotection can be readily converted into oxime groups available for other chemical reactions), or new oxime groups via oxime exchange reactions.

B. Enhancing Affinity for Serum Albumin

Various molecules can also be fused to the non-natural amino acid polypeptides described herein to modulate the half-life in serum. In some cases, molecules are linked or fused to the (modified) non-natural amino acid polypeptides described herein to enhance affinity for endogenous serum albumin in an animal.

For example, in some cases, a recombinant fusion of a polypeptide and an albumin binding sequence is made. In other cases, the (modified) non-natural amino acid polypeptides described herein are acylated with fatty acids. In other cases, the (modified) non-natural amino acid polypeptides described herein are fused directly with serum albumin (including but not limited to, human serum albumin). Those of skill in the art will recognize that a wide variety of other molecules can also be linked to non-natural amino acid polypeptides, modified or unmodified, as described herein, to modulate binding to serum albumin or other serum components. Further discussion regarding the enhancement affinity for serum albumin is described in U.S. Patent Application Nos. 60/638,418, 60/638,527, 60/639,195, 60/696,210, 60/696,302, and 60/696,068; PCT Publication WO 05/074650 entitled "Modified Four Helical Bundle Polypeptides and Their Uses," which are incorporated by reference in their entirety.

C. Glycosylation of Non-natural Amino Acid Polypeptides Described Herein

The methods and compositions described herein include polypeptides incorporating one or more non-natural amino acids bearing saccharide residues. The saccharide residues may be either natural (including but not limited to, N-acetylglucosamine) or non-natural (including but not limited to, 3-fluorogalactose). The saccharides may be linked to the non-natural amino acids either by an N- or O-linked glycosidic linkage (including but not limited to, N-acetylgalactose-L-serine) or a non-natural linkage (including but not limited to, an oxime or the corresponding C- or S-linked glycoside).

The saccharide (including but not limited to, glycosyl) moieties can be added to the non-natural amino acid polypeptides either in vivo or in vitro. In some cases, a polypeptide comprising a carbonyl-containing non-natural amino acid is modified with a saccharide derivatized with an aminooxy group to generate the corresponding glycosylated polypeptide linked via an oxime linkage. Once attached to the non-natural amino acid, the saccharide may be further elaborated by treatment with glycosyltransferases and other enzymes to generate an oligosaccharide bound to the non-natural amino acid polypeptide. See, e.g., H. Liu, et al. *J. Am. Chem. Soc.* 125: 1702-1703 (2003).

D. Use of Linking Groups and Applications, Including Polypeptide Dimers and Multimers In addition to adding functionality directly to the non-natural amino acid polypeptide, the non-natural amino acid portion of the polypeptide may first be modified with a multifunctional (e.g., bi-, tri, tetra-) linker molecule that then subsequently is further modified. That is, at least one end of the multifunctional linker molecule reacts with at least one non-natural amino acid in a polypeptide and at least one other end of the multifunctional linker is available for further functionalization. If all ends of the multifunctional linker are identical, then (depending upon the stoichiometric conditions) homomultimers of the non-natural amino acid polypeptide may be formed. If the ends of the multifunctional linker have distinct chemical reactivities, then at least one end of the multifunctional linker group will be bound to the non-natural amino acid polypeptide and the other end can subsequently react with a different functionality, including by way of example only: a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic excitable moiety; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; and any combination of the above.

Further use of linking groups and applications, including polypeptide dimers and multimers are further described in U.S. Patent Application Nos. 60/638,418, 60/638,527, 60/639,195, 60/696,210, 60/696,302, and 60/696,068; PCT Publication WO 05/074650 entitled "Modified Four Helical Bundle Polypeptides and Their Uses," which are incorporated by reference in their entirety.

E. Example of Adding Functionality: Easing the Isolation Properties of a Polypeptide A naturally-occurring or non-natural amino acid polypeptide may be difficult to isolate from a sample for a number of reasons, including but not limited to the solubility or binding characteristics of the polypeptide. For example, in the preparation of a polypeptide for therapeutic use, such a polypeptide may be isolated from a recombinant system that has been engineered to overproduce the polypeptide. However, because of the solubility or binding characteristics of the polypeptide, achieving a desired level of purity often proves difficult. The methods, compositions, techniques and strategies further described in U.S. Patent Application Nos. 60/638,418, 60/638,527, 60/639,195, 60/696,210, 60/696,302, and 60/696,068; PCT Publication WO 05/074650 entitled "Modified Four Helical Bundle Polypeptides and Their Uses," which are incorporated by reference in their entirety provide a solution to this situation.

F. Example of Adding Functionality: Detecting the Presence of a Polypeptide

A naturally-occurring or non-natural amino acid polypeptide may be difficult to detect in a sample (including an in vivo sample and an in vitro sample) for a number of reasons, including but not limited to the lack of a reagent or label that can readily bind to the polypeptide. The methods, compositions, techniques and strategies further described in U.S. Patent Application Nos. 60/638,418, 60/638,527, 60/639,195, 60/696,210, 60/696,302, and 60/696,068; PCT Publication WO 05/074650 entitled "Modified Four Helical Bundle Polypeptides and Their Uses," which are incorporated by reference in their entirety provide a solution to this situation.

G. Example of Adding Functionality: Improving the Therapeutic Properties of a Polypeptide A naturally-occurring or non-natural amino acid polypeptide will be able to provide a certain therapeutic benefit to a patient with a particular disorder, disease or condition. Such a therapeutic benefit will depend upon a number of factors, including by way of example only: the safety profile of the polypeptide, and the pharmacokinetics, pharmacologics and/or pharmacodynamics of the polypeptide (e.g., water solubility, bioavailability, serum half-life, therapeutic half-life, immunogenicity, biological activity, or circulation time). In addition, it may be advantageous to provide additional functionality to the polypeptide, such as an attached cytotoxic compound or drug, or it may be desirable to attach additional polypeptides to form the homo- and heteromultimers described herein. Such modifications preferably do not destroy the activity and/or tertiary structure of the original polypeptide. The methods, compositions, techniques and strategies further described in U.S. Patent Application Nos. 60/638,418, 60/638,527, 60/639,195, 60/696,210, 60/696,302, and 60/696,068; PCT Publication WO 05/074650 entitled "Modified Four Helical Bundle Polypeptides and Their Uses," which are incorporated by reference in their entirety provide solutions to these issues.

X. Therapeutic Uses of Modified Polypeptides

The (modified) non-natural amino acid polypeptides described herein, including homo- and hetero-multimers thereof find multiple uses, including but not limited to: therapeutic, diagnostic, assay-based, industrial, cosmetic, plant biology, environmental, energy-production, and/or military uses. As a non-limiting illustration, the following therapeutic uses of (modified) non-natural amino acid polypeptides are provided.

The (modified) non-natural amino acid polypeptides described herein are useful for treating a wide range of disorders. Administration of the (modified) non-natural amino acid polypeptide products described herein results in any of the activities demonstrated by commercially available polypeptide preparations in humans. Average quantities of the (modified) non-natural amino acid polypeptide product may vary and in particular should be based upon the recommendations and prescription of a qualified physician. The exact amount of the (modified) non-natural amino acid polypeptide is a matter of preference subject to such factors as the exact type of condition being treated, the condition of the patient being treated, as well as the other ingredients in the composition. The amount to be given may be readily determined by one skilled in the art based upon therapy with the (modified) non-natural amino acid polypeptide.

A. Administration and Pharmaceutical Compositions

The non-natural amino acid polypeptides, modified or unmodified, as described herein (including but not limited to, synthetases, proteins comprising one or more non-natural amino acid, etc.) are optionally employed for therapeutic uses, including but not limited to, in combination with a suitable pharmaceutical carrier. Such compositions, for example, comprise a therapeutically effective amount of the non-natural amino acid polypeptides, modified or unmodified, as described herein, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are well known in the art and can be applied to administration of the non-natural amino acid polypeptides, modified or unmodified, as described herein.

Therapeutic compositions comprising one or more of the non-natural amino acid polypeptides, modified or unmodified, as described herein are optionally tested in one or more appropriate in vitro and/or in vivo animal models of disease, to confirm efficacy, tissue metabolism, and to estimate dosages, according to methods known to those of ordinary skill in the art. In particular, dosages can be initially determined by activity, stability or other suitable measures of non-natural to natural amino acid homologues (including but not limited to, comparison of a polypeptide (modified) to include one or more non-natural amino acids to a natural amino acid polypeptide), i.e., in a relevant assay.

Administration is by any of the routes normally used for introducing a molecule into ultimate contact with blood or tissue cells. The non-natural amino acid polypeptides, modified or unmodified, as described herein, are administered in any suitable manner, optionally with one or more pharmaceutically acceptable carriers. Suitable methods of administering the non-natural amino acid polypeptides, modified or unmodified, as described herein, to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions described herein.

Non-natural amino acid polypeptides may be administered by any conventional route suitable for proteins or peptides, including, but not limited to parenterally, e.g. injections including, but not limited to, subcutaneously or intravenously or any other form of injections or infusions.

Polypeptide compositions (including the various polypeptides described herein) can be administered by a number of routes including, but not limited to oral, intravenous, intraperitoneal, intramuscular, transdermal, subcutaneous, topical, sublingual, or rectal means. Compositions comprising non-natural amino acid polypeptides, modified or unmodified, as described herein, can also be administered via liposomes. Such administration routes and appropriate formulations are generally known to those of skill in the art. The non-natural amino acid polypeptide may be used alone or in combination with other suitable components such as a pharmaceutical carrier.

The non-natural amino acid polypeptides, modified or unmodified, as described herein, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for EPO, IFN, GM-CSF, IFNs, interleukins, antibodies, and/or any other pharmaceutically delivered protein), along with formulations in current use, provide preferred routes of administration and formulation for the non-natural amino acid polypeptides, modified or unmodified, as described herein.

The dose administered to a patient, in the context compositions and methods described herein, is sufficient to have a beneficial therapeutic response in the patient over time. The dose is determined by the efficacy of the particular formulation, and the activity, stability or serum half-life of the non-natural amino acid polypeptides, modified or unmodified, employed and the condition of the patient, as well as the body weight or surface area of the patient to be treated. The size of the dose is also determined by the existence, nature, and extent of any adverse side-effects that accompany the administration of a particular formulation, or the like in a particular patient.

In determining the effective amount of the formulation to be administered in the treatment or prophylaxis of disease (including but not limited to, cancers, inherited diseases, diabetes, AIDS, or the like), the physician evaluates circulating plasma levels, formulation toxicities, progression of the disease, and/or where relevant, the production of anti-non-natural amino acid polypeptide antibodies.

The dose administered, for example, to a 70 kilogram patient, is typically in the range equivalent to dosages of currently-used therapeutic proteins, adjusted for the altered activity or serum half-life of the relevant composition. The pharmaceutical formulations described herein can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, the pharmaceutical formulations described herein are administered at a rate determined by the LD-50 or ED-50 of the relevant formulation, and/or observation of any side-effects of the non-natural amino acid polypeptides, modified or unmodified, at various concentrations, including but not limited to, as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, including but not limited to, diphenhydramine. Meperidine is used for more severe chills and muscle aches that do not quickly respond to antipyretics and antihistamines. Cell infusion is slowed or discontinued depending upon the severity of the reaction.

Non-natural amino acid polypeptides, modified or unmodified, as described herein, can be administered directly to a mammalian subject. Administration is by any of the routes normally used for introducing a polypeptide to a subject. The non-natural amino acid polypeptides, modified or unmodified, as described herein, include those suitable for oral, rectal, topical, inhalation (including but not limited to, via an aerosol), buccal (including but not limited to, sublingual), vaginal, parenteral (including but not limited to, subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend on the nature and severity of the condition being treated. Administration can be either local or systemic. The formulations can be presented in unit-dose or multi-dose sealed containers, such as ampoules and vials. The non-natural amino acid polypeptides, modified or unmodified, as described herein, can be prepared in a mixture in a unit dosage injectable form (including but not limited to, solution, suspension, or emulsion) with a pharmaceutically acceptable carrier. The non-natural amino acid polypeptides, modified or unmodified, as described herein, can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

Freeze-drying is a commonly employed technique for presenting proteins which serves to remove water from the protein preparation of interest. Freeze-drying, or lyophilization, is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. Biopharm. 3(9)26-30 (1990) and Arakawa et al. Pharm. Res. 8(3):285-291 (1991).

The spray drying of pharmaceuticals is also known to those of ordinary skill in the art. For example, see Broadhead, J. et al., "The Spray Drying of Pharmaceuticals," in Drug Dev. Ind. Pharm, 18 (11 & 12), 1169-1206 (1992). In addition to small molecule pharmaceuticals, a variety of biological materials have been spray dried and these include: enzymes, sera, plasma, micro-organisms and yeasts. Spray drying is a useful technique because it can convert a liquid pharmaceutical preparation into a fine, dustless or agglomerated powder in a one-step process. The basic technique comprises the following four steps: a) atomization of the feed solution into a spray; b) spray-air contact; c) drying of the spray; and d) separation of the dried product from the drying air. U.S. Pat. Nos. 6,235,710 and 6,001,800, which are incorporated by reference herein, describe the preparation of recombinant erythropoietin by spray drying.

The pharmaceutical compositions described herein may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) for the non-natural amino acid polypeptides, modified or unmodified, described herein, (see, e.g., *Remington's Pharmaceutical Sciences*, 17$^{th}$ ed. 1985)). Suitable carriers include buffers containing succinate, phosphate, borate, HEPES, citrate, imidazole, acetate, bicarbonate, and other organic acids; antioxidants including but not limited to, ascorbic acid; low molecular weight polypeptides including but not limited to those less than about 10 residues; proteins, including but not limited to, serum albumin, gelatin, or immunoglobulins; hydrophilic polymers including but not limited to, polyvinylpyrrolidone; amino acids including but not limited to, glycine, glutamine, asparagine, arginine, histidine or histidine derivatives, methionine, glutamate, or lysine; monosaccharides, disaccharides, and other carbohydrates, including but not limited to, trehalose, sucrose, glucose, mannose, or dextrins; chelating agents including but not limited to, EDTA; divalent metal ions including but not limited to, zinc, cobalt, or copper; sugar alcohols including but not limited to, mannitol or sorbitol; salt-forming counter ions including but not limited to, sodium; and/or nonionic surfactants including but not limited to Tween™ (including but not limited to, Tween 80 (polysorbate 80) and Tween 20 (polysorbate 20), Pluronics™ and other pluronic acids, including but not limited to, and other pluronic acids, including but not limited to, pluronic acid F68 (poloxamer 188), or PEG. Suitable surfactants include for example but are not limited to polyethers based upon poly(ethylene oxide)-poly(propylene oxide)-poly(ethylene oxide), i.e., (PEO-PPO-PEO), or poly(propylene oxide)-poly(ethylene oxide)-poly(propylene oxide), i.e., (PPO-PEO-PPO), or a combination thereof. PEO-PPO-PEO and PPO-PEO-PPO are commercially available under the trade names Pluronics™, R-Pluronics™, Tetronics™ and R-Tetronics™ (BASF Wyandotte Corp., Wyandotte, Mich.) and are further described in U.S. Pat. No. 4,820,352 incorporated herein in its entirety by reference. Other ethylene/polypropylene block polymers may be suitable surfactants. A surfactant or a combination of surfactants may be used to stabilize a (modified) non-natural amino acid polypeptide against one or more stresses including but not limited to stress that results from agitation. Some of the above may be referred to as "bulking agents." Some may also be referred to as "tonicity modifiers."

The non-natural amino acid polypeptides, modified or unmodified, as described herein, including those linked to water soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., *J. Biomed. Mater. Res.*, 15: 267-277 (1981); Langer, *Chem. Tech.*, 12: 98-105 (1982), ethylene vinyl acetate (Langer et al., supra) or poly-D-(-)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamate (Sidman et al., *Biopolymers*, 22, 547-556 (1983), poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218,121; Eppstein et al., *Proc. Natl. Acad. Sci. U.S.A.*, 82: 3688-3692 (1985); Hwang et al., *Proc. Natl. Acad. Sci. U.S.A.*, 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544, 545; and EP 102,324. All references and patents cited are incorporated by reference herein.

Liposomally entrapped polypeptides can be prepared by methods described in, e.g., DE 3,218,121; Eppstein et al., *Proc. Natl. Acad. Sci. U.S.A.*, 82: 3688-3692 (1985); Hwang et al., *Proc. Natl. Acad. Sci. U.S.A.*, 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. Composition and size of liposomes are well known or able to be readily determined empirically by one of ordinary skill in the art. Some examples of liposomes as described in, e.g., Park J W, et al., *Proc. Natl. Acad. Sci. USA* 92:1327-1331 (1995); Lasic D and Papahadjopoulos D (eds): MEDICAL APPLICATIONS OF LIPOSOMES (1998); Drummond D C, et al., Liposomal drug delivery systems for cancer therapy, in Teicher B (ed): CANCER DRUG DISCOVERY AND DEVELOPMENT (2002); Park J W, et al., *Clin. Cancer Res.* 8:1172-1181 (2002); Nielsen U B, et al., *Biochim. Biophys. Acta* 1591 (1-3):109-118 (2002); Mamot C, et al., *Cancer Res.* 63: 3154-3161 (2003). All references and patents cited are incorporated by reference herein.

The dose administered to a patient in the context of the compositions, formulations and methods described herein, should be sufficient to cause a beneficial response in the subject over time. Generally, the total pharmaceutically effective amount of the non-natural amino acid polypeptides, modified or unmodified, as described herein, administered parenterally per dose is in the range of about 0.01 µg/kg/day to about 100 µg/kg, or about 0.05 mg/kg to about 1 mg/kg, of patient body weight, although this is subject to therapeutic discretion. The frequency of dosing is also subject to therapeutic discretion, and may be more frequent or less frequent than the commercially available products approved for use in humans. Generally, a polymer:polypeptide conjugate, including by way of example only, a PEGylated polypeptide, as described herein, can be administered by any of the routes of administration described above.

XI. Isolation and Purification

A. Chromatography

In any of the embodiments herein, the isolation of peptides, (modified) non-natural amino acid polypeptides, binding partners or receptors to polypeptides can occur by chromatography. Chromatography is based on the differential absorption and elution of polypeptides. The sample is dissolved in a mobile phase, which may be a gas, a liquid or a supercritical fluid. This mobile phase is then forced through an immiscible stationary phase, which is fixed in a column or on a solid surface. Examples of stationary phases include liquids adsorbed on a solid, organic species bonded to a solid surface, solid, ion exchange resin and liquid in interstices of a polymeric solid. The ability of a polypeptide to be purified by different chromatographic or other isolation/purification methods may be modulated by the addition or substitution of one or more non-natural amino acids with a non-natural amino acid optionally in combination with one or more natural amino acid substitutions. Thus, the properties of a polypeptide may be modified by altering the amino acid composition enabling an increase or decrease in its interaction with known matrices. Changes to the amino acid composition include, but are not limited to, hydrophobic amino acid content, hydrophilic amino acid content, and change in charge, pI, or other characteristics of the polypeptide. Such modifications may be useful in isolating membrane proteins which are difficult to isolate since they are hydrophobic in nature and keep in their native conformation.

Gas Chromatography

In one embodiment the isolation of polypeptides can occur by gas chromatography (GC). The sample is vaporized and injected onto the head of a chromatographic column. Examples of mobile gas phases include but are not limited to helium, argon, nitrogen, carbon dioxide, and hydrogen. In one embodiment, the sample is isolated by gas-solid chromatography, where the stationary phase is a solid. Examples of solid stationary phase are molecular sieves and porous polymers. In another embodiment the polypeptide is isolated by gas-liquid chromatography, where the stationary phase is a liquid immobilized on the surface of an inert solid. Examples of liquid stationary phases include Polydimethyl siloxane, Poly (phenylmethyldimethyl) siloxane (10% phenyl), Poly(phenylmethyl) siloxane (50% phenyl), Poly(trifluoropropyldimethyl) siloxane, Polyethylene glycol and Poly(dicyanoallyldimethyl) siloxane.

Conventional GC columns are either packed and open tubular or capillary. GC-chromatographic columns vary in length from less than 2 m to 50 m or more. Examples of material for their construction include stainless steel, metal, glass, fused silica and Teflon. Typically GC columns have an in inner diameter of roughly of 2 to 4 mm. Micro-GC has an inner diameter of roughly 1 mm. Capillary GC utilizes a capillary with an inner diameter of roughly 100 to 750 um. Nano-GC is available with an inner diameter of 50 um-1 mm Liquid Chromatography In one embodiment the isolation of polypeptides can occur by liquid chromatography (LC). LC involves the use of fluid carrier over a stationary phase. The majority of LC-columns range in length from 10 to 30 cm. LC columns are ordinarily constructed from smooth-bore stainless steel tubing, although heavy glass tubing in occasionally encountered. Conventional LC columns have an inner diameter of roughly 4.6 mm and a flow rate of roughly 1 ml/min. Micro-LC has an inner diameter of roughly 1.0 mm and a flow rate of roughly 40 µl/min. Capillary LC utilizes a capillary with an inner diameter of roughly 300 µm and a flow rate of approximately 5 µl/min. Nano-LC is available with an inner diameter of 50 µm-1 mm and flow rates of 200 nl/min. Nano-LC can vary in length, e.g., 5, 15, or 25 cm. Nano-LC stationary phase may also be a monolithic material, such as a polymeric monolith or a sol-gel monolith. Two basic types of packing material have been used in liquid chromatography, non-porous and porous particles. The beads or particles are generally characterized by particle and pore size. Particle sizes generally range between 3 and 50 microns. Larger particles will generate less system pressure and smaller particles will generate more pressure. The smaller particles generally give higher separation efficiencies. The particle pore size is measured in angstroms and generally range between 100-1000 Å. These can be covered with a porous layer of silica, alumina, ion exchange resin, organic surface layer, polymers, ligands, carbohydrates or a specific cofactor.

In one embodiment of the invention, the polypeptides can be isolated using HPLC technology. In another embodiment of the invention, the polypeptide can be isolated using column chromatography. In column chromatography, the solid medium is packed onto a chromatography column, and the initial mixture containing the polypeptide is run through the column to allow binding. A wash buffer is then run through the column, and the elution buffer is subsequently applied to the column for sample collection. These steps may be performed at ambient pressure. In another embodiment, binding of the polypeptides to a solid phase may be achieved using a Batch treatment, by adding the initial mixture to the solid phase in a vessel, mixing the two together, separating the solid phase (i.e. by centrifugation), removing the liquid phase, washing, re-centrifuging, adding the elution buffer, re-centrifuging and removing the eluate. In another embodiment of the invention, a hybrid method is employed in which the binding is done by the Batch method, the solid phase with the target molecule bound is then packed onto a column, and washing and elution are performed on the column. In yet another embodiment of the invention, the isolation of peptides occur in a microfluidic device. In another embodiment of the invention, the isolation of peptides occur in a nanofluidic device.

Partition Chromatography

In one embodiment the isolation of polypeptides occurs by partition chromatography. In one embodiment the isolation of the polypeptides occurs by liquid-liquid partition chromatography. With liquid-liquid partition chromatography, a liquid stationary phase is retained on the surface of the packing by physical adsorption. In another embodiment, the isolation of the polypeptides can occur by bonded-phase partition chromatography. With bonded-phase partition chromatography, the stationary phase is bonded chemically to the support surfaces.

In another embodiment, normal-phase chromatography is used to isolate the polypeptides. In normal-phase chromatography, a polar stationary phase is used together with a non-polar solvent. Examples of the stationary phase for normal phase chromatography include but are not limited to, water, alcohols and triethylene glycol. Examples of non-polar solvents for normal phase chromatography include but are not limited to, ethyl, ether, chloroform, tetrahydrofuran, fluoroalkanes, cyclohexane, 1-chlorobutane, carbon tetrachloride, toluene, diethyl ether, hexane and i-propylether. In one embodiment the partition chromatography uses reversed-phase packings; this is referred as reversed-phase chromatography. In reversed-phase chromatography, a non-polar stationary phase is used together with a polar mobile phase. Examples of stationary phases for reversed-phased chromatography include but are not limited to, hydrocarbons, ether, esters, ketones, aldehydes, amides, and amines. Examples of mobile stationary phases for reversed-phased chromatography include water, methanol, ethanol, ethyl acetate, dioxane, nitromethane, ethylene glycol, tetrahydrofuran and acetonitrile.

In one embodiment, the type of reversed chromatography that can be use to isolate polypeptides is ion-pair chromatography. The mobile phase in ion-pair chromatography consists of an aqueous buffer containing an organic solvent such as methanol or acetonitrile and an ionic compound containing a counter ion of opposite charge to the polypeptides. The counter ion binds to the polypeptide to form an ion pair, which is a neutral species that is retained by a reversed-phase packing. Elution of the ion pairs is then accomplished with an aqueous solution of methanol or another water soluble organic solvent like the one described above. Examples of counter-ions are $ClO_4^-$ $C_{12}H_{25}SO_3^-$, $(C_4H_9)_4N^+$, $(C_{16}H_{33})(CH_3)_3N^+$, $(C_4H_9)_4N^+$, Bis- (2-ethylhexyl)phosphate, and $(C_4H_9)_4N^+$.

In one embodiment, the polypeptides can be isolated using partition chromatography with a chiral stationary phase. Examples of types of chiral stationary phases include but are not limited to, protein based stationary phases, small molecular weight chiral, polymers of cellulose and amylose, macrocyclic glycopeptides and cyclodextrin based materials.

Adsorption Chromatography

In one embodiment the isolation of polypeptides can occur by adsorption chromatography. Adsorption is a process whereby material (contained in the mobile phase) interacts by physical forces (dispersive, polar or ionic) with a stationary phase, thereby, causing a layer (or layers) of the material to adhere to that stationary phase. The stationary phase in most cases will be a solid (e.g. silica gel, alumina, charcoal, etc.) or sometimes a liquid (e.g. surfactants on water surfaces). The surface layer(s) may be single, double or multiple. Examples of solvents that can be use in adsorption chromatography include water, methanol, ethanol, ethyl acetate, dioxane, nitromethane, ethylene glycol, tetrahydrofuran, acetonitrile, ethyl, ether, chloroform, tetrahydrofuran, fluoroalkanes, cyclohexane, 1-chlorobutane, carbon tetrachloride, toluene, diethyl ether, hexane and i-propylether.

Ion Exchange Chromatography

In one embodiment the isolation of polypeptides can occur by ion-exchange chromatography. In ion-exchange chromatography the isolation of polypeptides is based upon ion-exchange resin. The ion exchange resin can be an anion exchange resin or a cation exchange resin. The ion-exchange resin can be made by natural ion exchangers, such as clays and zeolites, or from synthetic ion exchangers. Examples of common active sites for cation exchange resins are the sulfonic acid group —$SO_3^-H^+$, the carboxylic acid group —$COO^-H^+$ and phosphoric acid —$PO_{32}^+H_2$. Examples of common active sites for anion exchange resins are quaternary amine groups —$N(CH_3)^+OH^-$ or primary amine groups —$NH_3^+OH^-$. The mobile phase in ion-exchange chromatography is generally an aqueous solution that may contain moderate amounts of methanol or other water miscible organic solvents; these mobile phases also contain ionic species in the form of a buffer.

In one embodiment the ion exchange column is eluted with a gradient of salt concentrations. In one example, pumps add increasing amounts of salt to the buffer as it goes onto the column so that there is a continuous steady increase in the ionic concentration going through the column. The proteins then "elute" or come off the column stationary phase when the ionic strength of the buffer neutralizes their charge. The least charged molecules come off first, and the most highly charged come off last. In another example, the column is thoroughly rinsed with buffers of increasing ionic strength until the desired protein elutes; this exact same sequence is repeated each time with the same amounts of buffer to give reproducible yields and purification of the protein.

In one embodiment, the sample will be subject removal of high salt concentrations after isolation the polypeptide of interest by ion exchange chromatography. In one embodiment the removal of high salt concentration will be performed by dialysis. Dialysis makes use of semi-permeable membranes. The main feature of the dialysis membrane is that it is porous. However, the pore size is such that while small salt ions can freely pass through the membrane, larger protein molecules cannot (i.e. they are retained). Thus, dialysis membranes are characterized by the molecular mass of the smallest typical globular protein which it will retain. Removal of high salt concentration can be achieved in a single or multiple dialysis steps. In another embodiment, the removal of high salt concentration is performed by electrodialysis. Electrodialysis is an electromembrane process in which ions are transported through ion permeable membranes from one solution to another under the influence of a potential gradient. Since the membranes used in electrodialysis have the ability to selectively transportions having positive or negative charge and reject ions of the opposite charge, electrodialysis is useful for concentration, removal, or separation of electrolytes.

In another embodiment, the removal of high concentration of salt is achieved by using desalting columns in gravity-flow gel filtration. Gravity-flow gel filtration involves the chromatographic separation of molecules of different dimensions based on their relative abilities to penetrate into a suitable stationary phase. Desalting columns are packed with small, porous cellulose beads. These columns have a wet bead with specific diameters. The diameter of the beads used will depend on the molecular weight of the peptide of interest. Different levels of separation can be achieved based on the pore size of the medium packed into the column. The medium can be chosen to totally exclude proteins or large molecules, while still including small solutes. Large molecules are excluded from the internal pores of the gel and emerge first from the column. The smaller molecules are able to penetrate the pores, and then progress through the column at a slower rate. These smaller molecules are subsequently flushed through the column with additional buffer volume.

Size-Exclusion Chromatography

In one embodiment the isolation of polypeptides can occur by size-exclusion chromatography, also known as gel permeation, or gel filtration chromatography. Molecules that are larger than the average pore size of the packing are excluded and thus suffer no retention. Examples of packings for size exclusion chromatography include silica, cellulose beads and polymer particles. Conventionally, porous glasses and silica particles have an average pore size ranging from 40 Å to 2500 Å. In some embodiments, the molecular weight exclusion limit of a polymer packing with an average pore size of 102 Å is 700. In another embodiment the molecular weight exclusion limit of a polymer packing with an average pore size of 103 Å is $(0.1 \text{ to } 20) \times 10^4$. In another embodiment the molecular weight exclusion limit of a polymer packing with an average pore size of 104 Å is $(1 \text{ to } 20) \times 10^4$. In another embodiment the molecular weight exclusion limit of a polymer packing with an average pore size of $10^5$ Å is $(1 \text{ to } 20) \times 10^5$. In yet another embodiment the molecular weight exclusion limit of a polymer packing with an average pore size of $10^6$ Å is $(5 \text{ to } 10) \times 10^6$. In some embodiments, the molecular weight exclusion limit of silica packing with an average pore size of 125 Å is $(0.2 \text{ to } 5) \times 10^4$. In another embodiment, the molecular weight exclusion limit of silica packing with an average pore size of 300 Å is $(0.03 \text{ to } 1) \times 10^5$. In another embodiment, the molecular weight exclusion limit of silica packing with an average pore size of 500 Å is $(0.05 \text{ to } 5) \times 10^5$. In yet another embodiment, the molecular weight exclusion limit of silica packing with an average pore size of 1000 Å is $(5 \text{ to } 20) \times 10^5$.

Thin-Layer Chromatography

In one embodiment the isolation of polypeptides can occur by thin-layer chromatography. Thin-layer chromatographic methods include paper chromatography, thin-layer chromatography and electrochromatography. Each makes use of a flat, thin layer of material that is either self supporting or that is coated on a glass, plastic, or metal surface. The mobile phase moves through the stationary phase by capillary action, sometimes assisted by gravity or electrical potential. In one embodiment, planar separation is performed on flat glass or plastic plates that are coated with a thin and adherent layer of finely divided particles; this layer constitutes the stationary phase. The stationary phase and mobile phase are similar to those discussed in adsorption, normal- and reversed-phase partition, ion-exchange, and size exclusion chromatography. In one embodiment, the polypeptides are located in the plate by spraying a solution that will react with organic compounds to yield dark products. Examples of this type of solution include ninhydrin, iodine solutions and sulfuric acid solution. In another embodiment, the polypeptides are located by incorporating a fluorescent material to the stationary phase. The plate is examined under ultraviolet light. The sample components quench the fluorescent material so that all of the plate fluoresces except where the non-fluorescing sample components are located.

Affinity Chromatography

In one embodiment the isolation of polypeptides can occur by affinity chromatography. Affinity chromatography relies on the ability to design a stationary phase that reversibly binds to a known subset of molecules. Affinity purification generally involves the following steps: 1) incubate crude sample with the immobilized ligand support material to allow the target molecule in the sample to bind to the immobilized ligand, 2) wash away nonbound sample components from solid support and 3) elute (dissociate and recover) the target molecule from the immobilized ligand by altering the buffer conditions so that the binding interaction no longer occurs. Examples of elution buffers used in affinity chromatography include but are not limited to 100 mM glycine.HCl, 100 mM citric acid, 50-100 mM triethylamine or triethanolamine, 150 mM ammonium hydroxide, 3.5-4.0 M magnesium chloride in 10 mM Tris, 5 M lithium chloride in 10 mM phosphate buffer, 2.5 M sodium iodide, 0.2-3.0 sodium thiocyanate, 2-6 M guanidine.HCl, 2-8 M urea, 1% deoxycholate, 1% SDS, 10% dioxane, 50% ethylene glycol, 0.1 M Glycine-NaOH, 0.1 M Glycine-NaOH with 50% ethyleneglycol, 3.0 M Potassium chloride, 0.1 M Tris-acetate with 2.0 M NaCl, 5.0 M Potassium iodide, 1% SDS, 1% Sodium deoxycholate, 2.0 M Urea, 6.0 M Urea, 2.0 M Guanadine-HCl, 1.0 M Ammonium thiocyanate and >0.1 M counter ligand or analog.

In one embodiment, the stationary phase includes a ligand including but not limited to, a specific carbohydrate or a cofactor. In one embodiment, the polypeptides can then be eluted with a high concentration of the carbohydrate or a specific cofactor. Mimics for binding sites can sometimes be used as affinity stationary phases. The specific sugars, inhibitor or cofactors used in the stationary phase will vary according to the properties of the polypeptide. The embodiments of the invention include any ligand, carbohydrate or cofactor known in the art.

In another embodiment, the immobilized stationary phase includes a dye. Examples of dyes commonly used for dye-ligand chromatography include Reactive Blue 2 (Cibacron© Blue 3GA), Reactive Red 120 (Procion© Red HE3B), Reactive Blue 4 (Reactive Blue MRB)$^{TC}$, Reactive Green 5 (Reactive Green H4G)$^{TC}$, Reactive Green 19 (Reactive Green HE4BD)$^{TC}$, Green 19A (Reactive Green HE4BD)$^{TC}$, Reactive Yellow 86 (Reactive Yellow M8G)$^{TC}$ and Reactive Brown 10 (Reactive Brown M4R)$^{TC}$.

In another embodiment, the stationary phase includes a metal chelate resin. In metal chelate chromatography metal ions such as $Zn^{2+}$, $Cu^{2+}$ and $Ni^{2+}$ are immobilized to a chromatography stationary phase by chelate bonding take part in a reversible interaction with electron donor groups situated in the surface of polypeptides. At a pH value at which the electron group donor is present at least partially in non-protonized form the polypeptide is bonded to the stationary phase and can be subsequently eluted by means of a buffer with lower pH value at which the electron group is protonized. Examples of chelate resins include 8-hydroxyquinoline, salicylic acid, diethylenetriamine, diethylenetriaminetetraacetic acid, ethylenediaminetetraacetic acid (EDTA), iminodiacetic acid and nitrilo-triacetic acid.

In another embodiment, the isolation of polypeptides can occur by immunoaffinity chromatography. The principle of immunoaffinity or immunoadsorption chromatography is based on the highly specific interaction of an antigen with its antibody. Immunoaffinity chromatography utilizes an antibody or antibody fragment as a ligand immobilized onto the stationary phase in a manner that retains its binding capacity. Elution of the retained polypeptide is achieved by alterations to the mobile-phase conditions that weaken the antibody-antigen interaction. Elution conditions are intended to break the ionic, hydrophobic and hydrogen bonds that hold the antigen and antibody together. Successful eluting conditions will be dependent upon the specific antigen-antibody interaction that is occurring.

Antibodies may be generated that recognize the non-natural amino acid present in the polypeptide. Such antibodies may be used in affinity chromatography to purify the non-natural amino acid polypeptides from a complex mixture or enable conjugation of the polypeptide with other molecules on a support such as a resin, in immunoassays to detect the presence of non-natural amino acid polypeptides, and other assays that use antibodies. Antibodies may be generated that recognize one or more non-natural amino acids present at the N or C terminus of a polypeptide or other portions of the polypeptide.

Non-natural amino acid polypeptides may be antibodies, antibody fragments, or antigen-binding polypeptides or fragments thereof, and used to isolate antigens by affinity chromatography.

In one embodiment the isolation of polypeptides can occur by hydrophobic-interaction chromatography. Polypeptides may contain hydrophilic and hydrophobic natural amino acids and hydrophilic and hydrophobic non-natural amino acids. Polypeptides are separated according to their relative hydrophobicity by their ability to reversibly bind to hydrophobic compounds. The polypeptides are eluted from the column with decreasing concentrations of salt in buffer. Examples of hydrophobic compounds include but are not limited to, hydrophobic fatty acid chains, compounds with n-butyl functional groups, compounds with n-octyl functional groups and compounds with phenyl functional groups.

Supercritical Fluid Chromatography

In one embodiment the isolation of polypeptides can occur by supercritical chromatography (SFC). In SFC, the sample is carried through a separating column by a supercritical fluid where the mixture is divided into unique bands based on the amount of interaction between the individual analytes and the stationary phase in the column. Conventional SFC columns are either packed and open tubular or capillary. Open-tubular columns vary in length from 10 m to 20 m or more. Typically open-tubular columns have an inner diameter of roughly of 0.05 to 4 mm. Pack columns vary in diameter from 0.5 mm or less to 4.6 mm, with particle diameter ranging from 3 to 10 um. Packed columns contain small deactivated particles to which the stationary phases adhere. The columns are conventionally stainless steel. Capillary columns are open tubular columns of narrow internal diameter made of fused silica, with the stationary phase bonded to the wall of the column. The coatings are similar to those used in partition chromatography. Examples of supercritical fluids used in SFC include but are not limited to, carbon dioxide, ethane, pentane, nitrous oxide, dichlorodifluoromethane, diethyl ether, ammonia, and tetrahydrofuran. In some applications, polar organic modifiers such as methanol are introduced in small concentrations (1-5%).

B. Precipitation

In one embodiment the isolation of peptides, (modified) non-natural amino acid polypeptides, binding partners or receptors to polypeptides can occur by precipitation. The solubility of polypeptides is a function of the ionic strength and pH of the solution. Polypeptides have isoelectric points at which the charges of their amino acid side groups balance each other. If the ionic strength of a solution is either very high or very low, proteins will tend to precipitate at their isoelectric point. In one embodiment, the ionic strength of the solution will be increased by adding salt. Examples of salts used in precipitation methods include but are not limited to ammonium sulfate and sodium sulfate. Any salt known in the art for protein precipitation can be used in any of the embodiments of the inventions. In another embodiment, polypeptides will be forced out of solution with polymers. One example of a polymer commonly used to precipitate polypeptides is polyethylene glycol. Any polymer known in the art for protein precipitation can be used in any of the embodiments of the inventions. In one embodiment the precipitated polypeptides are removed by centrifugation or filtration.

In one embodiment, after precipitation of the peptide of interest by the addition salts to the solution the sample will be subject removal of high salt concentrations. Desalting methods are discussed in the ion-exchange chromatography section.

Immunoprecipitation

In one embodiment of the invention the isolation of polypeptides can occur by immunoprecipitation (IP). IP refers to the small-scale affinity purification of antigen using a specific antibody. Classical immunoprecipitation involves the following steps: 1) incubate specific antibody with a sample containing antigen, 2) capture antibody-antigen complex with immobilized Protein A or G agarose gel (Protein A or G binds the antibody, which is bound to its antigen), 3) Wash the gel with buffer to remove non-bound sample components, 4) Elute the antigen (and antibody).

In one embodiment of the invention, classical IP is performed in a microcentrifuge tube with the polypeptide-containing sample using immobilized Protein A or G gel. The gel is pelleted by centrifugation after each step (washes and elution), and the supernatant is removed. Usually the eluted sample will always contain both antigen and antibody, and reducing gel electrophoresis of the eluted sample will yield both antigen bands and heavy and light chain antibody fragment bands. Methods to obtain polypeptides from electrophoresis gel separated are known to those of ordinary skill in the art.

In another embodiment of the invention, to avoid antibody contamination of the eluted antigen, modifications to the classical IP method can be made so that the antibody is permanently immobilized and will not elute with the antigen. In one example, the antibody is first bound to the Protein A or G gel and then the antibody is covalently cross-linked to the Protein A or G. In another example the antibody is directly coupled to an activated affinity support. Non-natural amino acid polypeptides may be antigen-binding polypeptides and used in immunoprecipitation.

In one embodiment the support material is a porous gel such as cross-linked beaded agarose or co-polymer of cross-linked bis-acrylamide and azlactone. In one embodiment of the invention polypeptides can be isolated by magnetic affinity separation. Samples containing the molecule of interest are incubated with magnetic beads that are derivatized with an antibody or other binding partner. A magnetic field is used to pull the magnetic beads out of solution and onto a surface. The buffer can be carefully removed, containing any nonbound molecules. Protocols using magnetic beads for isolation of molecules of interest are well known in the art. Magnetic beads can be derivatized to contain active groups, including but not limited to, carboxylic acids or primary amines, or specific affinity molecules such as streptavidin or goat anti-mouse, anti-rabbit or anti-rat IgG or Protein A or G. In another embodiment the support is a microplate.

C. Electrophoresis

In any of the embodiments herein, isolation of polypeptides can occur by electrophoresis. Electrophoresis is the separation of ionic molecules such as polypeptides by differential migration patterns through a gel based on the size and ionic charge of the molecules in an electric field. Electrophoresis can be conducted in a gel, capillary or on a chip. Examples of gels used for electrophoresis include starch, acrylamide, agarose or combinations thereof. A gel can be modified by its cross-linking, addition of detergents, immobilization of enzymes or antibodies (affinity electrophoresis) or substrates (zymography) and pH gradient. Methods to obtain polypeptides from electrophoresis gels are known to those of ordinary skill in the art.

Capillary Electrophoresis

In one embodiment the isolation of peptides, (modified) non-natural amino acid polypeptides, binding partners or receptors to polypeptides can occur by capillary electrophoresis (CE). CE may be used for separating complex hydrophilic molecules and highly charged solutes. Advantages of CE include its use of small samples (sizes ranging from 0.001 to 10 µL), fast separation, easy reproducibility, very high efficiencies, meaning hundreds of components can be separated at the same time, is easily automated, can be used quantitatively and consumes limited amounts of reagents. CE technology, in general, relates to separation techniques that use narrow bore fused-silica capillaries to separate a complex array of large and small molecules. High voltages are used to separate molecules based on differences in charge, size and hydrophobicity. Depending on the types of capillary and buffers used, CE can be further segmented into separation techniques such as capillary zone electrophoresis (CZE), capillary isoelectric focusing (CIEF) and capillary electrochromatography (CEC).

Capillary zone electrophoresis (CZE), also known as free-solution CE (FSCE), is the simplest form of CE. The separation mechanism of CZE is based on differences in the charge-to-mass ratio of the analytes. Fundamental to CZE are homogeneity of the buffer solution and constant field strength throughout the length of the capillary. The separation relies principally on the pH-controlled dissociation of acidic groups on the solute or the protonation of basic functions on the solute.

Capillary isoelectric focusing (CIEF) allows amphoteric molecules, such as polypeptides, to be separated by electrophoresis in a pH gradient generated between the cathode and anode. A solute will migrate to a point where its net charge is zero. At this isoelectric point (the solute's pI), migration stops and the sample is focused into a tight zone. In CIEF, once a solute has focused at its pI, the zone is mobilized past the detector by either pressure or chemical means.

CEC is a hybrid technique between traditional liquid chromatography (HPLC) and CE. In essence, CE capillaries are packed with HPLC packing and a voltage is applied across the packed capillary, which generates an electro-osmotic flow (EOF). The EOF transports solutes along the capillary towards a detector. Both differential partitioning and electrophoretic migration of the solutes occurs during their transportation towards the detector, which leads to CEC separations. It is therefore possible to obtain unique separation selectivities using CEC compared to both HPLC and CE. The beneficial flow profile of EOF reduces flow related band broadening and separation efficiencies of several hundred thousand plates per meter are often obtained in CEC. CEC also makes it is possible to use small-diameter packings and achieve very high efficiencies.

Micellar electrokinetic capillary chromatography (MECC) is a capillary electrophoretic method that allows the separation of uncharged solutes. In this technique, surfactants, such as sodium dodecyl sulfate, are added to the operating buffer in amounts that exceed the critical micelle concentration at which micelles form. The surface of anionic micelles of this type has a large negative charge, which give them a large electrophoretic mobility toward the positive electrode. Most buffers, however, exhibit such a high electroosmotic rate toward the negative electrode that the anionic micelles are carried toward the negative electrode, but at a much reduced rate. This form a fast moving aqueous phase and a slower moving micellar phase. When the sample is introduced into the system, the components distribute themselves between the aqueous phase and the hydrocarbon phase at the interior of the micelles.

Alternatively, isotachophoresis (ITP) is a method of concentrating samples by electrophoretic separation using a discontinuous buffer. In isotachophoresis, two different buffer systems are used to create zones which the analytes separate into. During an isotachophoresis experiment it is possible to separate either cations or anions, not both. In ITP, a large volume of sample is placed between a leading electrolyte and a terminating electrolyte. Analytes in the sample stack into narrow bands one after another according to their mobility. The technique can be used in conjunction with capillary electrophoresis where a discontinuous electrolyte system is employed at the site of sample injection into the capillary.

Moreover, transient isotachophoresis (tITP) is a variation of this technique commonly used in conjunction with capillary electrophoresis (CE). Foret, F., et al. in "Trace Analysis of Proteins by Capillary Zone Electrophoresis with On-Column Transient Isotachophoretic Preconcentration". *Electrophoresis* 1993, 14, 417-428 (1993) describe two electrolyte arrangements for performing tITP.

One configuration employs two reservoirs connected by a capillary. The capillary and one reservoir are filled with a leading electrolyte (LE), while the second reservoir is filled with terminating electrolyte (TE). The sample for analysis is first injected into the capillary filled with LE and the injection end of the capillary is inserted into the reservoir containing TE. Voltage is applied and those components of the sample which have mobilities intermediate to those of the LE and TE stack into sharp ITP zones and achieve a steady state concentration. The concentration of such zones is related to the concentration of the LE co-ion but not to the concentration of the TE. Once a steady state is reached, the reservoir containing TE is replaced with an LE containing reservoir. This causes a destacking of the sharp ITP zones, which allows individual species to move in a zone electrophoretic mode.

The other configuration discussed by Foret, F., et al. employs a similar approach but uses a single background electrolyte (BGE) in each reservoir. The mobility of the BGE co-ion is low such that it can serve as the terminating ion. The sample for analysis contains additional co-ions with high electrophoretic mobility such that it can serve as the leading zone during tITP migration. After sample is injected into the capillary and voltage is applied, the leading ions of higher mobility in the sample form an asymmetric leading and sharp rear boundary. Just behind the rear boundary, a conductivity discontinuity forms, and this results in a non-uniform electric field, and thus stacking of the sample ions. As migration progresses, the leading zone will broaden due to electromigration dispersion and the concentration of higher mobility salt will decrease. The result is decreasing differences of the electric field along the migrating zones. At a certain concentration of the leading zone, the sample bands will destack and move with independent velocities in a zone electrophoretic mode. Isolation of peptides can involve any procedure known in the art, such as capillary electrophoresis (e.g., in capillary or on-chip), or chromatography (e.g., in capillary, column or on a chip).

D. Procedures for Removal of Contaminants

In some embodiments of the invention following the primary purification procedure to obtain a polypeptide of interest, secondary purification steps to remove contaminants may be required. The contaminants can be inhibitors, interfering substances or inappropriate buffers. In one embodiment of the invention removal of contaminants will be achieved by specifically purifying their protein of interest away from a complex mixture of biological molecules. In another embodiment of the invention the removal of contaminants will be achieved by specifically removing contaminants from a sample containing a protein of interest. For example, immobilized Protein A can be used to selectively remove immunoglobulins from a sample where they are considered to be a contaminant. In yet another embodiment filters can be used to remove undesired components from a sample. Examples include but are not limited to size exclusion chromatography and ultrafiltration membranes that separate molecules on the basis of size and molecular weight. In yet another embodiment, ultracentrifugation is used for removing undesired components from a sample. Ultracentrifugation can involve centrifugation of a sample while monitoring with an optical system the sedimentation (or lack thereof) of particles. In another embodiment of the invention, electrodialysis is used to remove undesired components from the sample. Electrodialysis is an electromembrane process in which ions are transported through ion permeable membranes from one solution to another under the influence of a potential gradient. Since the membranes used in electrodialysis have the ability to selectively transportions having positive or negative charge and reject ions of the opposite charge, electrodialysis is useful for concentration, removal, or separation of electrolytes.

Removal of Endotoxin

In some embodiments of the invention it may be necessary to remove endotoxins from the sample. Endotoxins are pyrogenic lipopolysaccharide (LPS) components of Gram-negative bacteria. Because these bacteria are ubiquitous, it is not surprising that endotoxins are frequent contaminants of biochemical preparations. Endotoxin contamination usually is measured as endotoxin units (EU), where 1 EU corresponds to a concentration of endotoxin (usually about 0.1 ng/kg body weight) sufficient to generate a pyrogenic reaction. In one embodiment removal of endotoxin is performed by ultracentrifugation. In another embodiment removal of endotoxin is performed by using immobilized polymixin B. Methods for reducing endotoxin levels are known to one of ordinary skill in the art and include, but are not limited to, purification techniques using silica supports, glass powder or hydroxyapatite, reverse-phase, affinity, size-exclusion, anion-exchange chromatography, hydrophobic interaction chromatography, a combination of these methods, and the like. Methods for measuring endotoxin levels are known to one of ordinary skill in the art and include, but are not limited to, *Limulus* Amebocyte Lysate (LAL) assays.

Removal of Detergent

In some embodiments of the invention it may be necessary to remove some or all of the detergent in the sample. For example, although many water-soluble polypeptides are functional in detergent-solubilized form, other polypeptides may be modified and inactivated by detergent solubilization. In one embodiment detergent removal can occur by dialysis. Dialysis is effective for removal of detergents that have high CMCs (critical micelle concentrations) and/or small aggregation numbers, such as the N-octyl glucosides. In another embodiment removal of detergent from the sample can occur by sucrose density gradient separation. In yet another embodiment, detergents can be removed from the sample by size exclusion chromatography.

E. Recombinant Polypeptides

In one embodiment of the invention isolation of polypeptides may use genetic engineering techniques to synthesize of hybrid proteins. By fusing the coding sequence of a polypeptide of interest with the coding sequence of a polypeptide with high affinity to a ligand, a hybrid protein with an affinity tag can be produced directly by a microorganism. Examples of expression systems are *Escherichia coli, Bacillus subtilis, Pseudomonas fluorescens, Pseudomonas aeruginosa, Pseudomonas putida,* yeast, mammalian cells and the baculovirus system in insect cells. The affinity tag can then be used to recover the product from a culture medium, cell lysate, estract, inclusion bodies, periplasmic space of the host cells, cytoplasm of the host cells, or other material by affinity chromatography.

In one embodiment of the invention non-natural amino acid polypeptides which are secreted into the medium can be obtained by centrifugation or filtration. These solutions may be suitable for direct application to chromatography columns. In another embodiment of the invention polypeptides which are accumulated intracellularly are extracted prior to purification by chromatography. In one embodiment polypeptides are extracted by cell disruption. Examples of cell disruption techniques include mechanical desintegrators, such as glass bead mills and high-pressure homoganizers. In another embodiment of the invention polypeptides are extracted by cell permeabilization. Examples of permeabilization agents include but are not limited to guanidine hydrochloride and Triton X-100. In addition to chemical permeabilization cells can be permeabilized by enzymatic lysis. The clarification of the cell homogenate or crude extract obtained after cell permeabilization can be done by centrifugation or by different filtration methods, such as microfiltration or ultrafiltration.

Purification tags have been developed to be applied in ion exchange, hydrophobic interaction, affinity, immunoaffinity, and metal-chelate chromatography. For example, hybrid polypeptides with a polyarginine tag can be purified by ion exchange chromatography, hybrid peptides with a polyphenylalanine tag can be isolated by hydrophobic interaction chromatography, hybrid peptides with a β-Galactosidase tag can be isolated by affinity chromatography, hybrid peptides with a protein A tag can be isolated by IgG-affinity chromatography, hybrid peptides with an antigenic tag can be isolated by immunoaffinity chromatography and hybrid peptides with a polyhistidine can be isolated by metal chelate chromatography. Tags may be removed by chemical or enzymatic means. In some embodiments, the tag is removed via an intramolecular reaction. A linker molecule may or may not be released.

Similarly, non-natural amino acids may be used to generate purification tags and hybrid polypeptides with these tags can be purified using chromatography or other techniques. In one embodiment, multiple non-natural amino acids are included at a terminus of the polypeptide. Purification of this polypeptide with multiple non-natural amino acids may be purified by affinity chromatography or by other means depending on the properties of the non-natural amino acids.

To conjugate polypeptides with multiple non-natural amino acid tags with another molecule, the following procedure may be performed. After the binding of the polypeptide to a resin that binds to the non-natural amino acid tag, a reaction is performed to conjugate the polypeptide to another molecule such as PEG. The conjugated product may be released from the resin as a result of the conjugation or after the conjugation is complete. The conjugation may be performed under denaturing conditions and refolding of the polypeptide may be performed on the resin. The second molecule may be conjugated to the polypeptide at a natural or non-natural amino acid present in the polypeptide. The second molecule may be conjugated to the polypeptide at a natural or non-natural amino acid present in the non-natural amino acid tag.

In another embodiment, the multiple non-natural amino acids included at a terminus of the polypeptide are metal-binding amino acids. Purification of this polypeptide may be performed using methods similar to those used for His-tagged proteins. In another embodiment, the polypeptide comprises two or more non-natural amino acids in that one or more non-natural amino acid is used to bind the polypeptide to a resin and the second non-natural amino acid is used to conjugate the polypeptide to another molecule, including but not limited to, PEG. Other materials useful in purification techniques may be used instead of resins. Tags may be removed by chemical or enzymatic means. In some embodiments, the tag is removed via an intramolecular reaction. A linker may or may not be released.

In another embodiment, a hybrid polypeptide may have a non-natural amino acid at the junction of the polypeptide and the tag. This non-natural amino acid may be used to separate the polypeptide from the tag by chemical cleavage, for example during or after the binding of the tag to a column. This non-natural amino acid may be used to separate the polypeptide from the tag by enzymatic cleavage or by an intramolecular chemical reaction.

In another embodiment, a "prodrug" type approach is used. A non-natural amino acid polypeptide is bound to a purification matrix, and a portion or all of the polypeptide is released after an event, including but not to, an intramolecular reaction, exposure to UV light (light activated molecule for release), chemical cleavage, or enzymatic cleavage.

In another embodiment a specific cleavage site at the junction between parts of a polypeptide could be introduced. This enables, for example, cleavage of the hybrid molecule to yield the protein of interest free of an affinity tag. Removal of a fusion sequence may be accomplished by enzymatic or chemical cleavage. To split off the affinity tag from the polypeptide of interest, a specific chemical or enzymatic cleavage site may be engineered into the fusion proteins. Enzymatic removal of fusion sequences may be accomplished using methods known to those of ordinary skill in the art. The choice of enzyme for removal of the fusion sequence will be determined by the identity of the fusion, and the reaction conditions will be specified by the choice of enzyme as will be apparent to one of ordinary skill in the art. Chemical cleavage may be accomplished using reagents known to those of ordinary skill in the art, including but not limited to, cyanogen bromide, TEV protease, and other reagents. Examples of cleavage reagents include but are not limited to, formic acid, hydroxylamine, collagenase, factor Xa, enterokinase, renin, carboxypeptidase A and carboxypeptidase B. The cleaved hGH polypeptide may be purified from the cleaved fusion sequence and cleavage reagents by methods known to those of ordinary skill in the art. Such methods will be determined by the identity and properties of the fusion sequence and the polypeptide, as will be apparent to one of ordinary skill in the art. Methods for purification may include, but are not limited to, size-exclusion chromatography, hydrophobic interaction chromatography, ion-exchange chromatography or dialysis or any combination thereof.

Figure 10:
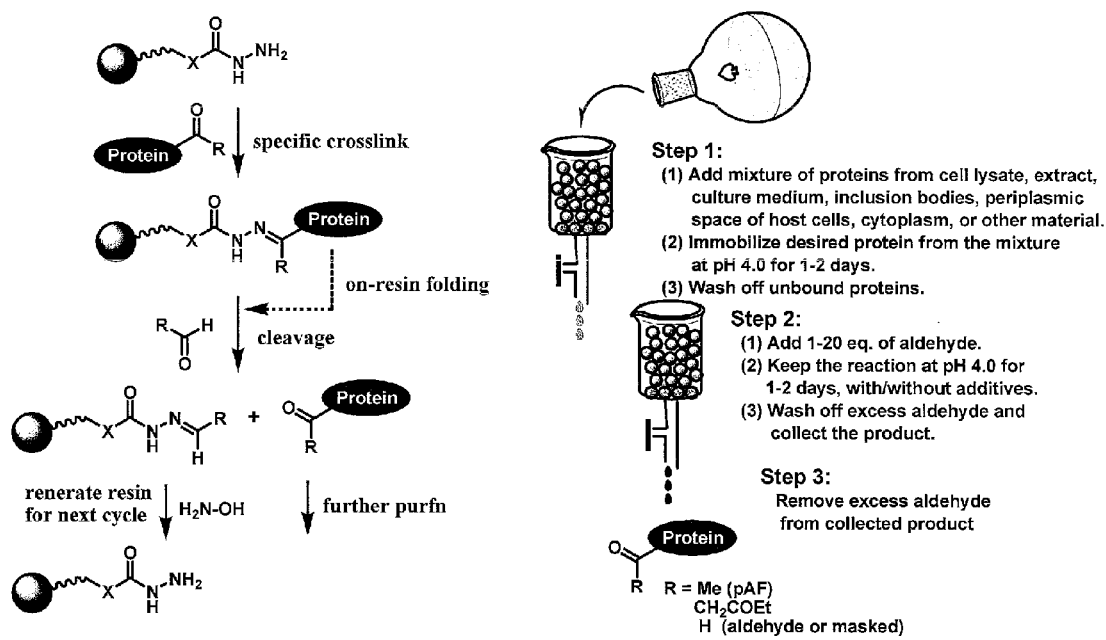
FIG. 10 shows an example of a purification method for a non-natural amino acid polypeptide utilizing a resin that reacts with the non-natural amino acid.
Figure 11:
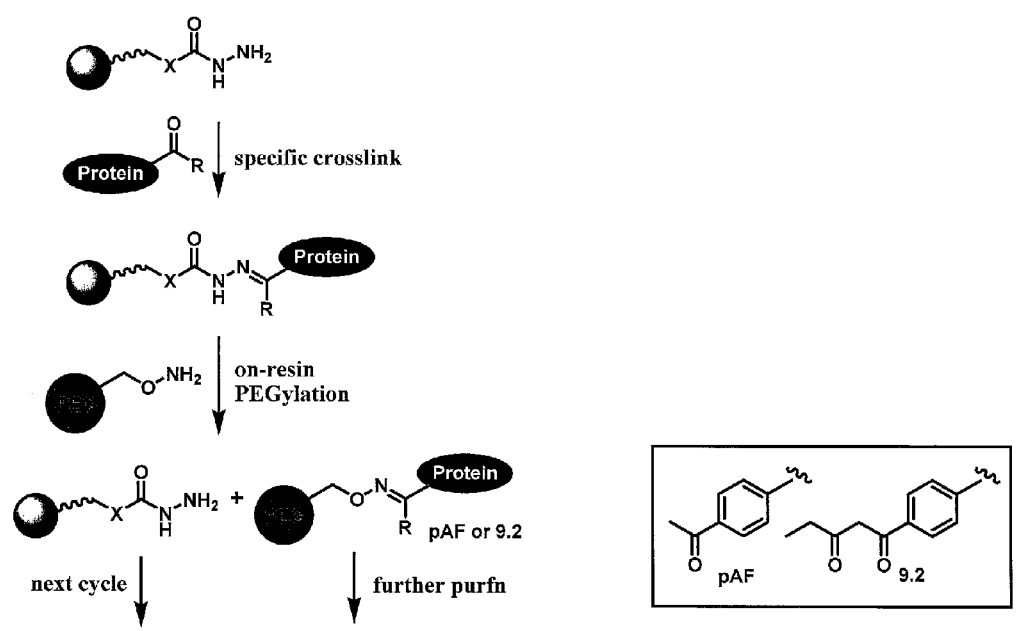
FIG. 11 shows an example of a method in which the purification of a non-natural amino acid polypeptide and conjugation of the polypeptide is performed in "one pot".
Figure 13:
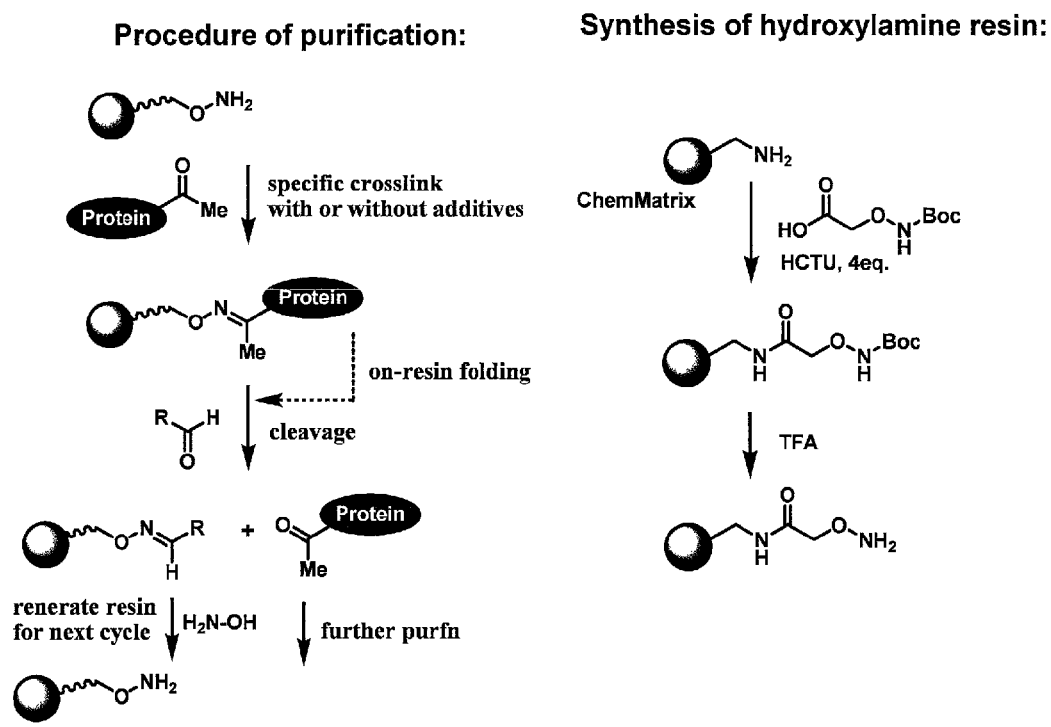
FIG. 13 shows an example of affinity purification of a non-natural amino acid polypeptide using hydroxylamine resin.

With an increasing number of protein and peptide therapeutics in development, there is a demand for an efficient, economic, and large-scale protein purification method that is not costly and difficult to scale up. Resins or other materials known to those skilled in the art may be used to isolate polypeptides. FIG. 10 shows an example of a purification method for a non-natural amino acid polypeptide utilizing a resin that reacts with the non-natural amino acid. A covalent linkage is formed between a chemically specific affinity tag on the resin and a non-natural amino acid present in the protein. Such linkages are stable under a broad range of pH and purification conditions. The separation step may be performed in alternate modes, including but not limited to a bath mode, enabling the large-scale purifications. The resin and the affinity tags are physically and chemically stable, and thus, can be reused to reduce the cost of protein purification upon scale-up. The separation can be performed in conjunction with conjugation of the polypeptide to molecules including but not limited to, PEG. This "one-pot" method further simplifies the conjugation process and reduces the cost of production of proteins, including but not limited to target therapeutic proteins (FIG. 11). Resins can be selected and functionalized according to the non-natural amino acid present in the polypeptide. FIG. 12 shows an example of resin selection and functionalization. Resins or other matrixes for purification can be functionalized with different functional groups depending on the non-natural amino acid in the polypeptide. For example, FIG. 13 shows an example of affinity purification of a non-natural amino acid polypeptide using hydroxylamine resin. FIG. 14 shows an example of purification of a non-natural amino acid polypeptide using an aldehyde resin. The ability to regenerate the matrix used in purification methods also provides advantages for large-scale production.

Figure 15:
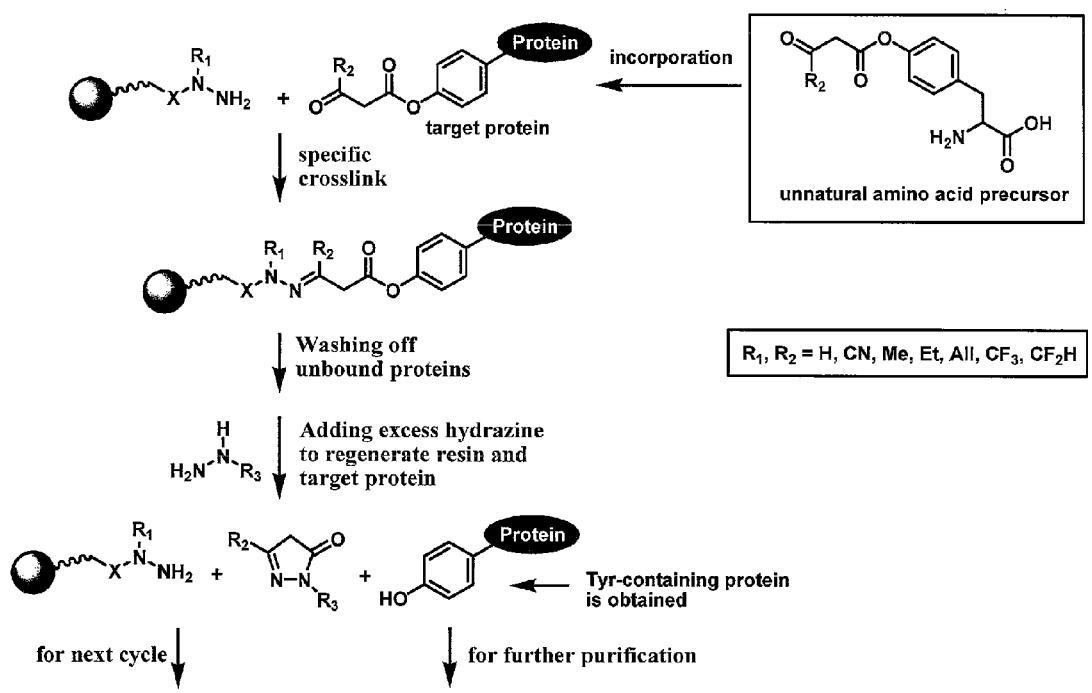
FIG. 15 shows an example of purification of native proteins from a non-natural amino acid precursor that is converted to tyrosine after cleavage.
Figure 16:
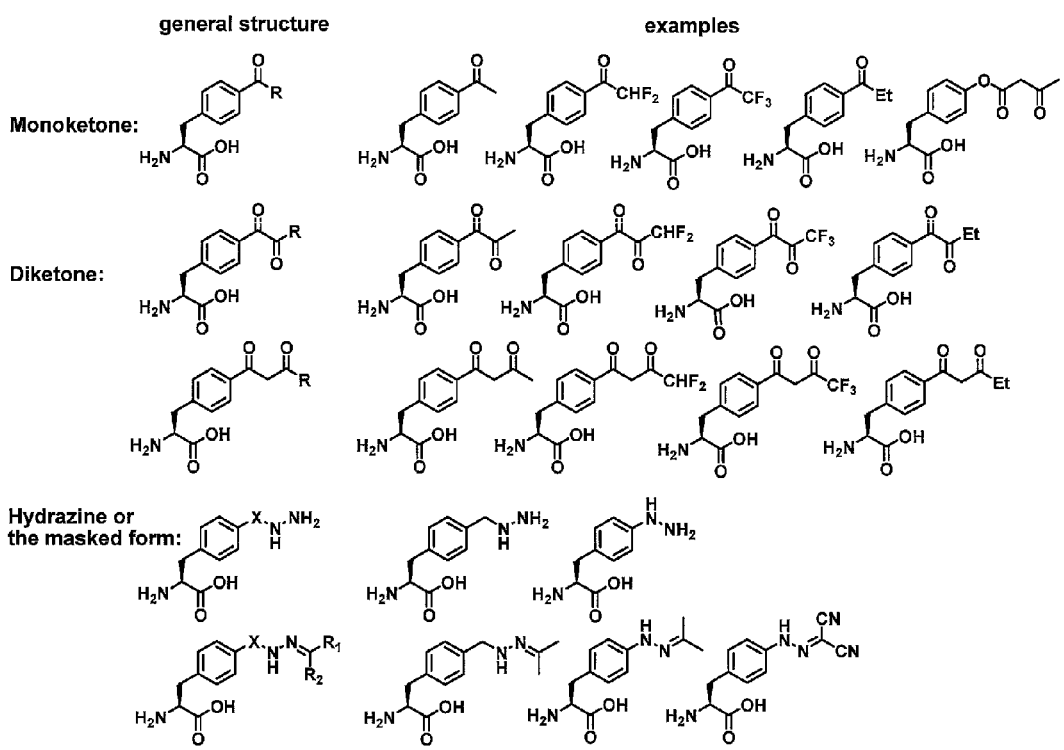
FIG. 16 shows non-limiting examples of non-natural amino acids.

In some embodiments, the purification process changes one or more non-natural amino acids present in the polypeptide to one or more natural amino acids. FIG. 15 shows an example of purification of native proteins from a non-natural amino acid precursor. The non-natural amino acid is converted to tyrosine after release from the resin used in the purification process. FIG. 16 shows non-limiting examples of non-natural amino acids.

Non-natural amino acids present in a set of two or more proteins may be used to purify complexes of polypeptides. The non-natural amino acids may be bonded to each other or joined via a linker, a polymer, or another molecule to enable purification of a complex of polypeptides. Polypeptides that may be isolated in this fashion include but are not limited to multiple subunit receptors or enzymes. Techniques used to isolate complexes may utilize one or more additional non-natural amino acids present in one or more of the polypeptides. Techniques for isolating large proteins are known to one of ordinary skill in the art. Dissociation of the polypeptide complex may be performed using one or more non-natural amino acids present in one or more of the polypeptides. One or more of the non-natural amino acids may be reacted with another molecule with a functional group that causes separation of the polypeptides in the complex.

In some embodiments, the polypeptides may form a complex due to non-covalent interactions that involve one or more non-natural amino acids present in the polypeptide.

In some embodiments, electro/chemical interaction such as electrical or magnetic fields may be used to purify polypeptides due to one or more non-natural amino acids present in the polypeptide. In other embodiments, single cell purification or isolation may be achieved using non-natural amino acid polypeptide.

XII. Library Screening

1. High Throughput Screening

The technological approaches for the screening process of the non-natural amino acids, non-natural amino acid polypeptides, modified non-natural amino-acid polypeptides and fragments thereof disclosed herein, include, but not limited to, multiwell-plate based screening systems, cell-based screening systems, microfluidics-based screening systems, and screening of soluble targets against solid-phase synthesized drug components.

Automated multiwell formats are developed high-throughput screening systems. Automated 96-well plate-based screening systems are widely used. The plate based screening systems can be made to reduce the volume of the reaction wells further, thereby increasing the density of the wells per plate. Other types of high-throughput assays, such as miniaturized cell-based assays can also be used in the present invention. Miniaturized cell-based assays have the potential to generate screening data of quality and accuracy, due to their in vivo nature. Microfluidics-based screening systems that measure in vitro reactions in solution make use of ten to several-hundred micrometer wide channels. Micropumps, electroosmotic flow, integrated valves and mixing devices control liquid movement through the channel network.

Libraries for screening can be grouped as, by way of example only, General Screening or Template-Based such as Groups with common heterocyclic lattices; Targeted such as Mechanism based selections, for example, Kinase Modulators, GPCR Ligands, Anti-infectives, Potassium Channel Modulators, and Protease Inhibitors; Privileged Structure such as Compounds containing chemical motifs that are more frequently associated with higher biological activity than other structures; Diversity such as Compounds pre-selected from available stock with maximum chemical diversity; Plant Extracts; Natural Products/Natural Product-Derived, etc.

A. Chemical Libraries

Combinatorial chemical libraries are a means to assist in the generation of new chemical compound leads. A combinatorial chemical library is a collection of diverse chemical compounds generated by either chemical synthesis or biological synthesis by combining a number of chemical "building blocks" such as reagents. Millions of chemical compounds can be synthesized through such combinatorial mixing of chemical building blocks. LogP, molecular weight, number of H-bond donors and acceptors, as set forth in the Lipinski "rule of five" requirements, help to determine strong candidates for drug-like characteristics. Lipinski "rule of five" requires the compound to have these properties: five or fewer hydrogen bond donors, molecular weight less than or equal to 500 Da, calculated LogP less than or equal to 5), and ten or fewer hydrogen bonding acceptors. High throughput screening technologies coupled with compound libraries obtained through combinatorial chemistry and/or high throughput synthesis methods can be utilized to rapidly identify and optimize ligands for non-natural amino acids, non-natural amino acid polypeptides, modified non-natural amino acid polypeptides and fragments thereof, as disclosed herein.

Chemical diversity libraries of organic compounds include, but are not limited to: benzodiazepines, diversomers such as hydantoins, benzodiazepines and, analogous organic syntheses of small compound libraries, oligomeric libraries such as peptide, N-alkyl glycine, polycarbamate and polyureas, oligocarbamates, and/or peptidyl phosphonates, carbohydrate libraries, chiral compound libraries, and small organic molecule libraries. A wide variety of heterocyclic compound libraries have been synthesized by solid phase methods. These include, by way of example only, benzodiazepins, pyrrolidines, hydantoins, 1,4-dihydropyridines, isoquinolinones, diketopiperazines, benzylpiperazines, quinolones, dihydro- and tetrahydroisoquinolines, 4-thiazolidinones, b-lactams, benzisothiazolones, pyrroles and imidazoles.

Combinatorial libraries of inorganic compounds include, but not limited to, (a) Oxides of metals and main group elements, including transition metal oxides such as zirconia, titania, manganese oxide, rare earth oxides such as ceria and lanthanum oxide; binary, ternary, and more complex solid state oxides and ceramic phases; various forms of alumina, silica, aluminosilicates and aluminophosphates; (b) Natural and synthetic forms of aluminosilicate and silicate zeolites such as ZSM-5, Beta, zeolite Y, and ferrierite, various forms of molecular sieves such as aluminophosphates and titanosilicates; natural or synthetic clays and related minerals such as kaolin, attapulgite, talc, montmorillonite, and Laponite®; (c) Non-oxide ceramics such as metal carbides and nitrides; (d) Various forms of carbons such as activated carbon, carbon molecular sieves, graphite, fullerenes, carbon nanotubes, and carbon black; (e) Various organic polymers, oligomers, or resins, such as polyethylene, polypropylene, polystyrene, polyamides, halo hydrocarbon polymers, polyesters, etc.; (f) Metals such as precious metals and/or transition metals deposited, mixed with, or exchanged into any support such as any of the materials described in (a)-(e) above. Examples of such phases include Pt/alumina, Pd/alumina, and Cu-ZSM-5.

B. Biological Libraries

Peptide library by using microorganisms—Antibodies and immune cell receptors of the immune system are representative biological libraries. In the immune system, all the processes of library design, synthesis, and optimization are controlled by the organism itself. Only structures of antigens and genetic information to form embryonic factors are external conditions, but the rest is controlled spontaneously by internal factors. Because the immune system uses protein structure libraries, they are libraries using amino acids as basic factors. Because peptides or proteins made of amino acids are the first products of synthesis by translating genetic information, through genetic engineering technologies, proteins of desired sequences can be easily obtained by inserting modified genetic information into microorganisms like bacteria or virus. Microorganism library synthesis brings several advantages. It is possible to clone microorganisms to make only one kind of proteins per microorganism, and even though only one cell is acquired, the number of clones can be easily increased by cell multiplication. The other advantage of using microorganisms is that they can self-propagate whenever there is enough supply. After synthesizing a DNA strand that makes the desired protein sequence, its complementary strand is synthesized, by enzymes if needed. For synthesized DNA to replicate and translate properly in microorganisms, it needs to be packed with vector and inserted into microorganisms. Proteins expressed on the surface of the microorganism, and to find desired proteins is the next step.

To make library various genetic information is needed. Random DNA synthesis or cutting cDNA or the whole genomic DNA of a particular organism can be used. A portion of DNA sequence that makes particular protein can be modified to make mutated protein library. Considering volume limitations and expression rates of microorganism incubation, $10^9$ (one billion) kinds of libraries can be made. Compared to $10^6$ to $10^7$ kinds of synthesis libraries, it is a huge number. The number of 5-unit peptides is $20^5$ (3.2 millions), that of 6-unit ones is 64 millions, and for 7-unit peptides the number passes one billion. Therefore, if more than 7 amino acids are changed incomplete library that does not contain all the possible combinations is made. For long proteins, 7 different amino acids can be selected separately and replaced. When DNA is randomly synthesized, DNA codes can be repeated and designate the same amino acid, and generation frequency changes. Therefore, to make all the possible combinations, much more quantities of clones are required.

A linear combinatorial biological library such as a polypeptide library is formed by combining a set of chemical building blocks called amino acids in every possible way for a given compound length (i.e., the number of amino acids in a polypeptide compound). The proteins may be members of a protein family such as a receptor family (examples: growth factor receptors, catecholamine receptors, amino acid derivative receptors, cytokine receptors, lectins), ligand family (examples: cytokines, serpins), enzyme family (examples: proteases, kinases, phosphatases, ras-like GTPases, hydrolases), transcription factors (examples: steroid hormone receptors, heat-shock transcription factors, zinc-finger, leucine-zipper, homeodomain), HIV proteases or hepatitis C virus (HCV) proteases, and antibody or antibody fragment (Fab, for example). Other examples are, such as, peptoids, encoded peptides, random biooligomers, dipeptides, vinylogous polypeptides, nonpeptidal peptidomimetics with Beta D Glucose scaffolding, antibody libraries, and peptide nucleic acid libraries.

Bacteriophage library—It is one of a number of protein library methods. Bacteriophage is living in a host bacterium and a kind of virus with genetic materials and capsids. M13 and Lambda viruses are the most famous.

A M13 is a thin, long virus and due to its small genome size, numerous libraries can be made easily. Different from other viruses, it can come out to outside of host cells without damaging them or inhibiting their growth. It is known that M13 amplifies its genetic information in the host cell and wears the capsid when emerging. It makes 10 kinds of proteins and pVIII and pIII capsids are commonly used in library synthesis among them. A pVIII protein surrounds the whole body and has about 50 amino acids. Usually 2700 per a virus are expressed. Because its amino end protrudes toward outside of the capsid, it can be modified to express a different peptide on it. Usually a long peptide cannot be expressed, but it is possible for 6-unit peptides. Because large amount of the same library molecules are expressed at the same time, in spite of its relatively short size, it is appropriate for a reaction with various ligands. A pIII protein is expressed at the end of a virus, and usually 3 to 5 proteins of 406 amino acids are expressed. It can express quite large proteins so that it is used for the whole protein or antibody molecule libraries. A normal antibody uses Fab, an antigen recognition region, or a Fvs chain. Bacteriophage Library and hybridoma are the most famous methods to make antibodies. M13 is ideal to make random peptide libraries and the virus is stable enough to be precipitated and concentrated so that screening $10^9$ libraries in a volume of 1-10 µL is possible.

Different from the M13, a Lambda virus coats itself with a capsid in the cytoplasm and comes out of its host cell when there is an enough number, instead of wearing a capsid when emerging. In other words, if a different protein is expressed, it will probably emerge in a folded shape with proper functions. A pV and D proteins are commonly used for the library synthesis. As proteins that can be expressed on a bacteriophage surface, there are random peptide, natural protein fragments, mutated particular protein libraries, and partial antibody fragments and they are used for chromatography materials, protein-protein mutual reactions, receptor binding site searching, and drug discoveries.

Phage display is a widely utilized technique to make peptide libraries. These peptide libraries are useful for screening to identify peptides that have a particular desired activity, such as binding to another polypeptide or other molecule. In phage display the peptide library is fused to a bacteriophage protein, typically a coat protein, that is displayed on the surface of the phage. The library of peptide bearing phage is contacted with an immobilized binding partner, such as a cell surface or a purified protein, and specific binders are then isolated. Phage display techniques and libraries are described in U.S. Pat. Nos. 5,580,717, 5,702,892, 5,750,344, 5,821,047, 5,962,255, 6,140,471, 6,475,806, 5,427,908, 5,667,988, 5,733,743, 5,750,373, 5,824,520, 6,096,551, 6,225,447, 6,492,160, which are incorporated in their entirety by reference herein. U.S. Pat. No. 5,750,373, which is incorporated by reference herein, describes a method for selecting novel proteins such as growth hormone and antibody fragment variants having altered binding properties for their respective receptor molecules. The method comprises fusing a gene encoding a protein of interest to the carboxy terminal domain of the gene III coat protein of the filamentous phage M13.

Bacteria and yeast libraries—Not only viruses with capsids, but also bacteria with cell walls and membranes can be used for library expression as well. Both the gram-positive bacteria and gram-negative bacteria can be used to express proteins on cell surfaces, and *E. coli*, a gram-negative bacterium, is commonly used. Bacteria library can find an antigen that strongly binds to a certain antibody and use it as a vaccine, or it can express diagnostic antibodies or receptor libraries for analysis of particular materials.

It is called translational modification that the higher animal's protein is modified by phosphorylation or sugar addition after the protein synthesis. But a bacterium, a prokaryote, does not have such a function, and when even a protein is synthesized, it either precipitates due to its bad solubility or is inactivated in most cases. Therefore, *S. cerevisiae*, a eukaryote, is used. Even though *S. cerevisiae* is unicellular like bacteria, it has translational modification function and very similar proteins to the original can be made.

Different from viruses, it has a micron size cell so that FACS (fluorescence-activated cell sorting) can be used. Fluorescence labeled target molecules are added to the library of proteins expressed on a cell surface and flow through thin tubes of FACS machine. FACS sorts each cells by fluorescent colors and intensities as alive. It is possible to screen different target molecules with different colors and also possible to sort cells of different intensities and selectivity. Another advantage is a liquid-phase screening. It is not necessary to separate strongly clung molecules. Sorted cells multiply again and they are re-screened.

Yeast surface display techniques are also widely utilized to product and display peptide libraries. Yeast surface display may be utilized in combination with fluorescence activated cell sorting to select cells displaying the desired peptides. Yeast surface display techniques and libraries are described in U.S. Pat. Nos. 6,083,693, 6,406,863, 6,410,271, 6,232,074, 6,410,246, 6,610,472, which are incorporated in their entirety by reference herein.

Bacterial surface display has been used in a variety of forms to display peptides on the cell surface or in the periplasm. A variety of bacterial hosts are available for use in this system, as are a variety of polypeptide anchoring domains to anchor the displayed peptide to the cell surface. Bacterial surface display techniques and libraries are described in U.S. Pat. Nos. 5,348,867, 5,866,344, 6,277,588, 5,635,182, 6,180,341, which are incorporated in their entirety by reference herein.

Other in vivo systems are utilized to make libraries of polypeptides and identify changes in activities, such as target protein binding modulation, resulting from changes in amino acid sequences. Examples of in vivo systems include, but are not limited to, the yeast two hybrid system (Schneider, S et al., Nat. Biotechnol., 17, 170-175 (1990)), and the dihydrofolate reductase protein-fragment complementation assay (Pellitier, N. J. et al., Nat. Biotechnol., 17, 683-690, (1990)), which are hereby incorporated by reference herein.

Bio-panning—A synthesized microorganism library may be used to find a peptide that binds to a particular molecule with high affinity.

Target molecules, such as non-natural amino acids, non-natural amino acid polypeptides, modified non-natural amino acid polypeptides and fragments thereof as disclosed herein, may be evenly placed on a test plate. The prepared microorganism library may be added to the plate. Only the microorganisms that strongly bind to the target molecules will remain and the rest will be in the solution. After a while, unbound microorganisms may be discarded, and then weakly or accidentally bound microorganisms may be washed with appropriate solutions. The target molecule's binding affinity determines the washing process. Still remaining microorganisms can be taken apart by addition of low pH or high concentrated target molecules, and the quantity is amplified by re-incubation. Sometimes it may be difficult to separate them without killing bacteria when the affinity is too strong. If it is a bacteriophage, instead of separation, one can infect its host cell directly. Because there still can be some undesired microorganisms bound accidentally, the first amplified microorganisms may go through repeated screening and amplification processes to increase the number of clones containing active proteins. Finally after they are incubated in low concentration, each clone may be separated and usually tens of clones may be selected and used for DNA sequence analysis. It is successful if peptide structures from DNA information are recognizable and most of clones show accord peptide sequences. However, because proteins can have toxicity up to kinds of clones and DNA expression rate can vary, there may be a possibility that faster multiplying and well-expressed clones are selected than desired screening results. Therefore, a confirmation step is necessary by measurement of peptide synthesis and binding affinity.

The microorganism protein library technology fundamentally uses a living organism's self-reproduction ability. That is, by amplifying (feeding) a small quantity of obtained candidate molecules, one can increase purity and quantity.

Ribosome display—Ribosome display and mRNA display techniques are also widely utilized to make peptide libraries. Ribosome display and mRNA display are in vitro techniques that couple the mRNA encoding a peptide to the encoded peptide either on the ribosome or by using puromycin. Ribosome display and mRNA display techniques and libraries are described in U.S. Pat. Nos. 6,416,950, 6,436,665, 6,602,685, 6,660,473, 6,429,300, 6,489,116, 6,623,926, 6,589,741, 6,348,315, 6,207,446, 6,258,558, 6,416,950, 6,440,695, 6,228,994, 6,281,344, 6,429,300, 6,660,473, 5,580,717, 5,688,670, 6,238,865, 6,261,804, 6,518,018, 6,281,344, 6,258,558, 6,214,553, which are incorporated in their entirety by reference herein.

DNA, RNA library—Development of PCR, DNA amplification technology, has enabled using nucleic acids as libraries. Because DNA and RNA are made of 4 units, 10 oligomers have 410 (about $10^6$=a million) kinds and 20 oligomer library can have about 1012. By using automated solid-phase DNA synthesizer, 5' end and 3' end are fixed in a sequence and A, T, C, and G are randomly placed as each take about 25% of the sequence. When one strand is made, it may be replicated by using enzymes or amplified by PCR. Commonly about 1014-15 molecules are made and used, but occasionally there are about 40 places (1024 kinds) for random introduction, sometimes they start with incomplete set of library. For DNA library, DNA themselves are simply used, but for RNA library, T7 RNA Polymerase is needed to transcript.

Prepared libraries are sorted by target molecule binding screening; amplified by PCR for DNA and by RT-PCR for RNA. Non-natural aminoacids, non-natural amino acid polypeptides, modified non-natural amino acid polypeptides and fragments thereof as disclosed herein, can be used as target molecules. Screening and amplification of the amplified library is repeated until the beginning number of $10^{14-15}$ is narrowed to several hundreds, and then sequences of acquired candidate molecules are analyzed and each binding affinity is measured. Such acquired DNA and RNA are called aptamers, and they show strong affinity toward protein target molecules. The aptamer inhibits the target molecule's function in vivo, but it is quickly destroyed by in vivo nucleases. To solve the problem, some parts of library are substituted with artificial nucleic aids to increase resistance against nucleases.

Few examples of biological libraries include, but not limited to, Bioactive Lipid Library; Endocannabinoid Library-compounds having activity at cannabinoid (CB) and vanniloid (VR) receptors which includes various classes of ligands, for example, Amides, Ethanolamides, Lipo-amino acids, Acyl-GABAs, and Acyl-dopamines etc.; Known Bioactives Library, such as, GPCR ligands, second messenger modulators, nuclear receptor ligands, actin & tubulin modulators, kinase inhibitors, protease inhibitors, ion channel blockers, gene regulation agents, lipid biosynthesis inhibitors, etc.; Ion Channel Ligand Library; Kinase/Phosphatase Inhibitor Library; Natural Products Library-Natural products are an unsurpassed source of chemical diversity and are an ideal starting point for any screening program for pharmacologically active small molecules; Neurotransmitter Library-CNS Receptor Ligands, such as, Adrenergics, Dopaminergics, Serotonergics, Opioids (& Sigma ligands), Cholinergics, Histaminergics (& Melatonin Ligands), Ionotropic Glutamatergics, Metabotropic Glutamatergics, GABAergics, and Purinergics (& Adenosines) etc.; Nuclear Receptor Ligand Library-Nuclear Receptor Ligand Library contains compounds with at nuclear receptors. Receptor agonists and antagonists may be included; Orphan Ligand Library-Orphan ligand library contains compounds with biological activity but whose protein binding partners have not been identified. For example, trace Amines, neurotransmitter metabolites, endogenouse β-carbolines, urinary metabolites, nicotine congeners, and D-Amino Acids etc.

2. Methods of Screening

The present invention provides methods to identify candidate agents that bind to a protein or act as a modulator of the binding characteristics or biological activity of a protein. Assays may be conducting in a variety of ways including screening a library of non-natural amino acid polypeptides with a known molecule or vice versa. In one embodiment, the method is performed in single test tubes or on a modest scale. In another embodiment, the method is performed in plurality simultaneously. For example, the method can be performed at the same time on multiple assay mixtures in a multi-well screening plate. Thus, in one aspect, the invention provides a high throughput screening system. With regards to assaying for interactions in one embodiment, fluorescence or absorbance readouts are utilized to determine activity. Other biological activities to assays by way of example only are acetylation, carboxylation, acylation, phosphorylation, dephosphorylation, ubiquitination, glycosylation, lipid modification, ADP-ribosylation, bioavailability and half-life.

There are many methods known to those skilled in the art which can also be used to detecting interaction between a non-natural amino acid polypeptide and another molecule within a screening assay. These methods may include by way of example only, fluorescent bind-binding assays, thermal shift assays, electrophoretic mobility shift assays, protein-protein binding assays, biochemical screening assays, immunoassays (i.e. immunoprecipitation) and cell based assays (i.e. two- or three-hybrid screens, GST pull down, TAP-TAG system), expression assays, protein-DNA binding assays, functional assays (phosphorylation assays, etc.) and the like. See, e.g., U.S. Pat. No. 6,495,337, incorporated herein by reference. Other methods may also include protein chip systems which can screen enzymes, receptor proteins or antibodies which aid conducting protein-protein interaction studies, ligand binding studies, or immunoassays (MacBeath and Schreiber, *Science* 2000 289: 1760-1763). Another embodiment may involve, profiling drug which can effect in intact cells, that are introduced with functional non-natural amino acid polypeptides, by probing the cell physiology using fluorescent stains for DNA and other proteins known to interact with the non-natural amino acid polypeptide and using fluorescent microscopes generated pictures so as to measure changes in the cells' behavior (Mayer, T. U., Kapoor, T. M., Haggarty, S. J., King, R. W., Schreiber, S. L., Mitchison, T. J. (1999). *Science*. 286, 971-4.)

In particular, there are numerous methods by which detection of binding of a test ligand to a non-natural amino acid polypeptide (and, thus, by which identification of a ligand of the non-natural amino acid polypeptide) can be carried out. Useful methods are those by which the folded non-natural amino acid polypeptide can be distinguished from unfolded non-natural amino acid polypeptide. The methods described below are by way of example only some of the means by which this can be done. In each case, the detection method is carried out on a test combination (test ligand-non-natural amino acid polypeptide combination) after sufficient time has passed for binding of a non-natural amino acid polypeptide to its ligand and on a control combination (which is the same as the test combination except that no test ligand is present).

A. Methods for Determining the Presence of Folded Non-Natural Amino Acid Polypeptide In the present method, a test ligand may be combined with a non-natural amino acid polypeptide for which a ligand (i.e., an agent which binds the non-natural amino acid polypeptide) is to be identified. The resulting combination is a test ligand-non-natural amino acid polypeptide combination or test combination. In general, the test ligand is present in excess molar amounts, relative to the non-natural amino acid polypeptide. The present method can be carried out in solution or, in some embodiments of the method, the non-natural amino acid polypeptide can be present on a solid phase (e.g., linked covalently through a linker or otherwise to a bead). The test ligand and non-natural amino acid polypeptide are combined under conditions (e.g., temperature, pH, salt concentration, time) appropriate for binding of the non-natural amino acid polypeptide to a ligand. In addition, conditions under which test ligand and non-natural amino acid polypeptide are combined are generally such that, for non-natural amino acid polypeptide that unfolds reversibly, a substantial fraction of non-natural amino acid polypeptide is present in the absence of the test ligand in the unfolded form, although the fraction can vary, depending on the detection method used. In the case of non-natural amino acid polypeptide which unfold irreversibly, conditions are generally such that the non-natural amino acid polypeptide unfolds at a substantial rate in the absence of ligand. These conditions are chosen to ensure that the non-natural amino acid polypeptide unfolds to an appropriate extent; thus, the observed signal (e.g., digestion by a protease; binding to antibody, chaperonin or surface) can be measured conveniently. If too little non-natural amino acid polypeptide is unfolded, the observed signal will occur at too low a level or rate to be conveniently measured. For each test ligand-non-natural amino acid polypeptide combination assessed, the conditions under which the present method is carried out will be determined empirically, using known methods. Such conditions include reaction temperature and the chaotropic agent(s) or denaturant(s) used. The temperature at which the method is carried out is determined by the non-natural amino acid polypeptide being used and can be determined empirically using known methods. To adjust or optimize the fraction of unfolded non-natural amino acid polypeptide, denaturing conditions may be required for some non-natural amino acid polypeptide. Such denaturing conditions might include the use of elevated temperatures, the addition of protein denaturants (e.g., urea, guanidine) to the incubation mixture or use of both. In addition, the stability of some non-natural amino acid polypeptide might be adjusted through engineering destabilizing or stabilizing amino acid substitutions in the non-natural amino acid polypeptide. The test ligand and non-natural amino acid polypeptide are combined, maintained under appropriate conditions and for sufficient time for binding of the non-natural amino acid polypeptide to a ligand. The time necessary for binding of non-natural amino acid polypeptide to ligand will vary depending on the test ligand, non-natural amino acid polypeptide and other conditions used. In some cases, binding will occur instantaneously (e.g., essentially simultaneous with combination of test ligand and non-natural amino acid polypeptide), while in others, the resulting test ligand-non-natural amino acid polypeptide combination is maintained for a longer time before binding is detected. In the case of non-natural amino acid polypeptide which unfolds irreversibly, the rate of unfolding must also be taken into consideration in determining an appropriate time for binding of test ligand. Binding of a test ligand to the non-natural amino acid polypeptide is assessed in one of several ways: by determining the extent to which folded non-natural amino acid polypeptide is present in the test ligand-non-natural amino acid polypeptide combination; by determining the extent to which unfolded non-natural amino acid polypeptide is present in the test ligand-non-natural amino acid polypeptide combination or by determining the ratio of folded non-natural amino acid polypeptide to unfolded non-natural amino acid polypeptide in the combination. That is, the difference between the amount of folded non-natural amino acid polypeptide, the amount of unfolded non-natural amino acid polypeptide or the ratio of folded non-natural amino acid polypeptide to unfolded non-natural amino acid polypeptide in the presence of the test ligand and in its absence is determined. If a test ligand binds the non-natural amino acid polypeptide (i.e., if the test ligand is a ligand for the non-natural amino acid polypeptide), there will be more folded non-natural amino acid polypeptide and less unfolded non-natural amino acid polypeptide (and, thus, a higher ratio of folded to unfolded non-natural amino acid polypeptide and a lower ratio of unfolded to folded non-natural amino acid polypeptide) than is present in the absence of a test ligand which binds the non-natural amino acid polypeptide. It is not necessary to determine the quantity or fraction of a folded and unfolded non-natural amino acid polypeptide. It is only necessary to know that there is a difference in the amount of folded or unfolded protein (a change in equilibrium of the two forms) in the presence and absence of a ligand or a change in the rate of unfolding. This difference can be determined by comparing the extent to which folded and/or unfolded non-natural amino acid polypeptide is present in a test combination (test ligand-non-natural amino acid polypeptide combination) With the extent to which they are present in a control combination (non-natural amino acid polypeptide in the absence of test ligand). Alternatively, for reversible unfolding, the difference between the extent to which the two forms occur in the absence of a test ligand can be assessed by determining their occurrence initially (e.g., prior to addition of a test ligand to a solution of non-natural amino acid polypeptide or to solid support-bound test protein) and then after the test ligand has been combined with the non-natural amino acid polypeptide under conditions appropriate for non-natural amino acid polypeptide-ligand binding to occur. In either case, determination of the two forms of non-natural amino acid polypeptide can be carried out using a variety of known methods, which are described below. A test ligand which is shown by the present method to bind a non-natural amino acid polypeptide is referred to as a ligand of the non-natural amino acid polypeptide.

1. Determining Ligand Binding Using Proteolysis

In one embodiment of the present method, binding of test ligand to non-natural amino acid polypeptide is detected through the use of proteolysis. In this embodiment, a protease which acts preferentially upon unfolded non-natural amino acid polypeptide is combined with the test ligand-non-natural amino acid polypeptide combination (test combination) and the resulting test combination-protease mixture is assayed after an appropriate period of incubation, using one of the methods described in detail below, to determine the difference between intact or degraded non-natural amino acid polypeptide in the presence and in the absence of the test ligand. An identical assay is performed on a test ligand-non-natural amino acid polypeptide combination and on a control combination and results of the two assays are compared. More intact protein or less degraded protein in the test combination than in the control combination indicates that the test ligand has bound the non-natural amino acid polypeptide and, thus, indicates that the test ligand is a ligand of the non-natural amino acid polypeptide. Similarly, a higher ratio of intact non-natural amino acid polypeptide to degraded protein in the test combination than in the control indicates the test ligand is a ligand of the non-natural amino acid polypeptide.

A wide variety of proteases, such as trypsin, chymotrypsin, V8 protease, elastase, carboxypeptidase, proteinase K, thermolysin and subtilisin, can be used in this embodiment. It is only necessary that the protease used be able to act upon (hydrolyze the peptide bonds of) the non-natural amino acid polypeptide used under the chosen incubation conditions and that this action be preferentially directed toward the unfolded form of the protein. To avoid interference by target ligands which directly inhibit the protease, more than one protease can be used simultaneously or in parallel assays.

In order to be efficiently digested the peptide bonds, the peptide substrate—the non-natural amino acid polypeptide—must have access to the enzyme active site of the chosen protease. Because the atoms in a folded protein molecule are tightly packed, the majority of the susceptible peptide bonds are sterically blocked from entering a protease active site when the protein is in the folded state. In the unfolded state, the peptide bonds are more exposed and are therefore relatively more susceptible to protease action.

Consequently, the addition of a test ligand which binds the folded non-natural amino acid polypeptide, stabilizing it in the protease-resistant form, changes the rate of proteolysis. Thus, by incubating the test ligand with the non-natural amino acid polypeptide, adding a protease to preferentially degrade the unfolded proteins, and then employing an assay to quantify the intact or the degraded non-natural amino acid polypeptide, it is possible to ascertain whether the test ligand bound the non-natural amino acid polypeptide and, thus, is a ligand of the non-natural amino acid polypeptide, indicating that it is potentially therapeutically useful.

Alternatively, the protease may be intrinsic to the unpurified or partially purified non-natural amino acid polypeptide sample.

2. Determining Ligand Binding Through Detection of Surface Binding

In another embodiment of the present method, the propensity of unfolded proteins to adhere to surfaces is utilized. This embodiment relies on the fact that folded proteins are held in specific three dimensional arrangements and, thus, are not as likely as their unfolded counterparts to bind a surface. If a test ligand binds a non-natural amino acid polypeptide (i.e., is a ligand of the non-natural amino acid polypeptide), it will stabilize the folded form of the non-natural amino acid polypeptide. Thus, the ability of a test ligand to bind a non-natural amino acid polypeptide can be determined by assessing the extent to which non-natural amino acid polypeptide is bound to an appropriate solid surface in the presence and in the absence of the test ligand. The methods described in detail below can be used for this purpose.

In this embodiment, the non-natural amino acid polypeptide, a test ligand and a surface that preferentially binds unfolded protein are combined and maintained under conditions appropriate for binding of the non-natural amino acid polypeptide to a ligand and binding of unfolded non-natural amino acid polypeptide to the surface. There are numerous suitable surfaces for this purpose, including microtiter plates constructed from a variety of treated or untreated plastics, plates treated for tissue culture or for high protein binding, nitrocellulose filters and PVDF filters.

If a test ligand binds the non-natural amino acid polypeptide, more folded non-natural amino acid polypeptide and less unfolded non-natural amino acid polypeptide is present in the test ligand-non-natural amino acid polypeptide combination than is present in a comparable control combination. That is, in the presence of a test ligand that is a ligand for a non-natural amino acid polypeptide, less unfolded protein is available to bind a surface that preferentially binds unfolded protein than in the absence of a ligand for the non-natural amino acid polypeptide. Determination of the amount of surface-bound non-natural amino acid polypeptide or the amount of non-natural amino acid polypeptide remaining in solution can be carried out using one of the methods described below. If more non-natural amino acid polypeptide is not surface bound (i.e., if more non-natural amino acid polypeptide is in solution) in the presence of a test ligand than in the absence of the test ligand, the test ligand is a ligand of the non-natural amino acid polypeptide. The ratio of non-natural amino acid polypeptide in solution to surface-bound non-natural amino acid polypeptide is greater if a test ligand is a ligand for the non-natural amino acid polypeptide than if it is not. Conversely, the ratio of surface-bound non-natural amino acid polypeptide to non-natural amino acid polypeptide in solution is less if a test ligand is a ligand for the non-natural amino acid polypeptide than if it is not.

3. Determining Ligand Binding Using Antibody Binding

In a third embodiment, the extent to which folded and unfolded non-natural amino acid polypeptide are present and, thus, binding of test ligand to non-natural amino acid polypeptide, are assessed through the use of specific antibodies directed against only the unfolded state ("denatured-specific antibodies" or "DS antibodies") or only the folded state ("nature specific antibodies" or "Nantibodies"). When a non-natural amino acid polypeptide is in the folded state, and stabilized in that state by test ligand which is a ligand for the non-natural amino acid polypeptide, the DS antibody's apparent binding affinity will be reduced (Breyer, (1989) "Production and Characterization of Mono-clonal Antibodies to the N-terminal Domain of the Lambda Repressor", *J. Biol. Chem.*, 264(5):13348-13354) and that of the NS antibody will be enhanced. If DS antibody binding to non-natural amino acid polypeptide is less or if NS antibody binding is greater in the presence of a test ligand than in its absence the test ligand is a ligand for the non-natural amino acid polypeptide.

There are numerous methods known in the art for producing antibody that binds to a particular protein (Harlow, E. & D. Lane, ANTIBODIES: A LABORATORY MANUAL, Cold Spring Harbor Laboratory, 1988, incorporated herein by reference). To prepare antibody specific for the denatured state, animals can be immunized with a peptide from a region of the protein that is buried in the native state. If the structure of the protein is unknown, antibodies can be prepared against several peptides and then the antibodies can be screened for preferential binding to the denatured state. Antibody production is by standard techniques, such as the technique for production of mono-clonal antibodies described in detail in Zola, Monoclonal Antibodies: A Manual of Techniques, CRC Press, Inc., Boca Raton, Fla. (1987), incorporated herein by reference.

There are at least three basic methods by which DS or NS antibodies can be utilized to detect a ligand-induced change in the occurrence of folded non-natural amino acid polypeptide, the occurrence of unfolded proteins or the ratio of one to the other.

In one approach, a test solution containing the DS antibody directed against the unfolded non-natural amino acid polypeptide, the non-natural amino acid polypeptide, and the test ligand is incubated, such as in a microtiter plate coated with the denatured non-natural amino acid polypeptide or a peptide fragment thereof, under conditions appropriate for binding of the non-natural amino acid polypeptide with its ligand and binding of the DS antibody to unfolded non-natural amino acid polypeptide. A control solution, which is the same as the test solution except that it does not contain test ligand, is processed in the same manner as the test solution. By comparing the amount of antibody bound to the plate or the amount remaining in solution in the test and control solutions, the difference in non-natural amino acid polypeptide folding is detected. The amount of antibody bound to the plate or remaining in solution can be measured as described below.

In a second approach, a test solution containing the DS antibody, the test ligand, and the non-natural amino acid polypeptide is incubated in a plate coated with a second antibody, referred to as a solid phase antibody, which cannot bind to the non-natural amino acid polypeptide simultaneously with the DS antibody, and is specific for the non-natural amino acid polypeptide, but is either specific for the folded state ("native specific" or "NA antibody") or unable to differentiate between the native and denatured states ("non-differentiating" or "ND antibody"). The resulting test combination or solution is maintained under conditions appropriate for binding of the non-natural amino acid polypeptide with a ligand of the non-natural amino acid polypeptide and for binding of the antibodies to the proteins they recognize (are specific for). A control solution, which is the same as the test solution except that it does not contain test ligand, is processed in the same manner as the test solution. In both solutions, denatured (unfolded) non-natural amino acid polypeptide binds the DS antibody and is inhibited from binding the solid phase antibody. The ability of the test ligand to bind the non-natural amino acid polypeptide can be gauged by determining the amount of non-natural amino acid polypeptide that binds to the solid phase antibody in the test solution and comparing it with the extent to which non-natural amino acid polypeptide binds to the solid phase antibody in the absence of test ligand, which in turn reflects the amount of non-natural amino acid polypeptide in the folded state. The amount of non-natural amino acid polypeptide bound to the plate via the second antibody or remaining in solution can be detected by the methods described below. This approach may be used in a comparable manner with NS antibody as the in solution antibody and DS or ND antibody on the solid phase.

In a third approach, a test solution containing the non-natural amino acid polypeptide and the test ligand is incubated in a container, such as a microtiter well which has been coated with a DS or NS antibody and maintained under conditions appropriate for binding of non-natural amino acid polypeptide to its ligand and for binding of the antibody to non-natural amino acid polypeptide. Alternatively, the antibody can be present on the surfaces of beads. The ability of the test ligand to bind the non-natural amino acid polypeptide is gauged by determining the extent to which non-natural amino acid polypeptide remains in solution (unbound to the antibody) or on the solid surface (bound to the antibody), or the ratio of the two, in the presence and in the absence of test ligand. If the test ligand binds the non-natural amino acid polypeptide (is a ligand of the non-natural amino acid polypeptide), there will be less non-natural amino acid polypeptide bound to a DS antibody or more bound to an NS antibody (i.e., more non-natural amino acid polypeptide will be in solution in the case of DS antibody or less in solution for NS antibody) than is bound to the antibody in the control solution. In a further embodiment, the antibody can be present in solution and the non-natural amino acid polypeptide can be attached to a solid phase, such as a plate surface or bead surface.

4. Determining Ligand Binding Using Molecular Chaperones

In a fourth embodiment, molecular chaperones are used to determine binding of a test ligand to a non-natural amino acid polypeptide. Chaperones are a variety of protein that bind unfolded proteins as part of their normal physiological function. They are generally involved in assembling oligomeric proteins, in ensuring that certain proteins fold correctly, in facilitating protein localization, and in preventing the formation of proteinaceous aggregates during physiological stress. Hardy, (1991) "A Kinetic Partitioning Model of Selective Binding of Nonnative Proteins by the Bacterial Chaperone SecB", *Science* 251:439-443 These proteins have the ability to interact with many unfolded or partially denatured proteins without specific recognition of defined sequence motifs.

One molecular chaperone, found in *E. coli*, is SecB. SecB has a demonstrated involvement in export of a subset of otherwise unrelated proteins. Competition experiments have shown that SecB binds tightly to all the unfolded proteins tested, including proteins outside of its particular export subset, but does not appear to interact with the folded protein.

In this embodiment, a test solution containing the test ligand and the target is incubated on a microtiter plate or other suitable surface coated with molecular chaperones, under conditions appropriate for binding of non-natural amino acid polypeptide with its ligand and binding of the molecular chaperones used to unfolded non-natural amino acid polypeptide. The unfolded non-natural amino acid polypeptide in the solution will have a greater tendency to bind to the molecular chaperone-covered surface relative to the ligand-stabilized folded non-natural amino acid polypeptide. Thus, the ability of the test ligand to bind non-natural amino acid polypeptide can be determined by determining the amount of non-natural amino acid polypeptide remaining unbound, or the amount bound to the chaperone-coated surface, using the methods detailed below.

Alternatively, a competition assay for binding to molecular chaperones can be utilized. A test solution containing purified non-natural amino acid polypeptide, the test ligand, and a molecular chaperone can be incubated in a container, such as a microtiter well coated with denatured (unfolded) non-natural amino acid polypeptide, under conditions appropriate for binding non-natural amino acid polypeptide with its ligand and binding of the molecular chaperones to unfolded non-natural amino acid polypeptide. A control solution which is the same as the test solution except that it does not contain test ligand is processed in the same manner. Denatured non-natural amino acid polypeptide in solution will bind to the chaperonin and, thus, inhibit its binding to the denatured non-natural amino acid polypeptide bound to the container surface (microtiter well surface). Binding of a test ligand to non-natural amino acid polypeptide will result in a smaller amount of unfolded non-natural amino acid polypeptide, and, thus, more chaperones will be available to bind to the solid-phase denatured non-natural amino acid polypeptide than is the case in the absence of binding of test ligand. Thus, binding of test ligand can be determined by assessing chaperones bound to the surface or in solution in the test solution and $i_D$ the control solution and comparing the results. Binding of chaperone to solid-phase denatured non-natural amino acid polypeptide to a greater extent in the test solution than in the control solution is indicative of test ligand-non-natural amino acid polypeptide binding (i.e., is indicative of identification of a ligand of the non-natural amino acid polypeptide). In this assay, the molecular shaperones are generally not provided in excess, so that competition for their binding can be measured.

Alternatively, test solution containing the non-natural amino acid polypeptide, the test ligand and a molecular chaperone can be incubated in a container, such as a microtiter well, whose surface is coated with antisera or a monoclonal antibody specific for the folded non-natural amino acid polypeptide (NS antibody) and unable to bind the non-natural amino acid polypeptide bound to the chaperone. Unfolded non-natural amino acid polypeptide will bind chaperone in solution and thus be inhibited from binding the solid phase antibody. By detecting non-natural amino acid polypeptide in the solution or bound to the well walls and comparing the extent of either or both in an appropriate control (the same combination without the test ligand), the ability of the test ligand to bind non-natural amino acid polypeptide can be determined. If the test ligand is a ligand for the non-natural amino acid polypeptide, more non-natural amino acid polypeptide will be bound to the antisera or monoclonal antibody bound to the container surface in the test solution than in the control solution. Conversely, less non-natural amino acid polypeptide will be present unbound (in solution) in the test solution than in the control solution. Detection and comparison of bound non-natural amino acid polypeptide, unbound non-natural amino acid polypeptide or a ratio of the two in the test solution and control solution indicate whether the test ligand is a ligand of the non-natural amino acid polypeptide or not.

5. Determining Ligand Binding Through Measurements of Protein Aggregation

The higher the fraction of protein in the folded form, the greater the amount of protein that is available to bind to a ligand that binds exclusively to the folded state. Consequently, if a protein has a known ligand, it is possible to increase the binding of the protein to the known ligand by adding a ligand that binds another site on the protein. In this approach, a ligand known to bind to the non-natural amino acid polypeptide is immobilized on a solid substrate. A solution containing the non-natural amino acid polypeptide is then added, along with test ligand or ligands. An increase in the amount of non-natural amino acid polypeptide that binds to the immobilized ligand relative to an identical assay in the absence of test ligand indicates that the test ligand binds the non-natural amino acid polypeptide. The amount of non-natural amino acid polypeptide bound to the solid substrate can be assessed by sampling the solid substrate or by sampling the solution, using the detection methods outlined below.

6. Determining Ligand Binding Through Measurements of Protein Aggregation

For proteins that unfold irreversibly, unfolded protein often forms insoluble aggregates. The extent of protein aggregation can be measured by techniques outlined below such as light scattering, centrifugation, and filtration. In this approach, non-natural amino acid polypeptide and test ligand are incubated and the amount of protein aggregation is measured over time or after a fixed incubation time. The extent of protein aggregation in the test mixture is compared to the same measurement for a control assay in the absence of test ligand. If a test ligand binds a non-natural amino acid polypeptide, the rate of unfolding of non-natural amino acid polypeptide will be lower than in the absence of test ligand. For measurements over time, the rate of increase of unfolded protein and hence of aggregated protein will be lower if the test ligand is a ligand for the non-natural amino acid polypeptide than if it is not. For measurements at a fixed time, there will be less unfolded protein add therefore less aggregated protein if the test ligand is a ligand for the non-natural amino acid polypeptide than if it is not. Thus, the ability of a test ligand to bind a non-natural amino acid polypeptide can be determined by assessing the extent of protein aggregation in the presence and absence of test ligand.

XIV. Protein Detection Techniques

Figure 1A:
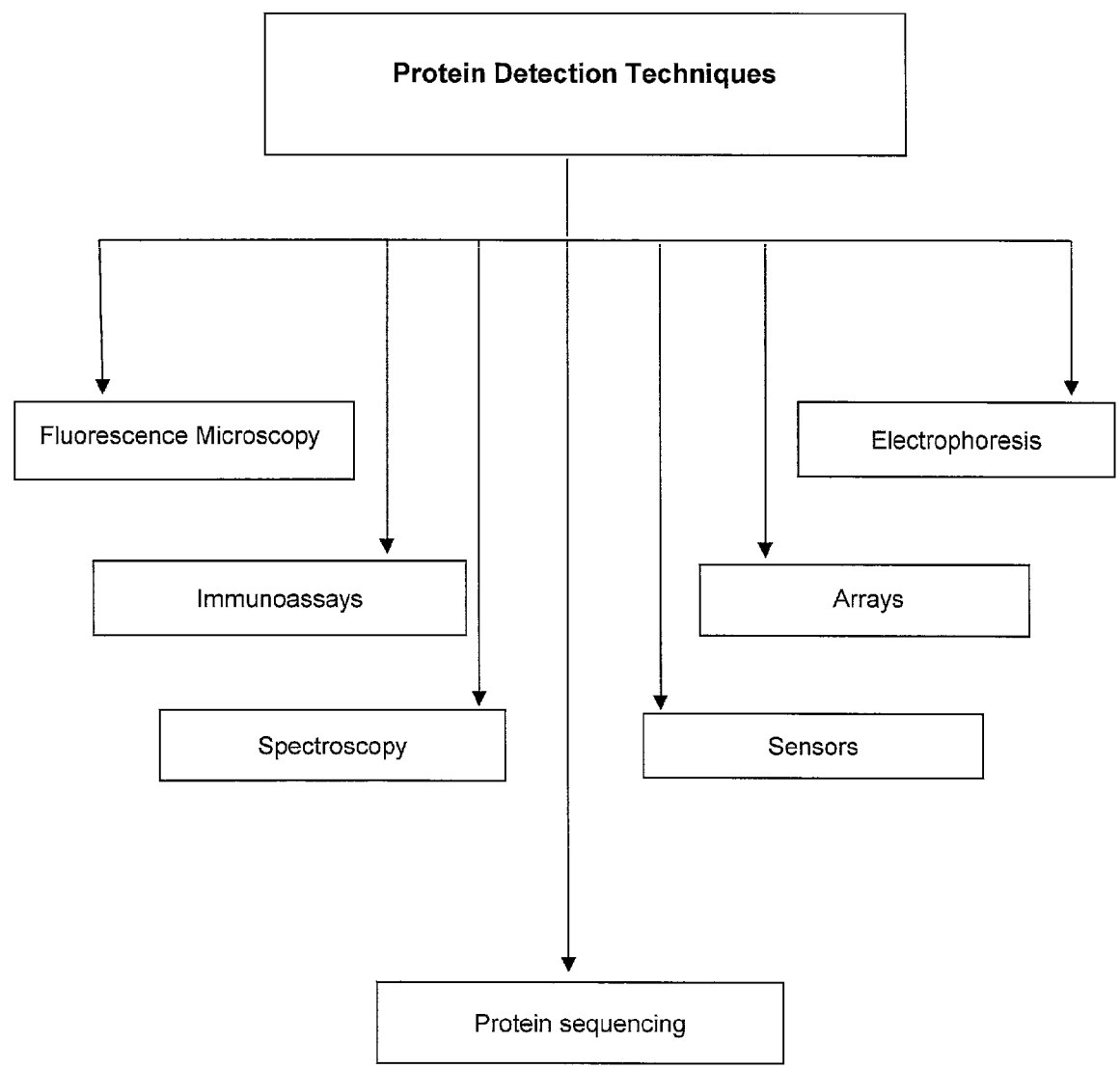
FIG. 1a presents various protein detection techniques.

Methods known in the art to detect the presence or absence of protein, small peptides or free amino acids can be used in the present method for detecting non-natural amino acids, non-natural amino acid polypeptides, modified non-natural amino acid polypeptides and fragments thereof. The method used can be determined by the product (proteins, peptides, free amino acids) to be detected. For example, techniques for detecting protein size can be used to determine the extent of proteolytic degradation of the non-natural amino acid polypeptide. Radio-labeling, fluorescence labeling, and enzyme-linked labeling can detect the presence or absence either in solution or on a substrate by measurement of radioactivity, fluorescence or enzymatic activity. Immunologic methods can detect the presence or absence of a known non-natural amino acid polypeptide in solution or on a substrate such as by binding of an antibody specific for that protein. FIG. 1a presents various protein detection techniques that can be used to detect non-natural amino acids, non-natural amino acid polypeptides, modified non-natural amino acid polypeptides and fragments thereof.

A. Fluoroscence Microscopy

Methods for protein detection disclosed herein, include fluorescence microscopy to detect non-natural amino acids, non-natural amino acid polypeptides, modified non-natural amino acid polypeptides and fragments thereof. Fluorescence Microscopy is a widely used microscopy technique that enables the molecular composition of the structures being observed to be identified through the use of fluorescently-labelled probes of high chemical specificity. Such probes may be antibodies, antibody fragments, or antigen-binding polypeptides that comprise a non-natural amino acid. Fluorescence microscopy may be used in studies of fixed specimens. For proteins that can be extracted and purified in reasonable abundance, a fluorophore may be conjugated to a protein and the conjugate introduced into a cell. A fluorophore may be conjugated to a non-natural amino acid in the polypeptide. It is assumed that the fluorescent analogue behaves like the native protein and can therefore serve to reveal the distribution and behavior of this protein in the cell. Along with NMR, infrared spectroscopy, circular dichroism and other techniques, protein intrinsic fluorescence decay and its associated observation of fluorescence anisotropy, collisional quenching and resonance energy transfer are key techniques for protein detection.

Measuring the fluorescence decay allows the dynamics of structural changes in a protein to be observed directly. Moreover, excitation of the native fluorescence of proteins emanating from the amino acids tyrosine and tryptophan eliminates the possibility of perturbation of the local environment when using extrinsic fluorescent probes.

A development in the use of fluorescent probes for biological studies has been the use of naturally fluorescent proteins as fluorescent probes. Naturally occurring dyes, so-called fluorescent proteins (GFP, YFP, CFP, TOPAS, GFT, RFP), were discovered in the late 1990s (Clonetech, USA). These dyes are distinguished by their reduced influence on specimens. They are therefore particularly suitable for labeling cell regions in living preparations.

The jellyfish *Aequorea victoria* produces a naturally fluorescent protein known as green fluorescent protein (GFP). The fusion of these fluorescent probes to a target protein enables visualization by fluorescence microscopy and quantification by flow cytometry. Because they are genetically encoded and require no auxiliary cofactors, GFP tags can be used to analyze protein expression and localization in living cells and whole organisms. The gene for this protein has been cloned and can be transfected into other organisms. GFP tags may be used for localizing regions in which a particular gene is expressed in an organism, or in identifying the location of a particular protein. In many cases these chimeric proteins preserve their original function. It is therefore often possible, for example, to use this technique to visualize the intracellular distribution of a protein, including but not limited to a cytoskeletal protein. With GFP, unstained or unfixed samples can be observed. There are presently several variants of GFP which provide spectrally separable emission colors. Mutations to GFP have resulted in blue-, cyan- and yellow-fluorescent light emitting versions. Fluorescent proteins which can be used to label the present non-natural amino acid peptides, polypeptides, antibodies, and antibody fragments include but are not limited to, green fluorescent protein (GFP), cyan fluorescent protein (CFP), red fluorescent protein (RFP), yellow fluorescent protein (YFF), enhanced GFP (EGFP), enhanced YFP (EYFP), and the like. New versions of GFP have been developed via mutation, including a "humanized" GFP DNA, the protein product of which has increased synthesis in mammalian cells (see Cormack, et al., (1996) Gene 173, 33-38; Haas, et al., (1996) Current Biology 6, 315-324; and Yang, et al., (1996) Nucleic Acids Research 24, 4592-4593). One such humanized protein is "enhanced green fluorescent protein" (EGFP). GFP, variants of GFP, or other naturally occurring dyes may be coupled to non-natural amino acid polypeptides.

GFP can be used as a biosensor, reporting the results of levels of ions or pH by fluorescing in characteristic ways. One molecule that can be used to sense the level of zinc ions is a blue fluorescent protein shown as PDB (Protein Data Bank) entry 1kys. The protein fluoresces twice as brightly creating an easily detectable visible signal once zinc binds to the modified chromophore. Construction of other peptide and protein biosensors comprising a non-natural amino acid may exhibit altered fluorescence properties in response to changes in their environment, oligomeric state, conformation upon ligand binding, structure, or direct ligand binding. Appropriately labeled fluorescent biomolecules allow spatial and temporal detection of biochemical reactions inside living cells. See for example Giuliano, K. A., et al., *Annu. Rev. Biophys. Biomol Struct.* 1995, 24:405-434; Day, R. N. *Mol. Endocrinol.* 1998, 12:1410-9; Adams, S. R., et al., *Nature* 1991, 349:694; Miyawaski, A., et al., *Nature* 1997, 388:882-7; Hahn, K., et al., *Nature* 1992, 359:736; Hahn, K. M., et al., *J. Biol. Chem.* 1990, 265:20335; and Richieri, G. V., et al., *Mol. Cell. Biochem.* 1999, 192:87-94. U.S. Pat. No. 6,951,947, which is incorporated by reference herein, discusses biosensors and fluorophores that detect environmental changes.

At present the technology is driven by new applications of existing probes and the design and synthesis of new and innovative probes. Without limiting the scope of the present invention, some of the probes are as following:

Labels: Sensitivity and safety (compared to radioactive methods) of fluorescence has been increasingly used for specific labelling of nucleic acids, proteins and other biomolecules. Besides Fluorescein, there are other fluorescent labels that cover the whole range from 400 to 820 nm. By way of example only, some of the labels include, but are not limited to, Fluorescein and its derivatives, Carboxyfluoresceins, Rhodamines and their derivatives, Atto labels, Fluorescent red and Fluorescent orange: Cy3/Cy5™ alternatives, Lanthanide complexes with long lifetimes, Long wavelength labels—up to 800 nm, DY cyanine labels, Phycobili proteins. Fluorescent molecules that are capable of absorbing radiation at one wavelength and emitting radiation at a longer wavelength include but are not limited to Alexa-532, Hydroxycoumarin, Aminocoumarin, Methoxycoumarin, Coumarin, Cascade Blue, Lucifer Yellow, P-Phycoerythrin, R-Phycoerythrin, (PE), PE-Cy5 conjugates, PE-Cy7 conjugates, Red 613, Fluorescein, BODIPY-FL, BODIPY TR, BODIPY TMR, Cy3, TRITC, X-Rhodamine, Lissamine Rhodamine B. PerCP, Texas Red, Cy5, Cy7, Allophycocyanin (APC), TruRed, APC-Cy7 conjugates, Oregon Green, Tetramethylrhodamine, Dansyl, Dansyl aziridine, Indo-1, Fura-2, FM 1-43, DilC18(3), Carboxy-SNARF-1, NBD, Indo-1, Fluo-3, DCFH, DHR, SNARF, Monochlorobimane, Calcein, N-(7-nitrobenz-2-oxa-1,3-diazol-4-yl) amine (NBD), ananilinonapthanele, deproxyl, phthalamide, amino pH phthalamide, dimethylamino-naphthalenesulfonamide, probes comparable to Prodan, Lordan or Acrylodan and derivatives thereof. Coumarin fluorescent dyes include, for example, amino methylcoumarin, 7-diethylamine-3-(4'-(1-maleimidyl)phenyl)-4-methylcoumarin (CPM) and N-(2-(1-maleimidyl)ethyl)-7-diethylaminocoumarin-3-Carboxamide (MDCC). Other useful molecules include those that display fluorescence resonance energy transfer (FRET). Many such donor-acceptor pairs are known, and include fluorescein to rhodamine, coumarin to fluorescein or rhodamine, etc. Still another class of useful label pairs includes fluorophore-quencher pairs in which the second group is a quencher, which decreases the fluorescence intensity of the fluorescent group. Some known quenchers include acrylamide groups, heavy atoms such as iodide and bromate, nitroxide spin labels such as TEMPO, etc. Labels such as these may be conjugated to non-natural amino acid polypeptides.

Fluorophores that are be conjugated to a non-natural amino acid polypeptide may fluoresce all of the time or only when the polypeptide is bound to a target. Other types of fluorophores include Conjugates: By way of example only, some of the conjugates include but are not limited to, Isothiocyanate conjugates, streptavidin conjugates, and Biotin conjugates. Antibody conjugates have been widely used to track biomolecules in living cells and whole organisms They can be generated with specificity for virtually any epitope and are therefore, in principle, applicable to imaging a wide range of biomolecules. Conjugates including but not limited to antibody conjugates may comprise a non-natural amino acid.

Enzyme Substrates: Enzyme substrates include but are not limited to fluorogenic and chromogenic substrates.

Micro- and Nanoparticles: Various techniques allow the preparation of a wide variety of fluorescent microspheres ranging in size, matrix chemistry, type of fluorochrome, fluorescence intensity, and surface functional groups. By way of example only, some of the fluorochromes used are: FITC (green fluorescence, Excitation/Emission=506/529 nm), Rhodamine B (orange fluorescence, Excitation/Emission=560/584 nm), Nile Blue A (red fluorescence, Excitation/Emission=636/686 nm)

Fluorescent nanoparticles are promising tools for both optical data storage and other technical applications, for example, in biochemical, bioanalytical and medical areas. Current medical and biological fluorescent imaging methods are mainly based on dye markers, which are limited in light emission per molecule, as well as photostability. Nanoparticles overcome those problems offering strong and stable fluorescence. Fluorescent nanoparticles have been successfully used for various types of immunoassays. Fluorescent nanoparticles are based on different materials, such as, polyacrylonitrile, and polystyrene, etc.

Molecular Rotors: Fluorescent Molecular Rotors are sensors of microenvironmental restriction that become fluorescent only if their rotation is constrained. The change of fluorescence intensity is caused by the restriction of intramolecular rotational relaxation about the donor-acceptor bond of the fluorophores. Examples of molecular constraint include but are not limited to increased dye (aggregation), binding to antibodies, or being trapped in the polymerization of actin.

IEF-Markers: IEF (Isoelectric Focusing) is a powerful analytical tool for the separation of ampholytes, mainly proteins. In order to ensure the high performance of analysis, standards of pI (pI markers) are needed. An advantage for IEF-Gel electrophoresis with Fluorescent IEF-Marker is the possibility to directly observe the formation of gradient. Fluorescent IEF-Marker can also be detected by UV-absorption at 280 nm (20° C.).

Any or all of these fluorescent probes can be used for the detection of non-natural amino acids, non-natural amino acid polypeptides, modified non-natural amino acid polypeptides and fragments thereof. FIG. 9 presents non-limiting examples of molecules that are site specifically attached to proteins through oxime formation between carbonyl of non-natural amino acid incorporated into a polypeptide and the hydroxylamine of the molecule. The molecules shown are fluorophores, biotin, and chelators.

Bio-Orthogonal Chemical reporters: Small molecules have better access to intracellular and extravascular compartments. Their use as imaging agents requires a means to selectively target the small probe to a desired biomolecule. Nucleophilic functionality occurs in most types of biopolymers, permitting facile derivatization with biotin, fluorophores and numerous other small-molecule reporters. Established bioconjugation protocols have made these operations trivial for purified biopolymers in vitro. It is an alternative strategy for tagging biomolecules that blends the simplicity of genetically encoded tags with the specificity of antibody labeling and the versatility of small-molecule probes. This approach involves the incorporation of unique chemical functionality—a bioorthogonal chemical reporter—into a target biomolecule using the cell's own biosynthetic machinery. Bioorthogonal chemical reporters are non-native, non-perturbing chemical handles that can be modified in living systems through highly selective reactions with exogenously delivered probes. This two-step labeling process can be used to outfit a target biomolecule for detection or isolation, depending on the nature of the probe.

Examples of bio-orthogonal coupling reactions include but are not limited to, the Staudinger ligation of azides with triaryl phosphines, the ketone/aldehyde-hydrazine reaction, and Huisgen's 1,3-dipolar azide-alkyne cycloaddition. Replacement of the bulky fluorescent tag with a sterically inconspicuous azide group may furnish probes that are more able to distribute in an unbiased manner within a living cell, tissue, or organism. Likewise, the variable and often antagonistic effect of the fluorescent tag on probe binding affinity for specific proteins is also eliminated. Finally, the use of azide-alkyne cycloaddition chemistry can streamline probe synthesis by removing the need to generate and purify large quantities of structurally diverse fluorophore-tagged reagents. Coupling reactions utilizing non-natural amino acid polypeptides may provide probes that are alternatives to fluorescently tagged polypeptides. Huisgen's 1,3-dipolar azide-alkyne cycloaddition may be used to attach other molecules or provide other methods for polypeptide purification or detection.

Peptide libraries can be synthesized on solid supports and, by using coloring receptors, dyed solid supports can be selected one by one. If receptors cannot indicate any colors, their binding antibodies can be dyed. Because it is possible to separate solid supports by tweezers under microscopes or even magnifiers, the method can be not only be used on protein receptors, but also on screening binding ligands of synthesized artificial receptors and screening new metal binding ligands as well. This method is useful to search new lead compounds, because it enables the screening of a large amount of compounds.

However, determination of activity depending on dye intensity may not be accurate, and large amount of solid supports may not be always treated one by one. Therefore, automated methods for high throughput screening (HTS) are required and a FACS (Fluorescence Activated Cell Sorter) method can be used. This machine originally runs cells through a capillary tube and separates cells by detecting their fluorescent intensities. The same method may be used on solid supports instead of cells. Because it is designed for cells, small resins of cell size may be run, but normal sizes of solid supports (50~200 pmol) need specially modified machines. Partial or entire isolation of compounds may also be done. For partial isolation of compounds, time controlled photodecomposition or several functional groups to cleave in different conditions are used. In the meanwhile, one can scatter solid supports on soft agar and isolate some of compounds by photodecomposition. The isolated compounds then spread out around solid supports so that screening and solid support separation can be done at a time.

B. Immunoassays

Methods for protein detection disclosed herein, include immunoassays to detect non-natural amino acids, non-natural amino acid polypeptides, modified non-natural amino acid polypeptides and fragments thereof. Immunoassays combine the principles of chemistry and immunology enabling scientific tests, e.g. enzyme immunoassays and immunoblotting for a specific and sensitive detection of the analytes (non-natural amino acids, non-natural amino acid polypeptides, modified non-natural amino acid polypeptides and fragments thereof) of interest. The basic principle of these assays is the specificity of the antibody-antigen reaction. Similar to the Western blot, a single protein can be identified by its antibody with immunoblotting. Competitive binding immunoassays may be done in which analyte competes with a labelled antigen for a limited pool of antibody molecules (eg. radioimmunoassay, EMIT). Immunoassays can be non-competitive such that antibody is present in excess and is labelled. As analyte antigen is increased, the amount of labeled antibody-antigen complex also increases (e.g. ELISA). Antibodies can be polyclonal if produced by antigen injection into experimental animal, or monoclonal if produced by cell fusion and cell culture techniques. In immunoassays the antibody serves as a specific reagent for the analyte antigen. The antigen may be non-natural amino acid polypeptides, modified non-natural amino acid polypeptides and fragments thereof). On the other hand, the antibodies or fragments thereof used in immunoassays may be non-natural amino acid polypeptides, and may be used in the detection of antigens that may or may not comprise a non-natural amino acid.

Without limiting the scope and content of the present invention, some of the types of immunoassays are, by way of example only, RIAs (Radioimmunoassay) and enzyme immunoassays like ELISA (Enzyme-linked immunosorbent assay), EMIT (Enzyme Multiplied Immunoassay Technique), Microparticle Enzyme Immunoassay (MEIA), LIA (luminescent immunoassay), and FIA (fluorescent immunoassay). These techniques can be used to detect non-natural amino acids, non-natural amino acid polypeptides, modified non-natural amino acid polypeptides and fragments thereof. The antibodies—either used as primary or secondary antibodies—may be labeled with radioisotopes (e.g. $^{125}$I), fluorescent dyes (e.g. FITC) or enzymes (e.g. HRP or AP) which catalyze fluorogenic or luminogenic reactions.

1. EMIT (Enzyme Multiplied Immunoassay Technique)

EMIT is a competitive binding immunoassay that avoids a separation step. A type of immunoassay in which the protein is labeled with an enzyme, and the enzyme-protein-antibody complex is enzymatically inactive, allowing quantitation of unlabeled protein.

2. ELISA (Enzyme Linked Immunosorbent Assay)

Methods for protein detection disclosed herein, include ELISA to detect non-natural amino acids, non-natural amino acid polypeptides, modified non-natural amino acid polypeptides and fragments thereof. Enzyme linked immunosorbent assays are based on selective antibodies attached to solid supports combined with enzyme reactions to produce systems capable of detecting low levels of proteins. It is also known as enzyme immunoassay or EIA. The antigen, including but not limited to a protein, is detected by antibodies that have been made against it; that is, for which it is the antigen. Monoclonal antibodies are often used.

The test may require the antibodies to be fixed to a solid surface, such as the inner surface of a test tube; and a preparation of the same antibodies coupled to an enzyme. The enzyme is one (e.g., β-galactosidase) that produces a colored product from a colorless substrate. The test, for example, is performed by filling the tube with the antigen solution (e.g., protein) to be assayed. Any antigen molecules present may bind to the immobilized antibody molecules. The antibody-enzyme conjugate is added to the reaction mixture. The antibody part of the conjugate binds to any antigen molecules that were bound previously, creating an antibody-antigen-antibody "sandwich". After washing away any unbound conjugate, the substrate solution is added. After a set interval, the reaction is stopped (e.g., by adding 1 N NaOH) and the concentration of colored product formed by reaction of the substrate with molecules conjugated to the secondary antibody is measured in a spectrophotometer. The intensity of color is proportional to the concentration of bound antigen.

ELISA can also be adapted to measure the concentration of antibodies, in which case, the wells are coated with the appropriate antigen. The solution (e.g., serum) containing antibody is added. After it has had time to bind to the immobilized antigen, an enzyme-conjugated anti-immunoglobulin is added, consisting of an antibody against the antibodies being tested for. After washing away unreacted reagent, the substrate is added. The intensity of the color produced is proportional to the amount of enzyme-labeled antibodies bound (and thus to the concentration of the antibodies being assayed).

3. Radioimmunoassays

Methods for protein detection disclosed herein, include radioimmunoassays to detect non-natural amino acids, non-natural amino acid polypeptides, modified non-natural amino acid polypeptides and fragments thereof. Radioimmunoassays are highly sensitive. Using antibodies of high affinity (eg., $K_0=10^8-10^{11}$ $M^{-1}$), it is possible to detect a few picograms (10-12 g) of antigen in the tube.

Radioactive isotopes can be used to study in vivo metabolism, distribution, and binding of small amount of compounds. Radioactive isotopes of $^1H$, $^{12}C$, $^{31}P$, $^{32}S$, $^{127}I$ are used such as $^3H$, $^{14}C$, $^{32}P$, $^{35}S$, $^{125}I$. Radioactive isotopes have almost same chemical properties as unradioactive ones, so that they can be converted easily. Also because their radiation energy is relatively large, only a little amount is needed.

Receptor Fixation Method—For a 96 well plate format, receptors are fixed in each well by using antibody or chemical methods, and radioactive labeled ligands are added to each well to induce binding. Unbound ligands are washed out and then the standard is determined by the quantitative analysis of the radioactivity of bound ligands or that of washed-out ligands. The addition of target compounds for screening induces competitive binding reactions with receptors. If target compounds show higher affinity to receptors than standard radioactive ligands, most of the radioactive ligands do not bind to receptors and are left in solution. Therefore, by analyzing the quantity of bound radioactive ligands (or washed-out ligands), the affinity of target compounds to receptors can be easily indicated.

A filter membrane method may be used when receptors cannot be fixed to 96 well plates or ligand binding must be performed in solution phase. With this method, after the ligand-receptor binding reaction is done in solution, the reaction solution is filtered through nitrocellulose filter paper. Small molecules including ligands will go through the filter paper, and only protein receptors will be left on the paper. Only ligands that are strongly bound to receptors will stay on the filter paper, and the relative affinity of added compounds can be identified by quantitative analysis of the standard radioactive ligands. This method can also be used to screen protein kinase inhibitors as well. In this case, $\gamma$-$^{32}$P-ATP can be used as a phosphoric acid group supplier, and by checking radioactive labeled protein substrate, enzymatic activity can be analyzed. Radioactive ATP that does not react will be filtered and removed.

By way of example only, radioimmunoassays can be performed by preparing a mixture of radioactive antigen and antibodies against that antigen. Iodine atoms can be introduced into tyrosine residues in a protein, the radioactive isotopes $^{125}$I or $^{131}$I are often used. Known amounts of unlabeled ("cold") antigen can be added to samples of the mixture. These compete for the binding sites of the antibodies. At increasing concentrations of unlabeled antigen, an increasing amount of radioactive antigen is displaced from the antibody molecules. The antibody-bound antigen is separated from the free antigen in the supernatant fluid, and the radioactivity of each is measured. From these data, a standard binding curve can be drawn. The samples to be assayed ("the unknowns") are run in parallel. After determining the ratio of bound to free antigen in each unknown, the antigen concentrations can be read directly from the standard curve.

Other methods of radioimmunoassays that can be used for detecting non-natural amino acids, non-natural amino acid polypeptides, modified non-natural amino acid polypeptides and fragments thereof are, by way of example only, precipitating the antigen-antibody complexes by adding a "second" antibody directed against the first. For example, if a rabbit IgG is used to bind the antigen, the complex can be precipitated by adding an anti-rabbit-IgG antiserum (e.g., raised by immunizing a goat with rabbit IgG). Alternatively, the antigen-specific antibodies can be coupled to the inner walls of a test tube. After incubation, the unbound contents are removed; the tube is washed, and the radioactive of the unbound and bound material are both measured. The antigen-specific antibodies can be coupled to particles, like Sephadex. Centrifugation of the reaction mixture separates the bound counts (in the pellet) from the free counts in the supernatant fluid.

4. Fluorescence Immunoassays

Methods for protein detection disclosed herein, include fluorescence immunoassays to detect non-natural amino acids, non-natural amino acid polypeptides, modified non-natural amino acid polypeptides and fragments thereof. Fluorescence based immunological methods are based upon the competitive binding of labeled ligands versus unlabeled ones on highly specific receptor sites. It is a very important tool for clinical and analytical biochemistry in the analysis of proteins.

This technique can be used for immunoassays based on changes in fluorescence lifetime with changing analyte concentration. This technique works with dyes with a short lifetime like fluorescein isothiocyanate (FITC) (the donor) whose fluorescence is quenched by energy transfer to Eosin (the acceptor). A number of molecular species have been used for causing energy transfer from a donor molecule to an acceptor molecule. In particular, sandwich type immunocomplex formation can be used with this technique.

A number of photoluminescent compounds may be used in the method of the invention and include the compounds listed above in fluorescence microscopy, as well as groups such as cyanines, oxazines, thiazines, porphyrins, phthalocyanines, fluorescent infrared-emitting polynuclear aromatic hydrocarbons, phycobiliproteins, squaraines and organometallic complexes, hydrocarbons and azo dyes.

Fluorescence based immunological methods can be, for example, heterogenous or homogenous. Heterogenous Immunoassays comprise a physical separation of bound from free labeled analyte. The analyte or antibody may be attached to a solid surface. The technique can be competitive (for a higher selectivity) or noncompetitive (for a higher sensitivity). Detection can be direct (only one type of antibody used) or indirect (a second type of antibody is used). Homogenous Immunoassays comprise no physical separation. Double-Antibody Fluorophore-labeled antigen participates in an equilibrium reaction with antibodies directed against both the antigen and the fluorophore. Labeled and unlabeled antigens compete for a limited number of anti-antigen antibodies.

Simple Fluorescence Labelling method—It can be used for receptor-ligand binding, enzymatic activity by using pertinent fluorescence, and as a fluorescent indicator of various in vivo physiological changes such as pH, ion concentration, and electric pressure. Self-fluorescence of amino acids such as tyrosine and tryptophan result in background radiation, and to overcome such weak points fluorescent compounds of absorption UV length longer than 520 nm such as cyanine are often used.

FRET: Fluorescence Resonance Energy Transfer—FRET may be used to measure the interaction of two proteins in vivo and can measure nanometer scale distances and distance (conformation) changes. Therefore, it has been used to measure simple protein-protein interactions and changes in protein folding, conformation, and stability (see Philipps, B.; Hennecke, J.; Glockshuber R. Mol Biol. 2003, 327, 239-249; Riven, I.; Kalmanzon, E.; Segev, L.; Reuveny E. Neuron. 2003, 38, 225-235). Two different fluorescent molecules (fluorophores) are conjugated to the two proteins of interest. Non-natural amino acid polypeptides conjugated to fluorophores may be used in FRET. When two fluorescent compounds are used instead of a single fluorescent compound, non-fluorescent energy transfer occurs. When the emission wavelength of a fluorescent donor is similar to absorption wavelength of an acceptor, the donor in its excited state will transfer its energy to the acceptor instead to emitting fluorescent light, and consequently emission occurs at emission wavelength of the acceptor. A number of different fluorophore pairs have been used for FRET analysis including GFP (green fluorescent protein) variants CFP (cyan) and YFP (yellow) fused to the proteins of interest.

Distance R0 of 50% FRET effect depends on the overlap of the emission range of donors, absorption range of the acceptors, and the acceptor's quantum yields and solvent. If two fluorescent molecules are at a shorter distance from each other than R0, when the donor's absorption light is emitted, theoretically the acceptor's fluorescence will be stronger. If the distance becomes longer than R0, when the same light is emitted, the donor's fluorescence will be detected as stronger. Therefore, enzymatic activity can be measured easily if fluorescent molecules are linked to the ends of small peptides, which can be used as kinases such as protease. BRET (Bioluminescene resonance energy transfer) was developed by Xu et al (Proc. Natl. Acad. Sci. U.S.A. 1999, 96, 151-156). It acts on a principle similar to FRET and is based on the finding that the emission spectrum of *Renilla* luciferase is similar to that of CFP. These techniques allow the study of interactions within specific subcellular compartments, including membrane protein-protein interactions, when utilizing organelle targeted fluorescent protein variants. Also post-translational modification events can be studied in mammalian cells.

TRF: Time Resolved Fluorescence—To reduce fluorescent background, Time Resolved Fluorescence was developed. The lifetime of excited states of common fluorescent molecules is usually only a few microseconds, but Lanthanide series elements have milliseconds of life time. TRF is a method that selectively measures the fluorescence of the Lanthanide series after the emission of other fluorescent molecules has finished. TRF can be also with FRET, and Lanthanide series become donors or acceptors.

5. Various Assay Formats

Various assay formats may be used for the detection of the non-natural amino acids, non-natural amino acid polypeptides, modified non-natural amino acid polypeptides, and fragment thereof, disclosed herein, including "sandwich" immunoassays and probe assays. For example, in a first assay format, a polyclonal or monoclonal antibody or fragment thereof, or a combination of these antibodies, which has been coated on a solid phase, is contacted with a test sample, to form a first mixture. This first mixture is incubated for a time and under conditions sufficient to form antigen/antibody complexes. Then, an indicator reagent comprising a monoclonal or a polyclonal antibody or a fragment thereof, or a combination of these antibodies, to which a signal generating compound has been attached, is contacted with the antigen/antibody complexes to form a second mixture. This second mixture then is incubated for a time and under conditions sufficient to form antibody/antigen/antibody complexes. The presence of antigen in the test sample and captured on the solid phase, if any, is determined by detecting the measurable signal generated by the signal generating compound. The amount of antigen present in the test sample is proportional to the signal generated.

In an alternative assay format, a mixture is formed by contacting: (1) a polyclonal antibody, monoclonal antibody, or fragment thereof, which specifically binds to antigen, or a combination of such antibodies bound to a solid support; (2) the test sample; and (3) an indicator reagent comprising a monoclonal antibody, polyclonal antibody, or fragment thereof, which specifically binds to a different epitope (or a combination of these antibodies) to which a signal generating compound is attached. This mixture is incubated for a time and under conditions sufficient to form antibody/antigen/antibody complexes. The presence, if any, of antigen present in the test sample and captured on the solid phase is determined by detecting the measurable signal generated by the signal generating compound. The amount of antigen present in the test sample is proportional to the signal generated.

In another assay format, one or a combination of at least two monoclonal antibodies of the invention can be employed as a competitive probe for the detection of antibodies to antigen. For example, unnatural amino acid polypeptides disclosed herein, either alone or in combination, are coated on a solid phase. A test sample suspected of containing antibody to antigen then is incubated with an indicator reagent comprising a signal generating compound and at least one monoclonal antibody for a time and under conditions sufficient to form antigen/antibody complexes of either the test sample and indicator reagent bound to the solid phase or the indicator reagent bound to the solid phase. The reduction in binding of the monoclonal antibody to the solid phase can be quantitatively measured.

In yet another detection method, the monoclonal or polyclonal antibodies can be employed in the detection of antigens in tissue sections, as well as in cells, by immunohistochemical analysis. The tissue sections can be cut from either frozen or chemically fixed samples of tissue. If the antigens are to be detected in cells, the cells can be isolated from blood, urine, breast aspirates, or other bodily fluids. The cells may be obtained by biopsy, either surgical or by needle. The cells can be isolated by centrifugation or magnetic attraction after labeling with magnetic particles or ferrofluids so as to enrich a particular fraction of cells for staining with the antibodies. Cytochemical analysis wherein these antibodies are labeled directly (with, for example, fluorescein, colloidal gold, horseradish peroxidase, alkaline phosphatase, etc.) or are labeled by using secondary labeled anti-species antibodies (with various labels as exemplified herein) to track the histopathology of disease also are within the scope of the present invention.

Combinations of the monoclonal antibodies (and fragments thereof) also may be used together as components in a mixture or "cocktail" along with antibodies which specifically bind to other regions of unnatural amino acid polypeptides disclosed herein, each antibody having different binding specificities. The polyclonal antibodies used in the assays can be used either alone or as a cocktail of polyclonal antibodies. Since the cocktails used in the assay formats are comprised of either monoclonal antibodies or polyclonal antibodies having different binding specificity to unnatural amino acid polypeptides disclosed herein, they are useful for the detecting, diagnosing, staging, monitoring, prognosticating, in vivo imaging, preventing or treating, or determining the predisposition to, various diseases and conditions.

It is contemplated and within the scope of the present invention that unnatural amino acid amino acids disclosed herein, may be detected in assays by use of a recombinant antigen as well as by use of a synthetic polypeptide or purified polypeptide, which polypeptide comprises an amino acid sequence of unnatural amino acid polypeptides disclosed herein. It also is within the scope of the present invention that different synthetic, recombinant or purified polypeptides, identifying different epitopes of unnatural amino acid polypeptides disclosed herein, can be used in combination in an assay for the detecting, diagnosing, staging, monitoring, prognosticating, in vivo imaging, etc. In this case, all of these polypeptides can be coated onto one solid phase; or each separate polypeptide may be coated onto separate solid phases, such as microparticles, and then combined to form a mixture of polypeptides which can be later used in assays. Polypeptides coated on solid phases or labeled with detectable labels are then allowed to compete with those present in a sample for a limited amount of antibody. A reduction in binding of the synthetic, recombinant, or purified peptides to the antibody (or antibodies) is an indication of the presence of unnatural amino acid polypeptides disclosed herein. Variations of assay formats are known to those of ordinary skill in the art.

6. Scanning Probe Microscopy (SPM) for Immunoassays

Methods for protein detection disclosed herein, include SPM to detect non-natural amino acids, non-natural amino acid polypeptides, modified non-natural amino acid polypeptides and fragments thereof. In scanning probe microscopy, in the capture phase, for example, at least one of the monoclonal antibodies is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes.

The use of SPM to monitor specific binding reactions can occur in many ways. In one embodiment, one member of a specific binding partner (analyte specific substance which is the monoclonal antibody) is attached to a surface suitable for scanning. The attachment of the analyte specific substance may be by adsorption to a test piece which comprises a solid phase of a plastic or metal surface. Covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Also, polyelectrolyte interactions may be used to immobilize a specific binding partner on a surface of a test piece by using techniques and chemistries. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

C. Spectroscopy

1. Nuclear Magnetic Resonance (NMR)

Methods for protein detection disclosed herein, include NMR to detect non-natural amino acids, non-natural amino acid polypeptides, modified non-natural amino acid polypeptides and fragments thereof.

NMR spectroscopy is capable of determining the structures of biological macromolecules like proteins and nucleic acids at atomic resolution. In addition, it is possible to study time dependent phenomena with NMR, such as intramolecular dynamics in macromolecules, reaction kinetics, molecular recognition or protein folding. Methods for protein detection disclosed herein, include NMR to detect non-natural amino acid polypeptides and modified non-natural amino acid polypeptides and fragments thereof.

Progress in the theoretical and practical capabilities of NMR, led to increasingly efficient utilization of the information content of NMR spectra. Parallel developments in the biochemical methods (recombinant protein expression) allow the simple and fast preparation of protein samples. Heteronuclei like $^{15}N$, $^{13}C$ and $^2H$, can be incorporated in proteins by uniformly or selective isotopic labeling. Spectra from these samples can be drastically simplified. Additionally, some new information about structure and dynamics of macromolecules can determined with these methods. All these developments currently allow the structure determination of proteins with a mass of up to 30 kDa or more.

2. X-ray Crystallography

Methods for protein detection disclosed herein, include X-ray crystallography to detect non-natural amino acids, non-natural amino acid polypeptides, modified non-natural amino acid polypeptides and fragments thereof.

X-ray crystallography is a technique in crystallography in which the pattern produced by the diffraction of X-rays through the closely spaced lattice of atoms in a crystal is recorded and then analyzed to reveal the nature of that lattice. This generally leads to an understanding of the material and molecular structure of a substance. The spacings in the crystal lattice can be determined using Bragg's law. The electrons that surround the atoms, rather than the atomic nuclei themselves, are the entities which physically interact with the incoming X-ray photons. This technique is widely used in chemistry and biochemistry to determine the structures of an immense variety of molecules, including inorganic compounds, DNA and proteins. X-ray diffraction is commonly carried out using single crystals of a material, but if these are not available, microcrystalline powdered samples may also be used, although this requires different equipment and is much less straightforward.

For X-ray crystallography, the molecule must be crystallized. One photon diffracted by one electron cannot be reliably detected, however, because of the regular crystalline structure; the photons are diffracted by corresponding electrons in many symmetrically arranged molecules. Because waves of the same frequency whose peaks match reinforce each other, the signal becomes detectable. To determine a structure, crystals of the molecule of interest are grown using some method of crystallization. The crystals are harvested and often frozen with liquid nitrogen. Freezing crystals both reduces radiation damage incurred during data collection and decreases thermal motion within the crystal. Crystals are placed on a diffractometer, a machine that emits a beam of X-rays. The X-rays diffract off the electrons in the crystal, and the pattern of diffraction is recorded on film and scanned into a computer. These diffraction images are combined and eventually used to construct a map of the electron density of the molecule that was crystallized, atoms are then fitted to the electron density map and various parameters such as position are refined to best fit the observed diffraction data.

3. Fluorescence Spectroscopy

Methods for protein detection disclosed herein, include fluorescence spectroscopy to detect non-natural amino acids, non-natural amino acid polypeptides, modified non-natural amino acid polypeptides and fragments thereof.

Besides the standard fluorescence measurements a variety of other methods have been developed. Conventional Fluorometry involves measurements of emission light intensities at defined wavelengths for a certain emission maxima of a fluorophore. Total Fluorometry involves a collection of data for a continuum of absorption as well as emission wavelengths. In Fluorescence Polarization, polarized light is used for excitation and binding of fluorochrome-labeled antigens to specific antibodies affects polarization extent. Line Narrowing Spectroscopy involves low-temperature solid-state spectroscopy that derives its selectivity from the narrow-line emission spectra it provides.

Time-dependent Fluorescence Spectroscopy comprises time-resolved measurements containing more information than steady-state measurements, since the steady-state values represent the time average of time-resolved determinations. It is a single photon timing technique in which the time between an excitation light pulse and the first photon emitted by the sample is measured.

Frequency-Domain Fluorescence Spectroscopy is an alternative to the time-resolved methods. The time decay of fluorescence is typically measured using a light source with an intensity modulated sinusoidally at a given frequency, by determining the phase delay and the relative modulation of the fluorescence signal with respect to the exciting light.

4. Matrix Assisted Laser Desorption Ionization Time-of-flight Mass Spectrometry (MALDI TOF-MS)

Methods for protein detection disclosed herein, include MALDI TOF-MS to detect non-natural amino acids, non-natural amino acid polypeptides, modified non-natural amino acid polypeptides and fragments thereof.

Linear TOF-MS—Mass spectrometry has emerged as an important tool for analyzing and characterizing large biomolecules of varying complexity. The matrix assisted laser desorption/ionization (MALDI) technique, developed in 1987, has increased the upper mass limit for mass spectrometric analyses of biomolecules to over 300,000 Da and has enabled the analyses of large biomolecules by mass spectrometry to become easier and more sensitive. TOF mass spectrometers operate on the principle that when a temporally and spacially well defined group of ions of differing mass/charge (m/z) ratios are subjected to the same applied electric field (K.E.=[mv2]/2=zeEs where K.E.=kinetic energy; m=the mass of the ion; v velocity of the ion; z=number of charges; e=the charge on an electron in coulombs; E=electric field gradient; and s=the distance of the ion source region) and allowed to drift in a region of constant electric field, they will traverse this region in a time which depends upon their m/z ratios.

Reflectron TOF-MS—Improved mass resolution in MALDI TOF-MS has been obtained by the utilization of a single-stage or a dual-stage reflectron (RETOF-MS). The reflectron, located at the end of the flight tube, is used to compensate for the difference in flight times of the same m/z ions of slightly different kinetic energies by means of an ion reflector. This results in focusing the ion packets in space and time at the detector. In the reflectron mass spectrum, the isotopic multiplet is well resolved producing a full width half maximum (FWHM) mass resolution of about 3400. Mass resolutions up to 6000 (FWHM) have been obtained for peptides up to about 3000 Da with RETOF-MS. Enhancing the mass resolution can also increase the mass accuracy when determining the ion's mass.

Historically, both linear and reflectron MALDI-TOF-MS have been utilized primarily for molecular weight determinations of molecular ions and enzymatic digests leading to structural information of proteins. These digests are typically mass analyzed with or without purification prior to molecular weight determinations. Varieties of methodologies have been developed to obtain primary sequence information for proteins and peptides utilizing MALDI TOF-MS. Two different approaches can be taken. The first method is known as protein ladder sequencing and is employed to produce structurally informative fragments of the analyte prior to insertion into the TOF mass spectrometer and subsequent analysis. The second approach utilizes the phenomenon of metastable ion decay that occurs inside the TOF mass spectrometer to produce sequence information.

Ladder Sequencing with TOF-MS-Proteins or peptides can be sequenced using MALDI-TOF-MS with a ladder sequencing technique which consists of either a time-dependent or concentration-dependent chemical degradation from either the N- or C-terminus of the protein or peptide into fragments, each of which differs by one amino acid residue. The mixture is mass analyzed in a single MALDI-TOF-MS experiment with mass differences between adjacent mass spectral peaks corresponding to a specific amino acid residue. This type of analysis can be thought of as simply determining the masses of a series of peptides/proteins that are present in a single MALDI sample. The order of occurrence in the mass spectrum defines the sequence of amino acids in the original protein or peptide.

Post-Source Decay with RETOF-MS MALDI—It has historically been considered a "soft" ionization technique that produces almost exclusively intact protonated pseudo-molecular ion species. A significant degree of metastable ion decay occurs after ion acceleration and prior to detection. The ion fragments produced from the metastable ion decav of peptides and proteins typically include both neutral molecule losses (such as water, ammonia and portions of the amino acid side chains) and random cleavage at peptide bonds. The observance of these metastable ion decay products in MALDI mass spectra is dependent on the TOF instrumental configuration.

MALDI TOF-MS has developed into a valuable tool in the biosciences for obtaining both accurate mass determinations and primary sequence information. Methods for protein detection disclosed herein, include MALDI TOF-MS to detect non-natural amino acid polypeptides and modified non-natural amino acid polypeptides and fragments thereof. The sequence information obtained from the mass spectra whose sequence was known a priori by no means implies a straightforward scheme to deduce an unknown peptide or protein sequence from its metastable ion decay mass spectrum. These MALDI techniques are envisioned to be most useful in conjunction with conventional biochemical techniques such as protein digests. They may be applicable to identifying blocked amino termini, post-translational modifications and mutation sites in known proteins in this way. Also, with a total unknown, a significant amount of preliminary structure determination should be possible on very small (less than 10 pmol) amounts of analyte. For ladder sequencing and in-source fragmentation studies, it is important to minimize potential peptide impurities.

In-Source Decay with Linear TOF-MS—An alternative approach to RETOF-MS for studying metastable ion decay of MALDI generated ions is to utilize DE with linear TOF-MS. By employing the DE technique, primary structural information for peptides and proteins can also be obtained. Prompt ion fragmentation produced at the time of the desorption event (i.e., ion formation) is generally absent for MALDI generated peptide or protein ions. By incorporating a time delay between ion formation and ion extraction, ions in the source are allowed to fragment in a relatively short period of time (<100 ns) into smaller ions and neutrals prior to extraction. A drawout potential is then applied extracting the fragmented ions. Coherent mass spectral peaks are produced from these metastable decayed ions giving rise to significant structural information for peptides and proteins.

5. Surface-enhanced Laser Desorption Ionization-Time of Flight (SELDI-TOF)

Another proteomic technology involved in quantitative analysis of protein mixtures is known as surface-enhanced laser desorption ionization-time of flight (SELDI-TOF). Methods for protein detection disclosed herein, include SELDI-TOF to detect non-natural amino acids, non-natural amino acid polypeptides, modified non-natural amino acid polypeptides and fragments thereof.

This technique utilizes stainless steel or aluminum-based supports, or chips, engineered with chemical (hydrophilic, hydrophobic, pre-activated, normal-phase, immobilized metal affinity, and cationic or anionic) or biological (antibody, antigen binding fragments (including but not limited to, scFv), DNA, enzyme, or receptor) bait surfaces of 1-2 mm in diameter. These varied chemical and biochemical surfaces allow differential capture of proteins based on the intrinsic properties of the proteins themselves. Solubilized tissue or body fluids in volumes as small as 0.1 µl are directly applied to these surfaces, where proteins with affinities to the bait surface will bind. Following a series of washes to remove non-specifically or weakly bound proteins, the bound proteins are laser desorbed and ionized for MS analysis. Masses of proteins ranging from small peptides of less than 1000 Da up to proteins of greater than 300 kDa are calculated based on time-of-flight. As mixtures of proteins will be analyzed within different samples, a unique sample fingerprint or signature will result for each sample tested. Consequently, patterns of masses rather than actual protein identifications are produced by SELDI analysis. These mass spectral patterns are used to differentiate patient samples from one another, such as diseased from normal. While protein fingerprints can be analyzed for differential biomarker expression, this technology is currently unable to specifically identify proteins within a sample using MS. However, this situation is rapidly evolving as prototypes are being tested which couple the SELDI-TOF technology with tandem mass spectrometers. Coupling of these types of instruments will enable amino acid sequencing and subsequent protein identification.

6. UV-Vis

Methods for protein detection disclosed herein, include UV-Vis to detect non-natural amino acids, non-natural amino acid polypeptides, modified non-natural amino acid polypeptides and fragments thereof.

Optical absorption spectroscopy (UV/VIS) plays an important role for the determination of concentrations (proteins, DNA, nucleotides etc.). Organic dyes can be used to enhance the absorption and to shift it into the visible range (e.g. coomassie blue reagents). Understanding the forces that govern the interaction of proteins with one another assists in the understanding of such processes as macromolecular assembly, chaperone-assisted protein folding and protein translocation.

Resonance Raman Spectroscopy (RRS) is a tool which can be used to study molecular structure and dynamics. Resonance Raman scattering requires excitation within an electronic absorption band and results in a large increase of scattering. Few molecules have visible absorption bands; however everything absorbs in the deep UV. By using UV light it is possible to study a wide variety of colorless chromophores, and have the additional benefit of avoiding interference from fluorescence. Furthermore, electrons of different functional groups with different excitation wavelengths can be selectively excited. This approach helps to investigate specific parts of macromolecules by using different excitation wavelengths.

7. Liquid Chromatography (LC)

Liquid chromatography has been a powerful tool for isolating proteins, peptides, and other molecules from complex mixtures. Methods for protein detection disclosed herein, include LC to detect non-natural amino acids, non-natural amino acid polypeptides, modified non-natural amino acid polypeptides and fragments thereof. Liquid chromatography can be affinity chromatography, gel filtration chromatography, anion exchange chromatography, cation exchange chromatography, diaode array-LC and high performance liquid chromatography (HPLC).

Gel filtration chromatography separates proteins, peptides, and oligonucleotides on the basis of size. Molecules move through a bed of porous beads, diffusing into the beads to greater or lesser degrees. Smaller molecules diffuse further into the pores of the beads and therefore move through the bed more slowly, while larger molecules enter less or not at all and thus move through the bed more quickly. Both molecular weight and three dimensional shape contribute to the degree of retention. Gel Filtration Chromatography may be used for analysis of molecular size, for separations of components in a mixture, or for salt removal or buffer exchange from a preparation of marcromolecules.

Affinity chromatography is the process of bioselective adsorption and subsequent recovery of a compound from an immobilized ligand. This process allows for the highly specific and efficient purification of many diverse proteins and other compounds. The process requires the utilization of an appropriately selective ligand which will bind the desired compound generally with a dissociation constant in the range of $10^{-4}$ to $10^{-8}$, while permitting recovery under mild conditions. The ligand is generally immobilized on a beaded and porous matrix which may be in the form of a column packing or batchwise adsorption medium.

Ion exchange chromatography separates molecules based on differences between the overall charge of the proteins. It is usually used for protein purification but may be used for purification of oligonucleotides, peptides, or other charged molecules, The protein of interest must have a charge opposite that of the functional group attached to the resin in order to bind. For example, immunoglobulins, which generally have an overall positive charge, will bind well to cation exchangers, which contain negatively charged functional groups. Because this interaction is ionic, binding must take place under low ionic conditions. Elution is achieved by increasing the ionic strength to break up the ionic interaction, or by changing the pH of the protein.

HPLC can be used in the separation, purification and detection of non-natural amino acids, non-natural amino acid polypeptides, modified non-natural amino acid polypeptides and fragments thereof disclosed herein. Peptides: Use of reversed-phased chromatography (RPC) has become a common and important step in synthetic peptide production. RPC has also been used to purify natural sequences. Although analytical columns are used to carry out the process, the procedure can be preparative in nature due to the limited amount of "active" proteins in tissue. Some other advantages are that recovery of post-purification biological activity and reformation of secondary or tertiary structure after exposure to RPC are favored due to the abbreviated size of the peptides. Crude tissue extracts may be loaded directly onto the RPC system and mobilized by gradient elution. Rechromatography under the identical conditions is an option if further purification is warranted or necessary. RPC can also be utilized in the process of protein structure determination. The normal procedure of this process is 1) fragmentation by proteolysis or chemical cleavage; 2) purification; and 3) sequencing. A common mobile phase for RPC of peptides is a gradient of 0.1% trifluoroacetic acid (TFA) in water to 0.1% TFA in an organic solvent, such as acetonitrile, since the organic solvent 1) solubilizes the peptide, 2) allows detection at approximately 230-240 nm, and 3) can evaporate away from the sample. Biologically Active Proteins: The use of size-exclusion chromatography (SEC) and ion-exchange chromatography (IEC) is well-suited for use with biologically active proteins, such as enzymes, hormones, and antibodies, since each protein has its own unique structure and the techniques may be performed in physiological conditions. Full recovery of activity after exposure to the chromatography may be achieved, and currently, availability of SEC columns is diverse enough to allow fractionation from 10 to 1000 kilodaltons. Extremely basic or hydrophobic proteins may not exhibit true SEC character since the columns tend to have slight hydrophobicity and anionic character. The use of gradient elution with the IEC column is favorable because of equivalent resolution as polyacrylamide gel electrophoresis (PAGE) and increased loading capability when compared to SEC. In liquid affinity chromatography (LAC) interaction is based on binding of the protein due to mimicry of substrate, receptor, etc. The protein is eluted by introducing a competitive binding agent or altering the protein configuration which facilitates dissociation. Membrane Proteins: Membrane proteins are either peripheral (situated on the outer surface) or integral (partially span, entirely span, or lie completely within the membrane). The lipophilicity of the bilayer conveys the lipophilic character (i.e., hydrophobic amino acids) of the proteins within the membrane. RPC would be a logical choice in analysis and purification of these proteins, but IEC is also employed. Another procedure used in the separation of membrane proteins is the use of nonionic detergents, such as Triton X-100, or protein solubilization by organic solvents with IEC. HPLC may be coupled with MS.

Diode array detector-liquid chromatography (DAD-LC) provides complete, multiple spectra for each HPLC peak, which, by comparison, can provide indication of peak purity. These data can also assign presence of Tyr, Trp, Phe, and possibly others (His, Met, Cys) and can quantitate these amino acids by 2nd derivative or multi-component analysis. By a post-column derivatization, DAD-LC can also identify and quantitate Cys, His and Arg in individual peptides. Thus, it is possible to analyze for 6 of the 20 amino acids of each separated peptide in a single LC run, and information can be obtained about presence or absence of these amino acids in a given peptide in a single step. This is assisted by knowing the number of residues in each peptide. Also, by correction at 205 nm absorbance for side-chain chromophores, this technique can give much better estimation of relative amounts of each peptide.

D. Electrophoresis

Methods for protein detection disclosed herein, include electrophoresis to detect non-natural amino acids, non-natural amino acid polypeptides, modified non-natural amino acid polypeptides and fragments thereof. Electrophoresis can be gel electrophoresis or capillary electrophoresis.

Gel Electrophoresis: Gel electrophoresis is a technique that can be used for the separation of proteins. Separation of large (macro) molecules depends upon two forces: charge and mass. When a biological sample, such as proteins, is mixed in a buffer solution and applied to a gel, these two forces act together. The electrical current from one electrode repels the molecules while the other electrode simultaneously attracts the molecules. The frictional force of the gel material acts as a "molecular sieve," separating the molecules by size. During electrophoresis, macromolecules are forced to move through the pores when the electrical current is applied. Their rate of migration through the electric field depends on the strength of the field, size and shape of the molecules, relative hydrophobicity of the samples, and on the ionic strength and temperature of the buffer in which the molecules are moving. After staining, the separated macromolecules in each lane can be seen in a series of bands spread from one end of the gel to the other. Using this technology it is possible to separate and identify protein molecules that differ by as little as a single amino acid. Its advantage is that proteins can be visualized as well as separated, permitting a researcher to estimate quickly the number of proteins in a mixture or the degree of purity of a particular protein preparation. Also, gel electrophoresis allows determination of crucial properties of a protein such as its isoelectric point and approximate molecular weight.

Electrofocusing, or isoelectric focusing, is a technique for separating different molecules by their electric charge differences (if they have any charge). It is most commonly used on proteins. It is a type of zone electrophoresis that takes advantage of the fact that a molecule's charge changes as the pH of its surroundings changes. Molecules are distributed over a medium that has a pH gradient (usually created by aliphatic ampholytes). An electric current is passed through the medium, creating a "positive" and "negative" end. Negatively charged particles migrate through the pH gradient toward the "positive" end while positively charged particles move toward the "negative" end. As a particle moves into a pH that neutralizes its charge, it will stop following the current. Particles of the same initial charge will deposit (or focus) around the same place on the pH gradient.

Capillary Electrophoresis: Capillary electrophoresis is a collection of a range of separation techniques which involve the application of high voltages across buffer filled capillaries to achieve separations. The variations include separation based on size and charge differences between analytes (termed Capillary Zone Electrophoresis, CZE, or Free Solution CE, FSCE), separation of neutral compounds using surfactant micelles (Micellar electrokinetic capillary chromatography, MECC or sometimes referred to as MEKC) sieving of solutes through a gel network (Capillary Gel Electrophoresis, GCE), separation of cations (or anions) based on electrophoretic mobility (Capillary Isotachophoresis, CITP), and separation of zwitterionic solutes within a pH gradient (Capillary Isoelectric Focusing, CIEF). Capillary electrochromatography (CEC) is an associated electrokinetic separation technique which involves applying voltages across capillaries filled with silica gel stationary phases. Separation selectivity in CEC is a combination of both electrophoretic and chromatographic processes. Many of the CE separation techniques rely on the presence of an electrically induced flow of solution (electroosmotic flow, EOF) within the capillary to pump solutes towards the detector. GCE and CIEF are of importance for the separation of biomolecules such as proteins. Generally CE is performed using aqueous based electrolytes however there is a growing use of non-aqueous solvents in CE.

Operation of a CE system involves application of a high voltage (typically 10-30 kV) across a narrow bore (25-100 mm) capillary. The capillary is filled with electrolyte solution which conducts current through the inside of the capillary. The ends of the capillary are dipped into reservoirs filled with the electrolyte. Electrodes made of an inert material such as platinum are also inserted into the electrolyte reservoirs to complete the electrical circuit. A small volume of sample is injected into one end of the capillary. The capillary passes through a detector, usually a UV absorbance detector, at the opposite end of the capillary. Application of a voltage causes movement of sample ions towards their appropriate electrode usually passing through the detector. The plot of detector response with time is generated which is termed an electropherogram. A flow of electrolyte, known as electroendosmotic flow, EOF, results in a flow of the solution along the capillary usually towards the detector. This flow can significantly reduce analysis times or force an ion to overcome its migration tendency towards the electrode it is being attracted to by the sign of its charge.

E. Arrays

Methods for protein detection disclosed herein, include arrays to detect non-natural amino acids, non-natural amino acid polypeptides, modified non-natural amino acid polypeptides and fragments thereof.

Arrays involve performing parallel analysis of multiple samples against known protein targets. The development of various microarray platforms has remarkably enabled and accelerated the determination of protein abundance, localization, and interactions in a cell or tissue. Microarrays provide a platform that allows identification of protein interaction or function against a characterized set of proteins, antibodies, or peptides.

Protein-based chips array proteins on a small surface and can directly measure the levels of proteins in tissues using fluorescence-based imaging. Proteins can be arrayed on either flat solid phases or in capillary systems (microfluidic arrays), and several different proteins can be applied to these arrays. The most popular ones currently rely on antibody-antigen interactions, which can also detect antigen-protein interactions. The potential of antibody arrays is currently limited by the availability of antibodies that have both high specificity (to eliminate cross reactions with non-specific proteins within the sample) and high affinity for the target of interest (to allow detection of small quantities within a sample). Another challenge of protein array technology is the ability to preserve proteins in their biologically active shape and form. In addition to the use of antibodies as array probes, single-stranded oligonucleotides, whose specificity is optimized by in vitro elution (aptamers), offer a viable alternative. Aptamers allow their covalent attachment to cognate proteins by photo-crosslinking, thus reducing background. Nonspecific protein stains are then used to detect bound proteins. International Publication No. WO 04/58946 entitled "Protein Arrays," which is incorporated by reference herein, describes the attachment of non-natural amino acid polypeptides to solid supports.

Arrays include, but not limited to, bead arrays, bead based arrays, bioarrays, bioelectronic arrays, cDNA arrays, cell arrays, DNA arrays, gene arrays, gene expression arrays, frozen cell arrays, genome arrays, high density oligonucleotide arrays hybridization arrays, microcantilever arrays, microelectronic arrays, multiplex DNA hybridization arrays, nanoarrays, oligonucleotide arrays, oligosaccharide arrays, planar arrays, protein arrays, solution arrays, spotted arrays, tissue arrays, exon arrays, filter arrays, macroarrays, small molecule microarrays, suspension arrays, theme arrays, tiling arrays, and transcript arrays.

F. Sensors

Methods for protein detection disclosed herein, include sensors to detect non-natural amino acids, non-natural amino acid polypeptides, modified non-natural amino acid polypeptides and fragments thereof. Sensors can be used for both in vivo and in vitro detection. Sensors may be used to detect events such as binding of a non-natural amino acid polypeptide to its target, conformational changes in a non-natural amino acid polypeptide, and or measure other interactions, modifications, or changes to a non-natural amino acid polypeptide or its environment.

Sensors can be chemical sensors, optical sensors, and biosensors. Chemical sensors are miniaturized analytical devices which deliver real-time and online information on the presence of specific compounds or ions in complex samples. Optical sensors are based on measurement of either intrinsic optical properties of analytes, or of optical properties of indicator dyes or labeled biomolecules attached to solid supports. Biosensors can be affinity biosensor based on capabilities of enzymes to convert "substrates" into products; or catalytic biosensors.

The binding of a non-natural amino acid polypeptide to its target, including but not limited to, an antibody, antibody fragment, or antigen-binding polypeptide or fragment thereof, may be measured. The non-natural amino acid polypeptide is conjugated to a molecule such as a nanotransmitter. While bound to its target in-vivo, the nanotransmitter emits a signal that is read ex vivo by a medical imaging instrument.

G. Methods for Identifying Proteins from a Library Screen

In order to identify the protein(s) that interact with the non-natural amino acid polypeptide, many methods may be used. Protein separation aids to separate a complex mixture so that individual proteins are more easily processed with other techniques. Protein identification methods include but is not limited to low-throughput sequencing through Edman degradation, mass spectrometry techniques, peptide mass fingerprinting, de novo sequencing, antibody-based assays and protein quantification assays such as fluorescent dye gel staining, tagging or chemical modification methods (i.e. isotope-coded affinity tags—ICATS, combined fractional diagonal chromatography—COFRADIC). The purified protein may also be used for determination of three-dimensional crystal structure, which can be used for modeling intermolecular interactions. Common methods for determining three-dimensional crystal structure include x-ray crystallography and NMR spectroscopy. Detailed below are a few of the methods for identifying proteins.

Protein sequencing: N-terminal sequencing and C-terminal sequencing. N-terminal sequencing aids in the identification of unknown proteins; confirm recombinant protein identity and fidelity (reading frame, translation start point, etc.); aid the interpretation of NMR and crystallographic data; demonstrate degrees of identity between proteins; or provide data for the design of synthetic peptides for antibody generation, etc. N-terminal sequencing utilizes the well-established Edman degradative chemistry, sequentially removing amino acid residues from the N-terminus of the protein and identifying them by reverse-phase HPLC. Sensitivity is at the level of 100 s femtomoles and long sequence reads (20-40 residues) can often be obtained from a few 10 s picomoles of starting material. Pure proteins (>90%) generate easily interpreted data, but insufficiently purified protein mixtures may also provide useful data, subject to rigorous data interpretation. N-terminally modified (especially acetylated) proteins cannot be sequenced directly, as the absence of a free primary amino-group prevents the Edman chemistry. However, limited proteolysis of the blocked protein (e.g. using cyanogen bromide) may allow a mixture of amino acids to be generated in each cycle of the instrument, which can be subjected to database analysis in order to interpret meaningful sequence information.

C-terminal sequencing is recognized as an important post-translational modification, sometimes critically affecting the structure and activity of a protein. Various disease situations have been associated with impaired protein processing and C-terminal sequencing provides an additional tool for the investigation of protein structure and processing mechanisms.

Proteome analyses: With proteomics proteins can be identified primarily by computer search algorithms that assign sequences to a set of empirically acquired mass/ intensity data which are generated from conducting electrospray ionization (ESI), matrix-assisted laser desorption/ionization (MALDI), time-of-flight (TOF) instruments, or a three-dimensional quadrupole ion traps on the protein of interest.

Other Methods of Detection

Additional detection methods involve bipyridines, metal coordination, nanotechnology (gold), biotin-streptavidin/avidin, UV/Vis, 2 step systems that involve a binding event and a coupling event due to proximity of a non-natural amino acid to a target resulting in exmission from a fluorophore, small molecule based fluorescent/fluorogenic molecules bound to a non-natural amino acid present in a polypeptide, lipocalins (beta barrel), fatty acid binding proteins, and dark to light or light to dark fluorophores.

XV. Imaging and Diagnostics

Methods for imaging and diagnostics utilizing non-natural amino acids, non-natural amino acid polypeptides, modified non-natural amino acid polypeptides and fragments thereof, are disclosed herein.

Molecular Imaging is a multidisciplinary field involving the efforts from molecular and cell biology to identify the molecular imaging target, radiochemistry and bioconjugation chemistry to develop suitable imaging probes, pharmacology to optimize the probes for optimal targeting efficacy and favorable in vivo kinetics, and image-capture techniques to non-invasively monitor the fate of molecular imaging probes in vivo. Aside from its basic diagnostic applications, molecular imaging also plays roles in treatment efficacy assessment, drug discovery, and understanding of molecular mechanisms in living systems. Molecular imaging probes (monoclonal antibodies, minibodies, proteins, peptides and peptidomimetics) can be used for visualization and quantification of molecular targets. The combination of anatomical (microMRI and microCT) and molecular imaging techniques (microPET, microSPECT, and NIR fluorescence imaging) can allow obtaining molecular and functional information, and monitor specific molecular therapeutic efficacy. Bio-imaging methods can be used to detect spatial organization (i.e., distribution) and to quantify cellular and tissue natural constituents, structures, organelles and administered components such as tagging probes (e.g., fluorescent probes) and drugs using light transmission, reflection, scattering and fluorescence emission strategies, with high spatial and spectral resolutions.

In-vivo competition assays of unlabeled compounds with labeled probes for agents with known pharmacological characteristics and efficacy can be used in the drug evaluation process. Noninvasive characterization of drug targeting, receptor occupancy, concentrations required for effective receptor or enzyme inhibition, etc., can speed up the evaluation of lead compounds. As new drug candidates proceed through pharmacodynamic and pharmacokinetic studies, imaging analyses can quantitatively and repetitively monitor target accessibility, duration of retention at the target site and its correlation with drug efficacy, and clearance from irrelevant tissues.

In clinical trials, imaging assays can facilitate evaluation of non-natural amino acids, non-natural amino acid polypeptides, modified non-natural amino acid polypeptides and fragments thereof, for both their pharmacological properties and their therapeutic effectiveness in patients. By combining imaging probes with multimodality-imaging instruments that merge structural and functional data, physicians can perform multiple functional-imaging assays simultaneously with anatomic analyses. Information derived from structural studies and from noninvasive, repetitive monitoring of drug distribution and concentration can then be correlated with biological effects on signal transduction pathways, target enzyme activities, antigen levels, receptor activation, cell proliferation, proteasome activity, etc. These noninvasive assays can permit real-time monitoring and modification of targeted interventions and therapeutic strategies. Molecular-imaging technologies can be used to study mouse models in pre-clinical studies. For example, many drugs for cancer and other disorders exert their therapeutic effects by inducing apoptosis. The ability to repetitively image apoptotic responses in living animals can facilitate preclinical evaluation of these drugs. For studying transgenic mice, identification of founder mice that can express the transgene in the proper spatial and temporal pattern by noninvasive imaging can permit the identification of founders without breeding.

Molecular imaging can provide the location, magnitude, and duration of expression of the therapeutic gene for the optimization of gene-therapy protocols. Optical imaging can be coupled with targeted gene transfer. Molecular imaging of reporter genes can also be used to monitor the biodistribution and efficacy of cell-based therapies.

Imaging Probes

Imaging probes can be molecules labeled with radioisotopes or light- or nearinfrared (NIR)-emitting molecules. The concentration and/or spectral properties of molecular imaging probes are altered by the specific biological process under investigation. Two types of probes that can be used in functional imaging studies are, by way of example only, direct binding probes and indirect probes. Direct binding probes and indirect probes may be non-natural amino acid polypeptides. Examples of direct binding probes include but are not limited to antibodies, antibody fragments, antigen-binding polypeptides and fragments thereof and receptor ligands. Direct probes can be used to detect concentrations of their targets, since their binding is stoichiometric. Therefore, direct probes are useful in investigating targets that are overexpressed in pathological conditions, for example, before and after therapy. Indirect probes are used to monitor activities of their macromolecular targets, including catalytic activities. Examples of such probes are described by Herschman in Science 2003 302:605-608.

Probes can be developed to monitor endogenous targeted molecules and biological processes. Such probes may be (modified) non-natural amino acid polypeptides. Key mediators and/or indicators of endogenous processes may be investigated using imaging probes. Substrates for enzymes such as kinases or proteases may be labeled via radionuclides or fluorescent molecules such that events such as phosphorylation or protease cleavage are detected by molecular-imaging assays. Such fluorescent probes that emit NIR fluorescent light after protease cleavage may be referred to as "activatable" optical imaging probes.

Direct and indirect probes may be discovered by high-throughput screening of chemical libraries. Direct probes may also be discovered by screening large recombinant antibody and phage libraries. Such libraries may be composed of (modified) non-natural amino acid polypeptides.

Quantum dots: Methods for imaging and diagnostics utilizing non-natural amino acids, non-natural amino acid polypeptides, modified non-natural amino acid polypeptides and fragments thereof disclosed herein include fluorescent semiconductor nanocrystals (also known as quantum dots or qdots). Qdots can be used for the study of intracellular processes at the single-molecule level, high-resolution cellular imaging, long-term in vivo observation of cell trafficking, tumor targeting, and diagnostics.

Colloidal semiconductor quantum dots are single crystals a few nanometers in diameter whose size and shape can be precisely controlled by the duration, temperature, and ligand molecules used in the synthesis. This process may yield qdots that have composition- and size-dependent absorption and emission. Absorption of a photon with energy above the semiconductor band gap energy may result in the creation of an electron-hole pair (or exciton). The absorption may have an increased probability at higher energies (i.e., shorter wavelengths) and result in a broadband absorption spectrum, in marked contrast to standard fluorophores. For nanocrystals smaller than the so-called Bohr exciton radius (a few nanometers), energy levels may be quantized, with values directly related to the qdot size (an effect called quantum confinement, hence the name "quantum dots"). The radiative recombination of an exciton (characterized by a long lifetime, >10 ns) may lead to the emission of a photon in a narrow, symmetric energy band. The long fluorescence lifetime of qdots may enable the use of time-gated detection to separate their signal from that of shorter lived species (such as background autofluorescence encountered in cells).

Single qdots can be observed and tracked over an extended period of time with, for example, confocal microscopy, total internal reflection microscopy, or basic wide-field epifluorescence microscopy. Fluorescence correlation spectroscopy may allow determination of the brightness per particle and also provide a measurement of the average qdot size. Qdots can also be used as probes for two-photon confocal microscopy because they are characterized by a very large absorption cross section. They can be used simultaneously with standard dyes. Qdots have a potential as customizable donors of a fluorescence resonance energy transfer (FRET) pair.

For applications such as qdot tagging of a target molecule such as a non-natural amino acid polypeptide, a single recognition moiety can be grafted to the qdot (e.g., DNA oligonucleotide or aptamer, antibody, antibody fragment, antigen-binding polypeptide, etc.) or, used as the qdot solubilization ligand. Qdot ligands containing either an amine or a carboxyl group, for example, may offer a possibility of cross-linking molecules containing a thiol group or an N-hydroxysuccinimyl ester moiety by means of standard bioconjugation reactions. Another approach can be to use electrostatic interactions between qdots and charged adapter molecules, or between qdots and proteins modified to incorporate charged domains. These functionalization steps can be repeated to add or change functionality. For instance, streptavidin-coated qdots can be used in combination with biotinylated proteins or antibodies. A three-layer approach such as, using (i) an antibody against a specific target, (ii) a biotinylated secondary antibody against the first, and (iii) a streptavidin-coated qdot can allow qdot labeling of non-natural amino acids, non-natural amino acid polypeptides, modified non-natural amino acid polypeptides and fragments thereof, as disclosed herein.

A number of potential surface attachment groups can be used to "graft" different functionalities to individual qdots, resulting in multipotent probes. For instance, in addition to a recognition moiety, qdots can be equipped with a membrane-crossing or cell-internalization capability, and/or an enzymatic function. Peptides can be customized, and with a choice of sequence, a single-step surfactant exchange can yield necessary functions: (i) protect the core/shell structure and maintain the original qdot photophysics, (ii) solubilize qdots, (iii) provide a biological interface, and (iv) allow the incorporation of multiple functions. The resulting particles can have colloidal properties, photophysics, and biocompatibility, and this "peptide toolkit" can be tailored to provide additional functionalities. Such functionalities can be improved by molecular evolution.

Live-cell experiments such as, whole-cell labeling, labeling of membrane-bound proteins, and cytoplasmic or nuclear target labeling can be used for cell or pathogen detection, cell tracking, and cell lineage studies. This can be achieved without any functionalization through microinjection, electroporation, or phagocytosis of qdots. Different types of functionalization can be explored as a way to target qdots to cell surface proteins. Some examples include streptavidin, secondary, or primary antibodies, receptor ligands such as epidermal growth factor (EGF) or serotonin, recognition peptides, and affinity pairs such as biotin-avidin after engineering of the target protein. Another strategy may consist of cross-linking primary antibodies to qdots. Some proteins can be recognized by peptides, so peptides can be used for qdot functionalization. Microinjection can allow the delivery of qdots functionalized with the appropriate targeting peptide sequence to mitochondria or the cell nucleus. The long-term stability and brightness of qdots make them a candidate for live animal targeting and imaging.

In synthesis, new compositions could entail qdots with properties such as (i) sensitivity to electric or magnetic fields; (ii) narrower fluorescence emission and longer lifetimes (using lanthanide-doped qdots); (iii) smaller sizes and extension to the NIR spectrum, as demonstrated by ternary alloys; (iv) end-specific functionalizations of nanorod qdots; (v) suppression of blinking and quantum yield enhancement; and (vi) built-in on-off switches or photoelectric biotransducers.

Biotransducer, light-excited qdots could transfer their charge to bound enzymes functioning as electron or hole acceptors, enabling their control by light activation. Reciprocally, qdots could be lit up by electron or hole donor enzymes through chemiluminescence. Peptide coating of nano-materials can be a tool for imparting novel functions to the organic-inorganic interface. The simultaneous engineering of the semiconductor's band gap (by rational design) with the peptide's redox potential (by molecular evolution) could be used to optimize qdot compositions and peptide sequences for binding and desired optical, electronic, magnetic, and chemical properties. In summary, different shapes, end specificities, and compositions can lead to more complex bioinorganic architectures that could be exploited as an optoelectronic interface to the cellular machinery.

Qdots can be used as contrast reagents for functional imaging with a combination of MRI, PET, computed tomography, and IR fluorescence imaging (the latter by direct imaging through the epidermis or by a catheter-based confocal fiber microscope). In vivo optical biopsy could confirm the pathology, and therapy could then be performed selectively, locally, and temporally by depositing energy (monochromatic x-rays for k-shell absorption or laser IR radiation) into the targeted qdots. Alternatively, it may be possible to graft therapeutic enzymes to the qdot surface and activate them by light, or produce free radicals (such as singlet oxygen) by optically cycling the qdots.

Imaging Instrumentation

Various instrumentation can be used for imaging and diagnostics of non-natural amino acids, non-natural amino acid polypeptides, modified non-natural amino acid polypeptides and fragments thereof, as disclosed herein.

Monitoring the probes may consist of (1) a measurement system, and (2) an analysis software. The measurement system may include all of the optics, electronics and the manner in which the sample is illuminated (e.g., light source selection), the mode of measurement (e.g., fluorescence or transmission), as well as the calibration best suited for extracting the desired results from the measurement. The analysis software may include all of the software and mathematical algorithms necessary to analyze and display important results in a meaningful way. The measurement can be carried out using virtually any optical system attached to the system, for example, an upright or inverted microscope, a fluorescence microscope, a macro lens, an endoscope and a fundus camera. Furthermore, any standard experimental method can be used, including light transmission (bright field and dark field), auto-fluorescence and fluorescence of administered probes, etc. Fluorescence measurements can be made with any standard filter cube (consisting of a barrier filter, excitation filter and a dichroic mirror), or any customized filter cube for special applications, provided the emission spectra fall within the spectral range of the system sensitivity.

Spectral bio-imaging can also be used in conjunction with any standard spatial filtering method such as dark field and phase contrast, and even with polarized light microscopy. Radionuclide-labeled probes can be detected by PET or SPECT (single-photon emission tomography), probes emitting light (fluorescence, bioluminescence, or NIR emissions) can be detected by optical imaging, and radiowave emissions can be detected by MRI. Small-animal devices can be used for radionuclide-based imaging (e.g., microSPECT and microPET), optical imaging of visible light (using sensitive, cooled charged-coupled device (CCD) cameras), and NIR emissions. The combination of anatomical (microMRI and microCT) and molecular imaging techniques (microPET, microSPECT, and NIR fluorescence imaging) can help obtain molecular and functional information, and monitor specific molecular therapeutic efficacy.

Noninvasive reporter gene assays can be used for molecular-imaging studies of living animals. Radionuclide-labeled probes can be used to monitor, in living mice, the expression of reporter genes using the direct-binding FESP probe, or the herpes simplex virus type 1-thymidine kinase (HSV1-TK). HSV1-TK can be monitored with positron-labeled thymidine analogs. Like FDG, the indirect substrate probe for hexokinase, positron-labeled substrates for HSV1-TK can be retained in cells as a result of enzyme dependent phosphorylation. For optical-imaging assays, the light produced by the enzymes from their substrates can be monitored with sensitive CCD cameras. New reporter genes encoding fusion proteins that can be imaged with fluorescent, bioluminescent, or radionuclide probes can allow study of a single animal with a number of different imaging probes and instrumentation appropriate for distinct applications.

MicroPET instrumentation can provide better anatomic discrimination of functional assays: for example, pinpointing the locations of tumors within organs, determining the location of cell migration more accurately, etc. Fluorescence-mediated tomography can improve the resolution and quantitation of optical imaging procedures. Spectral-imaging technologies can discriminate emissions from multiple fluorescent probes, permitting simultaneous analysis of distinct optical probes and dramatically reducing background autofluorescence.

Non-Natural Amino Acid-Scanning of Polypeptides and Libraries.

The identification of amino acids to be substituted in order to modulate activities or properties of the polypeptide may be done by site-directed mutagenesis. Amino acids in the polypeptides and polypeptide libraries of the present invention that modulate function can be identified or modulated by substituting a non-naturally encoded amino acid in place of a natural amino acid at any or all positions of the polypeptide. Naturally encoded amino acids may be substituted into a selected position of a polypeptide by methods known in the art, such as site-directed mutagenesis or alanine-scanning mutagenesis (See, e.g., Cunningham et al. 1989), which disclosure is hereby incorporated by reference in its entirety. The alanine-scanning mutagenesis procedure introduces single alanine mutations at selected or every residue in the molecule. Instead of substituting the naturally encoded amino acid alanine, a non-naturally encoded amino acid is substituted for a naturally encoded amino acid in the polypeptide chain. The resulting mutant polypeptide molecules comprising a non-naturally encoded amino acid are then tested for biological activity using assays appropriate for measuring the function of the particular polypeptide or protein. Of special interest may be substitutions of non-naturally encoded charged amino acids or non-naturally encoded neutral amino acids for the naturally encoded charged and/or neutral amino acids. These substitutions may produce proteins with highly desirable improved or modulated characteristics, such as modulated receptor binding, modulated enzymatic activity, modulated antigen binding, or modulated aggregation or solubility.

EXAMPLES

The following examples are offered to illustrate, but not to limit the claimed invention.

Example 1

This example describes conjugates that may be formed with non-natural amino acid polypeptides. Molecules may be directly bonded to one or more non-natural amino acids in a polypeptide or may be attached via a linker, polymer, water soluble polymer, or biologically active molecule.

FIG. 9 presents non-limiting examples of molecules that are site specifically attached to polypeptides via a reaction that forms an oxime bond between the carbonyl of a non-natural amino acid incorporated into a polypeptide and the hydroxylamine of the molecule. Molecules including but not limited to, fluorophores, biotin, and chelators may be attached to non-natural amino acid polypeptides.

Example 2

Resins or other materials known to those skilled in the art may be used to isolate polypeptides. FIG. 10 shows an example of a purification method for a non-natural amino acid polypeptide utilizing a resin that reacts with the non-natural amino acid. A covalent linkage is formed between a chemically specific affinity tag on the resin and a non-natural amino acid present in the protein. Such linkages are stable under a broad range of pH and purification conditions. The separation step may be performed in alternate modes, including but not limited to a bath mode, enabling the large-scale purifications. The resin and the affinity tags are physically and chemically stable, and thus, can be reused to reduce the cost of protein purification upon scale-up.

The separation can be performed in conjunction with conjugation of the polypeptide to molecules including but not limited to, PEG. This "one-pot" method further simplifies the conjugation process and reduces the cost of production of proteins, including but not limited to target therapeutic proteins (FIG. 11). Other molecules that can be conjugated include but are not limited to fluorophores.

Resins or other materials for purification can be selected and functionalized according to the non-natural amino acid present in the polypeptide. FIG. 12 shows an example of resin selection and functionalization.

Resins or other materials for purification can be functionalized differently depending on the non-natural amino acid in the polypeptide. For example, FIG. 13 shows an example of affinity purification of a non-natural amino acid polypeptide using hydroxylamine resin. FIG. 14 shows an example of purification of a non-natural amino acid polypeptide using an aldehyde resin. Non-limiting examples of hydroxylamine and aldehyde resins are shown.

naturally-occurring GH amino acid sequence as well as the mature naturally-occurring GH amino acid sequence and naturally occurring mutant, see SEQ ID NO: 1, SEQ ID NO: 2 and SEQ ID NO: 3, incorporated by reference from Int'l Pub. No. WO 05/074650.

An introduced translation system that comprises an orthogonal tRNA (O-tRNA) and an orthogonal aminoacyl tRNA synthetase (O-RS) is used to express hGH containing a non-naturally encoded amino acid. The O-RS preferentially aminoacylates the O-tRNA with a non-naturally encoded amino acid. In turn the translation system inserts the non-naturally encoded amino acid into hGH, in response to an encoded selector codon.

TABLE 1

O-RS and O-tRNA sequences incorporated by reference from Int'l Pub. No. WO 05/074650.

| | | |
|---|---|---|
| SEQ ID NO: 4 | *M. jannaschii* mtRNA$_{CUA}^{Tyr}$ | tRNA |
| SEQ ID NO: 5 | HLAD03; an optimized amber supressor tRNA | tRNA |
| SEQ ID NO: 6 | HL325A; an optimized AGGA frameshift supressor tRNA | tRNA |
| SEQ ID NO: 7 | Aminoacyl tRNA synthetase for the incorporation of p-azido-L-phenylalanine p-Az-PheRS(6) | RS |
| SEQ ID NO: 8 | Aminoacyl tRNA synthetase for the incorporation of p-benzoyl-L-phenylalanine p-BpaRS(1) | RS |
| SEQ ID NO: 9 | Aminoacyl tRNA synthetase for the incorporation of propargyl-phenylalanine Propargyl-PheRS | RS |
| SEQ ID NO: 10 | Aminoacyl tRNA synthetase for the incorporation of propargyl-phenylalanine Propargyl-PheRS | RS |
| SEQ ID NO: 11 | Aminoacyl tRNA synthetase for the incorporation of propargyl-phenylalanine Propargyl-PheRS | RS |
| SEQ ID NO: 12 | Aminoacyl tRNA synthetase for the incorporation of p-azido-phenylalanine p-Az-PheRS(1) | RS |
| SEQ ID NO: 13 | Aminoacyl tRNA synthetase for the incorporation of p-azido-phenylalanine p-Az-PheRS(3) | RS |
| SEQ ID NO: 14 | Aminoacyl tRNA synthetase for the incorporation of p-azido-phenylalanine p-Az-PheRS(4) | RS |
| SEQ ID NO: 15 | Aminoacyl tRNA synthetase for the incorporation of p-azido-phenylalanine p-Az-PheRS(2) | RS |
| SEQ ID NO: 16 | Aminoacyl tRNA synthetase for the incorporation of p-acetyl-phenylalanine (LW1) | RS |
| SEQ ID NO: 17 | Aminoacyl tRNA synthetase for the incorporation of p-acetyl-phenylalanine (LW5) | RS |
| SEQ ID NO: 18 | Aminoacyl tRNA synthetase for the incorporation of p-acetyl-phenylalanine (LW6) | RS |
| SEQ ID NO: 19 | Aminoacyl tRNA synthetase for the incorporation of p-azido-phenylalanine (AzPheRS-5) | RS |
| SEQ ID NO: 20 | Aminoacyl tRNA synthetase for the incorporation of p-azido-phenylalanine (AzPheRS-6) | RS |

In some embodiments, one or more steps of the purification process modify one or more non-natural amino acids present in the polypeptide to one or more natural amino acids. FIG. 15 shows an example of purification of native proteins from a non-natural amino acid precursor. The non-natural amino acid is converted to tyrosine after release from the resin used in the purification process. FIG. 16 shows non-limiting examples of non-natural amino acids.

Example 3

Non-Natural Amino Acid-scanning Mutagenesis.

This example details cloning and expression of a hGH polypeptide including a non-naturally encoded amino acid in *E. coli*. This example also describes one method to assess the biological activity of modified hGH polypeptides.

Methods for cloning hGH and fragments thereof are detailed in U.S. Pat. Nos. 4,601,980; 4,604,359; 4,634,677; 4,658,021; 4,898,830; 5,424,199; and 5,795,745, which are incorporated by reference herein. cDNA encoding the full length hGH or the mature form of hGH lacking the N-terminal signal sequence are shown in SEQ ID NO: 21 and SEQ ID NO: 22 respectively. For the complete full-length The transformation of *E. coli* with plasmids containing the modified hGH gene and the orthogonal aminoacyl tRNA synthetase/tRNA pair (specific for the desired non-naturally encoded amino acid) allows the site-specific incorporation of non-naturally encoded amino acid into the hGH polypeptide. The transformed *E. coli*, grown at 37° C. in media containing between 0.01-100 mM of the particular non-naturally encoded amino acid, expresses modified hGH with high fidelity and efficiency. The His-tagged hGH containing a non-naturally encoded amino acid is produced by the *E. coli* host cells as inclusion bodies or aggregates. The aggregates are solubilized and affinity purified under denaturing conditions in 6M guanidine HCl. Refolding is performed by dialysis at 4° C. overnight in 50 mM TRIS-HCl, pH 8.0, 40 μM CuSO$_4$, and 2% (w/v) Sarkosyl. The material is then dialyzed against 20 mM TRIS-HCl, pH 8.0, 100 mM NaCl, 2 mM CaCl$_2$, followed by removal of the His-tag. See Boissel et al., (1993) 268:15983-93. Methods for purification of hGH are well known in the art and are confirmed by SDS-PAGE, Western Blot analyses, or electrospray-ionization ion trap mass spectrometry and the like.

The His-tagged mutant hGH proteins were purified using the ProBond Nickel-Chelating Resin (Invitrogen, Carlsbad, Calif.) via the standard His-tagged protein purification procedures provided by the manufacturer, followed by an anion exchange column prior to loading on the gel. To further assess the biological activity of modified hGH polypeptides, an assay measuring a downstream marker of hGH's interaction with its receptor was used. The interaction of hGH with its endogenously produced receptor leads to the tyrosine phosphorylation of a signal transducer and activator of transcription family member, STAT5, in the human IM-9 lymphocyte cell line. Two forms of STAT5, STAT5A and STAT5B were identified from an IM-9 cDNA library. See, e.g., Silva et al., Mol. Endocrinol. (1996) 10(5):508-518. The human growth hormone receptor on IM-9 cells is selective for human growth hormone as neither rat growth hormone nor human prolactin resulted in detectable STAT5 phosphorylation. Importantly, rat GHR (L43R) extra cellular domain and the G120R bearing hGH compete effectively against hGH stimulated pSTAT5 phoshorylation.

IM-9 cells were stimulated with hGH polypeptides of the present invention. The human IM-9 lymphocytes were purchased from ATCC (Manassas, Va.) and grown in RPMI 1640 supplemented with sodium pyruvate, penicillin, streptomycin (Invitrogen, Carlsbad, San Diego) and 10% heat inactivated fetal calf serum (Hyclone, Logan, Utah). The IM-9 cells were starved overnight in assay media (phenol-red free RPMI, 10 mM Hepes, 1% heat inactivated charcoal/dextran treated FBS, sodium pyruvate, penicillin and streptomycin) before stimulation with a 12-point dose range of hGH polypeptides for 10 min at 37° C. Stimulated cells were fixed with 1% formaldehyde before permeabilization with 90% ice-cold methanol for 1 hour on ice. The level of STAT5 phosphorylation was detected by intra-cellular staining with a primary phospho-STAT5 antibody (Cell Signaling Technology, Beverly, Mass.) at room temperature for 30 min followed by a PE-conjugated secondary antibody. Sample acquisition was performed on the FACS Array with acquired data analyzed on the Flowjo software (Tree Star Inc., Ashland, Oreg.). $EC_{50}$ values were derived from dose response curves plotted with mean fluorescent intensity (MFI) against protein concentration utilizing SigmaPlot.

Table 2 below summarizes the IM-9 data generated with mutant hGH polypeptides. Various hGH polypeptides with a non-natural amino acid substitution at different positions were tested with human IM-9 cells as described. Substitutions shown were made with p-acetyl phenylalanine at the positions indicated. The same assay was used to assess biological activity of hGH polypeptides comprising a non-natural amino acid that is PEGylated. From the data shown in the table, it is apparent that there are differences in receptor binding activity depending upon the position in which the non-naturally encoded amino acid was substituted for a naturally encoded amino acid.

TABLE 2

| GH | $EC_{50}$ (nM) | GH | $EC_{50}$ (nM) |
|---|---|---|---|
| WHO WT | 0.4 ± 0.1 (n = 8) | G120R | >200,000 |
| N-6His WT | 0.6 ± 0.3 (n = 3) | G120pAF | >200,000 |
| rat GH WT | >200,000 | G131pAF | 0.8 ± 0.5 (n = 3) |
| Y35pAF | 0.7 ± 0.2 (n = 4) | P133pAF | 1.0 |
| E88pAF | 0.9 | R134pAF | 0.9 ± 0.3 (n = 4) |
| Q91pAF | 2.0 ± 0.6 (n = 2) | T135pAF | 0.9 |
| F92pAF | 0.8 ± 0.4 (n = 9) | G136pAF | 1.4 |
| R94pAF | 0.7 | F139pAF | 3.3 |
| S95pAF | 16.7 ± 1.0 (n = 2) | K140pAF | 2.7 ± 0.9 (n = 2) |
| N99pAF | 8.5 | Y143pAF | 0.8 ± 0.3 (n = 3) |
| Y103pAF | 130,000 | K145pAF | 0.6 ± 0.2 (n = 3) |
| Y111pAF | 1.0 | A155pAF | 1.3 |

Example 4

This example details cloning and expression of a modified hIFN polypeptide in *E. coli*.

This example demonstrates how a hIFN polypeptide including a non-naturally encoded amino acid can be expressed in *E. coli*. See Nagata et. al., Nature, vol. 284, 316-320 (1980) and U.S. Pat. No. 4,364,863. cDNA encoding the full length hIFN and the mature form of hIFN lacking the N-terminal signal sequence are shown in SEQ ID NO: 23 and SEQ ID NO: 24, respectively incorporated by reference from Int'l Pub. No. WO 05/074650. The full length and mature hIFN encoding cDNA is inserted into the pBAD HISc, pET20b, and pET19b expression vectors following optimization of the sequence for cloning and expression without altering amino acid sequence.

An introduced translation system that comprises an orthogonal tRNA (O-tRNA) and an orthogonal aminoacyl tRNA synthetase (O-RS) is used to express hGH containing a non-naturally encoded amino acid. The O-RS preferentially aminoacylates the O-tRNA with a non-naturally encoded amino acid. In turn the translation system inserts the non-naturally encoded amino acid into hGH, in response to an encoded selector codon.

O-RS and O-tRNA sequences suitable for use with Interferon expression include those shown in Example 3. The transformation of *E. coli* with plasmids containing the modified hIFN gene and the orthogonal aminoacyl tRNA synthetase/tRNA pair (specific for the desired non-naturally encoded amino acid) allows the site-specific incorporation of non-naturally encoded amino acid into the hIFN polypeptide. The transformed *E. coli*, grown at 37° C. in media containing between 0.01-100 mM of the particular non-naturally encoded amino acid, expresses modified hIFN with high fidelity and efficiency. The His-tagged hIFN containing a non-naturally encoded amino acid is produced by the *E. coli* host cells and are affinity purified. Methods for purification of hIFN are well known in the art and are confirmed by SDS-PAGE, Western Blot analyses, or electrospray-ionization ion trap mass spectrometry and the like.

Binding Assays.

The hIFN receptor was prepared as described in U.S. Pat. Nos. 6,566,132; 5,889,151; 5,861,258; 5,731,169; 5,578, 707, which are incorporated by reference herein. For a non-PEGylated polypeptide comprising a non-natural amino acid, the affinity of the hormone for its receptor was measured by using a BLAcore™ biosensor (Pharmacia) technique, which is known in the art. BIAcore biosensor assays were used to measure the binding characteristics of hIFN molecules that comprised a non-naturally encoded amino acid substituted at the positions shown in Table 3, along with the receptor binding data. From the data shown in the table, it is apparent that there are differences in receptor binding activity depending upon the position in which the non-naturally encoded amino acid was substituted for a naturally encoded amino acid.

TABLE 3

| IFNα2A Variants | Kd (nM) | IFNα2A Variants | Kd (nM) |
|---|---|---|---|
| Sigma IFNαA | 11 | 6His-Q61pAF | 21 |
| 6His-IFNα2A | 6 | 6His-N65pAF | 7 |
| C1S IFNa2A | 11 | 6His-E78pAF | 7 |
| C1S E107pAF | 9 | 6His-Y89pAF | 9 |

TABLE 3-continued

| IFNα2A Variants | Kd (nM) | IFNα2A Variants | Kd (nM) |
|---|---|---|---|
| 6His-F36S | 1300 | 6His-E96pAF | 12 |
| 6His-F38L | 18 | 6His-I100pAF | 10 |
| 6His-F38S | 42 | 6His-G102pAF | 27 |
| 6His-L9pAF | 14 | 6His-V103pAF | 14 |
| 6His-R12pAF | 8 | 6His-T106pAF | 8 |
| 6His-R13pAF | 14 | 6His-E107pAF | 5 |
| 6His-M16pAF | 18 | 6His-P109pAF | 17 |
| 6His-I24pAF | 5 | 6His-L110pAF | 13 |
| 6His-F27pAF | 8 | 6His-E113pAF | 19 |
| 6His-K31pAF | 52 | 6His-L117pAF | 8 |
| 6His-H34pAF | 4 | 6His-R120pAF | 4 |
| 6His-G37pAF | 12 | 6HisY122S | 300 |
| 6His-P39pAF | 17 | 6His-R125pAF | 19 |
| 6His-E41pAF | 16 | 6His-K134pAF | 10 |
| 6His-N45pAF | 7 | 6His-R149pAF | 75 |
| 6His-Q48pAF | 17 | 6His-E159pAF | 3.5 |
| 6His-K49pAF | 10 | | |

Example 5

Conjugates and complexes between proteins and oligonucleotides have wide applications in diagnosis and therapeutic, such as immunoPCR, gene therapeutic and more recently targeted delivery of RNAi. Site-specific conjugation enables production of specifically designed molecules and nano structures that have novel functions. Currently, the site-specific conjugations have been achieved mainly through maleimide chemistry, in which an engineered protein surface cysteine selectively reacts with maleimide to form a thioether. The development of site-specific incorporation of unnatural amino acids into polypeptides has enabled a large array of chemistries for conjugation of molecules to proteins. Over 30 non-naturally encoded amino acids have been incorporated site-specifically into proteins. In this example using the unnatural amino acid described below as a handle, oligo nucleotides were conjugated to proteins site-specifically. Furthermore, using single strand DNA as template, the conjugated proteins were assembled in one dimension in a defined manner.

Protein used in this experiment was human growth hormone Y35 mutant, in which the tyrosine 35 was replaced by the non-naturally encoded amino acid 9.2 (Scheme 1). The single strand DNAs were stored as 25 mM solutions in water at −80° C. The sequence of ssDNA FTam27 is 5'-CAG CCA GCG TGC ACG (SEQ ID NO:21). The 5' of FTam27 was modified with hydrazide. The sequence for the templates are FTam28-d1: 5'-CGTGCACGCTGGCTGCGTGCACGCTGGCTG (SEQ ID NO:21); FTam-d2: 5'-CGTGCACGCTGGCTG T CGTGCACGCTGGCTG (SEQ ID NO:22); FTam28-d3: 5'-CGTGCACGCTGGCTG TT CGTGCACGCTGGCTG;FTam28-t1 (SEQ ID NO:23); 5'-CGTGCACGCTGGCTGCGTGCACGCTGGCTGCGTGCACGCTGGCTG (SEQ ID NO:24); FTam28-t2: 5'-CGTGCACGCTGGCTG T CGTGCACGCTGG T CTGCGTGCACGCTGGCTG (SEQ ID NO:25); FTam28-t3: 5'-CGTGCACGCTGGCTG TT CGTGCACGCTGG TT CTGCGTGCACGCTGGCTG (SEQ ID NO:26).

Protein-single Strand DNA Conjugation:

Protein (1 mg) was buffer exchanged into reaction buffer (150 mM NaCl, 20 mM NaOAc, 400 mM Arg, 5 mM EDTA, pH 4.0) using PD 10 gel filtration columns. The protein solution was concentrated to 90 μl using 10 kD MWCO CENTROCON (Vivascience). Five μl of the water solution of 25 mM ssDNA FTam27, which has a 5' modification of hydrazide, was dispensed in 40 μl of reaction buffer. The ssDNA solution was added slowly into the protein solution. Precipitation appeared initially, but dissolved. 20 hours after incubation at 28° C., 5 mM sodium cyanoborohydride was added. The reaction mixture was incubated for another 20 hours and subjected to analysis and purification.

Purification of Conjugate:

A 1 ml phenyl HIC column was employed for the FPLC purification of the conjugate. Buffer A: 2 M NaCl, 10 mM Tris.HCl, pH 7.0; Buffer B: 10 mM Tris.HCl, pH 7.0. The gradient used in the purification was: 10 column volume (CV) 0% B, 5 CV to 50% B, hold at 50% B for 5 CV, then 30 CV to 100% B. Purified conjugate was concentrated, buffer-exchanged to storage buffer (200 mM NaCl, 50 mM Tris.HCl, 1 mM EDTA, pH 8.0) and subjected to PAGE analysis using 4-12% SDS gel, at 200 V in MES buffer.

Hybridization:

Five μl of protein-ssDNA conjugate was added to the complementary ssDNA in storage buffer (200 mM NaCl, 50 mM Tris.HCl, 1 mM EDTA, pH 8.0). The mixtures were supplemented with storage buffer to give a final volume of 20 μl and heated at 42° C. for 30 seconds, then cooled to room temperature. The final products were analyzed by native TRIS-glycine gel electrophoresis at 125 V, 4° C. for 3 to 5 hours.

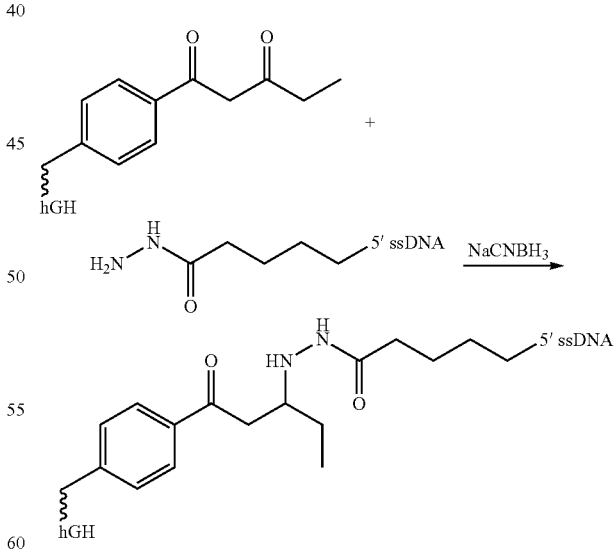

Figure 17:
FIG. 17 shows SDS-PAGE analysis of hGH-single strand DNA conjugate 1) Reaction mixture of the conjugation reaction; 2) Purified hGH-ssDNA conjugate by HIC column.

Scheme 1. Conjugation of hGH mutant (Y35/unnatural amino acid 9.2) with single strand DNA modified at 5' end with hydrazide Non-naturally encoded amino acid 9.2, which has a 1,3 diketone moiety, was incorporated into human growth hormone (hGH) at amino acid position 35, and used as a handle for the conjugation with a 15 mer single strand DNA, FTam27, modified at the 5' with hydrazide functional group (Scheme 1). This conjugation resulted in a hydrazone initially, which is further reduced with sodium cyanoborohydride to give an irreversible covalent linkage. With five fold excess of ssDNA, a 70% yield was obtained (FIG. 17). The conjugate was purified to about 90% pure using HIC column and subject to hybridization.

Figure 18:
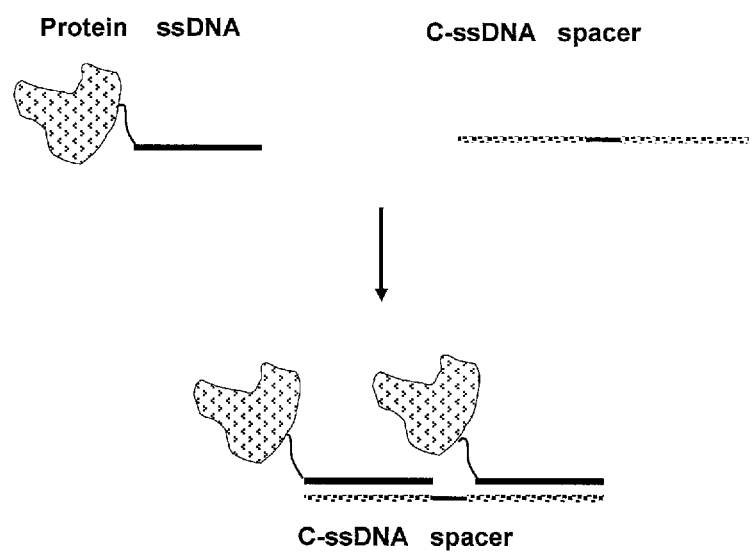
FIG. 18 shows protein-ssDNA conjugate hybridization.
Figure 19:
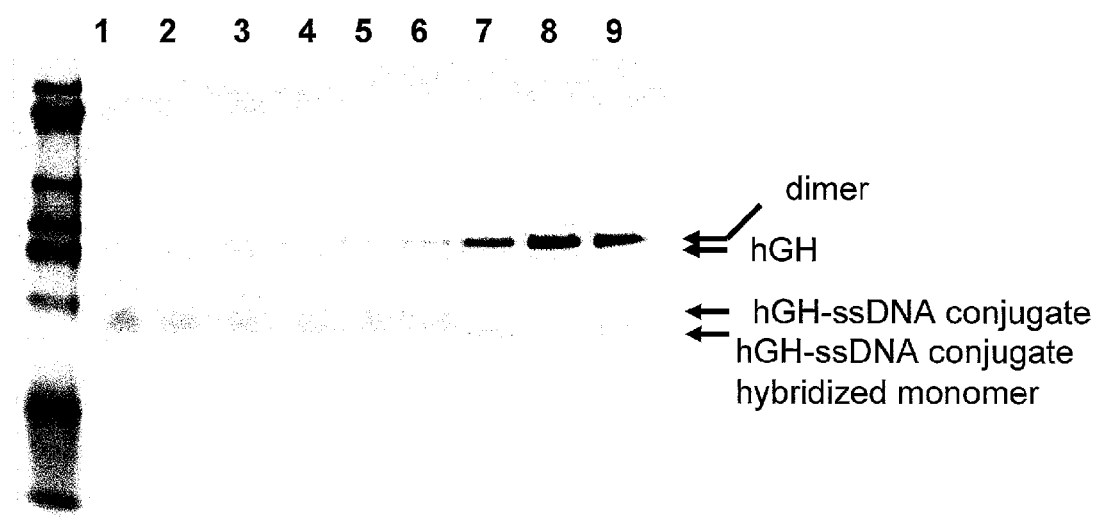
FIG. 19 shows native 14% glycine gel analysis of hGH-ssDNA conjugate hybridization; hGH-ssDNA conjugate (5 µl) with: 1) 0 µl; 2) 2 µl; 3) 4 µl; 4) 6 µl; 5) 8 µl; 6) 10 µl, of 1 µM FTam28d3; and 7) 2 µl; 8) 4 µl; 9) 8 µl, of 10 µM FTam28-d3.

The conjugate was designed to hybridize with ssDNAs that have two (d) or three (t) tandem complementary sequence (FTam28) repeats with zero (1), one (2) and two (3) bases T between them as spacers (FIG. 18). To determine the relative concentration of hGH-DNA conjugate, 5 µl of hGH-ssDNA conjugate was mixed with a series concentration of FTam28-d3, a single strand DNA that has two repeating sequences complementary to FTam27 and two T bases as a spacer between them. The result was analyzed with 14% native glycine gel electrophoresis, 125 V, 3 hr at 4° C. (FIG. 19). The most complete hybridization was with 5 µl hGH-ssDNA mixed with 4 µl of 10 µM FTam28-d3 which gave a conjugate concentration of about 16 µM. According to the gel, hGH-ssDNA and hGH-ssDNA hybrid monomer with FTam28-d3, were more mobile than hGH itself, presumably due to the large number of negative charges on the DNA backbone.

Figure 20:
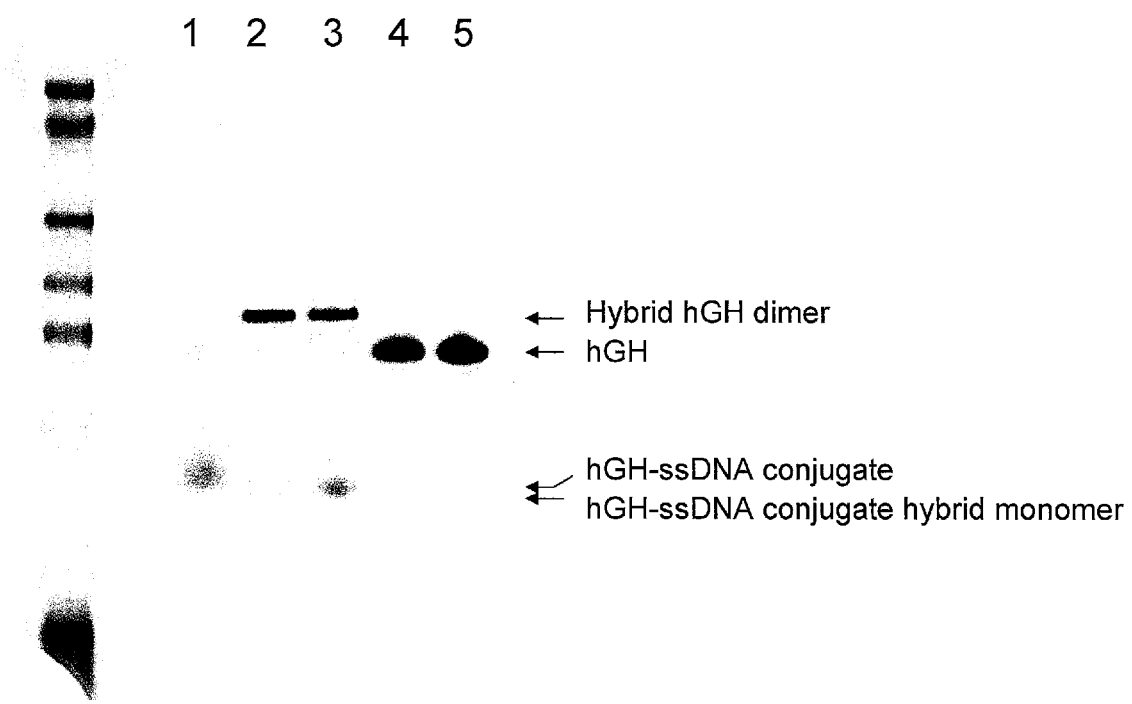
FIG. 20 shows native gel analysis of 5 µl of hGH-ssDNA mixed with 1) 0 µl; 2) 1 µl; 3) 4 µl, of 100 µM FTam28-d3; and hGH mixed with 4) 1 µl; 5) 0 µl, of 100 µM FTam28-d3.

These phenomena were also demontrated in a control experiment (FIG. 20). When hGH was mixed with 1 µl of 100 µM FTam28-d3, no hybridization was observed (lane 4). On the other hand, when 1 µl of 100 µM FTam28-d3 mixed with hGH-ssDNA conjugate, hGH dimer is formed through hybridization. There is no non-specific interaction between hGH and the DNA. The dimerization of conjugated hGH was the result of specific DNA hybridization. When a large excess of FTam28-d3 was added, more hybrid monomer and less hybrid dimer were formed. There was a substantial amount of hybrid dimer present when 80 pico mole of hGH-ssDNA conjugate was mixed with 10 equivalents of FTam28-d3 (lane 3). This indicated that the hybrid dimer was more stable than the hybrid monomer thermodynamically.

Figure 21:
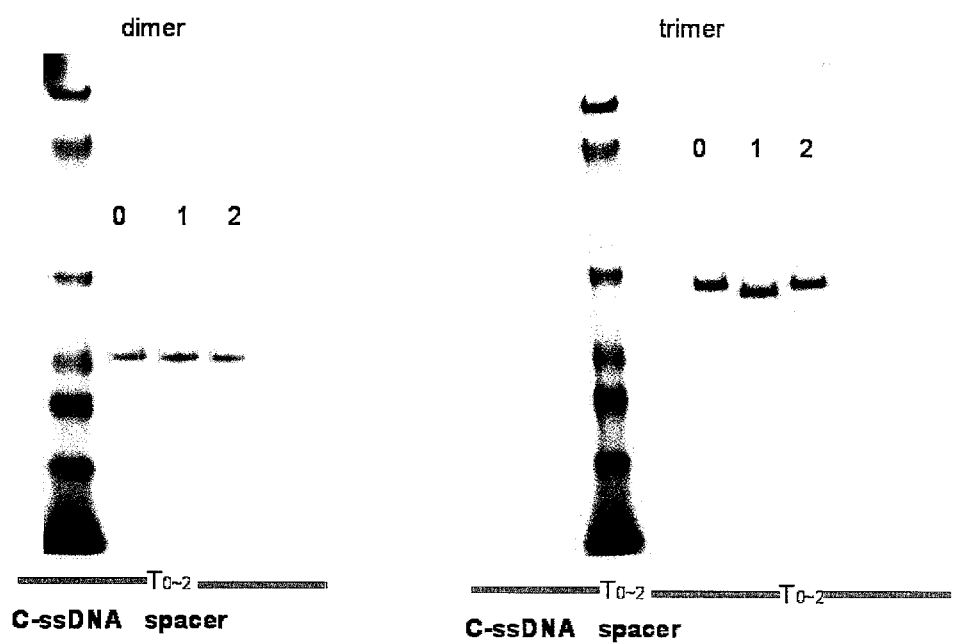
FIG. 21 shows assemblies of 1-D hGH structure using DNA as a template.

To demonstrate assembly of protein-ssDNA in a well-defined manner (FIG. 21), six one dimension structures of hGH using single strand DNA as templates were assembled. These structures varied by different valency and spacers between each hGH molecule. hGH-ssDNA conjugate was mixed with one equivalent of each of the DNA templates. The mixtures were incubated at 50° C. for 5 minutes, cooled to room temperature and analyzed on a native glycine gel. These 1-D structures were assembled highly efficiently. Lane 1 to lane 3 show the results of dimer formation with spacers of zero, one and two, respectively, T bases between the DNA sequence repeats. Lane 4 to lane 6 show the assembly results of trimer formation with spacers of zero, one and two T bases as spacer.

Using non-naturally encoded amino acids as a chemical handle, single strand DNA was conjugated to the protein surface site-specifically. This single strand DNA-protein conjugate can be used to assemble protein 1-D structures highly efficiently using DNA as a template. Site-specific oligonucleotide conjugation can also be used to assemble well defined 3-D structures creating novel nano structures with novel functions. Moreover, the protein-oligo nucleotide conjugation technology may be applied to create protein drug "plug and play" libraries. In this case, the oligonucleotide may be used as both a linkage and a "name tag" to encode the individual small molecule and/or protein. The protein-oligo nucleotide conjugate may be used in immunoPCR for diagnostic applications. This technology can also be used to create protein RNA or PNA conjugates which can be used in targeted RNAi therapeutics.

It is understood that the examples and embodiments described herein are for illustrative purposes only and that various modifications or changes in light thereof will be suggested to those of ordinary skill in the art and are to be included within the spirit and purview of this application and scope of the appended claims. While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A single stranded DNA polynucleotide-polypeptide conjugate comprising a polynucleotide covalently conjugated to a polypeptide, wherein the polynucleotide is at least 95% identical to SEQ ID NO: 26, wherein the polypeptide and polynucleotide are covalently conjugated via a non-naturally encoded amino acid in the amino acid sequence of the polypeptide, wherein the polypeptide is human growth hormone, and wherein the non-naturally encoded amino acid has the structure:

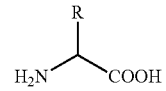

and wherein the R group is any substituent other than one used in the twenty natural amino acids.

2. The polynucleotide-polypeptide conjugate of claim 1 wherein the conjugate forms a dimer.

* * * * *